United States Patent
Wirth et al.

(10) Patent No.: US 9,988,626 B2
(45) Date of Patent: Jun. 5, 2018

(54) NEUROCALCIN DELTA INHIBITORS AND THERAPEUTIC AND NON-THERAPEUTIC USES THEREOF

(71) Applicant: Universität Zu Köln, Köln (DE)

(72) Inventors: Brunhilde Wirth, Bonn (DE); Markus Riessland, Köln (DE)

(73) Assignee: Universität Zu Köln, Köln (DE)

( * ) Notice: Subject to any disclaimer, the term of this patent is extended or adjusted under 35 U.S.C. 154(b) by 0 days. days.

(21) Appl. No.: 14/908,162

(22) PCT Filed: Jul. 29, 2014

(86) PCT No.: PCT/EP2014/066276
§ 371 (c)(1),
(2) Date: Jan. 28, 2016

(87) PCT Pub. No.: WO2015/014838
PCT Pub. Date: Feb. 5, 2015

(65) Prior Publication Data
US 2016/0208248 A1    Jul. 21, 2016

Related U.S. Application Data

(60) Provisional application No. 61/859,664, filed on Jul. 29, 2013.

(51) Int. Cl.
*A61K 48/00* (2006.01)
*C12N 15/113* (2010.01)
*A61K 31/713* (2006.01)
*A61K 35/30* (2015.01)
*A61K 45/06* (2006.01)
*C12N 5/0793* (2010.01)

(52) U.S. Cl.
CPC .......... *C12N 15/113* (2013.01); *A61K 31/713* (2013.01); *A61K 35/30* (2013.01); *A61K 45/06* (2013.01); *C12N 5/0619* (2013.01); *C12N 2310/11* (2013.01); *C12N 2310/14* (2013.01); *C12N 2310/3233* (2013.01); *C12N 2310/531* (2013.01); *C12N 2320/31* (2013.01); *C12N 2320/33* (2013.01); *C12N 2501/065* (2013.01); *C12N 2501/998* (2013.01)

(58) Field of Classification Search
CPC ..................................................... A61K 48/00
See application file for complete search history.

(56) References Cited

U.S. PATENT DOCUMENTS

2013/0047273 A1    2/2013 Sharma et al.

OTHER PUBLICATIONS

Bai et al. Mol Neurobiol (2016) 53:310-319.*

Ackermann et al., Plastin 3 ameliorates spinal muscular atrophy via delayed axon pruning and improves neuromuscular junction functionality. Hum Mol Genet. Apr. 1, 2013;22(7):1328-47.
Benjamini et al., Controlling the False Discovery Rate: a Practical and Powerful Approach to Multiple Testing. Journal of the Royal Statistical Society. Series B (Methodological). 1995;57(1):289-300.
Braunewell et al., Visinin-like proteins (VSNLs): interaction partners and emerging functions in signal transduction of a subfamily of neuronal Ca2+ -sensor proteins. Cell Tissue Res. Feb. 2009;335(2):301-16.
Buckingham et al., Sodium and potassium currents of larval zebrafish muscle fibres. J Exp Biol. Feb. 2004;207(Pt 5):841-52.
Burgoyne et al., Secretory granule exocytosis. Physiol Rev. Apr. 2003;83(2):581-632.
Burgoyne et al., The neuronal calcium sensor family of Ca2+-binding proteins. Biochem J. Jan. 1, 2001;353(Pt 1):1-12.
Dent et al., Dent EW, Gertler FB. Cytoskeletal dynamics and transport in growth cone motility and axon guidance. Neuron. Oct. 9, 2003;40(2):209-27.
Di Sole et al., Calcineurin homologous protein: a multifunctional Ca2+-binding protein family. Am J Physiol Renal Physiol. Jul. 15, 2012;303(2):F165-79.
Dodt et al., Visualizing unstained neurons in living brain slices by infrared DIC-videomicroscopy. Brain Res. Dec. 24, 1990;537(1-2):333-6.
Drapeau et al., Limits to the development of fast neuromuscular transmission in zebrafish. J Neurophysiol. Dec. 2001;86(6):2951-6.
Dunning et al., Statistical issues in the analysis of Illumina data. BMC Bioinformatics. Feb. 6, 2008;9:85.
Feldkoetter et al., Quantitative analyses of SMN1 and SMN2 based on real-time lightCycler PCR: fast and highly reliable; carrier testing and prediction of severity of spinal muscular atrophy. Am J Hum Genet. Feb. 2002;70(2):358-68.
Flanagan-Steet et al., Neuromuscular synapses can form in vivo by incorporation of initially aneural postsynaptic specializations. Development. Oct. 2005;132(20):4471-81.
Hao et al., Survival motor neuron affects plastin 3 protein levels leading to motor defects. J Neurosci. Apr. 11, 2012;32(15):5074-84.
Haucke et al., Protein scaffolds in the coupling of synaptic exocytosis and endocytosis. Nat Rev Neurosci. Mar. 2011;12(3):127-38.
Hidaka et al., Neurocalcin family: a novel calcium-binding protein abundant in bovine central nervous system. Neurosci Res. Feb. 1993;16(2):73-7.
Hsieh-Li et al., A mouse model for spinal muscular atrophy. Nat Genet. Jan. 2000;24(1):66-70.
Hua et al., Antisense correction of SMN2 splicing in the CNS rescues necrosis in a type III SMA mouse model. Genes Dev. Aug. 1, 2010;24(15)1634-44.
Hua et al., Peripheral SMN restoration is essential for long-term rescue of a severe spinal muscular atrophy mouse model. Nature. Oct. 5, 2011;478(7367):123-6.

(Continued)

*Primary Examiner* — Kimberly Chong
(74) *Attorney, Agent, or Firm* — Mintz Levin Cohn Ferris Glovsky and Popeo, P.C.; Ingrid A. Beattie

(57) ABSTRACT

The present invention relates to an inhibitor of neurocalcin delta (NCALD) for use in a method for the treatment or prevention of a patient suffering from a disorder associated with a pathological calcium homeostasis. Furthermore, the present invention refers to the use of such inhibitor of NCALD for inducing axon proliferation in vitro and to a method for the differentiation and/or maturation of neuronal stem cells (NSCs) in vitro and to the use of such inhibitor of NCALD to restore impaired endocytosis being a consequence of disturbed $Ca^{2+}$ homeostasis in synaptic terminals essential for development, maturation and maintenance of synapses and neuromuscular junctions (NMJs).

13 Claims, 44 Drawing Sheets

(56) References Cited

OTHER PUBLICATIONS

Huber et al., Variance stabilization applied to microarray data calibration and to the quantification of differential expression. Bioinformatics. 2002;18 Suppl 1:S96-104.
Iino et al., Neurocalcin-immunopositive nerve terminals in the muscle spindle, Golgi tendon organ and motor endplate. Brain Res. Oct. 19, 1998;808(2):294-9.
Ivings et al., Identification of Ca2+-dependent binding partners for the neuronal calcium sensor protein neurocalcin delta: interaction with actin, clathrin and tubulin. Biochem J. May 1, 2002;363(Pt 3):599-608.
Jablonka et al., Defective Ca2+ channel clustering in axon terminals disturbs excitability in motoneurons in spinal muscular atrophy. J Cell Biol. Oct. 8, 2007;179(1):139-49.
Kamiyama et al., Polymorphisms in the 3' UTR in the neurocalcin delta gene affect mRNA stability, and confer susceptibility to; diabetic nephropathy. Hum Genet. Nov. 2007;122(3-4):397-407.
Kariya et al., Reduced SMN protein impairs maturation of the neuromuscular junctions in mouse models of spinal muscular atrophy. Hum Mol Genet. Aug. 15, 2008;17(16):2552-69.
Kirshnan et al., Structural, biochemical, and functional characterization of the calcium sensor neurocalcin delta in the inner retinal neurons and its linkage with the rod outer segment membrane guanylate cyclase transduction system. Biochemistry. Mar. 16, 2004;43(10):2708-23.
Kleinhammer et al., Constitutive and conditional RNAi transgenesis in mice. Methods. Apr. 2011;53(4):430-6.
Kong et al., Impaired synaptic vesicle release and immaturity of neuromuscular junctions in spinal muscular atrophy mice. J Neurosci. Jan. 21, 2009;29(3):842-51.
Kruglyak et al., Parametric and nonparametric linkage analysis: a unified multipoint approach. Am J Hum Genet.; Jun. 1996;58(6):1347-63.
Kuebler et al., Actin and fimbrin are required for the internalization step of endocytosis in yeast. EMBO J. Jul. 1993;12(7):2855-62.
Le et al., SMNDelta7, the major product of the centromeric survival motor neuron (SMN2) gene, extends survival in mice with spinal muscular atrophy and associates with full-length SMN. Hum Mol Genet. Mar. 15, 2005;14(6):845-57.
McWhorter et al., Knockdown of the survival motor neuron (Smn) protein in zebrafish causes defects in motor axon outgrowth; and pathfinding. J Cell Biol. Sep. 1, 2003;162(5):919-31.
Murray et al., Selective vulnerability of motor neurons and dissociation of pre- and post-synaptic pathology at the neuromuscular junction in mouse models of spinal muscular atrophy. Hum Mol Genet. Apr. 1, 2008;17(7):949-62.
Oh et al., A novel role of hippocalcin in bFGF-induced neurite outgrowth of H19-7 cells. J Neurosci Res. May 15, 2008;86(7):1557-65.
Oprea et al., Plastin 3 is a protective modifier of autosomal recessive spinal muscular atrophy. Science. Apr. 25, 2008;320(5875):524-7.
Riessland et al., The benzamide M344, a novel histone deacetylase inhibitor, significantly increases SMN2 RNA/protein levels in spinal muscular atrophy cells. Hum Genet. Aug. 2006;120(1):101-10.
Rueschendorf et al., Alohomora: a tool for linkage analysis using 10K SNP array data. Bioinformatics. May 1, 2005;21(9):2123-5.
Ruiz et al., Altered intracellular Ca2+ homeostasis in nerve terminals of severe spinal muscular atrophy mice. J Neurosci. Jan. 20, 2010;30(3):849-57.
Schneggenburger et al., Presynaptic calcium and control of vesicle fusion. Curr Opin Neurobiol. Jun. 2005;15(3):266-74.
See et al., SMN deficiency alters Nrxn2 expression and splicing in zebrafish and mouse models of spinal muscular atrophy. Hum Mol Genet. Apr. 1, 2014;23(7):1754-70.
Smyth. Limma: Linear Models for Microarray Data. In: Gentleman R, Carey V, Dudoit S, Irizarry RA, Huber W (eds) Bioinformatics and Computational Biology Solutions using R and Bioconductor. Springer, New York, 2005;397-420.
Smyth. Linear models and empirical bayes methods for assessing differential expression in microarray experiments. Stat Appl Genet Mol Biol. 2004;3:Article3.
Stevens. Neurotransmitter release at central synapses. Neuron. Oct. 9, 2003;40(2):381-8.
Strauch et al., Parametric and nonparametric multipoint linkage analysis with imprinting and two-locus-trait; models: application to mite sensitization. Am J Hum Genet. Jun. 2000;66(6):1945-57.
Suedhof. Calcium control of neurotransmitter release. Cold Spring Harb Perspect Biol. Jan. 1, 2012;4(1):a011353.
Suszynska-Zajczyk et al., Hyperhomocysteinemia and bleomycin hydrolase modulate the expression of mouse brain proteins involved in neurodegeneration. J Alzheimers Dis. 2014;40(3):713-26.
Thiele et al., HaploPainter: a tool for drawing pedigrees with complex haplotypes. Bioinformatics. Apr. 15, 2005;21(8):1730-2.
Tsai. Therapy development for spinal muscular atrophy in SMN independent targets. Neural Plast. 2012;2012:456478.
Venkataraman et al., Neurocalcin delta modulation of ROS-GC1, a new model of Ca(2+) signaling. Biochemistry. Jun. 24, 2008;47(25):6590-601.
Voigt et al., Ultrastructural changes in diaphragm neuromuscular junctions in a severe mouse model for Spinal Muscular Atrophy and their prevention by bifunctional U7 snRNA correcting SMN2 splicing. Neuromuscul Disord. Nov. 2010;20(11):744-52.
Wirth et al., Mildly affected patients with spinal muscular atrophy are partially protected by an increased SMN2 copy number. Hum Genet. May 2006;119(4):422-8.
Yamatani et al., Proteomics analysis of the temporal changes in axonal proteins during maturation. Dev Neurobiol. Jun. 2010;70(7):523-37.
Mutihac et al., TARDBP pathogenic mutations increase cytoplasmic translocation of TDP-43 and cause reduction of endoplasmic reticulum $Ca^{2+}$ signaling in motor neurons. Neurobiol Dis. Mar. 2015;75:64-77.
Sun et al., ALS-causative mutations in FUS/TLS confer gain and loss of function by altered association with SMN and U1-snRNP. Nat Commun. Jan. 27, 2015;6:6171.
Cauchi RJ; "Gem depletion: amyotrophic lateral sclerosis and spinal muscular atrophy crossover" CNS Neurosci Ther. Jul. 2014;20(7):574-581.
Chan et al., "Mini-review on initiatives to interfere with the propagation and clearance of alpha-synuclein in Parkinson's disease" Translation Neurodegeneration, 2017, 6:33, pp. 1-5.
Colacurcio et al., "Dysfunction of autophagy and endosomal-lysosomal pathways: Roles in pathogenesis of Down syndrome and Alzheimer's Disease" Free Radical Biol. And Med., 2018, 114:40-51.
Liu et al., "Endocytosis regulates TDP-43 toxicity and turnover" Nature Communications, 2017, 8:2092, pp. 1-14.
Liu et al., "Common Membrane Trafficking Defects of Disease-Associated Dynamin 2 Mutations" 2011, 12: 1620-1633.
Schreij et al., "Endocytic membrane trafficking and neurodegenerative disease" Cellular and Molecular Life Sciences, 2016, 73:1529-1545.
Tadic et al., "The ER mitochondria calcium cycle and ER stress response as therapeutic targets in amyotrophic lateral sclerosis" Front Cell Neurosci. 2014, 30;8:147.

* cited by examiner

Fig. 12
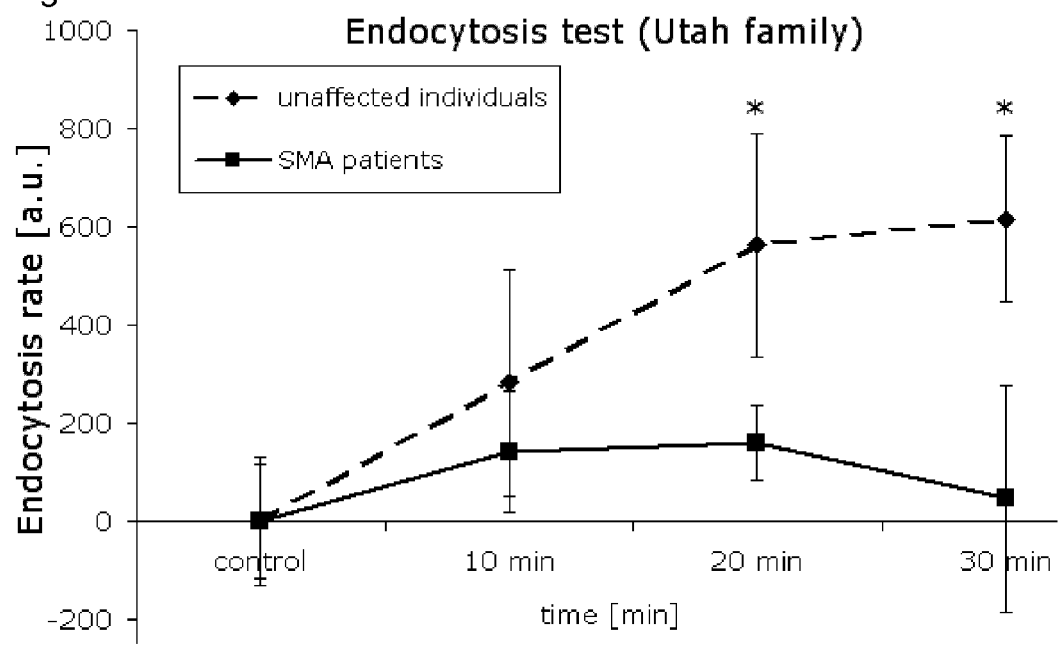
Fig. 13A Ncald protein expression (muscle)
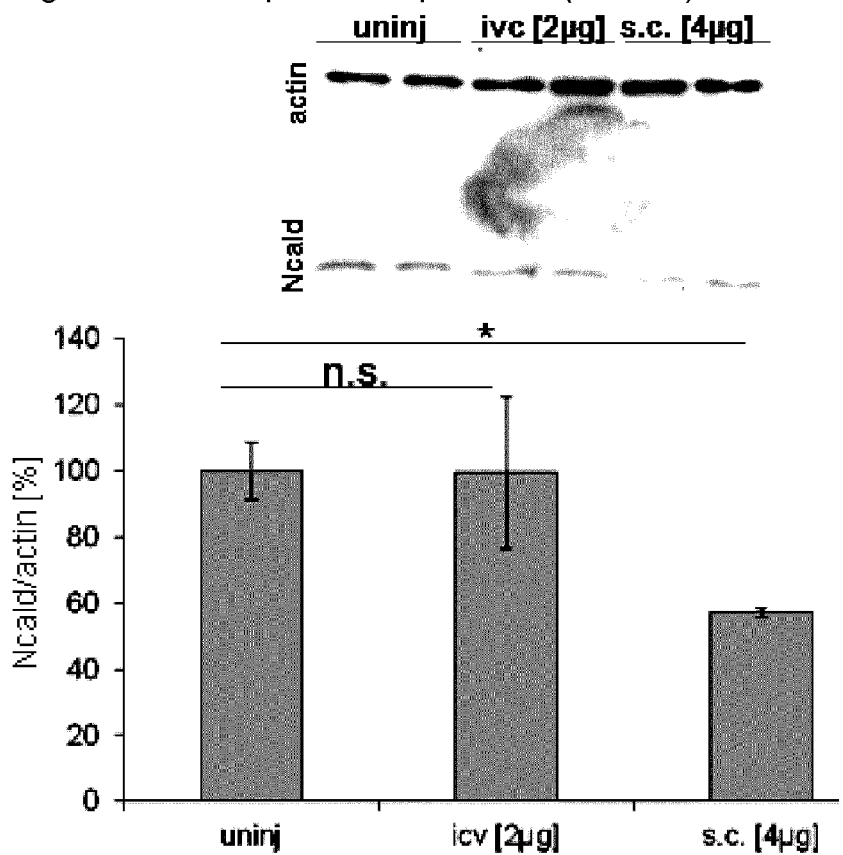

Fig. 13B Ncald protein expression (muscle)
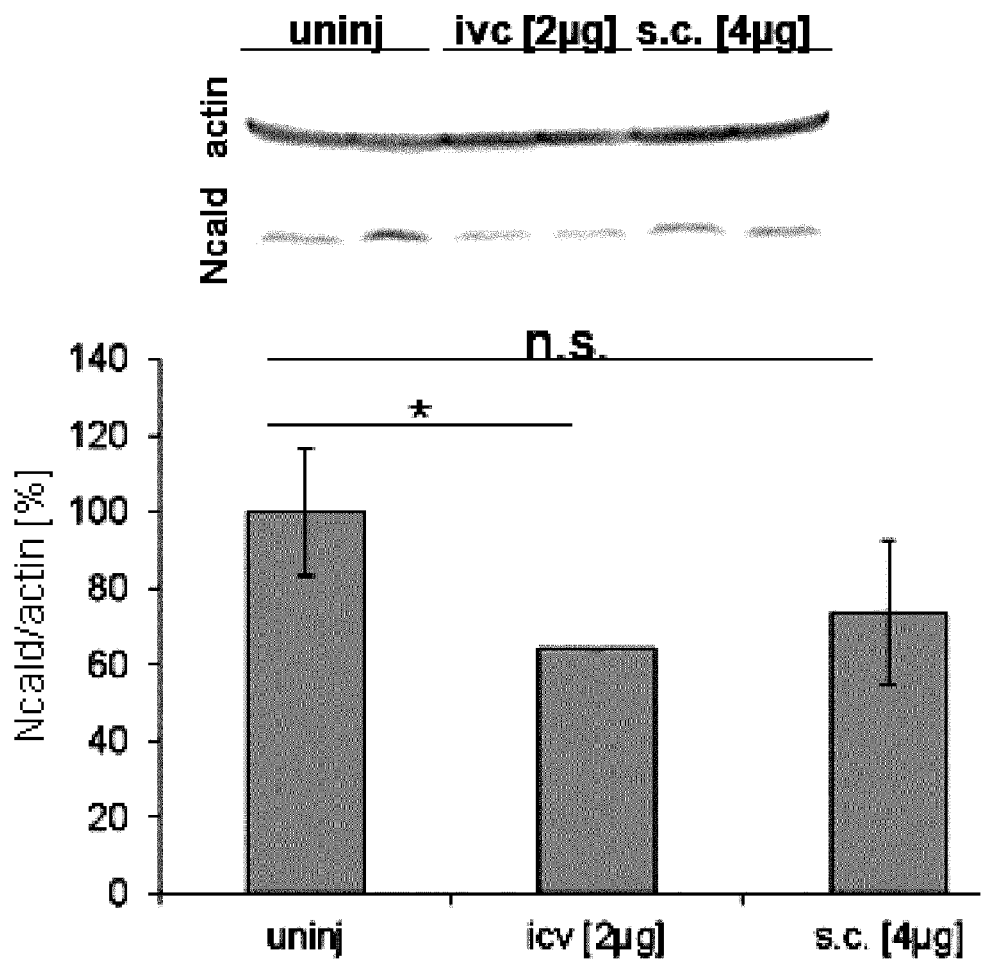
Fig. 14A
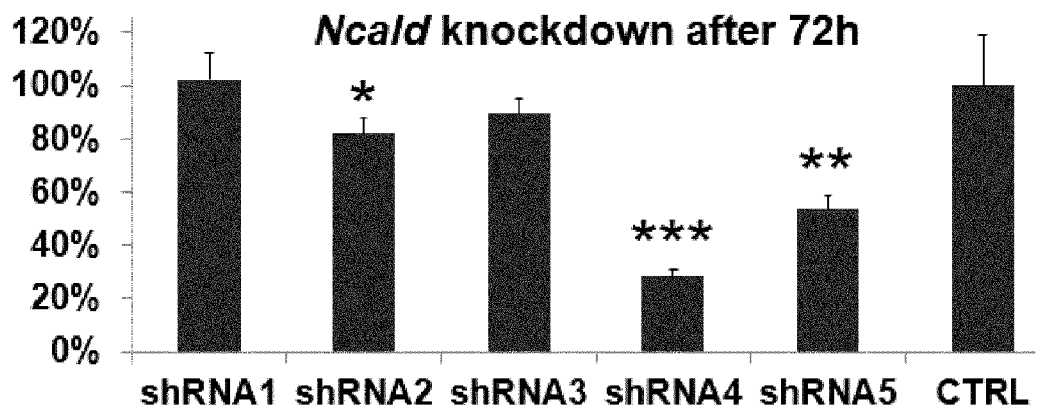

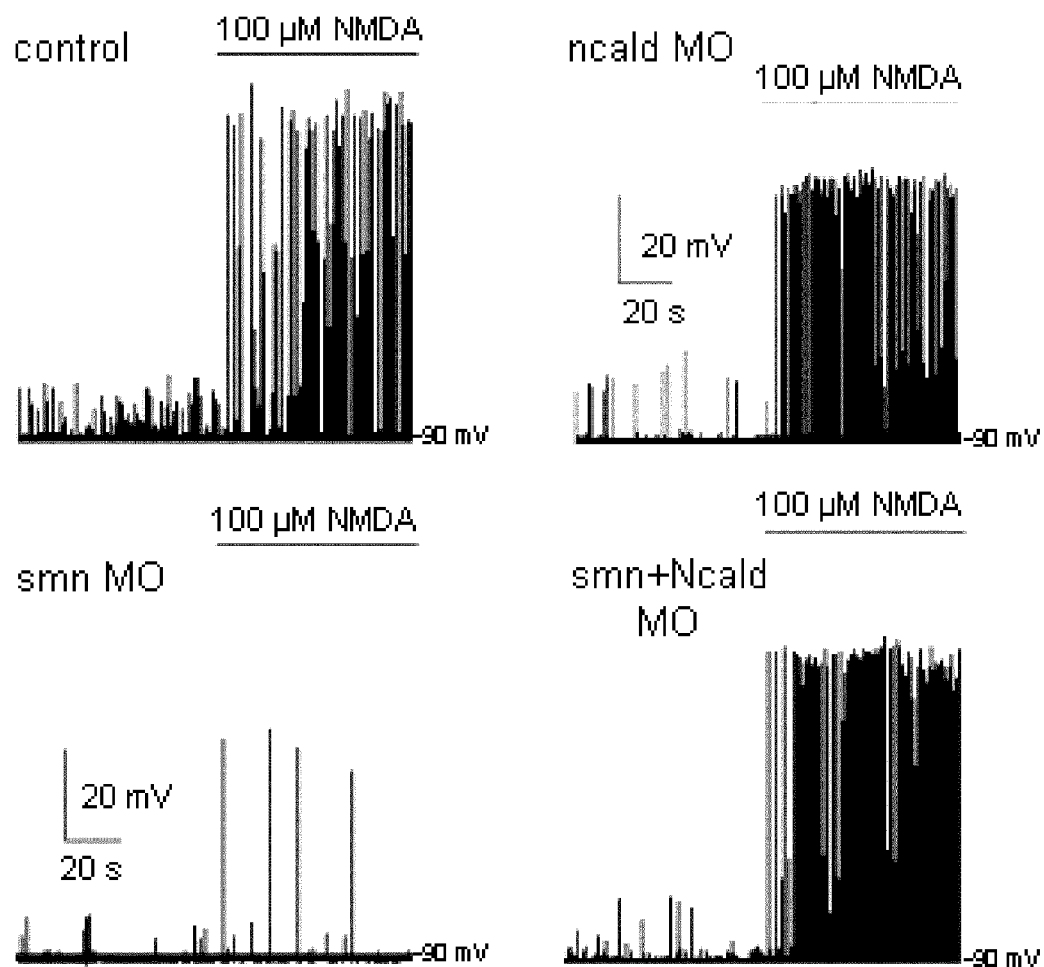

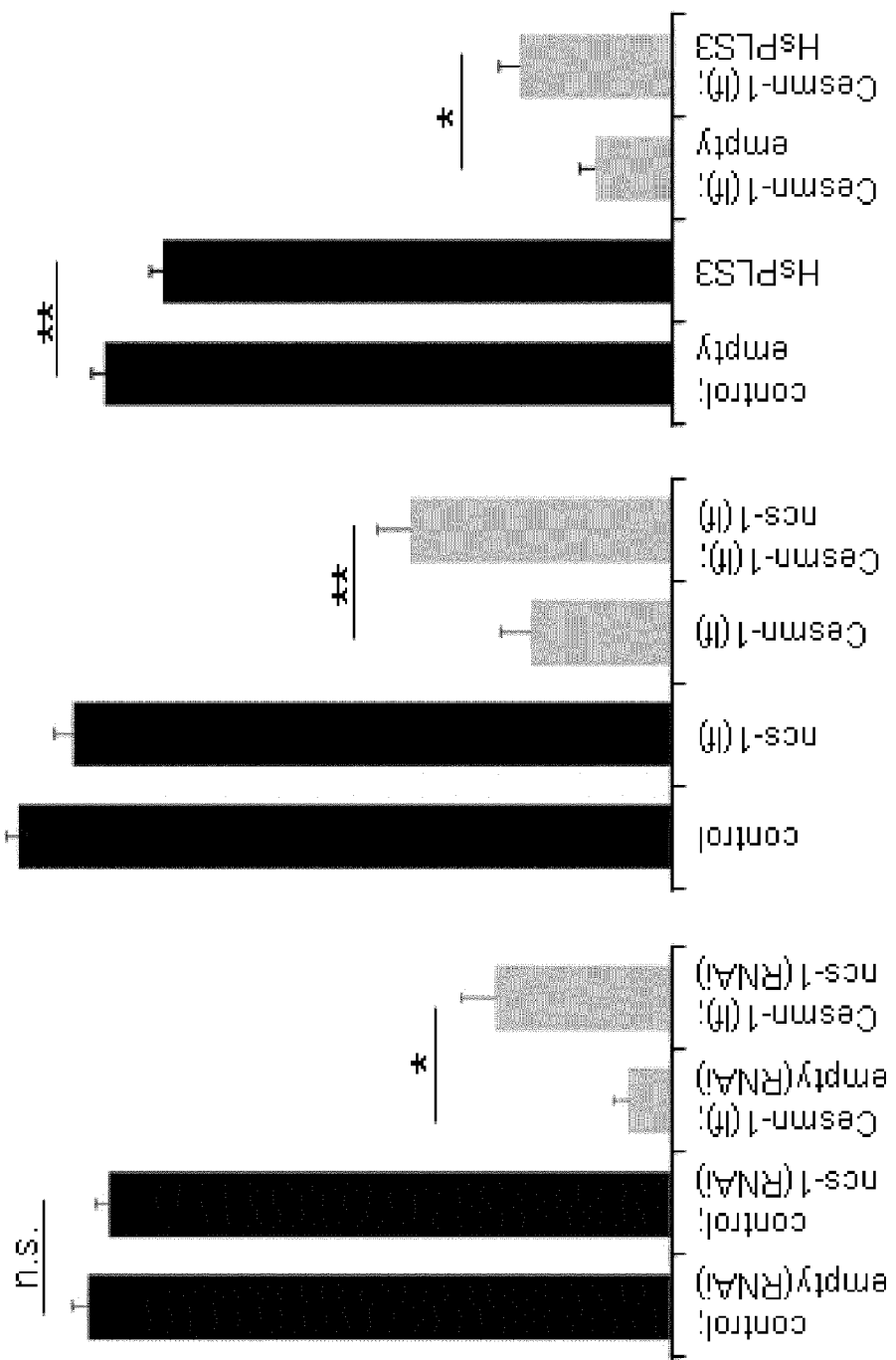
Fig. 18B-D

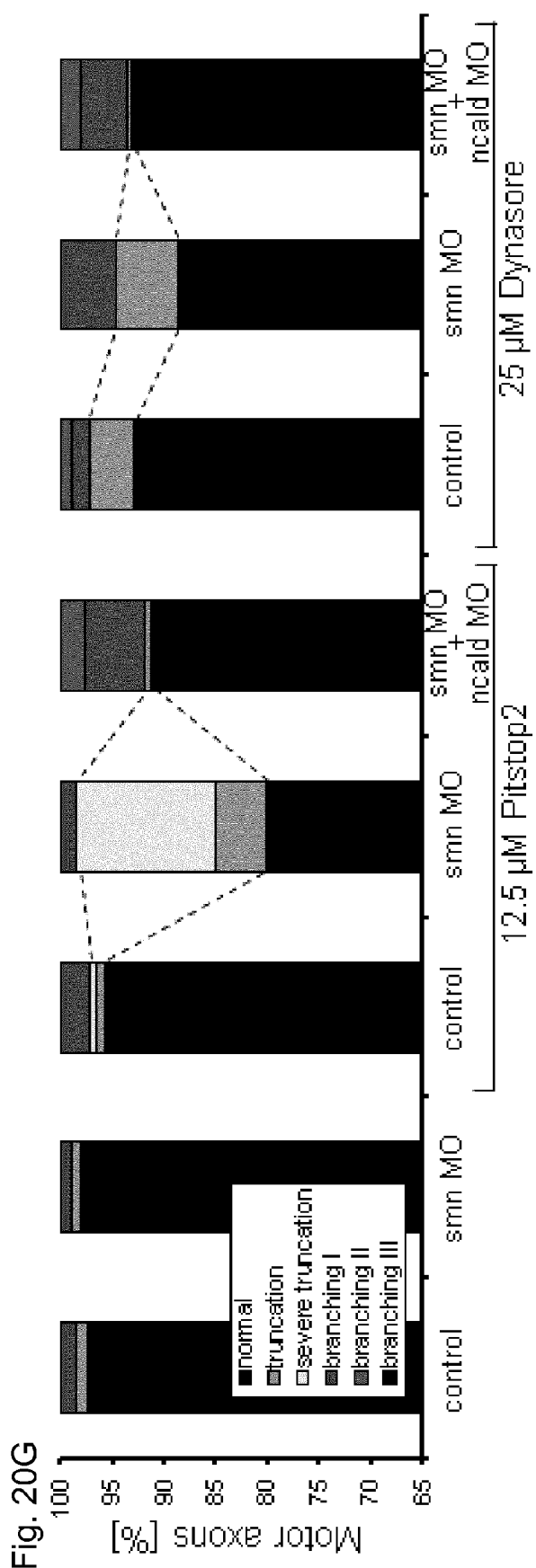

Fig. 25A
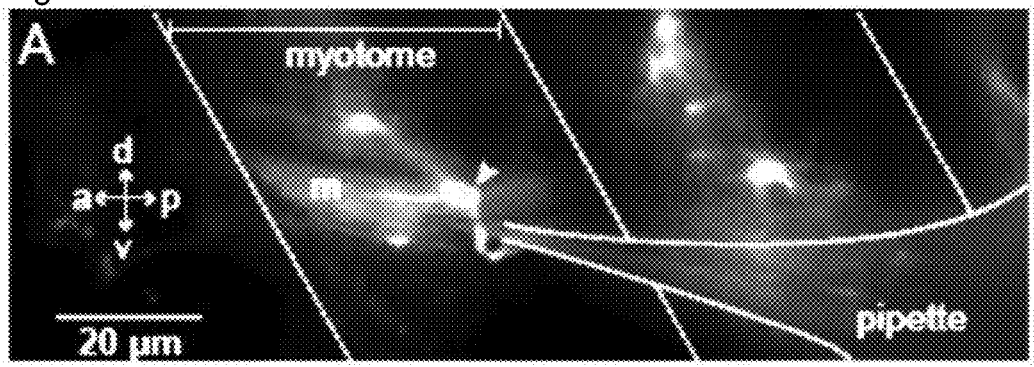
Fig. 25B
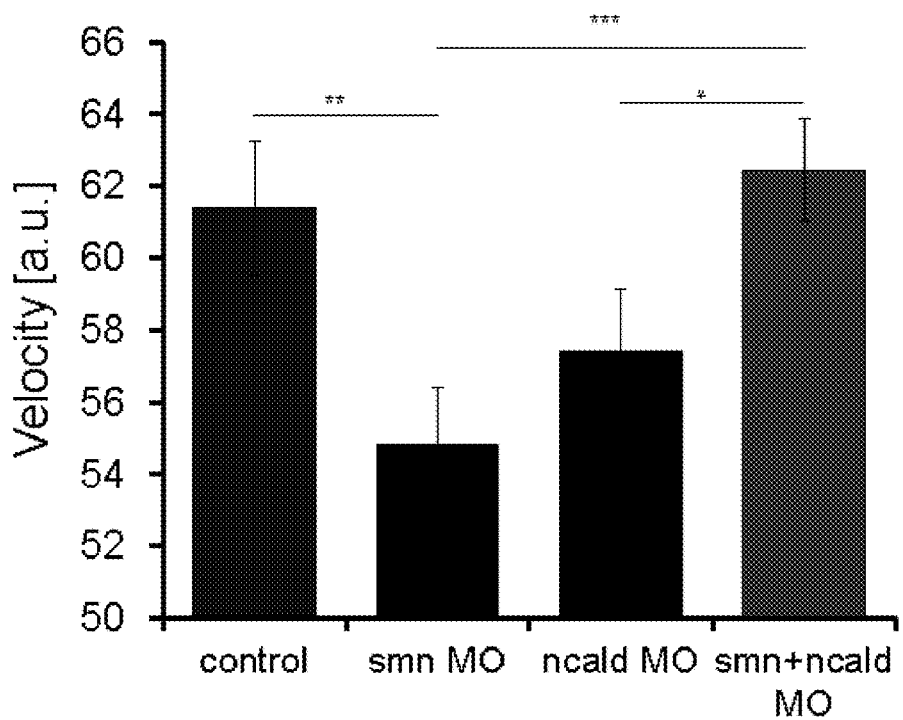
Fig. 25C and D
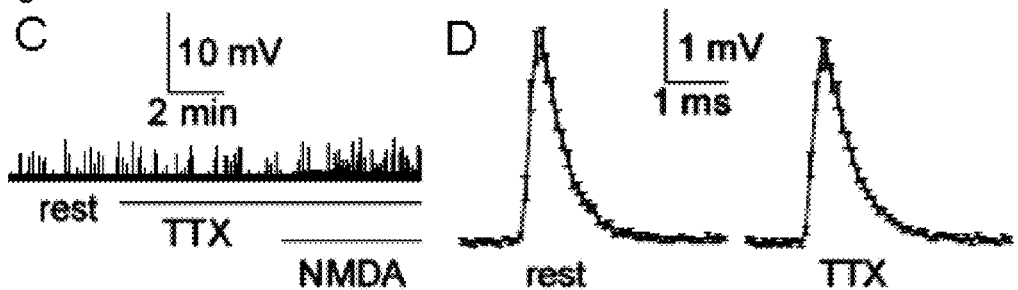

SEQUENCE LISTING

<160> NUMBER OF SEQ ID NOS: 43

<210> SEQ ID NO 1
<211> LENGTH: 192
<212> TYPE: PRT
<213> ORGANISM: human

<400> SEQUENCE: 1

```
Met Gly Lys Gln Asn Ser Lys Leu Arg Pro Glu Val Met Gln Asp Leu
1               5                   10                  15

Leu Glu Ser Thr Asp Phe Thr Glu His Glu Ile Gln Glu Trp Tyr Lys
            20                  25                  30

Gly Phe Leu Arg Asp Cys Pro Ser Gly His Leu Ser Met Glu Glu Phe
        35                  40                  45

Lys Lys Ile Tyr Gly Asn Phe Phe Pro Tyr Gly Asp Ala Ser Lys Phe
    50                  55                  60

Ala Glu His Val Phe Arg Phe Asp Ala Asn Gly Asp Gly Thr Ile Asp
65                  70                  75                  80

Phe Arg Glu Phe Ile Ile Ala Leu Ser Val Thr Ser Arg Gly Lys Leu
                85                  90                  95

Glu Gln Lys Leu Lys Trp Ala Phe Ser Met Tyr Asp Leu Asp Gly Asn
            100                 105                 110

Gly Tyr Ile Ser Lys Ala Glu Met Leu Glu Ile Val Gln Ala Ile Tyr
        115                 120                 125

Lys Met Val Ser Ser Val Met Lys Met Pro Glu Asp Glu Ser Thr Pro
130                 135                 140

Glu Lys Arg Thr Glu Lys Ile Phe Arg Gln Met Asp Thr Asn Arg Asp
145                 150                 155                 160

Gly Lys Leu Ser Leu Glu Glu Phe Ile Arg Gly Ala Lys Ser Asp Pro
            165                 170                 175

Ser Ile Val Arg Leu Leu Gln Cys Asp Pro Ser Ser Ala Gly Gln Phe
        180                 185                 190
```

<210> SEQ ID NO 2
<211> LENGTH: 25
<212> TYPE: DNA
<213> ORGANISM: artificial
<220> FEATURE:
<223> OTHER INFORMATION: NCALD zebrafish ATG

<400> SEQUENCE: 2

```
ggagcttgct gttttgtttt cccat                                       25

<210> SEQ ID NO 3
<211> LENGTH: 25
<212> TYPE: DNA
<213> ORGANISM: artificial
<220> FEATURE:
<223> OTHER INFORMATION: NCALD human ATG

<400> SEQUENCE: 3
gcttgctgtt ctgtttcccc atcct                                       25

<210> SEQ ID NO 4
<211> LENGTH: 25
<212> TYPE: DNA
<213> ORGANISM: artificial
<220> FEATURE:
<223> OTHER INFORMATION: NCALD mouse ATG

<400> SEQUENCE: 4
agcttgctgt tctgtttccc cattc                                       25

<210> SEQ ID NO 5
<211> LENGTH: 29
<212> TYPE: DNA
<213> ORGANISM: artificial
<220> FEATURE:
<223> OTHER INFORMATION: NCALD human and mouse

<400> SEQUENCE: 5
ggatgcttcc aaatttgcag agcatgtct                                   29

<210> SEQ ID NO 6
<211> LENGTH: 21
<212> TYPE: DNA
<213> ORGANISM: artificial
<220> FEATURE:
<223> OTHER INFORMATION: NCALD mouse 3'-UTR

<400> SEQUENCE: 6
caggtgattc acccattata a                                           21

<210> SEQ ID NO 7
<211> LENGTH: 20
<212> TYPE: DNA
<213> ORGANISM: artificial
<220> FEATURE:
<223> OTHER INFORMATION: SMN2 human ISS blocking

<400> SEQUENCE: 7
attcactttc ataatgctgg                                             20

<210> SEQ ID NO 8
<211> LENGTH: 18
<212> TYPE: DNA
<213> ORGANISM: artificial
<220> FEATURE:
<223> OTHER INFORMATION: SMN2 human ISS blocking ASO 10-27

<400> SEQUENCE: 8
tcactttcat aatgctgg                                               18

<210> SEQ ID NO 9
<211> LENGTH: 15
<212> TYPE: DNA
<213> ORGANISM: artificial
```

```
<220> FEATURE:
<223> OTHER INFORMATION: SMN2 human ISS blocking ASO 09-23

<400> SEQUENCE: 9
tttcataatg ctggc                                                  15

<210> SEQ ID NO 10
<211> LENGTH: 20
<212> TYPE: DNA
<213> ORGANISM: artificial
<220> FEATURE:
<223> OTHER INFORMATION: SMN2 human ISS blocking SMN2E7 (10-29)

<400> SEQUENCE: 10
attcactttc ataatgctgg                                             20

<210> SEQ ID NO 11
<211> LENGTH: 25
<212> TYPE: DNA
<213> ORGANISM: artificial
<220> FEATURE:
<223> OTHER INFORMATION: SMN2 human ISS blocking SMN2E7 (10-34)

<400> SEQUENCE: 11
gtaagattca ctttcataat gctgg                                       25

<210> SEQ ID NO 12
<211> LENGTH: 22
<212> TYPE: DNA
<213> ORGANISM: artificial
<220> FEATURE:
<223> OTHER INFORMATION: SMN2 human ISS blocking SMN2E7 (10-31)

<400> SEQUENCE: 12
agattcactt tcataatgct gg                                          22

<210> SEQ ID NO 13
<211> LENGTH: 21
<212> TYPE: DNA
<213> ORGANISM: artificial
<220> FEATURE:
<223> OTHER INFORMATION: SMN silencer

<400> SEQUENCE: 13
aagaaggaaa gtgctcacat a                                           21

<210> SEQ ID NO 14
<211> LENGTH: 22
<212> TYPE: DNA
<213> ORGANISM: artificial
<220> FEATURE:
<223> OTHER INFORMATION: oligonucleotide knocking down SMN

<400> SEQUENCE: 14
cgacatcttc tgcaccattg gc                                          22

<210> SEQ ID NO 15
<211> LENGTH: 59
<212> TYPE: DNA
<213> ORGANISM: artificial
<220> FEATURE:
<223> OTHER INFORMATION: oligonucleotide knocking down NCALD 1

<400> SEQUENCE: 15
ccggggccag gtgattcacc cattatctgg agataatggg tgaatcacct ggcttttg   59
```

-continued

<210> SEQ ID NO 16
<211> LENGTH: 58
<212> TYPE: DNA
<213> ORGANISM: artificial
<220> FEATURE:
<223> OTHER INFORMATION: oligonucleotide knocking down NCALD 2

<400> SEQUENCE: 16
ccggcctgaa gtcatgcagg acttactgga gtaagtcctg catgacttca ggttttttg    58

<210> SEQ ID NO 17
<211> LENGTH: 58
<212> TYPE: DNA
<213> ORGANISM: artificial
<220> FEATURE:
<223> OTHER INFORMATION: oligonucleotide knocking down NCALD 3

<400> SEQUENCE: 17
ccgggcaaac ggtgatggga caatactgga gtattgtccc atcaccgttt gcttttttg    58

<210> SEQ ID NO 18
<211> LENGTH: 58
<212> TYPE: DNA
<213> ORGANISM: artificial
<220> FEATURE:
<223> OTHER INFORMATION: oligonucleotide knocking down NCALD 4

<400> SEQUENCE: 18
ccggcgccag atggatacca atagactgga gtctattggt atccatctgg cgttttttg    58

<210> SEQ ID NO 19
<211> LENGTH: 58
<212> TYPE: DNA
<213> ORGANISM: artificial
<220> FEATURE:
<223> OTHER INFORMATION: oligonucleotide knocking down NCALD 5

<400> SEQUENCE: 19
ccgggcttcc aaatttgcag agcatctgga gatgctctgc aaatttggaa gcttttttg    58

<210> SEQ ID NO 20
<211> LENGTH: 22
<212> TYPE: DNA
<213> ORGANISM: Artificial Sequence
<220> FEATURE:
<223> OTHER INFORMATION: first primer for NCALD cDNA

<400> SEQUENCE: 20
ggaatgccca gagccccagt gt                                            22

<210> SEQ ID NO 21
<211> LENGTH: 22
<212> TYPE: DNA
<213> ORGANISM: artificial sequence
<220> FEATURE:
<223> OTHER INFORMATION: second primer for NCALD cDNA

<400> SEQUENCE: 21
gccccaaccc ccgagtctta cg                                            22

<210> SEQ ID NO 22
<211> LENGTH: 21
<212> TYPE: DNA
<213> ORGANISM: Mus musculus

<400> SEQUENCE: 22
aagaaggaaa gtgctcacat a                                    21

<210> SEQ ID NO 23
<211> LENGTH: 21
<212> TYPE: DNA
<213> ORGANISM: mus musculus

<400> SEQUENCE: 23
caggtgattc acccattata a                                    21

<210> SEQ ID NO 24
<211> LENGTH: 21
<212> TYPE: DNA
<213> ORGANISM: Rattus norvegicus

<400> SEQUENCE: 24
cccgacctgt gaagtagcta a                                    21

<210> SEQ ID NO 25
<211> LENGTH: 21
<212> TYPE: DNA
<213> ORGANISM: rattus norvegicus

<400> SEQUENCE: 25
agagacttcc tagcaattta a                                    21

<210> SEQ ID NO 26
<211> LENGTH: 21
<212> TYPE: DNA
<213> ORGANISM: artificial sequence
<220> FEATURE:
<223> OTHER INFORMATION: NCALD primer human forward

<400> SEQUENCE: 26
atggggaaac agaacagcaa g                                    21

<210> SEQ ID NO 27
<211> LENGTH: 19
<212> TYPE: DNA
<213> ORGANISM: artificial sequence
<220> FEATURE:
<223> OTHER INFORMATION: NCALD primer human reverse

<400> SEQUENCE: 27
gaactggccg gcactgctc                                       19

<210> SEQ ID NO 28
<211> LENGTH: 22
<212> TYPE: DNA
<213> ORGANISM: Danio rerio

<400> SEQUENCE: 28
cgacatcttc tgcaccattg gc                                   22

<210> SEQ ID NO 29
<211> LENGTH: 25
<212> TYPE: DNA
<213> ORGANISM: Danio rerio

<400> SEQUENCE: 29
ggagcttgct gttttgtttt cccat                                25

<210> SEQ ID NO 30

```
<211> LENGTH: 25
<212> TYPE: DNA
<213> ORGANISM: Danio rerio

<400> SEQUENCE: 30
cctcttacct cagttacaat ttata                                              25

<210> SEQ ID NO 31
<211> LENGTH: 30
<212> TYPE: DNA
<213> ORGANISM: homo sapiens

<400> SEQUENCE: 31
gaacgctagc atggatgaga tggctaccac                                         30

<210> SEQ ID NO 32
<211> LENGTH: 32
<212> TYPE: DNA
<213> ORGANISM: homo sapiens

<400> SEQUENCE: 32
caggggaatg aagagagtgt aacccggggt tc                                      32

<210> SEQ ID NO 33
<211> LENGTH: 23
<212> TYPE: DNA
<213> ORGANISM: artificial sequence
<220> FEATURE:
<223> OTHER INFORMATION: ncs-1 primer I

<400> SEQUENCE: 33
aaatcgtcta gctgtagtgt cgc                                                23

<210> SEQ ID NO 34
<211> LENGTH: 23
<212> TYPE: DNA
<213> ORGANISM: Artificial Sequence
<220> FEATURE:
<223> OTHER INFORMATION: ncs-1 primer II

<400> SEQUENCE: 34
ttgtgctccc tacactttgt ttt                                                23

<210> SEQ ID NO 35
<211> LENGTH: 21
<212> TYPE: DNA
<213> ORGANISM: Artificial Sequence
<220> FEATURE:
<223> OTHER INFORMATION: murine KO fw primer

<400> SEQUENCE: 35
ataacaccac cactcttact c                                                  21

<210> SEQ ID NO 36
<211> LENGTH: 21
<212> TYPE: DNA
<213> ORGANISM: Artificial Sequence
<220> FEATURE:
<223> OTHER INFORMATION: murine KO rev1 primer

<400> SEQUENCE: 36
agcctgaaga acgagatcag c                                                  21

<210> SEQ ID NO 37
<211> LENGTH: 20
```

```
<212> TYPE: DNA
<213> ORGANISM: Artificial Sequence
<220> FEATURE:
<223> OTHER INFORMATION: murine KO rev2 primer

<400> SEQUENCE: 37
tagccgtgat gccattgtca                                                    20

<210> SEQ ID NO 38
<211> LENGTH: 25
<212> TYPE: DNA
<213> ORGANISM: Artificial Sequence
<220> FEATURE:
<223> OTHER INFORMATION: Human SMN2 fw primer

<400> SEQUENCE: 38
cgaatcactt gagggcagga gtttg                                              25

<210> SEQ ID NO 39
<211> LENGTH: 25
<212> TYPE: DNA
<213> ORGANISM: Artificial Sequence
<220> FEATURE:
<223> OTHER INFORMATION: Human SMN2 rev primer

<400> SEQUENCE: 39
aactggtgga catggctgtt cattg                                              25

<210> SEQ ID NO 40
<211> LENGTH: 16
<212> TYPE: DNA
<213> ORGANISM: Homo sapiens

<400> SEQUENCE: 40
acacacacac acatat                                                        16

<210> SEQ ID NO 41
<211> LENGTH: 19
<212> TYPE: DNA
<213> ORGANISM: Homo sapiens

<400> SEQUENCE: 41
ttcctttctt tttccttcc                                                     19

<210> SEQ ID NO 42
<211> LENGTH: 17
<212> TYPE: DNA
<213> ORGANISM: Homo sapiens

<400> SEQUENCE: 42
ccagaagagg gctctga                                                       17

<210> SEQ ID NO 43
<211> LENGTH: 19
<212> TYPE: DNA
<213> ORGANISM: Homo sapiens

<400> SEQUENCE: 43
ttcctttctt tttccttcc                                                     19
```

NEUROCALCIN DELTA INHIBITORS AND THERAPEUTIC AND NON-THERAPEUTIC USES THEREOF

CROSS-REFERENCES TO RELATED APPLICATIONS

This application is a national stage application, filed under 35 U.S.C. § 371, of International Application No. PCT/EP2014/066276, filed on Jul. 29, 2014, and claims the benefit of, and priority to US Provisional Application No. 61/859,664, filed Jul. 29, 2013, the contents of each of which are incorporated hereby by reference in its entirety and for all purposes.

INCORPORATION-BY-REFERENCE OF SEQUENCE LISTING

The contents of the text file named "49839_502N01USSequenceListing.txt", which was created on Jan. 27, 2016, and is 9 KB in size, are hereby incorporated by reference in their entireties and for all purposes.

The present invention relates to an inhibitor of neurocalcin delta (NCALD) for use in a method for the treatment or prevention of a patient suffering from a disorder associated with a pathological calcium homeostasis. Furthermore, the present invention refers to the use of such inhibitor of NCALD for inducing axon proliferation in vitro and to a method for the differentiation and/or maturation of neuronal stem cells (NSCs) in vitro and to the use of such inhibitor of NCALD to restore impaired endocytosis being a consequence of disturbed $Ca^{2+}$ homeostasis in synaptic terminals essential for development, maturation and maintenance of synapses and neuromuscular junctions (NMJs).

Today, numerous disorders associated with a pathological calcium homeostasis are known of which many, in particular those that are neuronal disorders, are up to day not sufficiently curable.

Exemplarily, so far, no adequate and satisfactory therapy for spinal muscular atrophies (SMA), amyotrophic lateral sclerosis (ALS), hereditary motor neuropathies (HMN), Parkinson's disease, Alzheimer's disease, Morbus Huntington, and polyglutamic acid disease has been found. Although these disorders have a widespread incidence throughout the population, today, only few symptoms may be cured or even merely retarded, but there is still a lack of a comprehensive treatment and prevention of such disorders.

Autosomal recessive spinal muscular atrophy (SMA), for instance, has an incidence of approximately 1:6000 and is, therefore, after cystic fibrosis (mucoviscidosis), the second most often occurring autosomal recessive disorder found in human. Approximately one in 35 individuals beats a genetic disposition for developing SMA, which is frequently caused by the loss of the survival motor neuron 1 (SMN1) gene what typically leads to a malfunction of alpha-motoneurons in the spinal cord what may result in severe atrophy of the proximal musculature and, in roughly half of cases, even causes death in early childhood.

SMA is caused by loss of the survival motor neuron 1 (SMN1) gene. The severity of the disease is inversely correlated with the copy number of the main disease modifying gene survival motor neuron 2 (SMN2). However, in rare cases, other genetic factors are able to fully protect homozygously SMN1-deleted individuals from developing SMA. Overexpression of plastin 3, an actin-bundling protein has been shown to fully protect against SMA. So far, no effective therapeutic treatment or prevention of SMA is available.

In the view of the above, there are still unmet needs for either a therapeutic agent suitable for treating a patient suffering from a disorder associated with a pathological calcium homeostasis as well as for preventing a patient being at risk thereof.

Surprisingly, it has been found that inhibitors of neuiocalcin delta (NCALD) are suitable for treating and preventing such disorders in a patient in vivo and that said inhibitors are, likewise, effective tools for in vitro neuronal differentiation and maturation, and restoration of impaired endocytosis In a first aspect, the present invention relates to an inhibitor of neurocalcin delta (NCALD) for use in a method for the treatment or prevention of a patient suffering from or being at risk of developing a disorder associated with a pathological calcium homeostasis and/or disturbed neuromuscular transmission.

As used in the context of the present invention, the term "inhibitor" may be understood in the broadest sense as any molecular structure that is, in an adequate environment, able to reduce the expression and/or the functionality of NCALD. As used herein, the terms "inhibitor of neurocalcin delta" and "neurocalcin delta inhibitor" and "inhibitor of NCALD" and "NCALD inhibitor" may be understood interchangeably. As the NCALD is most typically present in cells, an adequate environment may preferably be an intracellular environment, most preferably a cytoplasmic and/or karyoplasmic environment. The molecular structure serving as an inhibitor may be a single molecule or may be a complex of molecules. Preferably, it is a single molecule or a dimer of two complementary oligomers. An oligomer in the sense of the present invention may be an oligonucleotide or a polypeptide, most preferably an oligonucleotide. The molecular structure may have a molecular weight of more than 500 Da or may be a small molecule of less than 500 Da. Alternatively, the molecular structure may also have a molecular weight of more than 500 Da, more than 1000 Da or even more than 2000 Da.

Most preferably, the inhibitor is an oligonucleotide. As used in the context of the present invention, the term oligonucleotide may be understood in the broadest sense as any nucleotide strand mainly composed of a consecutive strand of deoxyribonucleic acid (DNA) nucleotides and/or ribonucleic acid (RNA) nucleotides, wherein the strand is at least four nucleotide moieties (bases) in length and typically not longer than 100 bases. Preferably, the oligonucleotide is at least ten bases, more preferably at least 15, even more preferably at least 18, in particular of from approximately 18 to approximately 24 bases in length.

Alternatively, the inhibitor is a polypeptide of at least ten amino acids moieties, preferably of at least 15 amino acids moieties, more preferably of at least 20 amino acids moieties, even more preferably of at least 50 amino acids moieties, even, more preferably of at least 100 amino acids moieties in length.

Alternatively, the inhibitor, in particular when it is a polypeptide or a small molecule inhibitor, may bind to the NCALD polypeptide and may block its function by non-covalently or covalently binding that may be competitively, non-competitively or uncompetitively binding to a binding site (e.g., the calcium binding site, a second messenger binding site (e.g., the cyclic guanidine monophosphate (cGMP) binding site), and/or a cofactor binding site) of NCALD or by amending the NCALD polypeptide's three-dimensional structure sterically. A small molecule inhibitor may be exemplarily FK506 or a similar molecule.

Alternatively, the inhibitor may also be an antibody or an antibody fragment (e.g., a Fab fragment, a single chain antibody binding domain, a diabody or a triabody) directed against NCALD. This may bind to the NCALD non-covalently at a binding site (binding pocket, e.g., the calcium binding site or a cofactor binding site) of NCALD or by amending the NCALD polypeptide's three-dimensional structure sterically.

Alternatively, the inhibitor, may bind non-covalently or covalently to genomic DNA encoding for NCALD, to pre-mRNA comprising NCALD-encoding regions, to mature mRNA encoding for NCALD, to one or more transcription factor(s) triggering NCALD expression and/or to one or more translation factor(s) triggering NCALD expression and thereby reduces NCALD expression.

Optionally, in case the inhibitor may also be genetic material encoding for an oligonucleotide in the sense of the present invention or for a polypeptide inhibiting NCALD expression or the biological activity of the NCALD polypeptide. Then, the genetic material may optionally encode for an antisense or silencing oligonucleotide. As used in the context of the present invention, the term "genetic material" may be understood in the broadest sense as any carrier suitable for conveying genetic information into cells known in the art such as, e.g., DNA, RNA or any analogue thereof. Genetic material may be or include a linear consecutive strand mainly composed of nucleotide moieties and/or analogues thereof. Alternatively, it may also be a circular molecule (e.g., a plasmid). Optionally, such genetic material may be embedded into any vector known in the art such as, e.g., a plasmid, an episome, a virus, a vapid or a bacterial cell. In result, the patient and the cells, respectively, administered with the inhibitor then may produce the compounds inhibiting NCALD expression and/or functionality themselves.

"Neurocalcin delta" and its abbreviation "NCALD", respectively, as used herein is a neuronal calcium-binding polypeptide that belongs to the neuronal calcium sensor (NCS) family of proteins and is preferably expressed in mammalian brains. It is a member of the EF-Hand-containing-calcium binding proteins comprising a $Ca^{2+}$-myristoyl switch. NCALD may, beside other binding partners, interact with clathrin, alpha- and beta-tubulin and actin. The presence of NCALD may play a significant role in the growth, proliferation and branching of axons during embryogenesis, childhood, juvenility and in adults.

As used herein, the NCALD may be understood in the broadest sense as NCALD originating from any species, preferably mammalian NCALD, most preferably human NCALD.

As used herein, human NCALD preferably comprises a polypeptide having an amino acid sequence of at least 98% homology to SEQ ID NO: 1:

MGKQNSKLRPEVMQDLLESTDFTEHEIQEWYKGFLRDCPSGHLSMEEFKK

IYGNFFPYGDASKFAEHVFRFDANGDGTIDFREFIIALSVTSRGKLEQKL

KWAFSMYDLDGNGYISKAEMLEIVQAIYKMVSSVMKMPEDESTPEKRTEK

IFRQMDTNRDGKLSLEEFIRGAKSDPSIVRLLQCDPSSAGQF

More preferably, human NCALD comprises a polypeptide of SEQ ID NO: 1. Even more preferably, human NCALD is a polypeptide having an amino acid sequence of at least 98% homology to SEQ ID NO: 1. Most preferably, human NCALD is a polypeptide of SEQ ID NO: 1.

As used throughout the present invention, the term "homology" may be understood in the broadest sense as sequence homology. As used in the art, the terms "sequence homology" and "sequence identity" may be understood interchangeably. The percentage of sequence homology may typically be determined by sequence alignment. Methods for such sequence alignment for the purpose of sequence comparison are well known by those skilled in the art. Preferably, homology as used herein is determined by means of the open access National Center for Biotechnology Information (NCBI) Basic Local Alignment Search Tool (BLAST) available from several sources, including the National Center for Biotechnology Information (NCBI, Bethesda, Md.). In the context of amino acid sequences, the algorithm blastp, may preferably be used. In the context of nucleotide sequences, the algorithm blastn may preferably be used.

As used throughout the present invention, the term "polypeptide" may be understood interchangeably with the terms "peptide" and "protein" in the broadest sense as any molecule that is mainly composed of amino acid moieties linked by amide bonds with another and comprises at least four consecutive amino acid moieties. Herein, the terms "amide bond" and "peptidic bond" may be understood interchangeably. Likewise, also the terms "Moiety", "radical" and "residue" may be understood interchangeably.

As can be seen from the amino acid sequence of SEQ ID NO: 1, most preferably, NCALD essentially consists of 193 consecutive amino acid moieties. However, in particular in an individual suffering from a disorder associated with a pathological calcium homeostasis, NCALD may also optionally be modified such as by truncation and or by elongation. Therefore, the NCALD polypeptide may also comprise between 150 and 230 consecutive amino acids, more preferably between 160 and 220 consecutive amino acids, even more preferably between 170 and 210 consecutive amino acids, more preferably between 180 and 200 consecutive amino acids, even more preferably between 185 and 197 consecutive amino acids, even more preferably between 187 and 197 consecutive amino acids, even more preferably between 190 and 196 consecutive amino acids, even more preferably between 191 and 195 consecutive amino acids, even more preferably between 192 and 194 consecutive amino acids. Further, an individual suffering from a disorder associated with a pathological calcium homeostasis may also bear dimers, trimers or even complexes of higher order of NCALD that are also embraced by the definition of the NCALD of the present invention.

Preferably the polypeptide of the present invention essentially consists of a linear chain of consecutive amino acid moieties. Preferably, the majority of amino acid moieties are natural amino acid moieties linked via amide bonds with another. The amino acid backbone of the polypeptide may optionally be modified (e.g., by methylation, alkylation, oxidation, cyclization, dehydration). In particular the polypeptide may or may not be subjected to one or more posttranslational modification(s) and/or be conjugated with one or more non-amino acid moiety/moieties.

The termini of the polypeptide may, optionally, be capped by any means known in the art, such as, e.g., amidation, acetylation, methylation, acylation. Posttranslational modifications are well-known in the art and may be but may not be limited to lipidation, phosphorylation, sulfatation, glycosylation, truncation, oxidation, reduction, decarboxylation, acetylation, amidation, deamidation, disulfide bond formation, amino acid addition, cofactor addition (e.g., biotinylation, heme addition, eicosanoid addition, steroid addition) and complexation of metal ions, non-metal ions, peptides or small molecules and addition of iron-sulphide clusters. Moreover, optionally, co-factors, in particular cyclic guanidinium monophosphate (cGMP), but optionally also such as, e.g., ATP, ADP, NAD$^+$, NADH+H$^+$, NADP$^+$, NADPH+H$^+$, metal ions, anions, lipids, etc. may be bound to the polypeptide, irrespective on the biological influence of these co-factors.

As used in the context of the present invention, the term "patient" may be understood in the broadest sense as any living being, which is preferably any animal, more preferably a mammal including human, in particular a human being.

The term "suffering from" as used herein may be understood in the broadest sense in a way that the patient has developed a disorder associated with a pathological calcium homeostasis, i.e., that the disorder is present in the patient. The patient suffering from a disorder not necessarily but optionally bears medicinal symptoms such as, e.g., muscle weakness and atrophy, pain and/or one or more other perceptional complaint(s). The patient may also be asymptomatic.

The term "being at risk of developing" means that the patient has a certain risk of having a disorder associated with a pathological calcium homeostasis in the future. In this context, preferably, the patient has a higher risk compared to the average risk of developing a disorder associated with a pathological calcium homeostasis present in the entire population. More preferably, the risk is at least 1.1-fold increased, even more preferably the risk is at least 1.5-fold increased, even more preferably the risk is at least 2-fold increased, even more preferably the risk is at least 5-fold increased.

As used in the context of the present invention, a "disorder associated with a pathological calcium homeostasis" may be understood in the broadest sense as any pathological condition caused by or accompanied by a pathological calcium homeostasis. As used herein, the terra "disorder" may be understood in the broadest sense as any condition that differs from the healthy condition. Therefore, the terms "disorder" and "pathological condition" may be understood interchangeably. Preferably, a disorder is a "disease", thus a disorder accompanied by medicinal symptoms. In this context, the terms "disease", "illness" and "ailment" may be understood interchangeably.

Preferably, a disorder in the context of the present invention is a neuronal disorder, in particular a neuronal disorder selected from the group consisting of spinal muscular atrophies (SMA), amyotrophic lateral sclerosis (ALS), hereditary motor neuropathies (HMN) Parkinson's disease, Alzheimer's disease, Morbus Huntington, and polyglutamic acid disease.

Furthermore, a "disorder associated with a pathological calcium homeostasis" or "a disorder with a disturbed neuromuscular transmission" may also be understood as a disease with an impaired endocytosis, which may be restored by the use of inhibitors of NCALD as defined herein.

In the context of the present invention, in a disorder with disturbed neuromuscular transmission, the synaptic transmission may be disturbed at the neuromuscular endplate. In disorders associated with a pathological calcium homeostasis the synaptic transmission may be generally disturbed.

As used herein, the inhibitor may bear any mode of action. It may reduce the local amount of NCALD in a cell or may reduce the NCALD's biological activity. Preferably, the intracellular concentration of NCALD is reduced.

Therefore, in a preferred embodiment, the inhibitor reduces the expression rate of NCALD, preferably wherein said inhibitor knocks down the NCALD expression, in particular wherein knocking down is reducing the transcription rate of the NCALD gene, reducing the translation rate of the NCALD messenger ribonucleic acid (mRNA), reducing the transcript level of NCALD and/or reducing the NCALD function by pharmacological inhibitors.

In this context, knocking down the expression of NCALD may preferably be performed by one or more antisense oligonucleotide(s) (ASOs) and/or one or more analogue(s) thereof.

As used throughout the present invention, the term "knocking down the expression" may be understood in the broadest sense as reducing the production rate of a certain polypeptide, in particular by means of reducing the transcription rate, the rate of correct splicing and/or the translation rate regarding said polypeptide.

Knocking down the translation rate of the NCALD mRNA may preferably be performed by one or more interfering oligonucleotide(s).

Accordingly, in a preferred embodiment, the inhibitor is an oligonucleotide or an oligonucleotide analogue, in particular an oligonucleotide or an oligonucleotide analogue selected from the group consisting of:

(a) an antisense oligonucleotide, in particular an antisense deoxyribonucleic acid (asDNA), an antisense ribonucleic acid (asiRNA);

(b) an antisense oligonucleotide analogue, in particular an antisense 2'-O-methoxyethyl (2'MOE) oligonucleotide, an antisense morpholino, an antisense peptide nucleic acid (PNA), an antisense glycol nucleic acid (GNA), an antisense locked nucleic acid (LNA) or an antisense threose nucleic acid (TNA);

(c) an interfering oligonucleotide, more preferably small interfering ribonucleic acid (siRNA), short hairpin ribonucleic acid (shRNA) or micro ribonucleic acid (microRNA), in particular siRNA of from 18 to 24 bases in length;

(d) an oligonucleotide modifying the splicing of pre-mRNA, in particular wherein said oligonucleotide is single stranded deoxyribonucleic acid (ssDNA) or single stranded ribonucleic acid (ssRNA);

(e) an oligonucleotide analogue modifying the splicing of pre-mRNA, in particular wherein said oligonucleotide is a 2'MOE, morpholino, PNA, GNA, LNA or TNA; and (f) an oligonucleotide encoding for one or more of the aforementioned (a)-(e), optionally wherein said oligonucleotide is embedded in a vector or virus in particular a self complementary adeno associated viruses (scAAV).

As used in this context of the present invention, the term "antisense oligonucleotide" may be understood in the broadest sense as generally understood in the art. Therefore, an antisense oligonucleotide may be any single-stranded oligonucleotide complementary to the NCALD mRNA and may, therefore also be designated as "NCALD mRNA-interfering complementary oligonucleotides". It will be understood that an oligonucleotide according to the present invention may also comprise one or more modifications such as, e.g., one or more sulfur chemistry modification(s)/sulfatation (e.g., phosphorothioates), methylation, alkylation, oxidation, lipidation, phosphorylation, glycosylation, oxidation, reduction, deamidation and/or partial intramolecular cyclization Particularly preferably, an oligonucleotide according to the present invention comprises one or more nucleotide analogues shown in detail below.

Further, additionally or alternatively, the oligonucleotide may optionally comprise one or more non-nucleotide moiety/moieties and/or one or more non-natural nucleotide moiety/moieties. In particular, the termini of the oligonucleotide may, optionally, be capped by any means known in the art, such as, e.g., by sulfatation, amidation, acetylation, methylation, acylation, by one or more non-nucleotide moiety/moieties and/or by one or more non-natural nucleotide moiety/moieties. Optionally, the oligonucleotide may also be conjugated to any one of biotin, heme, eicosanoid(s), steroid(s), peptide(s) and/or small molecule(s). Preferably, such modified forms of oligonucleotide are those more stable against degradation in comparison with unmodified oligonucleotides.

An antisense oligonucleotide according to the present invention may be introduced into a cell to inhibit translation of NCALD by base pairing to the mRNA encoding it and physically/sterically obstructing the translation machinery regarding NCALD. Most typically, an antisense oligonucleotide according to the present invention may bind to the NCALD polypeptide-encoding region. However, an antisense oligonucleotide my also be complementary to an untranslated region (UTR) of the NCALD mRNA, in particular such located at the 3' end, or 5'UTR, in particular overlapping with the start codon (ATG) region. Typically but not necessarily, such region will be in a range of not more than 40 base pairs (bp), more preferably not more than 30 bp, even more preferably not more than 20 bp from the NCALD polypeptide-encoding region Particularly preferably, an antisense oligonucleotide in the sense of the present invention is antisense RNA (asiRNA). In this context, it may be noted that the 3'UTR of NCALD is comparably long and comprises several regulatory elements, which might be inhibited.

An antisense oligonucleotide analogue according to the present invention acts in away comparable with the action of an antisense oligonucleotide as laid out above. The only difference is that an antisense oligonucleotide analogue may typically be more stable against metabolic degradation. Therefore, the bonds between the moieties of the oligomers (monomers), thus, the nucleotide moiety analogues, of the antisense oligonucleotide analogue will typically be cleaved slower than the bonds between the corresponding nucleotide moieties, of the corresponding antisense oligonucleotide. Further, the rate of backbone and/or base modifications (e.g., acetylation, glycosylation) may preferably be lower in the antisense oligonucleotide analogues.

An antisense 2'-O-methoxyethyl (2'MOE) oligonucleotide may be any oligonucleotide analogue comprising at least one 2'-O-methoxyethyl nucleotide analogues, preferably an oligonucleotide analogue wherein at least 10% of the nucleotide moieties are 2'-O-methoxyethyl nucleotide analogues, more preferably an oligonucleotide analogue wherein at least 20% of the nucleotide moieties are 2'-O-methoxyethyl nucleotide analogues, even more preferably an oligonucleotide analogue wherein at least 50% of the nucleotide moieties are 2'-O-methoxyethyl nucleotide analogues, even more preferably an oligonucleotide analogue wherein at least 80% of the nucleotide moieties are 2'-O-methoxyethyl nucleotide analogues, even more preferably an oligonucleotide analogue wherein at least 90% of the nucleotide moieties are 2'-O-methoxyethyl nucleotide analogues, in particular even more preferably an oligonucleotide analogue wherein essentially all nucleotide moieties are 2'-O-methoxyethyl nucleotide analogues. This analogue nears an RNA-like structure.

A morpholino may also be designated as "phosphorediamidate morpholino oligonucleotide" or "PMO" and may typically interact with a comparably small region of the complementary pre-mRNA or mRNA of firm approximately 15 to approximately 30 bases in length. In a morpholino, the bases are bound to morpholine rings instead of ribose moieties in RNA and deoxynbose moieties in DNA, respectively. Accordingly, in a morpholino, the moieties are linked through phosphorodiamidate groups instead of phosphates.

As used throughout the present invention, the terms "peptide nucleic acid" and "PNA" may be understood in the broadest sense as any oligonucleotide analogue comprising repeating N-(2-aminoethyl)-glycine moieties linked by peptide bonds. Various purine and pyrimidine bases may be linked to the backbone by a methylene bridge ($-CH_2-$) and a carbonyl group ($-(C=O)-$).

As used throughout the present invention, the terms "glycol nucleic acid" and "GNA" may be understood in the broadest sense as any oligonucleotide analogue comprising 2,3-dihydroxypropylnucleoside analogues and repeating glycol moieties linked by phosphodiester bonds. Typically, in GNA, the Watson-Crick base pairing is comparably stable leading to comparably high melting temperatures of GNAs.

As used throughout the present invention, the terms "locked nucleic acid" and "INA" may be understood in the broadest sense as any oligonucleotide analogue wherein the ribose moiety is modified with an extra bridge connecting the 2' oxygen and 4' carbon. LNA may also be designated as "inaccessible RNA". This bridge "locks" the ribose in the 3'-endo (North) conformation, which is often found in the A-form duplexes. Typically, the locked ribose conformation enhances base stacking and backbone pre-organization leading to an increased melting temperature.

As used throughout the present invention, the terms "threose nucleic acid" and "TNA" may be understood in the broadest sense as any oligonucleotide analogue comprising a backbone comprising repealing threose sugars linked together by phosphodiester bonds. TNA may form the helical geometry similar to A-formRNA.

In the above inhibitors, nucleotide moiety analogues may be conjugated to DNA and/or RNA moieties in a single molecule then comprising one or more nucleotide moiety/moieties and one or more DNA and/or RNA moiety/moieties whenever desired. Furthermore, additionally or alternatively, such molecule or the above oligonucleotide analogues may be hybridized with one or more DNA and/or RNA oligonucleotide(s) whenever desired.

As used in this context of the present invention, the term "interfering oligonucleotide" may be understood in the broadest sense as generally understood in the art. Accordingly, most typically, the interfering oligonucleotide may be a double-stranded oligonucleotide molecule of from approximately 20 bp to approximately 25 bp in length. Particularly preferably, an interfering oligonucleotide in the sense of the present invention is interfering RNA (iRNA), in particular small interfering RNA (siRNA) suitable for the well-known technology of RNA interference (RNAi), also known as "post-transcriptional gene silencing" (PTGS), specifically interfering with the expression of NCALD encoded by a gene having a complementary nucleotide sequence. Such RNA may also be short shRNA and micro RNA. As used herein, the terms "small interfering RNA", "short interfering RNA" and "silencing RNA" may be understood interchangeably in the broadest sense as generally understood in the art. Accordingly, most typically, the siRNA may be a double-stranded RNA (dsRNA) molecule of from approximately 20 bp to approximately 25 bp in length.

As used herein, the term "precursor messenger RNA" (pre-mRNA) may be understood in the broadest sense as any immature single strand of messenger ribonucleic acid (mRNA). Typically, pre-mRNA is synthesized from a template of genomic DNA by transcription and comprises the bulk of heterogeneous nuclear RNA (hnRNA).

Once pre-mRNA has been completely processed, it is typically designated as "mature messenger RNA" (mature mRNA).

The person skilled in the art will immediately know that pre-mRNA may be processed further by splicing. Such splicing processes are well-known in detail by any person skilled in the art. Therefore, "splicing" in the context of the present invention may be understood in the broadest sense as a process of modifying nascent pre-mRNA that may take place after or concurrently with its generation by transcription of the genomic DNA. By splicing, introns may be removed whereas the exons may preferably remain in the mature mRNA. In many cases this may be needed before the mRNA can be used to produce a correct polypeptide strand by mean of translation of the mRNA. For many eukaryotic introns, splicing is performed in a series of reactions typically catalyzed by the spliceosome, a complex of small nuclear ribonucleoproteins (snRNPs), but the person skilled in the art will also know self-splicing introns wherein splicing may typically be performed directly in the nucleus. Any splicing process may, in principle, be modified by oligonucleotides according to the present invention.

The oligonucleotide encoding far one or more of the aforementioned (a)-(e) may be any genetic material as known in the art and exemplified above.

The person skilled in the art will notice that, optionally,
(i) two or more antisense oligonucleotides;
(ii) more than one interfering oligonucleotide(s);
(iii) more than one interfering oligonucleotide analogue(s);
(iv) more than one oligonucleotides modifying pre-mRNA splicing; or
(v) more than one oligonucleotide analogues modifying pre-mRNA, may be combined with another.

Moreover, the person skilled in the art will also notice that, optionally, one or more antisense oligonucleotide(s) may be combined with:
(i) one or more antisense oligonucleotide analogue(s);
(ii) one or more antisense oligonucleotide(s); and/or
(iii) one or more oligonucleotide(s) modifying pre-mRNA splicing.

Moreover, the person skilled in the art will also notice that, optionally, one or more antisense oligonucleotide(s) may be combined with:
(i) one or more oligonucleotide(s) modifying pre-mRNA splicing; and/or
(ii) one or more oligonucleotide analogue(s) modifying pre-mRNA splicing.

Moreover, the person skilled in the art will also notice that, optionally, one or more interfering oligonucleotide(s) may be combined with one or more oligonucleotide analogue(s) modifying pre-mRNA splicing;

Moreover, also one or more antisense oligonucleotide(s) and one or more antisense oligonucleotide analogue(s) may be combined with:
(i) one or more oligonucleotide(s) modifying pre-mRNA-splicing; or
(ii) one or more oligonucleotide analogue(s) modifying pre-mRNA-splicing.

Moreover, also one or more interfering oligonucleotide(s), one or more antisense oligonucleotide(s) and one or more oligonucleotide(s) modifying pre-mRNA splicing may be combined with another. Moreover, also one or more interfering oligonucleotide(s), one or more antisense oligonucleotide analogues(s) and one or more oligonucleotide(s) modifying pre-mRNA splicing may be combined with another. Moreover, also one or more interfering oligonucleotide(s), one or more antisense oligonucleotide(s) and one or more oligonucleotide analogues(s) modifying pre-mRNA splicing may be combined with another. Moreover, also one or more interfering oligonucleotide(s), one or more antisense oligonucleotide analogues(s) and one or more oligonucleotide analogues(s) modifying pre-mRNA splicing may be combined with another.

Furthermore, also four or even all of the above listed oligonucleotide and oligonucleotide analogue groups (a) to (f) may be combined with another.

The oligonucleotides in the sense of the present invention may be administered to cells and/or patients by any means known in the art. The person skilled in the art will know how many methods suitable for administering such molecules to cells and patients. Further, some of applicable methods are exemplified in the example section below.

Exemplarily, an oligonucleotide or an analogue thereof may be administered to cells by means of electroporation (e.g., single pulse or multi-pulse electroporation (e.g., nucleofection), one or more amphiphilic lipid(s), one or more cell-penetrating peptide(s) (e.g., the chariot peptide, a polyarginine (e.g., R7, R8, R9, R10, R11 or R12), the HIV tat peptide, a lactoferrin-derived peptide, or an antimicrobial peptide, a nucleic targeting sequence), one or more liposome(s), one or more micelle(s), one or more episome(s), one or more polymersome(s), one or more microbead(s), one or more nanobead(s), one or more amphiphilic polymer(s), one or more positively charged polymer(s) (e.g., polyethylene imine (PEI)), one or more virus(es) (e.g., self complementary adeno-associated viruses (scAAV), an altered herpes simplex virus (HSV)), one or more viroid(s), and/or gene gun technology (e.g., by using gold beads).

Exemplarily, an oligonucleotide or an analogue thereof may be administered to a patient by means of one or more amphiphilic lipid(s), one or more cell-penetrating peptide(s), one or more liposome(s), one or more micelle(s), one or more polymersome(s), one or more microbead(s), one or more nanobead(s), one or more amphiphilic polymer(s), one or more positively charged polymer(s), one or more virus(es) and/or one or more viroid(s)

The person skilled in the art will know how to administer the oligonucleotides and analogues thereof. Administration to a patient may be systemically and/or locally.

Preferably, the patients are injected intrathecally in order to directly target the brain and the spine and optionally concomitantly systemically (e.g., in the blood) in order to target the other organs.

Preferably, administration to a patient may include injecting the oligonucleotide(s) and/or analogue(s) thereof or the nasally uptake of these in order to circumvent the first pass effect.

Such oligonucleotide may be any one suitable for the purpose of the present invention, i.e., sewing as an inhibitor of NCALD.

In a preferred embodiment, the inhibitor is an oligonucleotide having a sequence homology of at least 80% to any of SEQ ID NOs: 2-6 or 15-19, preferably of at least 90% to any of SEQ ID NOs: 2-6 or 15-19, more preferably of at least 95% to any of SEQ ID NOs: 2-6 or 15-19, in particular wherein said oligonucleotide has a sequence of any of SEQ ID NOs: 2-6 or 15-19.

As used herein, the nucleotides of SEQ ID NOs: 2-6 or 15-19 have nucleic acid sequences of:

```
SEQ ID NO: 2:
GGAGCTTGCTGTTTTGTTTTCCCAT

SEQ ID NO: 3:
GCTTGCTGTTCTGTTTCCCCATCCT

SEQ ID NO: 4:
AGCTTGCTGTTCTGTTTCCCCATTC

SEQ ID NO: 5:
GGATGCTTCCAAATTTGCAGAGCATGTCT

SEQ ID NO: 6:
CAGGTGATTCACCCATTATAA

SEQ ID NO: 15:
CCGGGGCCAGGTGATTCACCCATTATCTGGAGATAATGG

GTGAATCACCTGGCTTTTTG

SEQ ID NO: 16:
CCGGCCTGAAGTCATGCAGGACTTACTGGAGTAAGTCCT

GCATGACTTCAGGTTTTTG

SEQ ID NO: 17:
CCGGGCAAACGGTGATGGGACAATACTGGAGTATTGTCC

CATCACCGTTTGCTTTTTG

SEQ ID NO: 18:
CCGGCGCCAGATGGATACCAATAGACTGGAGTCTATTGG

TATCCATCTGGCGTTTTTG

SEQ ID NO: 19:
CCGGGCTTCCAAATTTGCAGAGCATCTGGAGATGCTCTG

CAAATTTGGAAGCTTTTTG
```

As mentioned above, each of the sequences may be an oligonucleotide or a corresponding oligonucleotide analogue. Given are the DNA sequences. It will however the noted that also the corresponding RNA sequences are encompassed by the present invention. Then, the base "T" may be replaced by uracil ("U"). Highly preferably, the above sequences are:

SEQ ID NO: 2: NCALD zebrafish ATG-MO (morpholino vs. zebrafish NCALD)
SEQ ID NO: 3: NCALD human ATG-MO (morpholino vs. human NCALD)
SEQ ID NO: 4: NCALD mouse ATG-vivo-MO (vivo-morpholino vs. mouse NCALD)
SEQ ID NO: 5: NCALD human and mouse shRNA (shRNA vs. mouse and human NCALD)
SEQ ID NO: 6: NCALD mouse siRNA (siRNA vs. mouse NCALD (3 'UTR))
SEQ ID NOs: 15-19: shRNAs knocking down mouse NCALD Alternatively, the inhibitor may also be an oligonucleotide analogue corresponding to an oligonucleotide having a sequence homology of at least 80% to any of SEQ ID NOs: 2-6 or 15-19, preferably of at least 90% to any of SEQ ID NOs: 2-6 or 15-19, more preferably of at least 95% to any of SEQ ID NOs: 2-6 or 15-19, in particular wherein said oligonucleotide has a sequence of any of SEQ ID NOs: 2-6 or 15-19.

Furthermore, the use of the inhibitors of NCALD is exemplarily shown in the example section below.

The inhibitor of NCALD, in particular when it is an oligonucleotide, may be an unbound molecule or molecular complex or may be covalently and/or non-covalently bound to a high-molecular weight molecular structure. Such bonding may optionally stabilize the inhibitor, in particular when it is an oligonucleotide, against degradation when administered to a patient and/or to cells.

Therefore, in a preferred embodiment, the inhibitor is
(a) covalently and/or non-covalently bound to at least one cell-penetrating peptide and/or at least one membrane disrupting peptide;
(b) included in or covalently and/or non-covalently bound to a liposome;
(c) included in or covalently and/or non-covalently bound to a micelle;
(d) included in or covalently and/or non-covalently bound to a polymersome;
(e) included in an episome;
(f) covalently and/or non-covalently bound to or included in a microbead and/or nanobead and/or
(g) covalently and/or non-covalently bound to a non-toxic polymer, preferably, wherein said polymer is a water soluble polymer, in particular wherein said polymer is polyethylene glycol (PEG), polyethylene imine (PEI), polylactic acid (PLA), polyglycolic acid (PGA), poly (lactic-co-glycolic acid) (PLGA), hydroxypropyl methacrylate copolymer (HPMA) or a copolymer or block polymer of two or more thereof.

In case of a covalent bond, the terms "bound to", "conjugated to", "conjugated with" may be understood interchangeably. In case of a non-covalent bond, the terms "bound to", "complexed by", "complexed with", "attached to" and "associated with" may be understood interchangeably. A cell-penetrating peptide (CPP) may be understood interchangeably with a protein transduction domain (PTD) as any polypeptide that may facilitate cellular uptake such as, e.g., the chariot peptide, a polyarginine (e.g., hexaarginine, heptaarginine, octaarginine, nonaarginine, decaaiginine, etc.), the HIV tat peptide, a lactoferrin-derived peptide, or an antimicrobial peptide, a nucleic targeting sequence) that is typically between seven and 25 amino acids in length. A membrane disrupting peptide is most preferably an amphiphilic peptide such as an amphiphilic antimicrobial peptide.

Most preferably, the inhibitor is non-covalently bound to one or more of the above molecular structures that bear a positive net charge such as, e.g. polyarginine(s), positively charged liposomes and/or PEI.

As mentioned above, a disorder associated with a pathological calcium homeostasis may be any pathological condition caused by or accompanied by a pathological calcium homeostasis.

Experimentally, it could be demonstrated that downregulation of NCALD counteracts spinal muscular atrophy (SMA) (see experimental section below). Accordingly, an inhibitor of NCALD may be used for treating and/or preventing SMA in a patient.

Further, it could be experimentally demonstrated that neurocalcin delta (NCALD) has a significant impact on regulation of endocytosis acting as a $Ca^{2+}$-dependent regulator of endocytosis (see experimental section below). Surprisingly, it was found that upon reducing NCALD activity (and/or increasing plastin 3 (PLS3) activity), endocytosis may be restored in various species, including mammals. Therefore, inhibiting NCALD may be used to restore endocytosis. In this context, it may be noted that interestingly a number of neuronal disorders (in particular motoneuron diseases) are associated with impaired endocytosis, F-actin dynamics and/or $Ca^{2+}$-homeostasis. Such diseases may be treated in the context of the present invention.

With respect to Alzheimer's disease, the finding of the present application are further supported by the fact that NCALD is highly upregulated in Alzheimer disease(Suszynska-Zajczyk et at, 2014).

Therefore, an inhibitor of NCALD may be used for treating or preventing a number of disorders associated with a pathological calcium homeostasis and/or disturbed neuromuscular transmission, in particular neuronal disorders (e.g., motoneuron diseases, diseases with impaired synaptogenesis), in particular when such disorder is associated with impaired endocytosis, F-actin dynamics and/or $Ca^{2+}$-homeostasis.

Accordingly, in a preferred embodiment, the disorder is a neuronal disorder, preferably a motoneuron disease, in particular a disorder selected from the group consisting of spinal muscular atrophy (SMA), amyotrophic lateral sclerosis (ALS), hereditary motor neuron disease (HMN) or a neurodegenerative disorders particularly Parkinson's disease, Alzheimer's disease, Morbus Huntington, and polyglutamic acid disease.

As used herein, the terms "neuronal disorder" and "neurological disorder" may be understood interchangeably in the broadest sense as any pathological condition of the body's nervous system.

As used herein, the terms "motoneuron disease" and "motor neuron lesion" may be understood interchangeably in the broadest sense as any lesion which affects nerve fibers traveling from the anterior horn of the spinal cord to the relevant muscle(s), i.e., to the motor neuron. Preferably, a motoneuron disease is characterized by flaccid paralysis, i.e., paralysis accompanied by muscle atrophy. Symptoms may or may not include, e.g., muscle paresis or paralysis, fibrillations, fasciculations, hypotonia, atonia, areflexia and/or hyporeflexia.

The patient may be administered with the inhibitor of the present invention alone or may be administered with a combination of one or more inhibitor(s) according to the present invention and one or more further compound(s).

In a preferred embodiment, the patient is further administered with a compound selected from the group consisting of HDAC inhibitors.

As used throughout the present invention, the terms "HDAC inhibitor", "histone deacetylase inhibitor" and "HDIs" may be understood interchangeably in the broadest sense as a compound interfering with the function of histone deacetylase. In this context, the compound may also be valproic acid (VPA), phenylbutyrate (PB), TSA, SAHA, LBH589, JNJ-26481585

The person skilled in the art will notice that the patient may also be administered with one or more one or more inhibitor(s) according to the present invention and two, three or even more of the above compounds and/or also other compounds suitable for treating or preventing a disorder associated with a pathological calcium homeostasis. Examples for such combinations are shown in the example section below.

Moreover, alternatively or additionally, the patient may be further administered with one or more agent(s) increasing the activity of survival motor neuron (SMN).

Accordingly, in a preferred embodiment, the patient is further administered with an agent increasing survival motor neuron (SMN) activity, preferably wherein said agent is selected from the group consisting of:

(a) an agent increasing the expression rate of SMN, more preferably wherein said agent is an antisense oligonucleotide or an oligonucleotide analogue blocking a silencer or enhancing an enhancer of exon 7 inclusion of pre-mRNA of survival motor neuron 2 (SMN2), in particular wherein said agent is an oligonucleotide having a sequence homology of at least 80% to any of SEQ ID NOs: 7-6, preferably of at least 90% to any of SEQ ID NOs: 7-14, more preferably of at least 95% to any of SEQ ID NOs: 7-14, more in particular wherein the oligonucleotide has a sequence of any of SEQ ID NOs: 7-14;

(b) an agent increasing the rate of functional SMN, in particular wherein said agent is an oligonucleotide or an oligonucleotide analogue modifying pre-mRNA splicing;

(c) an agent comprising genetic material encoding for functional SMN, optionally wherein said genetic material is embedded in a vector, (d) an agent stabilizing the SMN; or inhibiting the proteasomal degradation of SMN;

(e) an agent that is increasing activity of the SMN; and (f) replacement by gene therapy expressing SMN1 in an self complementary adenovirus vector.

As used throughout the present invention, the term "increasing the SMN activity" may be understood in the broadest sense as boosting of the function of SMN. This may be achieved by increasing the amount/concentration of functional SMN and/or by activating SMN already present in a cell and/or in a patient.

The term "rate of functional SMN" as used herein refers to the fraction of SMN that is fully functional, i.e., has at least 10%, preferably at least 20%, more preferably at least 30%, even more preferably at least 40%, even more preferably at least 50%, even more preferably at least 60%, even more preferably at least 70%, even more preferably at least 80%, even more preferably at least 90% and most preferably approximately 100% or even more compared to SMN1.

As used herein, SMN may be survival of motor neuron 1 (SMN1) and/or survival of motor neuron 2 (SMN2). When herein referred to "SMN activity" in general, this may be understood as the overall activity of SMN1 and SMN2 together. Typically, the gene encoding SMN1 is considerably more expressed than a corresponding SMN2 gene.

As used throughout the present invention, the term "increasing the expression rate" may be understood in the broadest sense as boosting the production of a certain polypeptide, in particular by means of increasing the transcription rate, the rate of correct splicing and/or the translation rate regarding said polypeptide.

In this context, the terms "antisense oligonucleotide", "antisense oligonucleotide analogue", "interfering oligonucleotide", "oligonucleotide modifying pre-mRNA splicing" and "oligonucleotide analogue modifying pre-mRNA splicing" may be understood in the broadest sense as generally understood in the art and as laid out in the context of the respective SMN- and NCALD-related oligonucleotides and analogues thereof defined above. The person skilled in the art will know how to administer such molecules to cells and patients. This is further exemplified in the context of SMN- and NCALD-related oligonucleotides above.

An oligonucleotide modifying SMN2 pre-mRNA splicing or analogue thereof may cause the generation of an mRNA strand originating from the SMN2 gene encoding for a polypeptide that bears at least 60%, more preferably at least 70%, even more preferably at least 80%, even more preferably at least 90%, in particular approximately 100% or even more biological activity compared to SMN1. Most preferably said oligonucleotide modifying SMN2 premRNA splicing or analogue thereof facilitating exon 7 inclusion into the mRNA. As used throughout the invention, a silencer of SMN2 expression may be an intronic or exonic silencer and an enhancer may be an exonic or intronic enhancer.

Preferably, the oligonucleotide or analogue thereof may also be directed against a silencer in intron 7. Alternatively, the oligonucleotide or analogue thereof may also be directed against a silencer in intron 6 or is amplifying the exonic splice enhancer. When amplifying the exonic splice enhancer, the correct splicing of exon 7 may be regulated by several cis regulatory intronic an exonic enhancers and silencers. Further, several trans splicing factors binding to the cis elements may influence the splicing pattern (e.g., TRA2B, SRSF1, RBMX, HNRNPA1, TARDBP, SRSF9).

Accordingly, in a highly preferred embodiment, the patient is administered with an inhibitor of NCALD and with an agent increasing SMN activity. Particularly preferably, the patient is administered with an oligonucleotide or an oligonucleotide analogue knocking down NCALD and with an oligonucleotide or an oligonucleotide analogue knocking down a silencer region of the SMN2 gene (double knockdown of NCALD and SMN2 silencer) or alternative an oligonucleotide or an oligonucleotide analogue enhancing a splice enhancer of exon 7 of the SMN2 gene. The inhibitor of NCALD and the agent increasing SMN activity may be administered concomitantly or subsequently, preferably essentially concomitantly, i.e., within a time frame of not more than 24 h, preferably not more than 10 h, even more preferably not more than 5 h, in particular not more than 2 h.

Indeed, the presence of an SMN molecules in the patient and/or cell of interest may improve patient's health, such as, e.g., the health of a patient suffering from SMA. This may be achieved by increasing the expression of an SMN2 gene, by correcting the SMN2 pre-mRNA splicing, by increasing the SMN stability or by means of gene therapy (e.g., via a viral vector such as e.g., scAAV-SMN1).

As used herein, SEQ ID NOs: 7-14 refer to nucleic acid sequences of:

```
SEQ ID NO: 7:
ATTCACTTTCATAATGCTGG

SEQ ID NO: 8:
TCACTTTCATAATGCTGG

SEQ ID NO: 9:
TTTCATAATGCTGGC

SEQ ID NO: 10:
ATTCACTTTCATAATGCTGG

SEQ ID NO: 11:
GTAAGATTCACTTTCATAATGCTGG

SEQ ID NO: 12:
AGATTCACTTTCATAATGCTGG

SEQ ID NO: 13:
AAGAAGGAAAGTGCTCACATA

SEQ ID NO: 14:
CGACATCTTCTGCACCATTGGC
```

As mentioned above, each of these sequences may be an oligonucleotide or a corresponding oligonucleotide analogue. Given are the DNA sequences. It will however be noted that also the corresponding RNA sequences are encompassed by the present invention. Then, the base "T" may be replaced by uracil ("U"). Highly preferably, the above sequences are:

SEQ ID NO: 7: SMN2 human ISS blocking morpholino

SEQ ID NO: 8: SMN2 human ISS blocking ASO 10-27 2'-O-methoxyethyl-modified oligonucleotide with phosphorethioate backbone SEQ ID NO: 9: SMN2 human ISS blocking ASO 09-23 2'-O-methoxyethyl-modified oligonucleotide with phosphorethioate backbone SEQ ID NO: 10: SMN2 human ISS blocking phosporediaminidate morpholino oligonucleotide (PMO) SMN2E7 (-10-29)

SEQ ID NO: 11: SMN2 human ISS blocking phosporediaminidate morpholino oligonucleotide (PMO) SMN2E7 (-10-34)

SEQ ID NO: 12: SMN2 human ISS blocking phosporediaminidate morpholino oligonucleotide (PMO) SMN2E7 (-10-31)

SEQ ID NO: 13: SMN silencer, preferably, SMN-siRNA

SEQ ID NO: 14: morpholino knocking down SMN

Alternatively, the agent increasing SMN activity may also be an oligonucleotide analogue corresponding to an oligonucleotide having a sequence homology of at least 80% to any of SEQ ID NOs: 7-14, preferably of at least 90% to any of SEQ ID NOs: 7-14, more preferably of at least 95% to any of SEQ ID NOs: 7-14, in particular wherein said oligonucleotide has a sequence of any of SEQ ID NOs: 7-14.

The person skilled in the art will notice that the agent increasing SMN activity may also be covalently and/or non-covalently bound to one or more cell-penetrating peptide(s), membrane disrupting peptide(s), liposome(s), micelle(s) and/or non-toxic polymer(s) as described in the context of the inhibitor of NCALD above. Alternatively, the agent increasing SMN activity may also be a vector comprising a gene encoding for SMN (e.g., a viral vector such as, e.g., scAAV-SMN) or may be a vector (e.g., a viral vector) encoding for shRNA(s) or micreRNA(s). The agent increasing SMN activity may optional also be administered in combination with one or more other compound(s) as described above. Examples for such combinations are shown in the example section below.

The patient may be administered once or more often. Optionally, the patient may be administered once per day, twice per day or three times a day. Alternatively, the patient may be administered every second day, twice a week or even less frequently.

The inhibitor(s) of NCALD and optionally also the agent(s) increasing SMN2 activity and/or the further compound(s) may be administered to the patient by any means known in the art such as, e.g., by injection or by oral, nasal or transdermal administration. Administration may be local administration (e.g., intrathecally, intracerebreventricularly (icv), topically or intravitreally) or systemic administration (e.g., intravenously (i.v.), intraarterially (i.a.), intraperitoneally (i.p.), intramusculary (i.m.), subcutaneously (s.c.)). In particular when the inhibitor is an oligonucleotide or an analogue thereof, it is preferably administered to the patient by injection or nasally in order to circumvent the first past effect and the accompanied degradation. Preferably, administration is performed by injection, more preferably systemic injection, in particular intravenous injection.

The term "genetic material encoding for functional SMN" may be any genetic material that may convey genetic information known in the art such as, e.g., DNA, RNA or any analogue thereof. It may be a linear strand or may be circular (e.g., a plasmid). Optionally, it may be embedded into any vector known in the art such as, e.g., a plasmid, an episome, a virus, a viroid or a bacterial cell. Preferably, the genetic material may further comprise at least one promoter region and optionally one or more enhancer region(s).

In the context of the present invention, the inhibitors of NCALD according to the present invention can not only be used in a patient in vivo, but also in cell or tissue culture in vitro.

In a further aspect, the present invention also relates to a pharmaceutical composition comprising an inhibitor according to the present invention and a pharmaceutically acceptable carrier.

It will be noticed that the pharmaceutical composition may optionally further comprise one or more further compound(s) such as, e.g., an HDAC inhibitor and/or an agent increasing SMN activity.

As used herein, the term "pharmaceutically acceptable carrier" may refer to any substance that may support the pharmacological acceptance of the inhibitor. The pharmaceutical composition may be administered orally or may be injected. It may be pharmaceutically formulated in a dry form (e.g., as a powder, a tablet, a pill, a capsule, a chewable capsule, etc) or a liquid (e.g., a spray, a syrup, a juice, a gel, a liquid, a paste, an injection solution, an aerosol, an enema, etc.) A pharmaceutically acceptable carrier may be a solvent with no or low toxicity such as, e.g., an aqueous buffer, saline, water, dimethyl sulfoxide (DMSO), ethanol, vegetable oil, paraffin oil or combinations thereof. Furthermore, the pharmaceutically acceptable carrier may contain one or more detergent(s), one or more foaming agent(s) (e.g., sodium lauryl sulfate (SLS), sodium doceyl sulfate (SDS)), one or more coloring agent(s) (e.g., $TiO_2$, food coloring), one or more vitamin(s), one or more salt(s) (e.g., sodium, potassium, calcium, zinc salts), one or more humectant(s) (e.g., sorbitol, glycerol, mannitol, propylenglycol, polydextrose), one or more enzyme(s), one or more preserving agent(s) (e g., benzoic acid, methylparabene), one or more texturing agent(s) (e.g., carboxymethyl cellulose (CMC), polyethylene glycol (PEG), sorbitol), one or more emulsifier(s), one or more bulking agent(s), one or more glacing agent(s), one or more separating agent(s), one or more antioxidant(s), one or more herbal and plant extract(s), one or more stabilizing agent(s), one or more polymer(s) (e.g., hydroxypropyl methacrylamide (HPMA), polyethylene imine (PEI), carboxymethyl cellulose (CMC), polyethylene glycol (PEG)), one or more uptake mediator(s) (e.g., polyethylene imine (PEI), dimethyl sulfoxide (DMSO), a cell-penetrating peptide (CPP), a protein transduction domain (PTD), an antimicrobial peptide, etc.) one or more antibody/antibodies, one or more sweetener(s) (e.g., sucrose, acesulfam K, saccharin Na, stevia), one or more counterstain dye(s) (e.g., fluorescein, fluorescein derivatives, Cy dyes, an Alexa Fluor dyes, S dyes, rhodamine, quantum dots, etc.), one or more gustatory substance(s) and/or one or more fragrance(s).

Accordingly, in a further aspect, the present invention refers to the use of an inhibitor of NCALD for inducing axon proliferation in vitro.

A still further related aspect of the present invention refers to the use of an inhibitor of NCALD to restore impaired endocytosis being a consequence of disturbed $Ca^{2+}$ homeostasis in synaptic terminals contributing to development, maturation and maintenance of synapses and neuromuscular junctions (NMJs) and, thus, also for synaptic particular neuromuscular junction (NMJ) development, maturation and maintenance in vitro.

As used throughout the present invention, the terms "in vitro" and "ex vivo" may be understood interchangeably in the broadest sense as any use or method not considered as therapeutic or diagnostic use or method as defined by patent practice in the corresponding jurisdiction. Therefore, "in vitro" preferably means that there is no substantial health risk for a patient involved when carrying out the invention.

The axon proliferation may preferably be accompanied by a differentiation and/or maturation of precursor cells, in particular of neuronal stem cells (NSCs). Then, the use of an inhibitor of NCALD may include contacting it with precursor cells, in particular neuronal stem cells (NSCs). As used herein, the differentiation and/or maturation of precursor cells may preferably be the differentiation into motoneuronal cells. Most preferably, the use of an inhibitor of NCALD includes contacting said inhibitor with neuronal stem cells (NSCs) which, under influence of said inhibitor, differentiate and maturate into motoneuronal cells.

In the context of the use of the inhibitor of NCALD according to the present invention in vitro, all embodiments and specifications laid out above also apply.

Therefore, in a preferred embodiment, the inhibitor of NCALD is defined as in the context of the inhibitor above.

The use according to the present invention may also include the optional co-incubation of cells with the inhibitor of NCALD and with an HDAC inhibitor and/or with agent increasing SMN activity. This co-incubation may be concomitant incubation and/or subsequent incubation. This is further exemplified in the example section.

The use of an inhibitor of NCALD for inducing axon proliferation in vitro in the sense of the present invention may also be used for producing matured or partly matured motoneurons. As used herein, the teams "motoneuron" and "motor neuron" may be understood interchangeably. Such motoneurons may be used in many different applications such as for treating a pathological condition associated with disordered and/or injured spinal cord and/or nerve cord(s) in a patient suffering therefrom. Exemplarily, said pathological condition is spinal muscular atrophy. In the context of such pathological condition, neuronal stem cells (NSCs) may be obtained from a patient, differentiated into motoneurons in vitro and administered back into the same patient (autologous grafting) or another patient (heterologous grafting), preferably the same patient.

The use of an inhibitor of NCALD may be used for counteracting disturbed $Ca^{2+}$ homeostasis at synaptic terminals and/or growth cone, which may thereby improve development, maturation and maintenance of synapses and in particular neuromuscular junction (NMJs) in patients with motor neuron diseases (SMA, ALS, HMN) or neurodegenerative disorders (Parkinson's disease, Alzheimer's disease, Morbus Huntington or polyglutamine disorders).

Optionally, the obtained motoneuronal cells may be used in a method for treating or preventing a disorder associated with a pathological calcium homeostasis, preferably wherein said disorder is a neuronal disorder, more preferably a motoneuron disease, in particular a disorder selected from the group consisting of spinal muscular atrophies (SMA), amyotrophic lateral sclerosis (ALS), hereditary motor neuron (HMNN diseases or neurodegenerative disorders in particular Parkinson's disease, Alzheimer's disease, Morbus Huntington, and polyglutamic acid disease.

Furthermore, also in vitro, the inhibitor of NCALD may be combined with one or more further compounds, in particular those defined above, and/or with one or more agent(s) increasing SMN activity, in particular such as defined above. Examples for such combinations are shown in the example section below.

A still further aspect of the present invention relates to a method for the differentiation and/or maturation of neuronal stem cells (NSCs) in vitro comprising the following steps:
i) providing neuronal stem cells (NSCs);
ii) contacting said cells with an inhibitor of NCALD; and
iii) cultivating the cells under conditions allowing their differentiation and/or maturation.

In the context of this method according to the present invention, all embodiments and specifications hid out above also apply.

As used herein, the terms "neuronal stem cell", "NSC", "neuronal precursor cell", "NPC" and "induced pluripotent stem cells", "iPSC") may be understood interchangeably in the broadest sense as any self-renewing, multipotent cells that are able to generate the main phenotypes of the nervous system such as, e.g., neurons, astrocytes, and oligodendrocytes. Typically, NSCs are characterized by their capability to differentiate into multiple cell types via exogenous stimuli from their environment.

The person skilled in the art will notice that NCSs as used by the present invention are preferably not embryonic stem cells, in particular not human embryonic stem cells, but rather adult stem cells, in particular pluripotent adult stem cells or induced pluripotent stem cell (in particular such derived from a somatic cell, particular fibroblasts, keratinocytes).

As described in detail above, the NSCs may be contacted with the inhibitor by any means, such as, e.g., by means of co-incubation (i.e., admixing of the inhibitor into the culture medium), electreporation (e.g., single pulse or multi-pulse electroporation (e.g., nucleofection), one or more amphiphilic lipid(s), one or more cell-penetrating peptide(s) (e.g., the chariot peptide, a polyaiginine (e.g., R7, R8, R9, R10, R11 or R12), the HIV tat peptide, a lactoferrin-derived peptide, or an antimicrobial peptide, a nucleic targeting sequence), one or more liposome(s), one or more micelle(s), one or more polymersome(s), one or more microbead(s), one or more nanobead(s), one or more amphiphilic polymer(s), one or more positively charged polymer(s) (e.g., polyethylene imine (PEI)), one or more virus(es) (e.g., an altered herpes simplex virus (HSV)), one or more viroid(s), and/or gene gun technology (e.g., by using gold beads). Examples are further provided in the example section below.

The conditions for cultivating the cells allowing their differentiation and/or maturation may be any conditions suitable for this purpose. The person skilled in the art will know such conditions well. Typically, the cells may be cultivated at a temperature range of from approximately 20° C. to approximately 45° C., preferably at a temperature range of from approximately 25° C. to approximately 44° C., more preferably at a temperature range of from approximately 28° C. to approximately 43° C., even more preferably at a temperature range of from approximately 30° C. to approximately 42° C., even more preferably at a temperature range of from approximately 32° C. to approximately 41° C., even more preferably at a temperature range of from approximately 34° C. to approximately 40° C., even more preferably at a temperature range of from approximately 34° C. to approximately 39° C., even more preferably at a temperature range of from approximately 36° C. to approximately 38° C., in particular at a temperature of approximately 37° C. Typically, the cells may be cultivated in an aqueous buffer bearing a pH in the range of from approximately pH 6 to approximately pH 8, preferably in the range of from approximately pH 6.5 to approximately pH 7.8, more preferably in the range of from approximately pH 6.8 to approximately pH 7.6, even more preferably in the range of from approximately pH 7.0 to approximately pH 7.5, even more preferably in the range of from approximately pH 7.2 to approximately pH 7.5, in particular at a pH of approximately pH 7.4. Optionally, the pH may be adjusted by means of using an open buffer system such as a buffer system including gassing with carbon dioxide. The aqueous buffer may further comprise nutrients sufficient for cellular health such as, e.g., one or more carbohydrate source(s) (e.g., sugars), vitamins, amino acids, essential minerals and/or growth factors. The aqueous buffer may preferably be changed after certain time intervals in order to remove metabolic products and to add nutrients sufficient for cellular health. It will be noticed that any compounds toxic to the cells may preferably be avoided. Examples are further provided in the example section below.

Therefore, in a preferred embodiment, the inhibitor of NCALD is defined as in the context of the inhibitor and the in vitro use above.

Furthermore, also in the method performed in vitro, the inhibitor of NCALD may be combined with one or more further compounds, in particular those defined above, and/or with one or more agent(s) increasing SMN activity, in particular such as defined above.

Therefore, in a preferred embodiment, the method further comprises the step of administering to the cells at least one selected from the following:
(a) an agent increasing survival motor neuron (SMN) activity, preferably wherein said agent is selected from the group consisting of:
 (aa) an agent increasing the expression rate of SMN, more preferably wherein said agent is an antisense oligonucleotide or an oligonucleotide analogue blocking a silencer or enhancing an splice enhancer of exon 7 inclusion of survival motor neuron activity 2 (SMN2), in particular wherein said agent is an oligonucleotide having a sequence homology of at least 80% to any of SEQ ID NOs: 7-14, preferably of at least 90% to any of SEQ ID NOs: 7-14, more preferably of at least 95% to any of SEQ ID NOs: 7-14, more in particular wherein the oligonucleotide has a sequence of any of SEQ ID NOs: 7-14;
 (ab) an agent increasing the rate of functional SMN, in particular wherein said agent is an oligonucleotide or an oligonucleotide analogue modifying pre-mRNA splicing;
 (ac) an agent comprising genetic material encoding for functional SMN, optionally wherein said genetic material is embedded in a vector,
 (ad) an agent stabilizing the SMN; and inhibitory proteasomal degradation of SMN
 (ae) an agent that is increasing activity of the SMN; and
(b) an HDAC inhibitor.

Examples for such combinations are shown in the example section below.

The administration of an inhibitor of NCALD, in particular an oligonucleotide or oligonucleotide analogue knocking down NCALD, into the cells in vitro may, under suitable conditions, trigger the maturation of NSCs, i.e., trigger the differentiation from NSCs into motoneurons and improve development, maturation and maintenance of synapses and neuromuscular junctions (NMJs). In this context, the compound may also be an HDACi (VPA, PB, TSA, SAHA, LBH589, JNJ-26481585)

Therefore, the method according to the present invention laid out in detail above may also be used for producing matured or partly matured motoneurons. Such motoneurons may be used in many different applications such as for treating a pathological condition associated with disordered and/or injured spinal cord and/or nerve cord(s) in a patient suffering therefrom. Exemplarily, said pathological condition is spinal muscular atrophy.

Accordingly, a further aspect of the present invention relates to a matured cell obtainable from the method according to the present invention for use in a method for the treatment of a pathological condition associated with disordered and/or injured spinal cord and/or nerve cord(s) in a patient suffering therefrom, in particular wherein said pathological condition is spinal muscular atrophy.

As described above, most preferably, such matured cell is a motoneuron or a precursor thereof.

In the context of this aspect, the matured cells obtainable from the NSCs matured by means of the above method in vitro may be administered back into the same patient the NSCs had been obtained from (autologous grafting) or into another patient (heterologous grafting), preferably the same patient.

The pathological condition may also be any other kind of spinal marrow lesion or motoneuron-associated disease.

The matured cell obtainable from the method according to the present invention may be administered to the patient by any means known in the art for such purpose. Preferably the cell is injected. Administration may be local administration (e.g., intrathecally or intravitreally) or systemic administration (e.g., intravenously (iv.), intraarterially (i.a.), intraperitoneally (i.p.), intramusculary (i.m.), subcutaneously (s.c.)).

Further, a matured cell obtainable from the method according to the present invention may be used in a method for treating or preventing a disorder associated with a pathological calcium homeostasis, preferably wherein said disorder is a neuronal disorder, more preferably a motoneuron disease, in particular a disorder selected from the group consisting of spinal muscular atophy (SMA), amyotrophic lateral sclerosis (ALS), hereditary motor neuron diseases (HMN) or neurodegenerative disorders in particular Parkinson's disease, Alzheimer's disease, Morbus Huntington, and polyglutamic acid disease.

In a yet further aspect, the present invention relates to a method for the treatment or prevention of a patient suffering from or being at risk of developing a disorder associated with a pathological calcium homeostasis, wherein the patient is administered with an inhibitor of neurocalcin delta (NCALD) in an amount sufficient for treating or preventing said disorder.

A still further aspect of the present invention relates to a method for treating a pathological condition associated with disordered and/or injured spinal cord and/or nerve cord(s) in a patient suffering therefrom, wherein said patient is administered with matured cells obtainable from the method of the present invention in an amount sufficient for treating said pathological condition, or wherein said patient is administered the NCALD inhibitor as mentioned above, in particular wherein said pathological condition is a motoneuron disease.

The following examples as well as the accompanying figures are intended to provide illustrative embodiments of the present invention described and claimed herein. These examples are not intended to provide any limitation on the scope of the invented subject-matter. In example 2, the findings of Example 1 have been further elaborated.

BRIEF DESCRIPTION OF THE DRAWINGS

FIG. 3 demonstrates the neurite proliferation.

FIG. 6 depicts patching experiments.

FIG. 8 shows ultrastructural analysis of NMJs in zebrafish using TEM.

FIG. 9 shows the functional analysis of NMJs in zebrafish using electrophysiology.

FIG. 12 shows the diagrammatic presentation of endocytosis rate of two fibroblast cell lines derived from SMA-patients in comparison to two cell lines derived from asymptomatic SMN1-deleted individuals. *=p<0.05.

FIG. 13 shows an analysis of in vivo knockdown efficiency of morpholinos in mice. Quantification of muscular (gastrocnemius muscle) (FIG. 13A) and neuronal (whole brain lysate) (FIG. 13B) Ncald protein levels after either intracerebroventricular (icv) or subcutaneous (s.c.) injection. Left: representative Western blots; right: quantification of protein bands of three individual mice.

FIG. 14 shows the testing of the knockdown efficiency of five individual shRNA sequences. FIG. 14A demonstrates qRT-PCR-based quantification of Ncald levels, 72 h after knockdown using different shRNA sequences. Transient transfection of NSC34 cells. The respective sequences are SEQ ID NO: 15-19.

(A): Pedigree of the Utah family. Haplotype analysis of microsatellite makers in the 5q13 SMA region and SMN1/SMN2 copy numbers are shown. Black filled symbols. SMA-affected individuals, grey filled symbols: asymptomatic SMN1-deleted individuals and symbols with a dot: SMA carriers.

(B): Genome-wide linkage analysis identifies eight regions with positive LOD scores of 1.5. White arrow marks to genomic region of chromosome 8 where NCALD is located.

(C): Verification of microarray results (Table S1) of NCALD in lymphoblastoid cell lines of asymptomatic individuals (Utah family members n=5) versus SMA patients (Utah family members n=2) and unrelated SMA type III patients with four SMN2 copies (n=10) on RNA and protein level. Note the significant difference in expression on both RNA and protein level from three independent experiments including all 17 cell lines. *=p<0.05 (Student's t-test)

(D): Expression analysis of NCALD RNA and proteins in fibroblasts derived from Utah family members (asymptomatic, n=5; symptomatic, n=2); three independent experiments including all seven cell lines.  =p<0.01; * =p<0.001 (Student's t-test)

Figure 22:
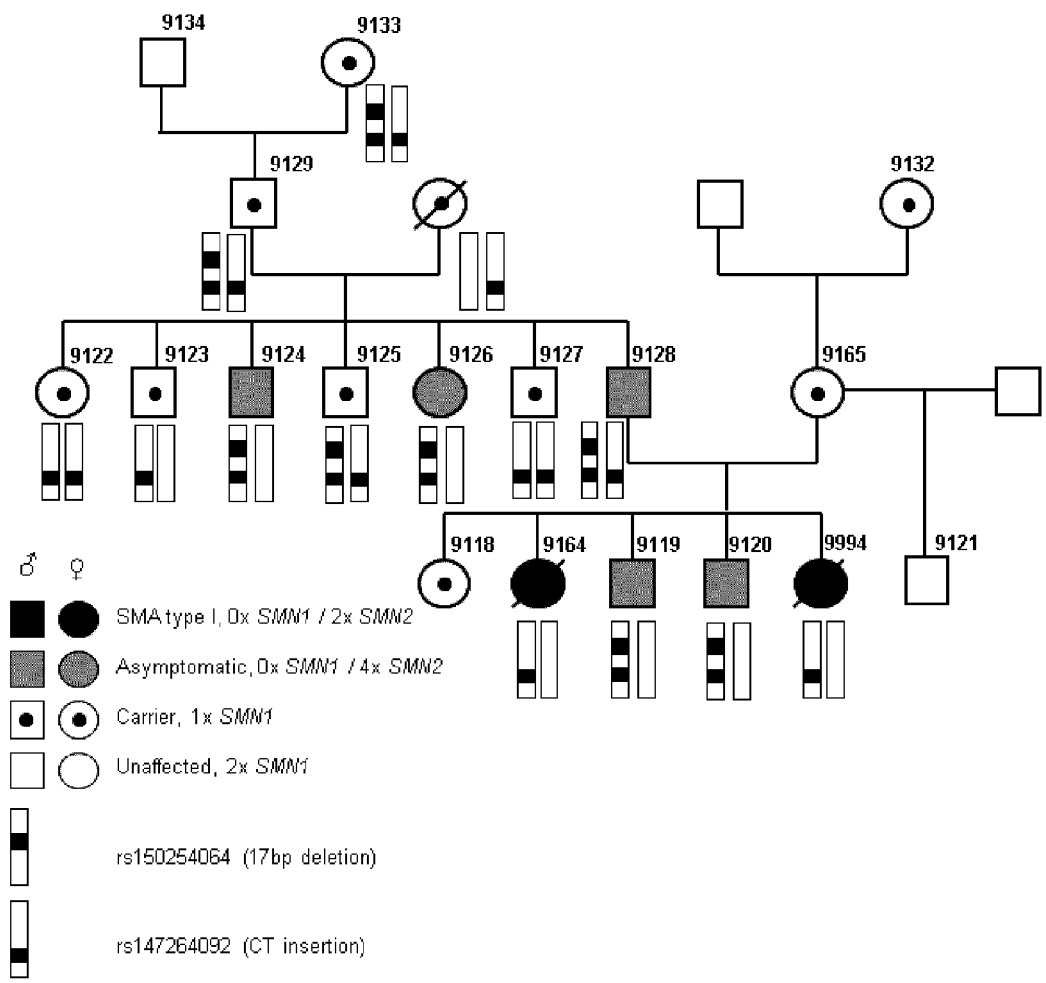

See also FIG. 22 and Table S1.

FIG. 16 shows that NCALD downregulation restores neurite outgrowth defect in SMN-deficient neuronal cells.

(A): Western Blot showing low NCALD level during initiation of neuronal differentiation and neuronal maturation of NSC34 cells treated with retinoic acid. Note also the shift of the ratio between $Ca^{2+}$-free (22kDa) versus $Ca^{2+}$-bound form (18kDa) during neuronal maturation.

(B): Ncald siRNA treated NSC34 cells show signs of differentiation (neurite outgrowth, positive Hb9 staining) even in absence of retinoic acid (right panel). As positive control, cells were differentiated with retinoic acid and treated with control (scrambled) siRNA (middle panel). Negative control was treated only with scrambled siRNA (left panel). Hb9 positive nuclei are marked with white arrows. Scale bar=100 μm.

(C): NSC34 cells were stained with Phalloidin-Alexafluor568. Four days after siRNA transfection and three days after retinoic acid treatment cells showed a neurite outgrowth phenotype. Note the reduced outgrowth in Smn siRNA-treated cells compared to control siRNA-treated cells. Cells transfected with both Smn and Ncald siRNA show an outgrowth comparable to cells treated with control siRNA (50 nM siRNA, 1 μM RA). Scale bar=200 μm.

(D): Neurite length as visualized under (C). The significant reduction of neurite length under Smn knockdown is restored by additional Ncald knockdown. n=100 per measurement *** =p<0.001 (Student's t-test); dashed line=mean (control siRNA: 138.32 μm; Smn siRNA: 101.35 μm; Ncald siRNA: 185.9 μm; Smn+Ncald siRNA: 150.36 μm), line=median (control siRNA: 122.5 μm; Smn siRNA: 87.5 μm; Ncald siRNA: 165 μm; Smn+Ncald siRNA: 135 μm).

(E): Primary MN from SMA or heterozygous murine embryos were cultivated for eigth days, fixed and stained with anti-neurofilament. Cells were co-stained with ChAT to verify motor neuronal fate (FIG. 23C). Scale bar=100 μm (F): Quantitative analysis of axon length of MN as visualized under (E). Note: siRNA-mediated Ncald knockdown restores axon length in MN derived from SMA embryos. (SMA: N=7, n=100 per measurement; HET: N=6, n=100; *** =p<0.001 (Student's t-test) ; dashed line=mean (SMA control siRNA: 549.63 μm; SMA Ncald siRNA: 727.93 μm; HET control siRNA: 778.01 μm; HET Ncald siRNA: 825.1 μm), line=median (SMA control siRNA: 493.42 μm; SMA Ncald siRNA: 641.84 μm; HET control siRNA: 744.45 μm; HET Ncald siRNA: 764.64 μm).

Figure 23A:
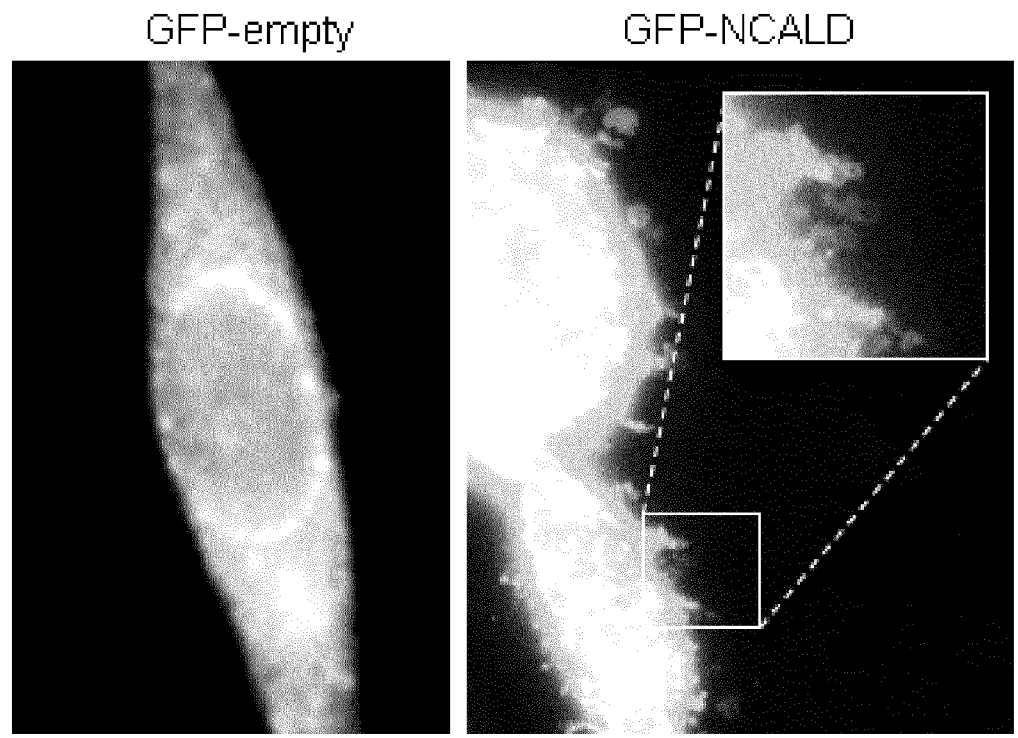
Figure 23B:
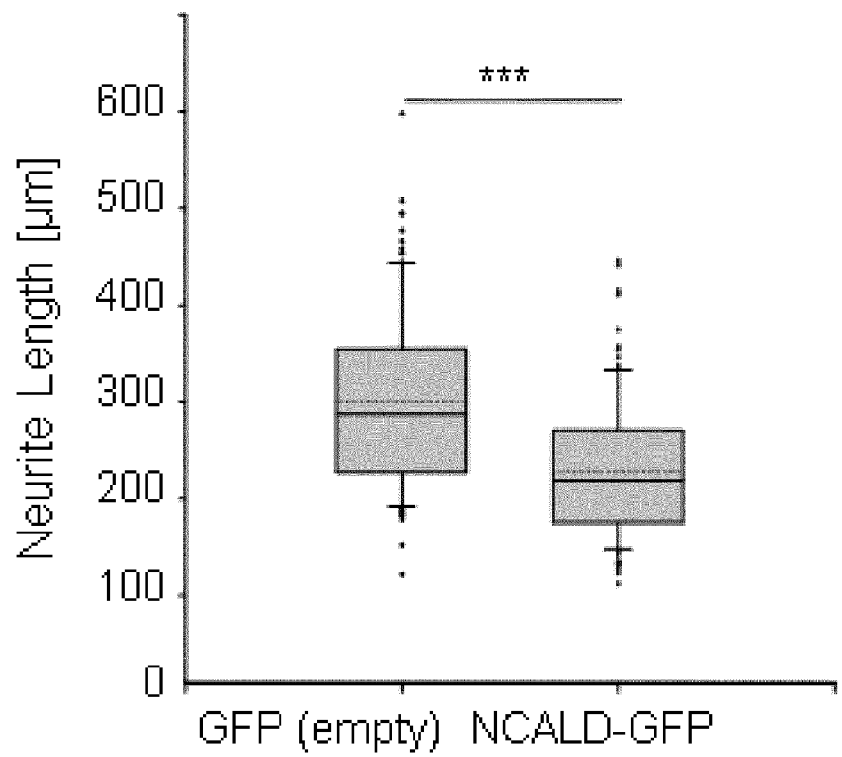
Figure 23C:
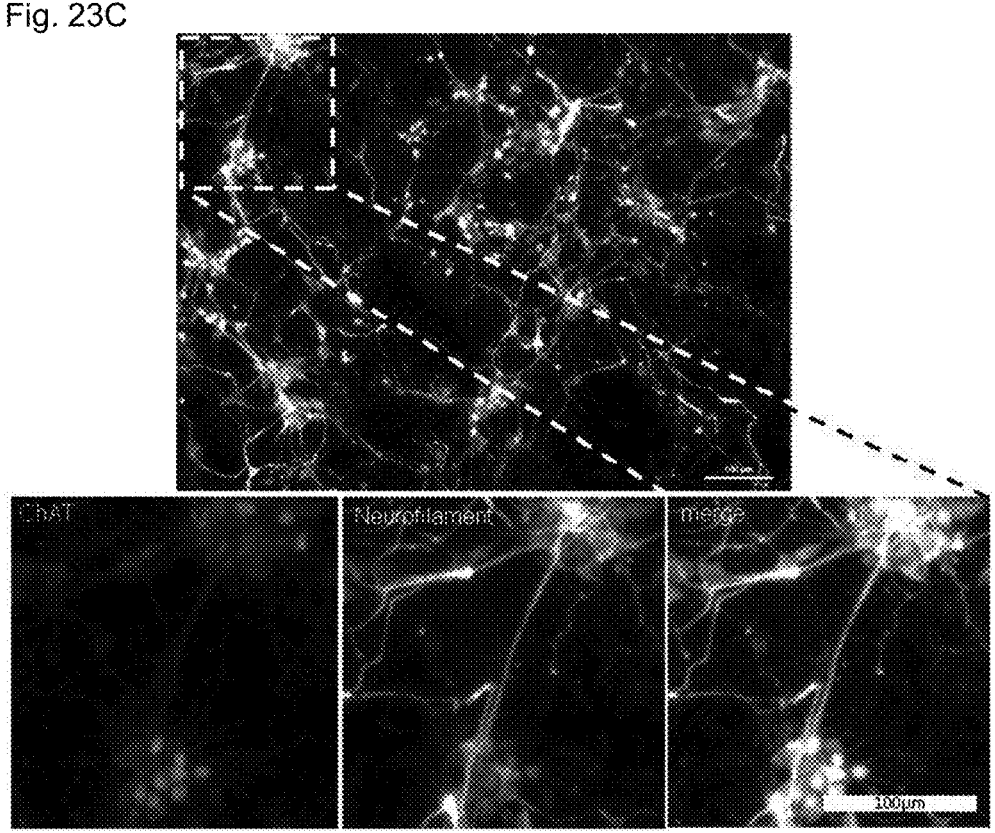

See also FIG. 23.

FIG. 17 shows an in vivo investigation of Ncald reduction in zebrafish. (A): First 10 motor axons posterior to the yolk globule of 34 hpf zebrafish embryos. Embryos were injected with respective morpholinos (MO). smn MO=4 ng; ncald MO=2 ng. Note the truncated motor axons (white arrows) under Smn reduction Arrowheads mark extensive branching in ncald or smn+ncald morphants; bright=znp 1 staining.

(B): Western Blot of proteins isolated from zebrafish larvae treated with indicated MO.

(C): Quantitative characterization of motor axon phenotype. Note the increased percentage of truncated motor axons in smn morphants, compared to control fish. Dashed lines between smn and smn+ncald morphants mark the significant rescue of the truncation phenotype (p<0.01 (Student's t-test)). Smn+ncald and ncald morphants show significant increase in branching. First 10 motor axons behind the yolk were evaluated in every fish. n>500 motor axons per MO injection. Branching phenotype: branching I: mild, branching II: intermediate, branching III: severe.

(D): Election microscopic images of NMJs of 48 hpf zebrafish larvae. Embryos were injected with respective MO. White arrows mark synaptic clefts including the basal lamina. Note reduced width of cleft within smn morphants, a sign of delayed NMJ maturation. Delayed maturation is restored in smn+ncald morphants. M=muscle fiber, T=nerve terminal, scale bar=100 nm.

(E): Width of synaptic cleft of individual MO-injected 48 hpf fish. Note significant reduction of synaptic cleft width under smn knockdown compared to control, which marks delayed maturation of NMJs. This phenotype is restored by additional Ncald knockdown. In comparison to smn morphants, smn+ncald morphants show massive increase in width of synaptic cleft, reflecting accelerated NMJ maturation, (per treatment N=3, n=5; **=p<0.01 (Student's t-test)); dashed line=mean (control 49.13 nm; smn MO: 30.26 nm; ncald MO: 42.38 nm; smn+ncald MO: 53.57 nm), line=median (control 59.63 nm; smn MO: 23.51 nm; ncald MO: 37.77 nm; smn+ncald MO: 56.1 nm).

See also FIG. 24.

(F): Whole cell current clamp recordings of resting and NMDA-induced (100 µM) EPPs in ventral fast muscle cells of wild-type controls, smn, ncald and smn+ncald morphants.

(G) Mean resting and NMDA-induced (100 µM) EPP frequencies of ventral fast muscle cells of wt controls, smn, ncald and smn+ncald morphants. The white portions of the bars reflect the mEPP frequencies. The grey portions reflect the frequency of the TTX-sensitive large EPPs. Paired Student's t-tests are given for the overall EPP (mEPP+lEPP) frequencies: wild type (p=0.0013, n=12); smn MO (p=0.4653, n=10); ncald MO (p=0.0076, n=11); smn+ncald MO (p=0004, n=12).

See also FIG. 25.

FIG. 18 shows that loss of the C elegans NCALD ortholog improves neuromuscular function in animals with SMN defects.

(A): RNAi knockdown of C elegans ncald ortholog ncs-1 increases the pharyngeal pumping rates of mutant smn-1 worms (smn-1 loss-of-function: Cesmn-1(lf)). Arrow points to the pharyngeal grinder, used to score a pumping event (B): The reduced pumping rate in Cesmn-1 worms is significantly rescued by knocking down ncs-1 via ncs-1 RNAi.)

(C): Loss of ncs-1 function significantly improves pumping rates in double mutant worms (Cesmn-1 (ok355);ncs-1 (qa401)).

(D): Overexpression of human PLS3 in Cesmn-1(lf) worms ameliorates the pumping rate, however to a less extent then ncs-1 eduction (compare with C). SEM is shown; Mann-Whitney U-test: *p<0.05, **p<0.01. For every experiment n≥25. RNAi studies were undertaken in a sensitized genetic background, which lowers pumping rates.

FIG. 19 shows that morpholino-driven downregulation of Ncald ameliorates SMA phenotype in mice.

(A): Survival curves for SMA and heterozygous (HET) mice treated with Ncald vivo MO (s. c. 2 mg/kg, starting at P1 and then every other day) in comparison to untreated SMA and HET mice. Mean survival is not rescued by Ncald MO treatment (P=n.s.) (unheated SMA: N=37; untreated HET: N=11; Ncald MO SMA: N=7 Ncald MO HET: N=20)

(B): Motor ability of SMA mice is restored to the level of HET mice by the treatment with vivo MO targeting Ncald (untreated SMA: N=13; untreated HET: N=11; Ncald MO SMA: N=7; Ncald MO HET N=20) (p-values: untreated SMA vs. Ncald MO SMA: PND5 to PND 10p<0.001; Student's t-test).

(C): Representative confocal pictures of neuromuscular junctions of TVA muscles from PND10 SMA or HET mice treated or untreated with vivo MO. Note the size difference between treated and untreated SMA mice (scale bar=20 µm).

(D) Quantification of NMJ area size of TVA muscle from SMA and HET animals with respective treatments at PND10. Reduced area size of SMA mice was restored (***=p<0.001) to control levels by NCALD reduction. (N=3, n=300, for every condition); dashed line=mean (untreated SMA: 183.14 µm$^2$; Ncald MO SMA: 199.94 µm$^2$; untreated HET: 198.55 µm$^2$; Ncald MO HET: 202.98 µm$^2$), line=median (untreated SMA: 181.08 µm$^2$; Ncald MO SMA: 195.64 µm$^2$; untreated HET: 194.99 µm$^2$; Ncald MO HET: 201.51 µm$^2$).

(E): HE staining of cross sections of quadriceps femoris muscles of PND10 SMA or HET mice. Note the size difference between untreated SMA and Ncald MO-treated SMA mice.

(F): Quantitative analysis of muscle fiber area size of quadriceps femoris from SMA and control animals with respective treatments at PND10. Reduced area size of SMA mice was restored (p<0.001; Student's t-test) to control levels by NCALD reduction (N=3, n=900, for every condition); dashed line=mean (untreated SMA: 209.53 µm$^2$; Ncald MO SMA: 232.19 µm$^2$; untreated HET: 240.45 µm$^2$; Ncald MO HET: 254.89 µm$^2$), line=median (untreated SMA: 198.23 µm$^2$; Ncald MO SMA: 211.92 µm$^2$; untreated HET: 226.63 µm$^2$; Ncald MO HET: 238.21 µm$^2$).

See also FIG. 26.

FIG. 20 shows interconnections between SMN, NCALD, voltage-dependent Ca$^{2+}$ influx, endocytosis and SMA.

(A): I-V relationships of Ca$^{2+}$ tail currents that were measured in differentiated NSC34 cells and NSC34 cells treated with respective siRNAs. The holding potential was −80 mV and neurons were depolarized for 5 ms to 60 mV in 5 mV increments. While the currents did not differ between wildtype (wt; n=7), control (scrambled siRNA; n=33) and Ncald knockdown (n=13), the currents were significantly reduced in Smn knockdown cells (n=15) at current pulses more depolarized than −35 mV (*). Knockdown of Smn+Ncald (n=12) did not rescue this phenotype. ANOVA followed by posthoc pairwise comparison was used to asses statistical significance (*=p<0.05; =p<0.01; *=p<0.001).

(B): Western blot of coimmunoprecipitation experiment. NCALD interacts with clathrin only in the absence of Ca$^{2+}$ (addition of EDTA to the cell lysate) but not in the presence. We also excluded interaction between NCALD and SMN.

(C): Immunogold staining of NMJs of 48hpf control zebrafish larvae. Ncald is visualized by secondary antibody labelled with 20 nm gold particle (big black dots) and clathrin with 6 nm gold particle (small black dots). Note the localization of Ncald (white arrows) to synaptic vesicles and the active zone (az) of the presynapse. Clathrin is localized to some synaptic vesicles (black arrows). Note the colocalization of Ncald and clathrin at synaptic vesicles (white arrowheads). M=muscle fiber, T=nerve terminal, scale bar=100 nm.

(D): Quantification of endocytosis by FITC-dextran uptake in fibroblasts. SMA derived fibroblasts (N=10) showed significant decrease in endocytosis as compared to controls (N=3), which was significantly ameliorated in asymptomatic individuals (N=5) of the Utah family, expressing low NCALD. PLS3 is not overexpressed in fibroblasts of discordant siblings (N=2) and consequently has no effect on endocytosis. Significance is given in comparison to SMA cells (*=p<0.05, **=p<0.01; Student's t-test). Note that there was no significant difference between control and asymptomatic (NCALD) cells. Cells counted for each time point for every cell line, n=50.

(E): FACS-based quantification of FITC signal in NSC34 cells treated with respective siRNA. Ncald downregulation resulted in elevated FITC-dextran endocytosis. Importantly, Smn downregulation decreased endocytosis (*=p<0.05, Student's t-test), which was fully restored by additional Ncald knockdown (Smn siRNA vs. Smn+Ncald siRNA: **=p<0.01 control siRNA vs. Smn+Ncald siRNA: n.s., Student's t-test). For every siRNA treatment biological samples N=6, with individual sample size of n=50.000 cells.

(F): Quantification of endocytosis in MEFs derived from mice embryos. Cells overexpressing transgenically PLS3 have increased endocytosis in both SMA and control mice as compared to cells without PLS3 overexpression (*=p<0.05; Student's t-test, N=3; n=150)

(G): Quantitative analysis of motor axon phenotype of zebrafish larvae treated with sub-phenotypical dosis of smn MO (2 ng), ncald MO (2 ng) and endocytosis inhibitors Pitstop2 and Dynasore, respectively. Dashed lines highlight the synergistic effect of smn MO and Pitstop and the effect of Dynasore on axon truncation. Additional ncald MO injection ameliorates the truncation phenotype (p<0.001 (Fisher's Exact Test)). First 10 motor axons posterior to the yolk globule were evaluated in every fish n≥100 motor axons per Pitstop2 treatment; n≥150 motor axons per Dynasore treatment Branching phenotype: branching I: mild, branching II: intermediate, branching III: severe.
See also FIG. 27.

Figure 21:
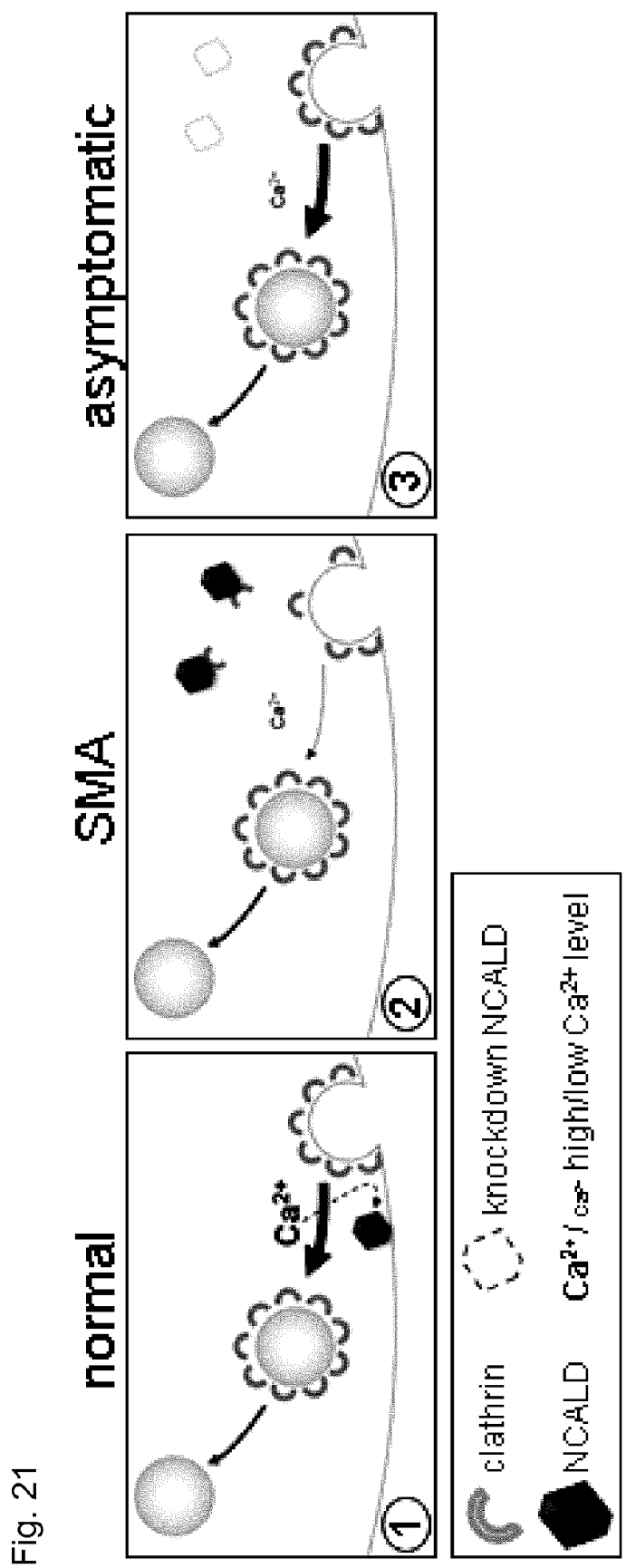

FIG. 21 shows that NCALD acts as a $Ca^{2+}$-dependent regulator of endocytosis in synaptic vesicle recycling. Diagrammatic presentation of the mode of action of NCALD in synaptic vesicle recycling in normal, SMA, and asymptomatic pre-synapse of neuronal cells. From left to right:
1) following neurotransmitter release, clathrin binds to empty vesicle membrane causing membrane bending and vesicle formation. High concentration (which is present after vesicle release (Burgoyne and Morgan, 2003) of local $Ca^{2+}$ causes NCALD conformational change and thereby a release of clathrin so that it can perform its function. NCALD may fine-tune recycling speed and help to coordinate proper clathrin coating
2) In SMA, voltage dependent $Ca^{2+}$ influx is reduced, decreasing NCALD-clathrin dissociation, thus inhibiting clathrin coating of vesicles. In our model NCALD regulates (increases) the $Ca^{2+}$ dependence of clathrin function.
3) When NCALD level is reduced the $Ca^{2+}$ dependence is reduced too and even at relative low intracellular $Ca^{2+}$ levels clathrin can mediate endocytosis.

FIG. 22 depicts a pedigree showing segregation of identified variants. This Figure is related to FIG. 15. Depicted is the pedigree of Utah family showing the segregation of the identified variations (CT insertion in intron1 of NCALD and 17 bp deletion upstream of NCALD) on chromosome 8.

FIG. 23 shows an overexpression of NCALD and verification of motor neuronal fate. This Figure is related to FIG. 16.

(A): Representative picture of an GFP (empty GFP-plasmid) and an NCALD-GFP overexpressing NSC34 cell. Significant membrane blebbing is present only in the NCALD-GFP overexpressing cell. Magnified subset shows detail of membrane blebbing.

(B): Quantification of neurite outgrowth length of NSC34 cells transfected either with empty control plasmid expressing only GFP, or NCALD-GFP plasmid overexpressing NCALD. Significant reduction of neurite length is observed in NCALD overexpressing cells. Cells were treated with retinoic acid for 3 days, fixed and stained with phalloidin-rhodamine. n=100; RA=retinoic acid; *** =p<0.001.

(C): Microscopic overview picture of primary motor neurons after eight days of in vitro cultivation. Magnified subset shows more detailed expression of ChAT. Cells are stained for neurofilament and ChAT to verify motor neuronal fate.

FIG. 24 shows an overview of motor neuron phenotype after downregulation or overexpression of NALD. This Figure is related to FIG. 17.

(A): Representative overview of motor axon outgrowth phenotype of 34hpf morphants (including pictures from main FIG. 17). Significant truncation phenotype of smn morphants is corrected by additional ncald knockdown.

(B): Representative overview of motor axon outgrowth phenotype of 34 hpf zebrafish after human NCALD mRNA injection. Note the dose-dependent truncation phenotype of zebrafish overexpressing NCALD.

(C): Quantitative characterization of motor axon phenotype. Note the dose-dependent increased percentage of truncated motor axons in zebrafish injected with NCALD mRNA, compared to control fish. First 10 motor axons posterior to the yolk were evaluated in every fish. n≥200 motor axons per mRNA injection.

FIG. 25 shows the characterization of electrophysiological properties of zebrafish muscles and swimming behaviour of zebrafish. This Figure is related to FIG. 17.

(A): Fluorescence image of the recording situation. A wild type ventral fast muscle cell was filled with rhodamine dextran during a whole cell patch clamp recording. The muscle cell (m) is innervated by GFP-labeled motor neurons (bright) indicated by the arrowhead. The muscle cell spans one myotome.

(B): Bar graph of high-speed camera swimming velocity measurement of 48 hpf zebrafish (n=30, per treatment) larvae. After lolitracker software evaluation, mean swimming velocity is given in arbitrary units.

(C): Whole cell current clamp recordings of zebrafish muscles. Diagramm shows original whole cell current clamp recordings of mEPPs: at rest, during 1 μM TTX-and during simultaneous TTX and 100 μM NMDA-application. NMDA application failed to increase muscle action potentials in the presence of TTX. mEEP amplitude and frequency are not TTX-sensitive.

(D): Means of 30 EPPs in the absence and the presence of 1 μM TTX.

FIG. 26 shows the localization of NCALD in murine NMJs and investigation of NCALD downregulation in SMA mice. This Figure is related to FIG. 19.

(A): Representative microscopic pictures of neuromuscular junctions (NMJ) from the transversus abdominis (TVA) of 10 PND SMA and heterozygous control mice. Showing co-localization of synaptic vesicle 2 (SV2) as pre-synaptical maker with NCALD. Bungarotoxin-Alexfluor350 is labeling post-synapse.

(B): Representative western blots of PND 5 control mice (n=12) to evaluate the efficacy of vivo-morpholino and its application regimen. As representative tissues, brain (as neuronal tissue) and muscle was chosen. Best down regulation in both tissue types was found after subcutaneous (s.c.) injection in comparision to intracerebroventricular (icv) injection Therefore, s.c. injection was chosen for further experiments.

(C): Representative pictures of sections of heart, lung and intestine (H&E staining). Note the different size of hearts from SMA and HET mice. SMA hearts are smaller and show thinner septa compared to HET. Vivo MO treatment had no effect on heart development. The lungs of SMA mice show ruptured alveolar septa (arrows) and enlarged alveolar spaces (arrowheads) in both treated and untreated mice compared to HET animals. The intestine of SMA mice reveal reduced numbers of villi and villi are shorter and show ruptures and edema in comparison to HET mice. Vivo MO treatment had no effect on intestine structure.

FIG. 27 shows the detailed electrophysiological characterization of Smn siRNA or Smn+Ncald siRNA Cells and impact of $Ca^{2+}$ on endocytosis. This Figure is related to FIG. 20.

(A): Ratiometric $Ca^{2+}$ imaging with fura-2 in differentiated PC12 cells showed a reduction of depolarization-induced (by KCl) increase of cytosolic $Ca^{2+}$ in SMN depleted cells (N=3, n=41) compared to wt control cells (N=2, n=38; p<0.001, unpaired t-test).

(B): Representative microscopic images of fibroblasts derived from Utah family members, SMA patients and controls after endocytosis assay. Starved cells were fed for 20 minutes with FITC-dextran and after fixation counter-stained with phalloidin-Alexafluor 568. Note the higher FITC-signal in asymptomatic cells. Scale bar=50 µm (C): Representative microscopic pictures of NSC34 cells treated with FITC-dextran in presence or absence of Ionomycin. Increase of intracellular $Ca^{2+}$ by Ionomycin leads to a significant increase in endocytosis as seen in representative pictures.

(D): Quantification of endocytosis assay of NSC34 cells treated with Ionomycin. Increased $Ca^{2+}$ resulted in significantly increased endocytosis (***=p<0.001, Student's t-test, n=50).

(E): Representative FACS diagrams from FITC-dextran-based endocytosis assay performed with NCS34 cells treated with the given siRNA. Note the red gating of the measured cells (marked with endo). This gate represents the living cells with the highest green fluorescence signal.

(F): Quantitative analysis of motor axon phenotype of 34 hpf zebrafish, subjected to the respective treatment: 1=ncald MO 2 ng, 2 =smn+ncald MO (2 ng), 3 =ncald MO+12.5 µM Pitstop2, 4 =control+25 µM Pitstop2, 5 =smn MO+25 µM Pitstop2, 6=smn MO+ncald MO+25 µM Pitstop2, 7=ncald MO+25 µM Dynasore. Note the rescue effect of ncald MO injection on the truncation phenotype of smn MO and 50 µM Pitstop2 treated fish (compare bar 5 and 6).

Figure 27A:
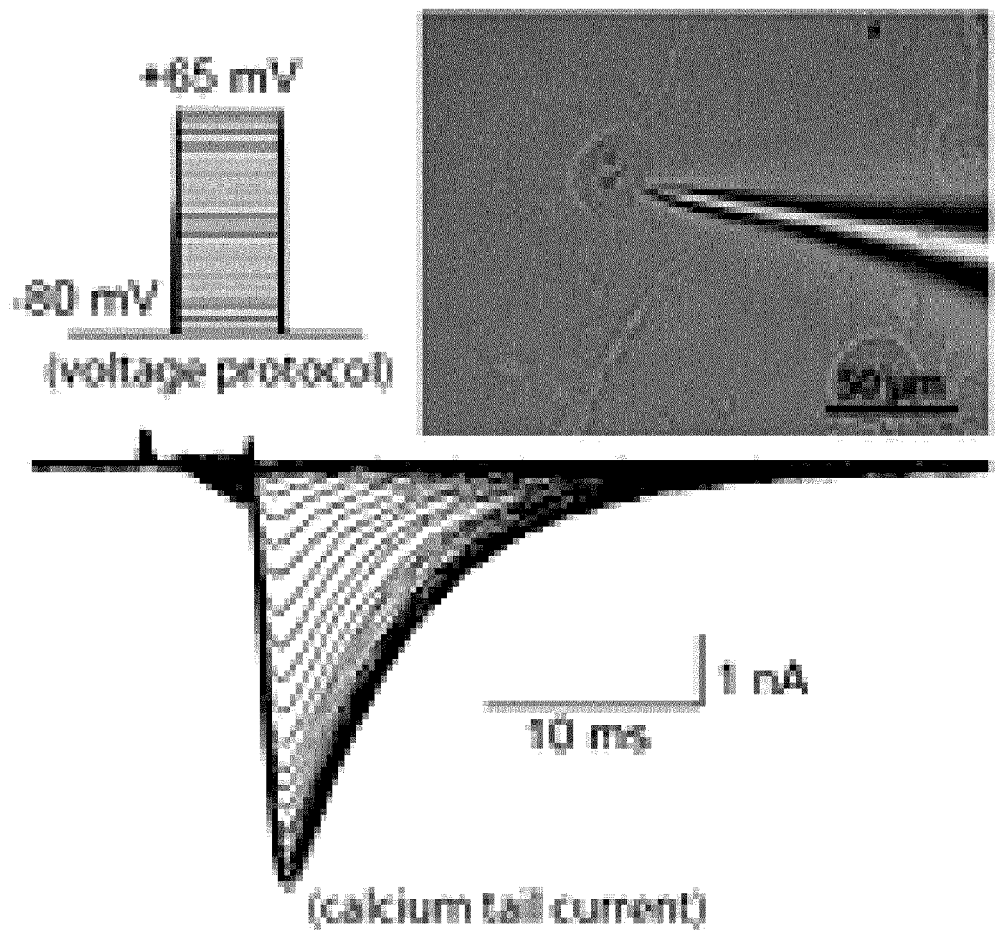
Figure 27B:
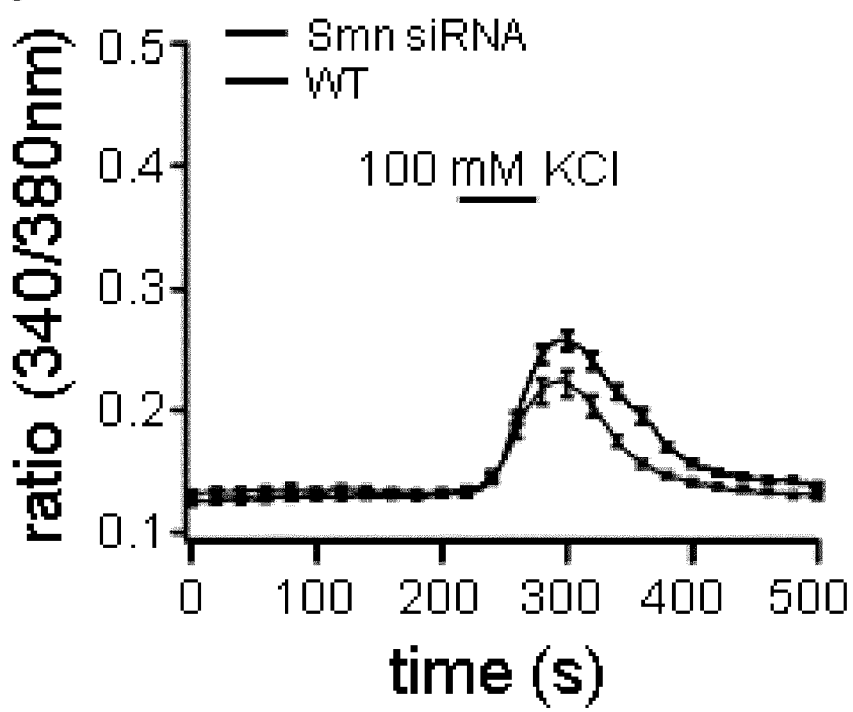
Figure 27C:
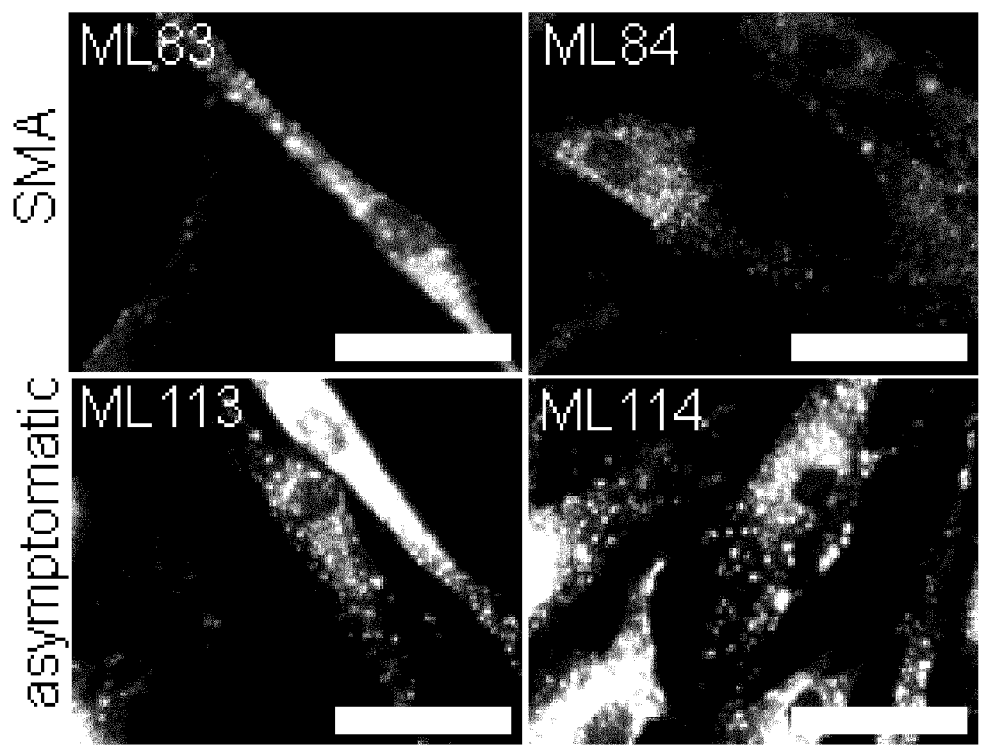
Figure 27D:
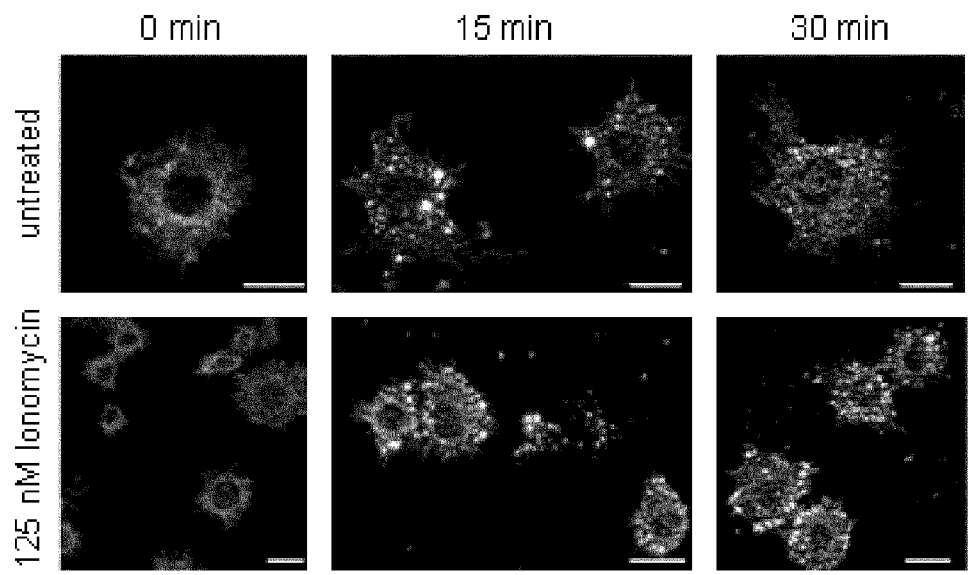
Figure 27E:
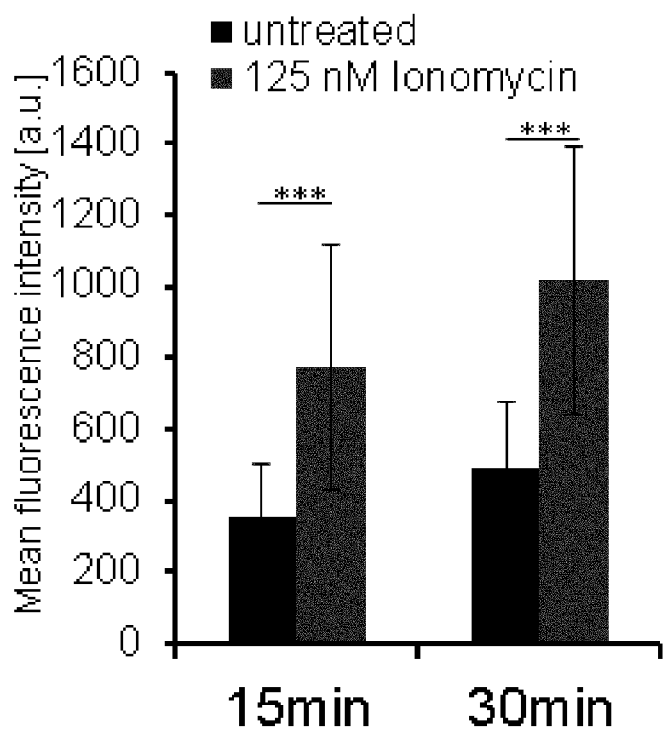
Figure 27F:
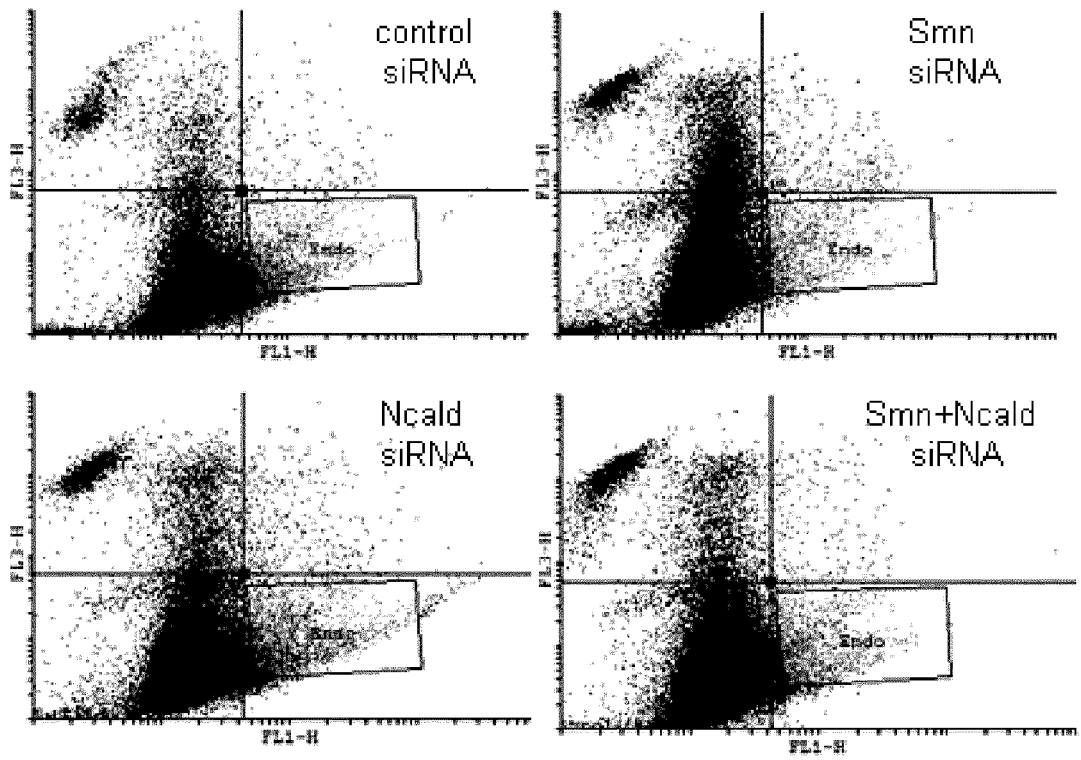
Figure 27G:
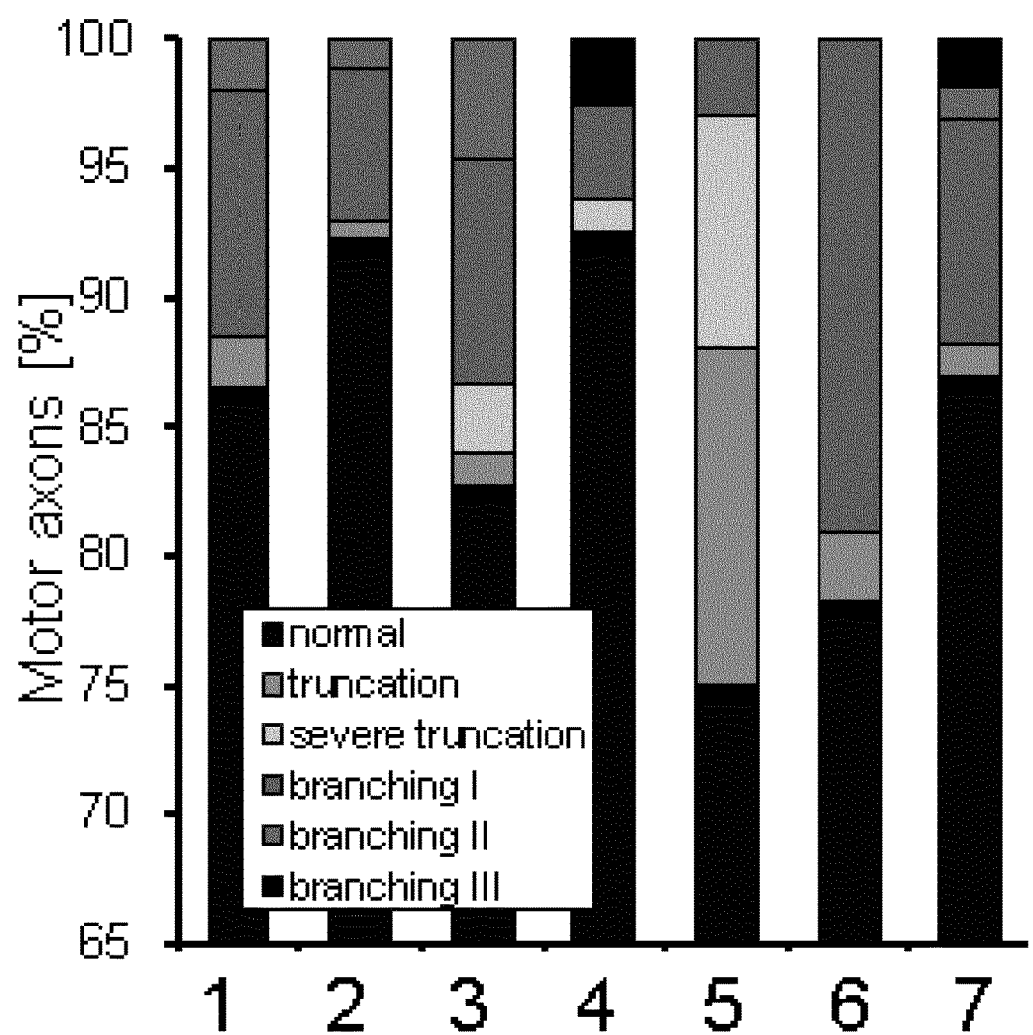

(G): Proportion of motor axons phenotypes in axons treated with a respective compound selected from compounds 1 to 7 as indicated in FIG. 27(F).

EXAMPLES

Example 1

Material and Methods
Genome-wide Linkage Analysis

DNA was extracted from peripheral blood samples using standard methods. The genome-wide scan was performed by genotyping 14 individuals of the Utah family using the GeneChip Human Mapping 10K Array Xba 131 (Affymetrix) according to manufactures guidelines. The mean intermarker distance was 210 kb, equivalent to 0.32 cM. Parametric linkage analysis was performed by a modified version of the program GENEHUNTER 2.1 through stepwise use of a sliding window with sets of 110 or 200 SNPs (Kruglyak et at 1996; Strauch et al. 2000). Haplotypes were reconstructed with GENEHUNTER 2.1 and presented graphically with HaploPainter (Thiele and Numberg 2005). All data handling was performed using the graphical user interface ALOHOMORA to facilitated linkage analysis with chip data (Ruschendorf and Numberg 2005).

Transcriptome Analysis

For expression profiling 400 ng of total RNA were linearly amplified and biotinylated using the Illumina® TotalPrep™ RNA Amplification Kits (Ambion) according to the manufacturer's instructions. Human HT-12v3 bead arrays (Illumina, San Diego, Calif.) were hybridized with 750 ng cRNA for 18 h at 58° C. according to the Illumina® Whole-Genome Gene Expression with IntelliHyb Seal System Manual. Arrays were washed three times with buffer E1BC, High-Temp Wash Buffer and 100% ethanol, respectively, stained with streptavidine-Cy3 and again washed with buffer E1BC. Raw fluorescence intensities were recorded on a BeadArray Reader GX (Illumina). Average signal intensities without background correction (Dunning et al. 2008) were performed with BeadStudio 3.1 software (Illumina) All subsequent data analysis steps were performed in the statistical programming environment R (version 2.10-0; www.r-project.org) with several bioconductor packages (version 2.6.1; www.bioconductor.org). First, signal intensities were normalized with VSN (Huber et al. 2002) and non-informative probes were removed based on detection p-values. The signals were then averaged for the individual subgroups and a linear model was designed capturing the influence of the patient group on gene expression levels (Smyth 2004, 2005). Differences between subgroups were extracted as contrasts and analyzed with the moderated F-test (empirical Bayes method) including a correction step for multiple testing with the 5%-FDR-based method of Benjamini and Hochberg. To attribute significant regulations to individual contrasts, a decision matrix was generated based on the function "decide tests" within the "limma" package, where significant up- or downregulations are represented by values of 1 or -1, respectively.

Cell Culture of Human Primary Fibroblasts and NSC34 Cells

All used fibroblast cell lines and NSC34 cells were grown as adherent cultures in D-MEM medium containing 10% FCS, amphotericin B and penicillin and streptomycin. Cells were grown as monolayer in tissue culture flask of either 25 cm² or 75 cm² surfaces and kept in a sterile cell incubator at normal cultivation growing conditions of an atmosphere with 5% CO2 at 37° C. Humidity in the incubator was warranted by evaporation of water from a special water reservoir. Depending on the cell division rate of the respective cell line the medium was either changed by default once or twice a week or when a cell line showed a very rapid growth or metabolism, the metabolic products changed the pH within the medium so that the indicator in the standard D-MEM turned the color from red to yellow indicating the necessity of a medium change. Each time a cell line was grown 70~80% confluent, the cells were splitted into new flasks, following the subsequent steps. First, the cell monolayer was washed with PBS (w/o $Ca^{2+}$, $Mg^{2+}$), then Trypsin-EDTA was added to the cells and incubated for 5 minutes in the cell incubator. After that, the trypsinization was stopped by addition of fresh culture medium and cells were split into several new flasks. To keep the growth of the cells dense but not confluent, cells were split, depending on the division rate of the respective cell line from one 75 cm² flask in two to three new 75 cm² flasks. For the longtime storage, cells were first pelleted after trypsinization in a centrifugation step for 8 min at 1200 rpm at 4° C. Then the pellet was resuspended in a sterile-filtered solution of FCS (90%) and DMSO (10%). The resuspended cells in the freezing medium were stored over night at −80° C. and then transferred to −196° C. liquid nitrogen and kept there for longtime storage. At any time, these aliquots can be thawn again and cells can be brought back to culture conditions. For the differentiation of NSC34, cells were seeded on Laminin (Sigma) coated cover slips and retinoic acid (50 μM, Sigma) was added to the medium. After 3 days of incubation cells show Neurite outgrowth.

Cell Culture of Primary Motor Neurons

Whole spinal cord of SMA mouse embryos or heterozygous control mouse embryos was prepared at embryonic day 14.5. Cells were singularized by trypsinization and plated out on poly-L-lysine (Sigma) and laminin (Sigma) coated cover slips in DMEM containing 0.6% glucose (Invitrogen). Next day, cells were transfected with siRNA according to the manufacturer's protocol (Qiagen, Dharmacon). After that, according on the adapted protocol by Kaech and Banker (Kaech and Banker 2006) cells were incubated with neurobasal medium containing B27 supplement and the growth factors BDNF, GDNF and CTNF (Invitrogen). After 8 days in culture, cells are fixed with 4% PFA containing 8% sucrose (Sigma). Subsequently, to identify motor neurons, cells were stained with anti-Hb9 antibody (1:200 Invitrogen) and with anti-neurofilament antibody for axon measurement (1:200 Hybridoma Bank). Finally, cells were imaged with an Axio Imager M2 (Zeiss) and the axonal length was measured with ZEN software (Zeiss). Subsequent statistical analysis was performed with Excel (Microsoft).

siRNA Knockdown

In order to knockdown the expression of a specific gene small interfering RNAs (siRNA) were used. The siRNA stocks (Qiagen) were first diluted to a final concentration of 1 μM in siRNA suspension buffer. Target sequences: Ncald-siRNA: 5'-CAGGTGATTCACCCATTATAA-3' (SEQ ID NO: 6), Smn-siRNA: 5'-AAGAAGGAAAGTGCTCA-CATA-3' (SEQ ID NO: 13). The lipofection substance Dharmafect 1 (Dharmacon) was used for all siRNA transfection experiments. The transfection experiments were performed according to the manufacturer's protocol. Beside the siRNA regarding the respective target gene, siTOX (Dharmacon) siRNA served as a transfection control and AllStars Negative Control siRNA (Qiagen) served as a negative control. All cells transfected with siTOX induced apoptosis. Subsequently to the respective incubation time, cells were harvested for protein isolation. Every knockdown experiment was performed in triplicates.

Immunohistochemistry

Zebrafish were dechorionated and fixed in 4% PFA-PBS 34 hours after fertilization. Collagenase digest was performed to permeabilize the larvae for the following antibody staining. In brief, fish were stained at 4° C. over night in 500 μl PBS-T/10% FCS containing znp-1 antibody (1:300, Hybridoma Bank). After all-day washing in PBS-T/1% FCS/1% BSA (changing solution every hour) fish were stained in PBS-T/1% DMSO/10% FCS containing secondary donkey anti-mouse antibody labelled with Alexafluor 488 (1:200, Invitrogen). After repeated washing, fish were stored in 80% glycerol/20% PBS in the dark at 4° C. Microscopic analysis of fish was performed in 80% glycerol on micro slides using a fluorescence microscope (Axioskop 2, Zeiss). The length of each of the first ten motoraxons behind the yolk was analyzed and evaluated. For NSC34 cell staining cells were fixed in 4% PFA for 15 min at RT. Following fixation, cells were rinsed 1× in PBS for 5 min. After another washing step with PBS, cells were permeabilized in 0.2% Triton X in PBS for 5 min. For blocking, cells were incubated in 5% BSA (Sigma) and 5% FCS (Biochrom) in PBS (blocking solution) for 2 h at RT. Next, primary antibodies (mouse anti Hb9 (1:200) in blocking solution was given to the cells over night. Following 3 washing steps in PBS for 15 min each, the secondary antibody donkey anti-mouse Alexa fluor 488 (1:250, Invitrogen) was co-diluted with Phalloidin Alexa568 (1:40, Invitrogen) in PBS containing 10% FCS and incubated for 4 h at RT. Finally, samples were mounted in mounting medium containing DAPI (Vectashield).

Western Blot Analysis

In case of zebrafish, 34hpf fish were manually dechorionated and deyolked in PBS. After gentle spin-down, larvae were lysed in RIPA buffer (Sigma) containing protease inhibitors (Complete Mini, Roche). For the protein analysis of cells (fibroblasts, NSC34), cells were lysed in PIPA buffer, by direct incubation of cells with RIPA. Cell lysates were immediately frozen at −80° C. or subsequently used for Western blot analysis. Western blots were performed as previously reported (Riessland et al. 2006). The following primary antibodies were used for overnight incubation: anti-beta-actin (zebrafish) (rabbit polyclonal, 1:1000, Anaspec); anti-NCALD (rabbit polyclonal, 1:1000, Proteintech), anti-beta actin (human) (mouse monoclonal, 1:10.000, Sigma), anti-SMN (mouse monoclonal, 1:3000, Hybridoma Bank). Following secondary antibodies were used (incubation 1 h, 1:10.000): anti-rabbit-HRP (GE Healthcare), anti-mouse-HRP (Sigma). Signal detection with Chemiluminescence reagent (Super Signal West Pico,Thermo Scientific) was carried out according to standard protocols.

Endocytosis Assay

Some 10.000 fibroblasts per well are plated out on 96-well plate (in 200 μl normal DMEM growth medium), to achieve ~100% confluency. Next day, the growth medium was replaced with starvation medium (DMEM transparent (HEPES), 2% FKS, Invitrogen) and incubated for 10 minutes. After that, starvation medium was replaced by FITC-dextran medium (starvation medium including FITC-dextran (5mg/ml), Sigma) and cell was incubated for 0, 10, 20 or 30 minutes at 37° C. Subsequently, cells were carefully washed three times with ice-cold PBS (Invitrogen) on ice and fixed with 4% PFA for 10 minutes. After fixation, cells were washed twice with PBS and each well was filled with exactly 200 μl of PBS. Finally, the 96-well plate was transferred to the TECAN plate reader and FITC fluorescence was determined.

Antisense Morpholino Injection

The used antisense Morpholino (MO) was designed against the translational start codon of the ncald gene (Gene Tools, LLC): 5'-GGAGCTTGCTGTTTTGTTTTCCCAT-3' (SEQ ID NO: 2). For smn knockdown, a previously published MO was chosen (5'-CGACATCTTCTGCACCAT-TGGC-3' SEQ ID NO: 14). After finding the right concentration, the embryos were injected with either 2 ng of ncald-MO alone, 4 ng of smn-MO alone, or in combination in aqueous solution containing 0.05% phenol red and 0.05% rhodamine-dextran. Zebrafish embryos were injected between the one- and four-cell stage. For direct control of the motor neuron phenotype, we used embryos obtained from TL/EK wildtype and TL/EK-hb9-GFP (Flanagan-Steet et al. 2005) crossings. Six hours after injection embryos were sorted according to homogeneity of the rhodamine fluorescence signal reflecting the equal distribution of the injected MO solution.

Electrophysiology

Experiments were conducted with zebrafish embryos (wildtype (wt) contras, smn-, ncald-, and smn/ncald-morphants) 72 hours post fertilization. The animals were anesthetized with 0.02% tricaine (in saline; E10521, Sigma-Aldrich, Taufkirchen, Germany) for 1-2 min and then rinsed with saline. The saline contained (in mM): 134 NaCl, 2.9 KCl, 2.1 CaCl$_2$, 1.2 MgCl$_2$, 10 HEPES, 10 Glucose adjusted to pH 7.8 with NaOH. The fish were decapitated and pinned under saline in a Sylgard-coated (SYLG184, Dow Coming, Midland, Mich.) recording chamber (~3 ml volume). The skin was peeled off using a sharp tungsten pin and fine forceps and the preparation was incubated in 3 M formamide (in saline; 6749.1, Carl Roth GmbH, Karlsruhe) for 2 min to prevent muscle contractions. After rinsing the preparation, the superficial layer of ventral slow muscle cells was removed by gently scratching with a fine tungsten pin to expose deeper lying fast skeletal muscle cells. Remaining superficial slow muscles in the segments of interest were removed with a low resistance pipette (~2 MΩ). If not stated otherwise the preparation was continuously superfused with saline at a flow rate of ~2 ml·min$^{-1}$. Experiments were carried out at ~25° C. Muscle cells were visualized with a fixed-stage upright microscope (Zeiss Axio Examiner, Carl Zeiss Microscopy GmbH, Jena, Germany), using a 40× water immersion objective (W Plan-Apochromat, 40×; 1.0 numerical aperture; 2.5 mm working distance; Zeiss) with infrared-differential interference contrast (Dodt and Zieglgansberger 1990) and fluorescence optics. Fast muscle cells were identified by their orientation to the spinal cord and by their ability to generate action potentials (Buckingham & Ali, 2004).

Whole-cell patch clamp recordings in current-clamp mode were performed with an EPC10 patch-clamp amplifier (HEKA-Elektronik, Lambrecht, Germany) that was controlled by the program Patchmaster (version 2.53, HEKA-Elektronik) running under Windows. The electrophysiological signals were low-pass filtered at 2.9 kHz with a 3-pole Bessel filter. The data were acquired at a rate of 10 kHz using Spike 2 software (version 6.02) and a CED Micro 1401 analog-to-digital board (both from Cambridge Electronic Design, Cambridge, England). Compensation of the offset potential and capacitance were performed using the 'automatic mode' of the EPC10 amplifier. The calculated liquid junction potential between intracellular and extracellular solution of 5.8 mV (calculated with Patcher's-Power-Tools plug-in from http://www.mpibpc.gwdg.de/abteilungen/140/software/index.html for Igor Pro 6 [Wavemetrics, Portland, Oreg., USA]) was also compensated. Whole-cell capacitance was determined by using the capacitance compensation (C-slow) of the EPC10. In current-clamp mode, the bridge was adjusted to 90%. Electrodes with tip resistance between 3 and 4.5 MΩ were fashioned from baosilicate glass (0.86 mm OD, 1.5 mm ID, GB150-8P, Science Products, Holheim, Germany) with a temperature controlled pipette puller (PIP5, HEKA-Elektronik), and filled with a solution containing (in mM): 120 KCl, 10 K-HEPES, and 5 K-BAPTA, adjusted to pH 7.4 with KOH. For muscle cell labeling, 0.02% tetraethylrhodamine-dextran (3000 MW; D3308, Life Technologies GmbH, Darmstadt, Germany) was added to the intracellular solution. The muscle cells were low frequency (1 Hz) voltage clamped to −90 mV to prevent inactivation of voltage dependent sodium channels N-methyl-d-aspartate (NMDA, M3262 Sigma-Aldrich, Taufkirchen, Germany) and tetrodotoxin (TTX, BN0517, Biotrend Chemikalien GmbH, Cologne, Germany) were bath-applied at a flow rate of ~2 ml min$_{-1}$.

Statistical Analysis

For the electrophysiological measurements, data were analyzed using Spike2 and statistical analysis was performed in GraphPad Prism (version 5.05, GraphPad Software, San Diego, Calif., USA). All calculated values are expressed as mean±standard error. The EEP frequencies for each cell were measured as mean frequencies over 30 s intervals. Frequencies before and during NMDA application were compared by a paired t-test for each group. A Kruskal-Wallis test followed by Dunns multiple comparisons was used to compare EPP frequencies in different groups. A significance level of 0.05 was accepted for all tests. For statistical analysis of protein and RNA quantification, anatomical analysis (motor neuron phenotype, width of synaptic cleft, motor neuron length) the Student's test was applied to compare individual groups.

Transmission Election Microscopy (TEM)

Whole zebrafish larvae were fixed in 4% PFA for 30 min and postfixed in 0.6% glutaraldehyde for 24 h. Larvae were embedded in Epoxy resin (Plano) and cross sections were performed according to previously described and adapted TEM protocol (Voigt et al. 2010). Thickness of semi-thin and ultra-thin sections was 0.5 μm and 0.1 μm, respectively. Image acquisition was performed as described in the supplement. Image acquisition was performed using the TEM CM10 (Philips) microscope with the Orius SC200W 1 Gatan camera and Digital Micrograph software.

Results

Identification of Neurocalcin delta in a Four Generation Discordant SMA Family

Figure 1:
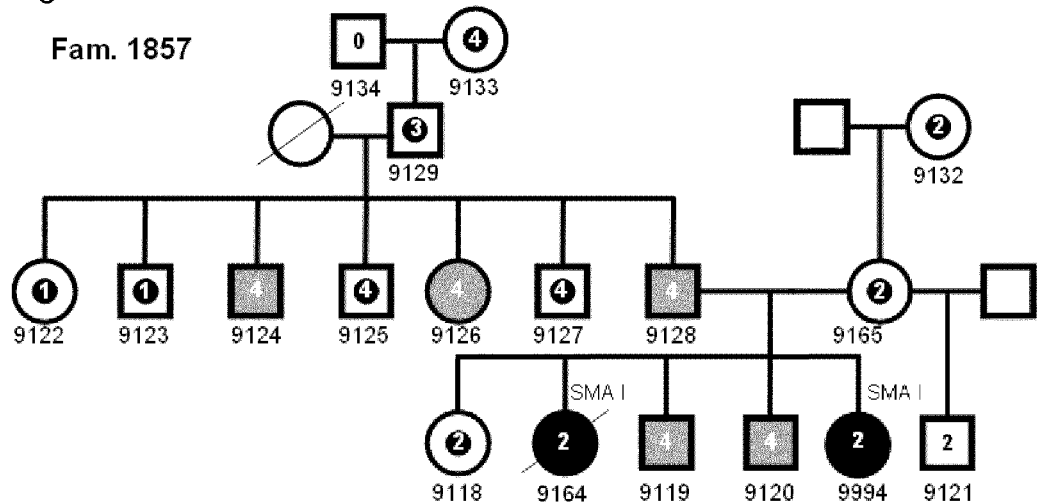
FIG. 1 shows the phenotypic discordant SMA family (Utah, USA). Gray symbols: asymptomatic SMN1-deleted individuals, black symbols: SMA type I patients. Numbers represent the SMN2 copy numbers. (asymptomatic Utah family members: 0x SMN1, 4x SMN2; SMA patients Utah family: 0x SMN1, 2x SMN2; unrelated SMA patients: 0x SMN1; 2x SMN2).

All preliminary research results which are presented in the following are based on material (blood, EBV-cell lines and fibroblasts) derived from a large 4 generation discordant SMA family and generously provided by Dr. Kathy Swoboda (Salt Lake City, Utah, USA). The family includes two SMA type I patients (females, 4$^{th}$ generation) and five asymptomatic (healthy) individuals (four males and one female in the 3$^{rd}$ and 4$^{th}$ generation), all of which are homozygously deleted for the SMN1 gene (FIG. 1). Although the discordant individuals carry four SMN2 copies, it has been shown that this is not sufficient to protect from developing SMA (Feldkotter et al. 2002; Wirth et al. 2006). Since we could prove via expression analysis that the asymptomatic family members are not protected by Plastin 3 expression, we hypothesize an unknown protective mechanism, most likely based on a novel modifying factor.

Figure 2:
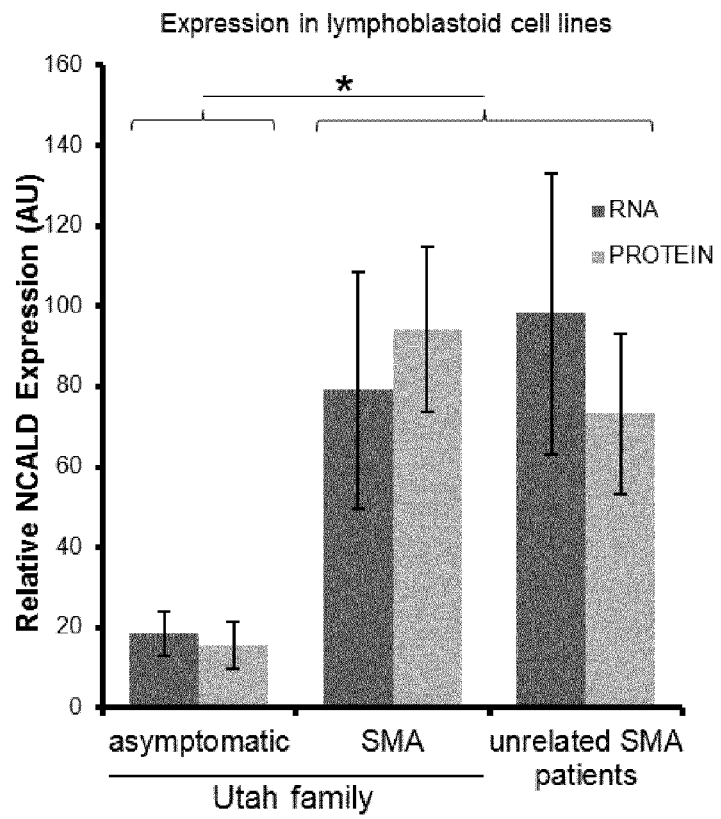
FIG. 2 shows the relative NCALD expression on RNA and protein level in asymptomatic (n=5) and symptomatic (n=2) members of the Utah-family and unrelated SMA patients carrying four SMN2 copies (n=5). All included individuals carry homozygous deletions of SMN1

To identify a potential modifier for SMA in the respective discordant family, we performed expression and linkage analyses. A microarray-based differential expression analysis (Illumina Human HAT-12 v3-Chip) was applied to compare cDNAs derived from the symptomatic and the asymptomatic family members, as well as the cDNAs from five independent SMA patients (SMA type III, 4 SMN2 copies). Neurocalcin delta was identified as significantly downregulated in the asymptomatic siblings. This finding was verified on RNA level by realtime-PCR and on protein level by semi-quantitative western blotting (FIG. 2). Second, to identify the genomic cause of discordance, a genome-wide linkage analysis was performed (250k SNP Affymetrix-Chip). This analysis revealed a co-segregation of a protecting allele containing the genomic region in which NCALD is located. These findings suggest a protective role of Neurocalcin delta in the asymptomatic SMA family.

NCALD Knockdown Experiments in Cell Culture

Figure 3A:
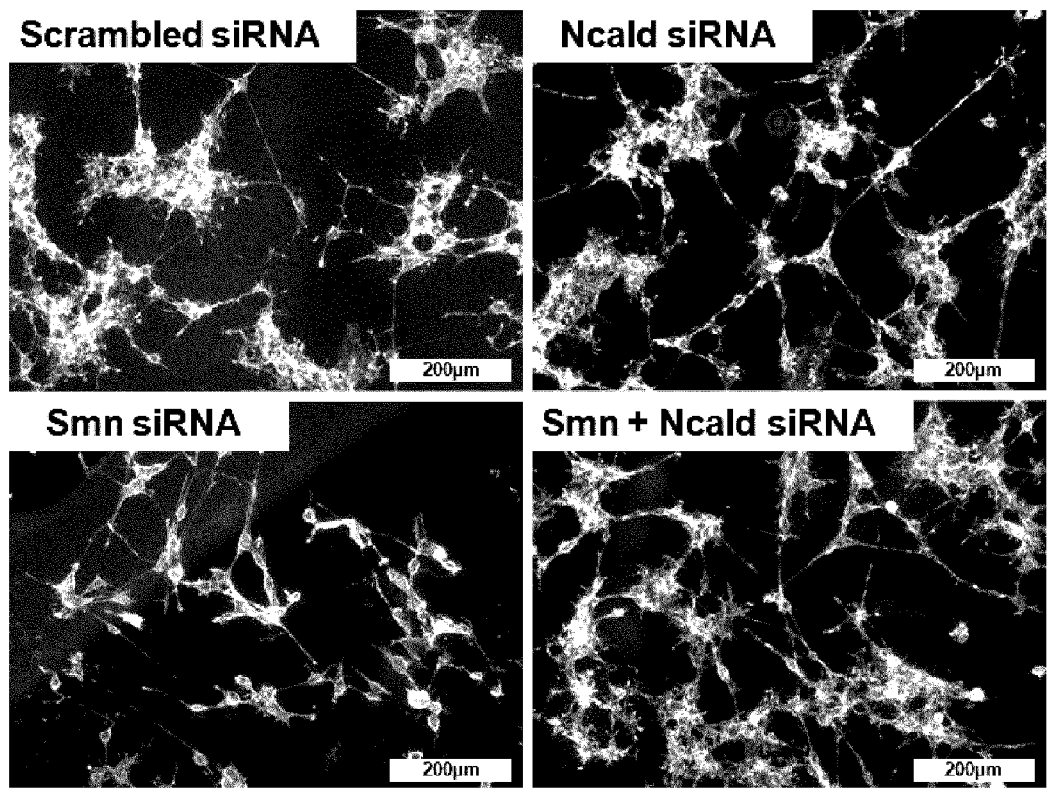
FIG. 3A depicts microscopic pictures of NSC34 cells (Phalloidin-Rhodamine staining) three days after transfection with scrambled-, Smn-, Ncald- or double-siRNA. Neurite outgrowth is reduced under Smn-siRNA transfection. This "SMA-phenotype" is rescued by a double knockdown.
Figure 3B:
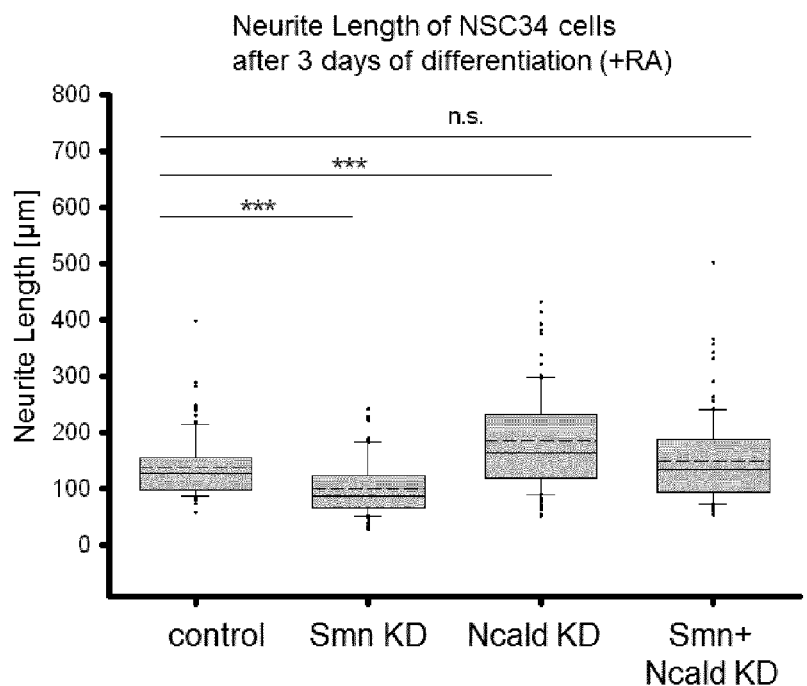
FIG. 3B shows a boxplot quantification of the neurite-length after retinoic acid treatment, under indicated siRNA knockdown conditions.

Next, we investigated the effect of Ncald downregulation on neuronal differentiation and neurite outgrowth. To do so, the murine motor neuron-like cell line NSC34 was applied, which shows neurite outgrowth under retinoic acid (RA) treatment. To investigate the protective effect of the Ncald reduction on a SMA background, a double knockdown approach was applied. Retinoic acid treated Smn-knockdown NSC34 cells revealed a significant reduction in neurite length compared to the control-siRNA transfected cells. Additionally, the Ncald-sIRNA cells showed a significant increase in neurite-length compared to control-siRNA cells. Most strikingly, the "SMA-phenotype"(short neurites) was rescued by the double knockdown of Smn and Ncald (FIG. 3). In the double knockdown situation the neurite length was not significantly different from the control-siRNA cells and therefore the SMA phenotype was rescued.

Figure 4:
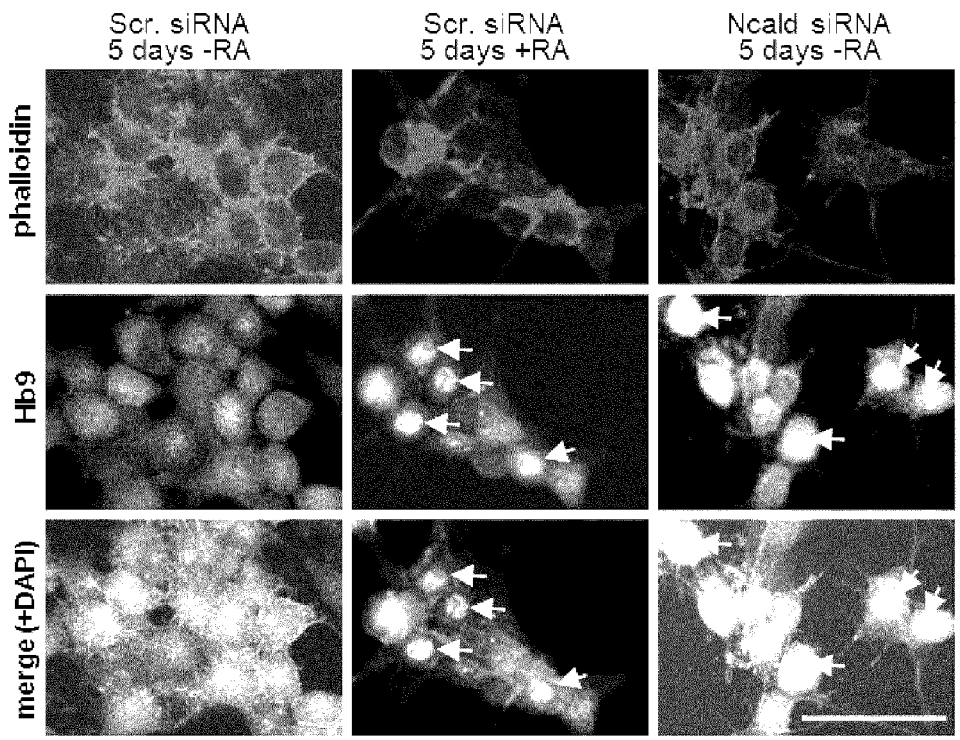
FIG. 4 demonstrates the differentiation of NSC34 cells under Ncald knockdown conditions, with or without RA. Microscopic pictures of NSC34 cells (Phalloidin-Rhodamine staining, red) five days after transfection with scrambled- or Ncald-siRNA. Note the obvious neurite outgrowth and Hb9 expression (bright nuclei, marked with white arrows) in the Ncald-knockdown cells (right).

Although the motor neuronal differentiation of NSC34 cells is triggered by retinoic acid treatment (RA), most interestingly, the siRNA knockdown of Ncald resulted in significant neurite outgrowth after 5 days, even without stimulation with retinoic acid (FIG. 4), Therefore we focused on the differentiation of NSC34 cells and observed expression of Hb9 (homeobox 9; a marker gene for motor neurons) upon Ncald reduction, which supports the hypothesis that these cells differentiate into MN-like cells and that the reduction of Ncald alone is sufficient to induce neuronal differentiation.

Figure 5:
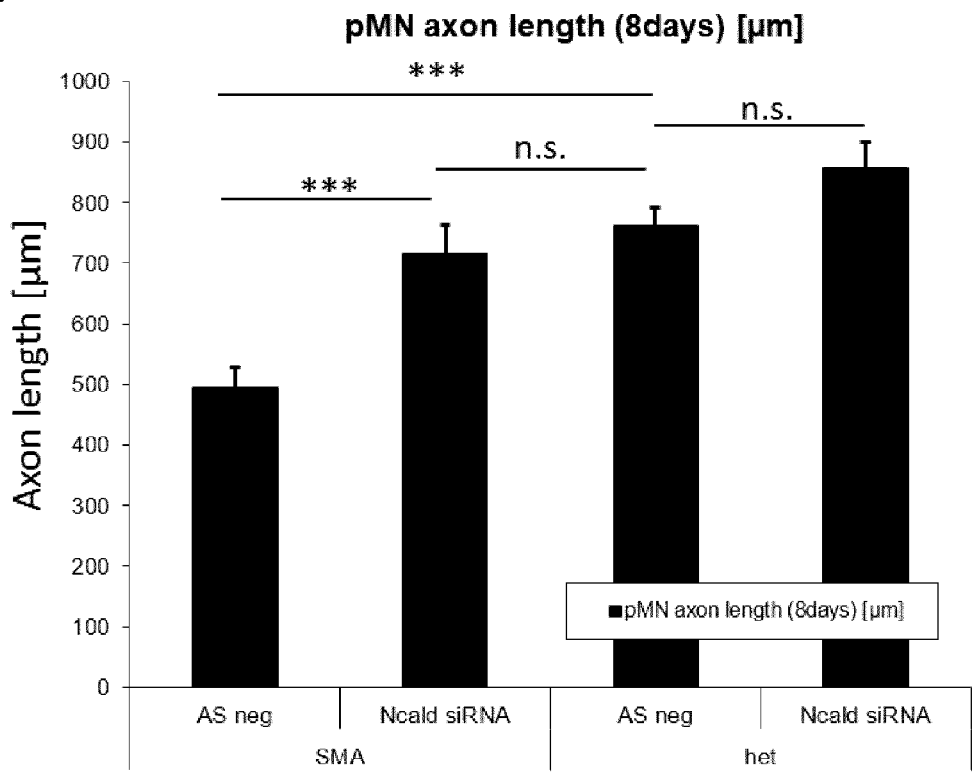
FIG. 5 depicts a bar graph showing the quantification of the axon-length of primary motor neurons after eight days of differentiation in culture under indicated siRNA knockdown conditions. Note the significantly reduced axon length in SMA cells which is rescued by Ncald knockdown. n.s.=not significant, ***=p<0.001, SMA=SMA-like mouse derived motor neurons ($Smn^{-/-}$; $SMN2^{tg/0}$), het=heterozygous control mouse derived motor neurons ($Smn^{-/+}$; $SMN2^{tg/0}$).

To investigate the effect on Ncald downregulation on an endogenous SMA background, we used primary motor neuron cultures derived from SMA mice. To do so, we made use of a well-described SMA mouse model (Taiwanese Hung mouse {Hsieh-Li, 2000 #164}) in which the murine Smn gene is homozygously deleted and two copies of the human SMN2 gene is integrated. These animals show a severe SMA-like phenotype with motor neuron degeneration, an NMJ phenotype, motor function deficits and survive on congenic FVB background for 10 days. Since the motor neurons of the mice closely resemble the situation in SMA patient motor neurons (the mainly affected tissue in patients), we isolated primary motor neurons from SMA-like ("SMA": $Smn^{-/-}$; $SMN2^{tg0}$) embryos and heterozygous control littermates ("het": $Smn^{-/+}$; $SMN2^{tg0}$) at embryonic day 14.5. Both cell types were subsequently transfected with either scrambled control siRNA (allstars negative, AS neg) or siRNA targeting Ncald (Ncald siRNA) and after 8 days of differentiation, motor neuron length was measured. Notably, SMA control cells showed significantly ($p<0.001$) reduced axon length (mean~495 μm) compared to heterozygous control cells (mean~762 μm). Most interestingly, the truncation phenotype of SMA cells was rescued by Ncald reduction (mean~714 μm) (FIG. 5). Moreover, heterozygous Ncald knockdown cells revealed also a small but not significant increase in axon length (mean~856 μm) compared to heterozygous control (AS neg) cells, pointing to a general effect of Ncald reduction on axonal outgrowth.

Investigation of Calcium Handling in NSC34 Cells

Figure 6A:
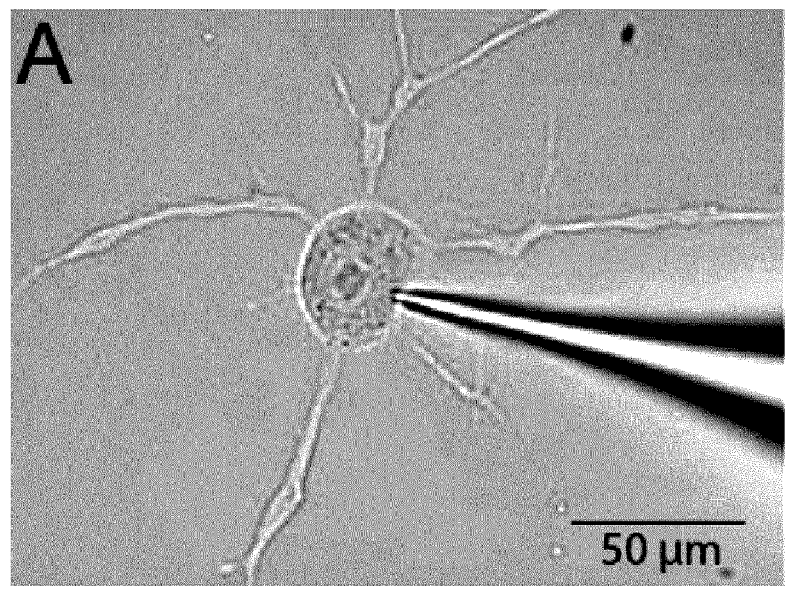
FIG. 6A depicts an exemplary microscope picture of NSC34 cell patched with glass pipette.
Figure 6B:
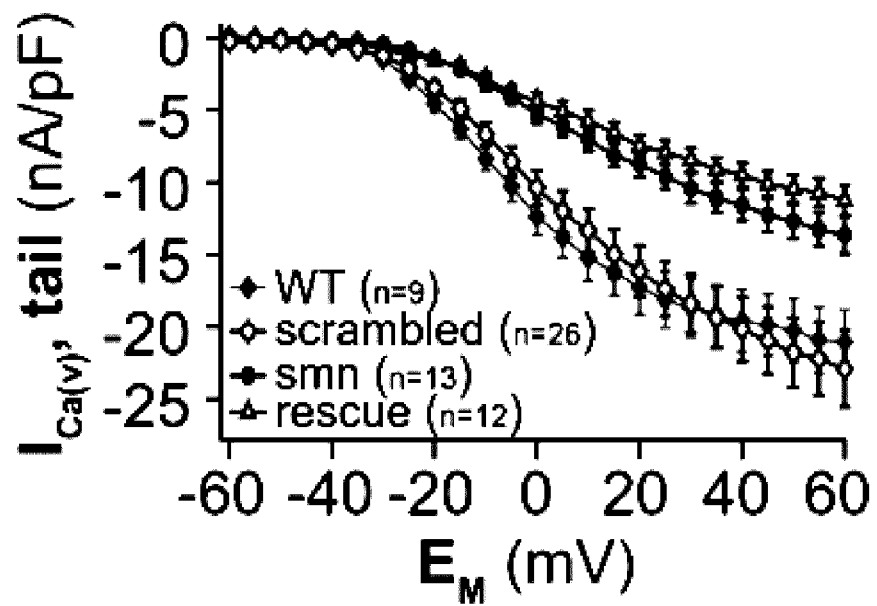
FIG. 6B shows a diagrammatic presentation of quantified of $Ca^{++}$ tail currents. Curves resemble the $Ca^{++}$ current density (nA/pF) of cells. WT=wild-type, smn=Smn siRNA, rescue=Smn+Ncald siRNA, n-numbers are given in brackets.

We next hypothesized that NCALD might have an impact on the calcium handling of the cells, since it has been described to have three functional calcium-binding EF-hands and to act as an calcium sensing protein (Burgoyne and Weiss 2001). To approach the calcium dynamics in differentiated NSC34 siRNA-treated cells, we applied patch-clamp-based electrophysiological measurements. The calcium current density resembling the calcium-ion influx into the cell was quantified by patch-clamp measurement. Therefore, the $Ca^{++}$ channel based tail currents were determined under controlled depolarization of the neuron. Strikingly, it was found that Smn depleted NSC34 show significantly reduced $Ca^{++}$ influx compared to wild-type NSC34 cells and also to cells treated with control siRNA. However, the double knockdown approach (Ncald+Smn siRNA) did not rescue this effect, indicating that Ncald is not a $Ca^{++}$ regulatory but indeed a $Ca^{++}$ sensor (FIG. 6B). Because of the calcium-binding capacity of NCALD it still may play a role in intracellular calcium-buffering or might be important only in certain subcompartments of the presynapse, so called $Ca^{++}$-microdomains which are important for synaptic vesicle release (Schneggenburger and Neher 2005). However, these measurements were not adequate to prove this hypothesis.

Morphological Effect of ncald Downregulation in Zebrafish

Figure 7:
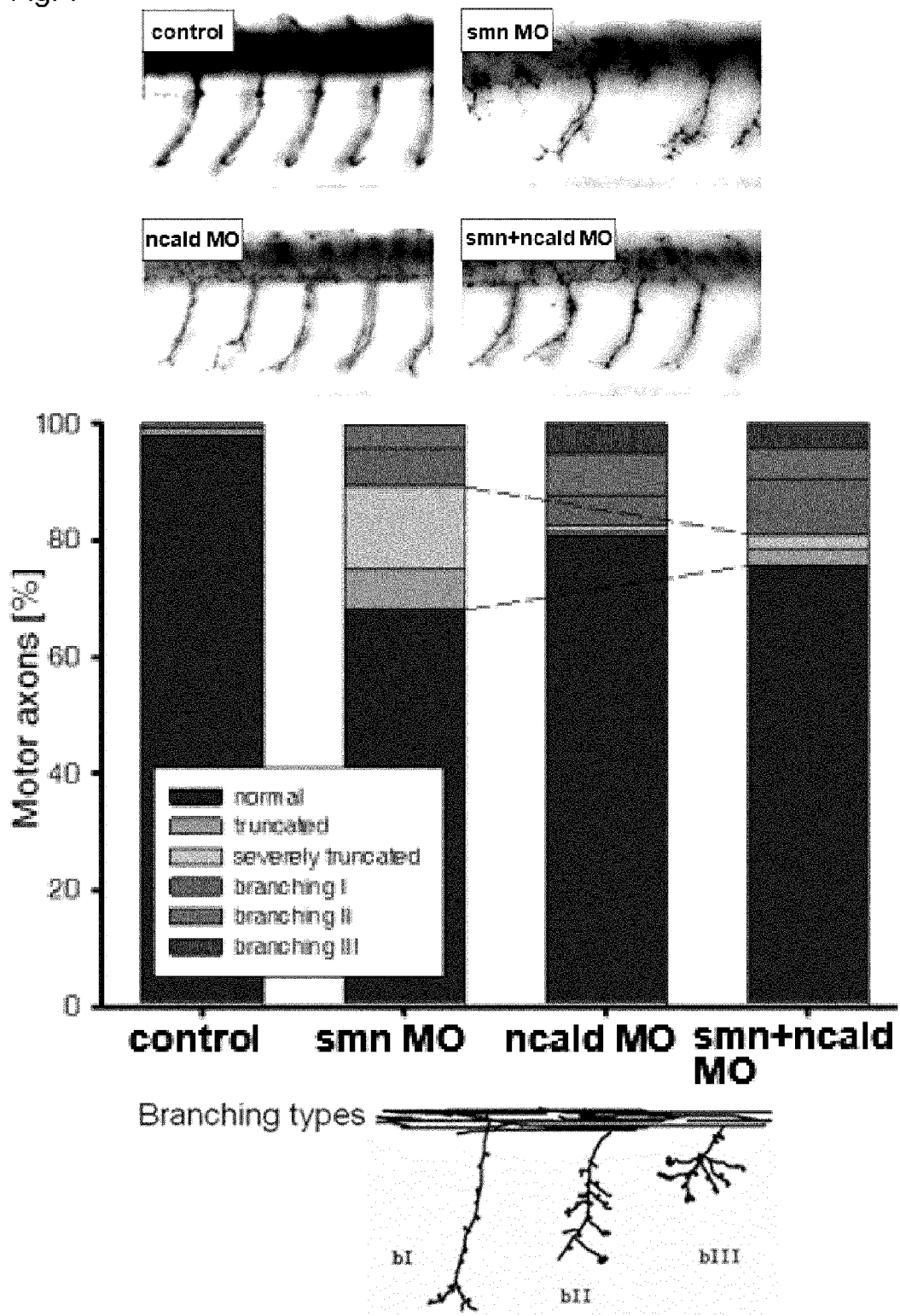
FIG. 7 shows exemplary pictures of differently treated zebrafish. Upper right: Quantification of classified motor axons (n=min. 350). Lower right: Legend for classification of motor axons. Exemplary western blot to determine the knockdown efficiency of the ncald morpholino. Motor axons were stained by DAB staining by using a znp-1 antibody.

Since we were able to prove the protective effect on the SMA phenotype in cell culture, we aimed to confirm this effect in vivo as well. To assess the in vivo effect of the simultaneous reduction of smn and ncald, a double knockdown approach in zebrafish was chosen, using morpholinos against the two respective genes. As previously described, the single knockdown of smn in zebrafish resulted in high numbers of severely truncated motor neuron axons (FIG. 7). However, the highly efficient morpholino knockdown of ncald resulted in high number of extremely branched motor axons, whereas truncations—which are prevalent in the smn knockdown situation (SMA phenotype (McWhorter et al. 2003; Oprea et al. 2008))—were hardly observed. Most interestingly, the double-knockdown (smn+ncald) resulted in a clear rescue of the SMA phenotype (FIG. 7). The number of truncated axons in the co-injected fish was significantly reduced, suggesting a SMA-modifying function of ncald.

Ultrastructural Investigation of Zebrafish NMJs

Figure 8A:
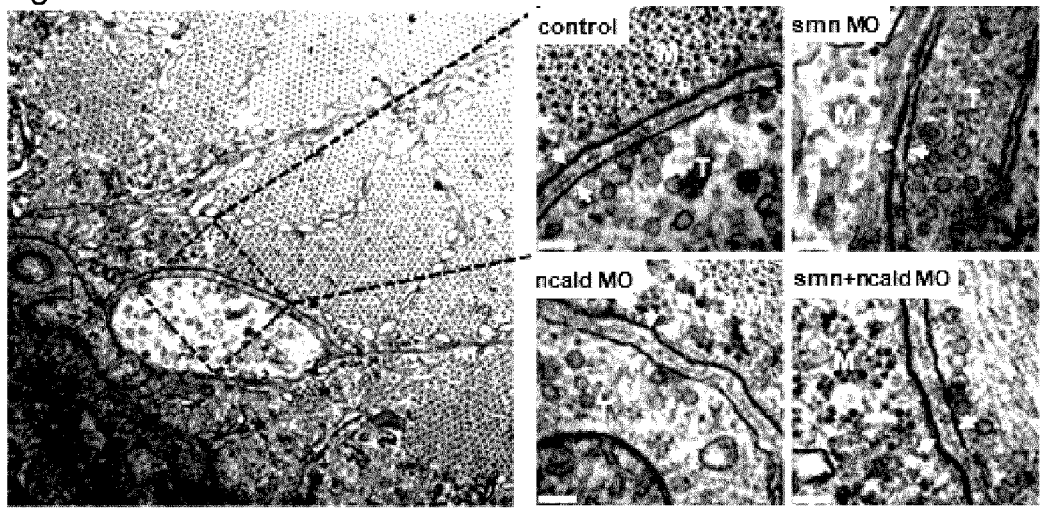
FIG. 8A depicts representative TEM images of NMJs of 34 hpf zebrafish larvae. Embryos were injected with respective morpholinos. White arrows mark synaptic clefts including the basal lamina. Note the reduced width of the synaptic cleft within smn morphants, a sign of delayed NMJ maturation. Delayed maturation is restored by co-injection of smn and ncald morpholinos. Single ncald MO injection increases the width of the synaptic cleft. M=muscle fiber, T=nerve terminal, scale bar=100 nm.
Figure 8B:
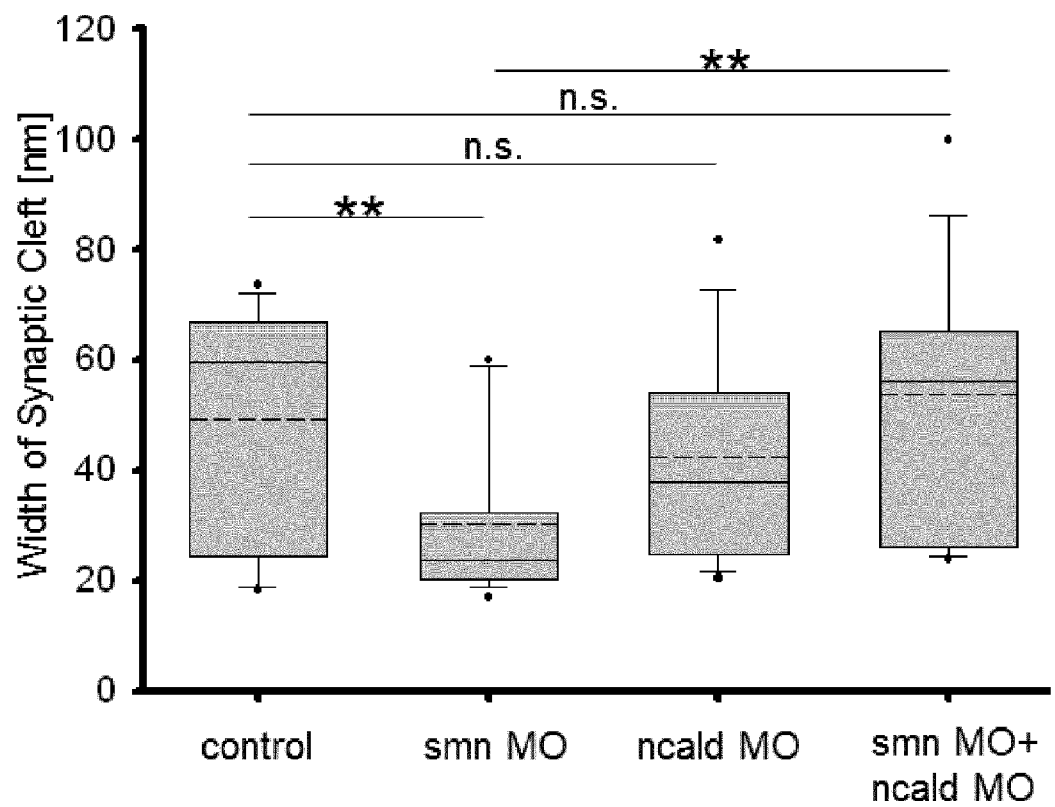
FIG. 8B shows a boxplot quantification of the width of the synaptic cleft of individual morpholino injected 34 hpf fish. Note significant reduction of synaptic cleft width under smn knockdown compared to control, which marks delayed maturation of NMJs. This phenotype is restored by additional ncald knockdown. Ncald and smn+ncald morphants show increase in width of synaptic cleft, reflecting accelerated NMJ maturation.

To investigate the impact of smn reduction on the development of neuromuscular junctions (NMJ), we applied transmission electron microscopy (TEM) and subsequent computer-based analyses (ImageJ) of the synaptic cleft. It has been published that the width of the synaptic cleft of neuromuscular junctions (NMJ) of zebrafish increases during normal development (Drapeau et al. 2001). We found that the morpholino-mediated downregulation of smn resulted in a significant reduction of the width of the synaptic cleft of NMJs, suggesting a delay of normal NMJ formation. Moreover, the additional reduction of ncald in the fish resulted in amelioration of the disrupted NMJ development and could restore the mean width of the synaptic cleft (FIG. 8). These findings prove the structural rescue of the SMA-phenotype in NMJs of zebrafish.

Electrophysiological Investigation of Zebrafish Neurotransmission

Figure 9A:
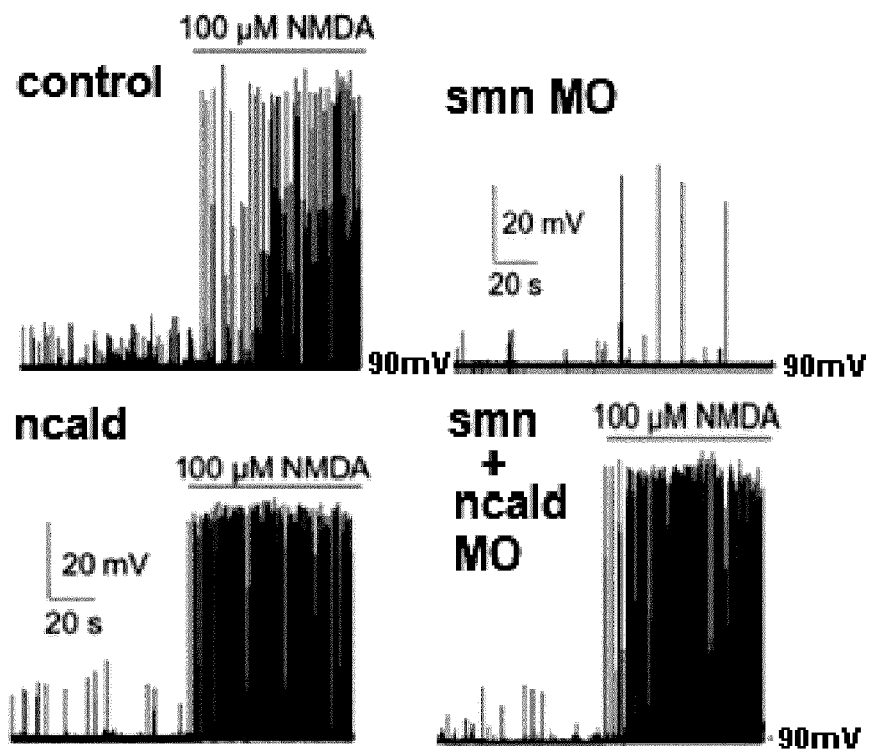
FIG. 9A depicts the original whole cell current clamp recordings of resting and NMDA-induced (100 μM) EPPs in ventral fast muscle cells of wild-type controls, smn, ncald and smn/ncald morphants.
Figure 9B:
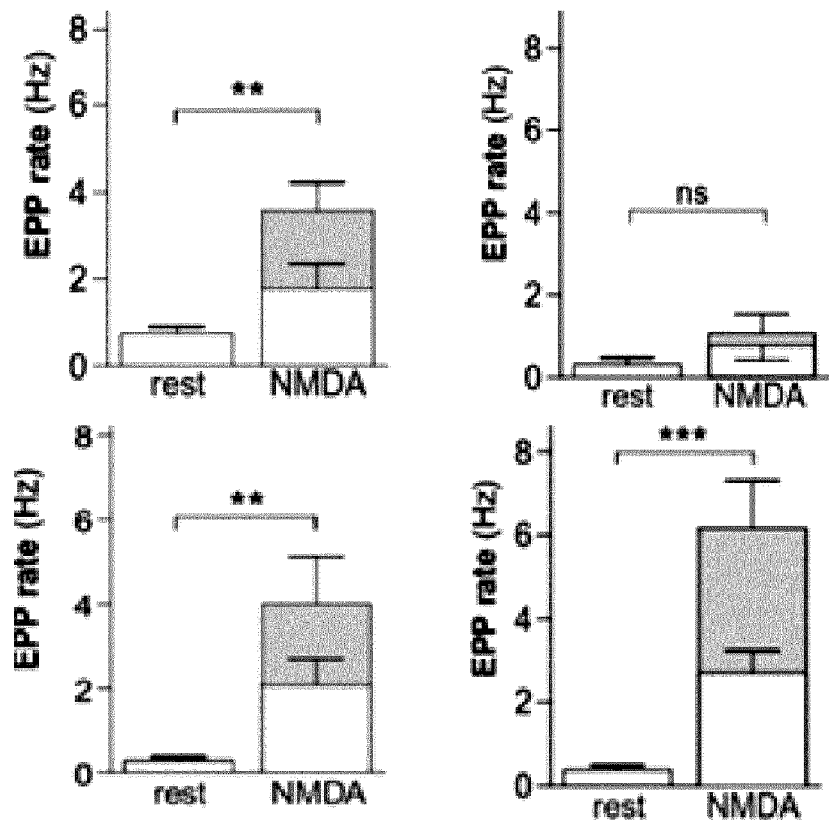
FIG. 9B shows the mean resting and NMDA-induced EPP frequencies of ventral fast muscle cells of wt controls, smn, ncald and smn/ncald morphants. The white portions of the bars reflect the mEPP frequencies. The grey portions reflect the frequency of the TTX-sensitive large EEPs. The significance makers are given for the overall EEP (mEEP+lEEP) frequencies.

Since we found at ultrastructural level that the abnormalities of SMA NMJs can be rescued by the reduction of ncald, we addressed the question whether the functionality of the NMJs is also restored to wild-type levels by reducing ncald. To investigate the functionality of NMJs, we performed electrophysiological measurements to evaluate the neuronal transmission from motor neuron to muscle in the zebrafish morphants. In close collaboration with the lab of Prof. Peter Kloppenburg (Cologne) we developed a new method to stimulate motor neurons and measure action potentials in the receiving muscle of zebrafish. In brief the whole spinal cord is stimulated with NMDA and the endplate potential (EPP) as well as the miniature endplate potential (mEPP) of the target muscle of a selected fish segment is measured by patch-clamp. The electrophysiological analysis of the morphants revealed a significant reduction of the mEPP and the EPP rate of smn morphants. This represents a significantly disturbed neuronal transmission, reflecting the structural aberrations of SMA fish. However, the combined knockdown approach with smn and ncald morpholinos restored the defect to wild-type levels (FIG. 9). These findings show the complete restoration of the functionality of zebrafish NMJs and underline the protective effect of ncald in this animal model.

Movement Behavior of smn, ncald and Rescue Morphants

Figure 10:
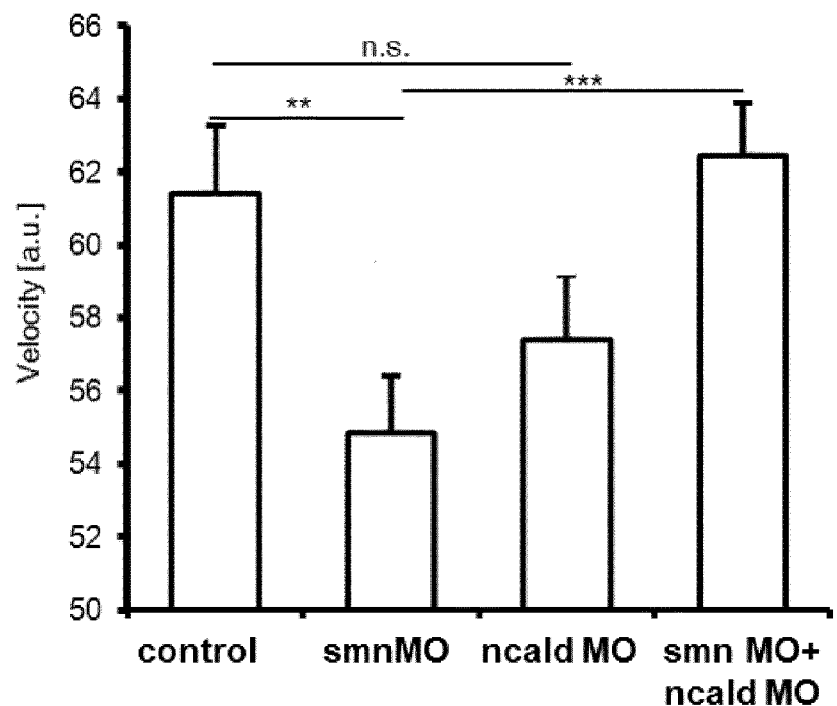
FIG. 10 shows the functional analysis of zebrafish movement ability. Bar graph represents the mean relative velocity of 30 fish after electric shock stimulation. Note the significantly reduced velocity of smn-morphants, which is completely rescued by the additional ncald downregulation (smn MO+ncald MO).

We showed that the reduction of ncald ameliorates the SMA phenotype in zebrafish: besides the restoration of the motor neuron outgrowth we proved the rescue of the NMJ structure and the rescue of the functionality at the NMJ level. Next we were interested in the gross movement ability of the different zebrafish morphants. Therefore we applied high-speed movement tracking of morpholino-injected zebrafish. High-speed video tracking and subsequent software-based analysis (Lolitrack) revealed a significantly reduced median swimming velocity of the smn-reduced morphants. Double knockdown of smn and ncald rescued the swimming ability and restored the speed to wild-type levels (FIG. 10).

NCALD is Involved in Endocytosis

Figure 11:
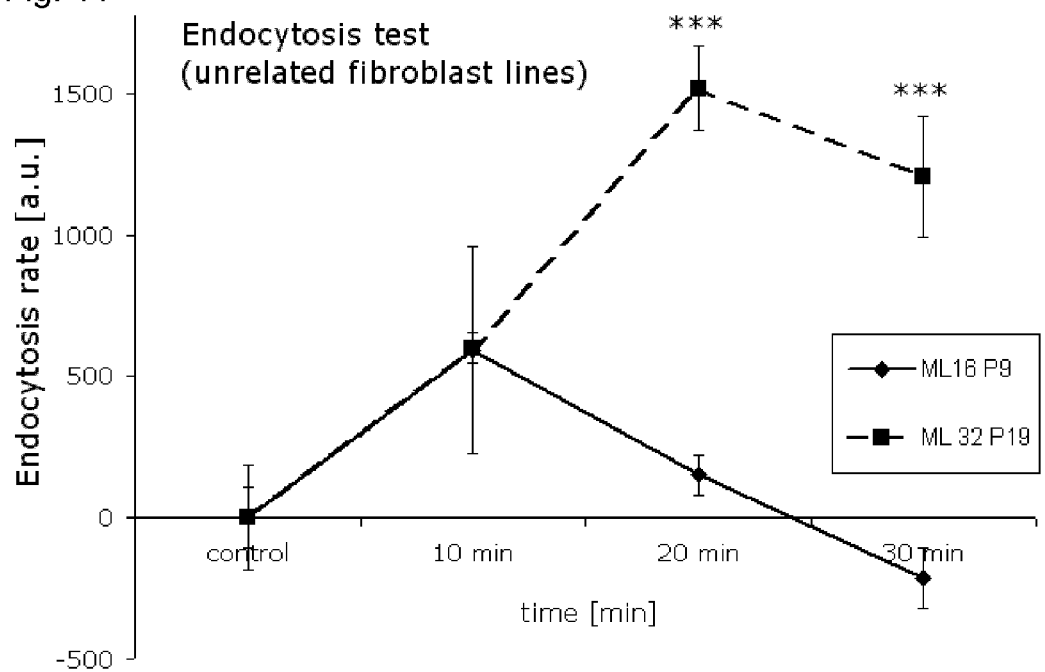
FIG. 11 shows the diagrammatic presentation of endocytosis rate of unrelated fibroblast cell lines derived from SMA-patient (ML16P9) vs. control (ML32P19). ***=p<0.001.

Since we found that NCALD plays important roles in neurogenesis and synaptic transmission, we asked to unravel the molecular mechanism how downregulation of NCALD can restore the neurotransmission phenotype of SMA zebrafish. Since it has been shown that the $Ca^{++}$ sensing molecule NCALD interacts $Ca^{++}$ dependently with membranes, beta-actin and clathrin, we assumed an important function of NCALD in the NMJ. Synaptic vesicle release and synaptic vesicle recycling are crucial steps for motor neuron-muscle transmission, which are highly $Ca^{++}$ regulated. Since clathrin is one of the most important players involved in vesicle recycling and interacts $Ca^{++}$ dependently with NCALD, we hypothesized that NCALD has a role in synaptic vesicle reuptake. Synaptic vesicle recycling and endocytosis resemble a very similar cellular process. Therefore, we investigated the endocytosis properties of control fibroblasts and compared them to SMA patient derived fibroblasts. In brief; we measured the endocytotic uptake of a fluorescent dye (FITC-dextran) over the time. Indeed the tested SMA cell line showed a significantly reduced endocytosis (FIG. 11). Next, we compared two SMA cell lines with two cell lines derived from asymptomatic SMN1-deleted individuals from the Utah family. Indeed, we found reduced endocytotic capacity in the SMA cells in comparison with the fibroblasts derived from the asymptomatic relatives (FIG. 12). Given that the cellular machinery involved in endocytosis and synaptic vesicle recycling is in many ways similar, we assume that the endocytosis phenotype in fibroblasts resembles the situation at the synaptic cleft in SMA patients and their discordant siblings.

In vivo Downregulation of Ncald in Mice

It has been published that a single intraventricular injection of antisense oligonucleotides (ASO), which can restore the coned splicing of SMN2, into the brain of SMA mice is well tolerated and can ameliorate the SMA phenotype (Hua et al. 2010). Since this therapeutic approach was shown to be safe and efficient, pre-clinical trials are in progress. As we observed downregulation of NCALD in the asymtomatic individuals, we aim to decrease the Ncald level in SMA mice by intraventricular antisense oligonucleotide (ASO) injection to rescue the SMA phenotype. Therefore, we designed ASOs targeting the murine Ncald and, after testing its in vitro efficacy in murine NSC34 cells, we injected ASOs either subcutaneously (s.c.) or into the $3^{rd}$ ventricle (icv) of control mice and monitored the in vivo downregulation of Ncald by semiquantitative immunoblotting of different mouse tissues. Subcutaneous injection of 4 μg ASO in newborn (P0) mice resulted in significant downregulation (to ~45%) in muscle tissue (FIG. 5a), but no significant downregulation of Ncald was observed in brain (down to ~70%). However, the direct injection of 2 μg ASO into the $3^{rd}$ brain ventricles resulted in significant downregulation Ncald in brain (to ~60%), but not in muscle tissue (FIG. 13). Therefore, a combination of both application methods will be tested for further analyses.

Generation of shRNA-Ncald Expressing Transgenic Mice

Figure 14B:
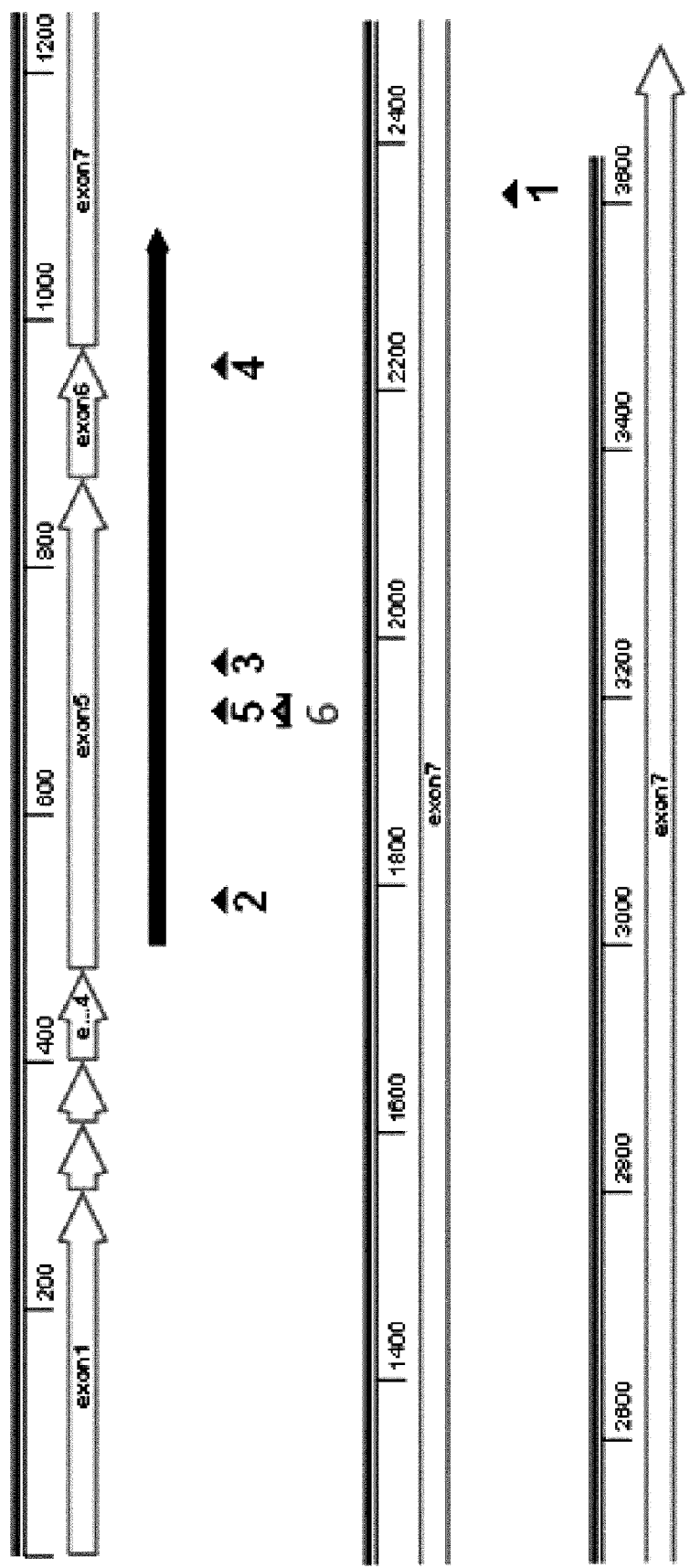
FIG. 14B provides a schematic overview of localization of the target binding regions of the individual shRNAs, binding the Ncald mRNA. Numbers represent the respective shRNA, as shown in FIG. 14A.

Based on the findings that the transient antisense knockdown approach did not lead to efficient reduction of Ncald, we are generating a transgenic mouse model with an inducible short hairpin RNA (shRNA) targeting Ncald, to test the protective function of Ncald on SMA in a mammal. Before starting the cloning of the targeting construct for the mouse generation, we constructed and tested five individual shRNA elements targeting the Ncald gene. To do so, we transiently transfected five different shRNA-Ncald constructs in murine NSC34 cells and analysed the knockdown efficiency after 72 h. Two (shRNA #4 and #5) of the five transfected constructs revealed sufficient knockdown efficacy (FIG. 14). For further testing, we cloned selected shRNA sequences into the vector pEx-H1tetO-CAG-tetR carrying all necessary elements of the tetO/R system which allow later induction of the shRNA-expression by administration of doxycycline (Dox) (Kleinhammer et al. 2011). Currently, after we could verify the dox-inducible capability of two shRNA constructs to knockdown Ncald, we are producing stable murine embryonic cell lines (ES cells) to subsequently generate two individual transgenic mouse strains containing inducible Ncald knockdown vectors. These mice will later be crossed on SMA background to investigate the protective ability of Ncald downregulation.

The knockdown efficiency of five individual shRNA sequences was tested by qRT-PCR-based quantification of Ncald levels, 72 h after knockdown using different shRNA sequences. Transient transfection of NSC34 cells. The respective sequences are those of SEQ ID NO: 15-19 as shown above.

Conclusions

After the identification of NCALD as a potential modifier of the pathological SMA phenotype in a SMA discordant family, we applied many different experimental approaches to unravel the biological mechanism of protection. Since NCALD was found to be downregulated in the SMA-protected individuals, we made use of different gene knockdown methods. By use of siRNA, morpholinos, shRNA and vivo-morpholinos, we were able to reduce the amount of NCALD in vitro and in vivo. The active downregulation of NCALD resulted in a phenotypic rescue of the SMA pathology in many ways. We showed that Ncald reduction in murine motor neuron-like cells (NSC34) did not only rescue the reduced neurite outgrowth, caused by Smn reduction, it also was able to trigger motor neuron differentiation even in the absence of retinoic acid. This finding supports the idea that Ncald reduction could also promote neuronal differentiation in vivo and could therefore be helpful in future therapies for diseases which cause other motor neuron degeneration like amyotrophic lateral sclerosis (ALS), hereditary motor neuropathies (HMN), or other neuronal degeneration (Parkinson, Fretotemporal lob dementia, Alzheimer, Poly-Q-diseases, ataxia etc.), or spinal cord injuries. This hypothesis is further encouraged by the finding that ncald knockdown in a zebrafish model for SMA, is not only rescuing the motor axon truncation phenotype, but also leads to an improvement in NMJ formation, restores the neuronal transmission to the target muscle and even rescues the gross movement phenotype of the zebrafish. The identification of the most likely affected cellular process, the synaptic vesicle recycling, might in future also lead to more applications of the Ncald knockdown regimen, for diseases in which this or a related mechanism is affected. Finally, we succeeded to actively downregulate the Ncald level in mice and are generating an Ncald-shRNA transgenic mouse model. The proof of concept that it is possible to downregulate Ncald by antisense technology in a mammalian animal model shows the feasibility for a potential future application in humans.

Indeed we here identified neurocalcin delta (NCALD) a $Ca^{2+}$-sensor as an SMA protective modifier by applying a combined genetic and expression strategy using the most advanced technologies. In asymptomatic SMN1-deleted individuals the negative effect of reduced SMN levels was counteracted by reduced NCALD. While low SMN levels disturb the $Ca^{++}$ homeostasis in the NMJs and impairs endocytosis, reduced NCALD levels restore endocytosis and NMJ function. This restores axonogenesis and facilitates the proper development of synaptic vesicles and active zones and a full restoration of the function of NMJs as shown by electrophysiology and behavioural tests in zebrafish.

Disturbed $Ca^{2+}$ homoeostasis at the synapse level has been associated with many neurological and MN diseases such as Parkinson, Alzheimer, ALS etc. The identification of NCALD as a crucial $Ca^{2+}$ regulator that counteracts the detrimental effect of reduced SMN levels and of disturbed $Ca^{2+}$ homeostasis to trigger SMA pathogenesis will have a significant impact on the development of further therapies for this devastating disorders.

References

Benjamini Y, Hochberg Y (1995) Controlling the False Discovery Rate: a Practical and Powerful Approach to Multiple Testing. Journal of the Royal Statistical Society B 57.: 289 -300

Burgoyne R D, Weiss J L (2001) The neuronal calcium sensor family of $Ca^{2+}$-binding proteins. Biochem J 353: 1-12

Dent E W, Gertler F B (2003) Cytoskeletal dynamics and transport in growth cone motility and axon guidance. Neuron 40: 209-27

Dodt H U, Zieglgansberger W (1990) Visualizing unstained neurons in living brain slices by infrared DIC-videomicroscopy. Brain Res 537: 333-6

Drapeau P, Buss R R, Ali D W, Legendre P, Rotundo R L (2001) Limits to the development of fast neuromuscular transmission in zebrafish J Neurophysiol 86: 2951-6

Dunning M J, Barbosa-Morais N L, Lynch A G, Tavare S, Ritchie M E (2008) Statistical issues in the analysis of Illumina data. BMC Bioinformatics 9:85

Feldkotter M, Schwarzer V, Wirth R, Wienker T F, Wirth B (2002) Quantitative analyses of SMN1 and SMN2 based on real-time lightCycler PCR: fast and highly reliable carrier testing and prediction of severity of spinal muscular atrophy. Am J Hum Genet 70: 358-68

Hua Y, Sahashi K, Hung G, Rigo F, Passini M A, Bennett C F, Krainer A R (2010) Antisense correction of SMN2 splicing in the CNS rescues necrosis in a type III SMA mouse model. Genes Dev 24: 1634-44

Huber W, von Heydebreck A, Sultmann H, Poustka A, Vingron M (2002) Variance stabilization applied to microarray data calibration and to the quantification of differential expression. Bioinformatics 18 Suppl 1:S96-104

Kleinhammer A, Wurst W, Kuhn R (2011) Constitutive and conditional RNAi transgenesis in mice. Methods 53: 430-6

Kruglyak L, Daly M J, Reeve-Daly M P, Lander E S (1996) Parametric and nonparametric linkage analysis: a unified multipoint approach. Am J Hum Genet 58:1347-63

Le T T, Pham L T, Butchbach M E, Zhang H L, Monani U R, Coovert D D, Gavrilina T O, Xing L, Bassell G J, Burghes A H (2005) SMNDelta7, the major product of the centromeric survival motor neuron (SMN2) gene, extends survival in mice with spinal muscular atrophy and associates with full-length SMN. Hum Mol Genet 14: 845-57

McWhorter M L, Monani U R, Burghes A H, Beattie C E (2003) Knockdown of the survival motor neuron (Smn) protein in zebrafish causes defects in motor axon outgrowth and pathfinding J Cell Biol162: 919-31

Oprea G E, Krober S, McWhorter M L, Rossoll W, Muller S, Krawczak M, Bassell G J, Beattie C E, Wirth B (2008) Plastin 3 is a protective modifier of autosomal recessive spinal muscular atrophy. Science 320: 524-7

Riessland M, Brichta L, Hahnen E, Wirth B (2006) The benzamide M344, a novel histone deacetylase inhibitor, significantly increases SMN2 RNA/protein levels in spinal muscular atrophy cells. Hum Genet 120:101-10

Ruschendorf F, Nurnberg P (2005) ALOHOMORA: a tool for linkage analysis using 10K SNP any data. Bioinformatics 21: 2123-5

Schneggenburger R, Neher E (2005) Presynaptic calcium and control of vesicle fusion. Curr Opin Neurobiol 15: 266-74

Smyth G K (2004) Linear models and empirical bayes methods for assessing differential expression in microarray experiments. Stat Appl Genet Mol Biol 3: Article3

Smyth G K (2005) Limma: linear models for microarray data. In: Gentleman R, Carey V, Dudoit S, Irizarry R A, Huber W (eds) Bioinformatics and Computational Biology Solutions using R and Bioconductor. Springer, New York, pp 397-420

Strauch K, Fimmers R, Kurz T, Deichmann K A, Wienker T F, Baur M P (2000) Parametric and nonparametric multipoint linkage analysis with imprinting and two-locus-trait models: application to mite sensitization. Am J Hum Genet 66:1945-57

Thiele H, Nurnberg P (2005) HaploPainter: a tool for drawing pedigrees with complex haplotypes. Bioinformatics 21: 1730-2

Voigt T, Meyer K, Baum O, Schumperli D (2010) Ultrastructural changes in diaphragm neuromuscular junctions in a severe mouse model for Spinal Muscular Atrophy and their prevention by bifunctional U7 snRNA correcting SMN2 splicing. Neuromuscul Disord 20: 744-52

Wirth B, Brichta L, Schrank B, Lochmuller H, Blick S, Baasner A, Heller R (2006) Mildly affected patients with spinal muscular atrophy are partially protected by an increased SMN2 copy number. Hum Genet 119: 422-8

Example 2

Homozygous loss of SMN1 causes spinal muscular atrophy (SMA) the most common and devastating childhood genetic motor neuron (MN) disease. Low expression from SMN2, present in every SMA patient is unable to counteract SMN1 loss. Here we found that low expression of neurocalcin delta (NCALD), a neuronal calcium sensor, acts as a protective SMA modifier in asymptomatic individuals carrying homozygous SMN1 deletions. We demonstrate that SMN loss reduces voltage-dependent $Ca^{2+}$ influx impaling endocytosis, both essential in synaptic neurotransmission. NCALD binds clathrin at low $Ca^{2+}$-levels, thus acting as a $Ca^{2+}$-dependent inhibitor of endocytosis. Pharmacological inhibition of endocytosis caused an SMA-like phenotype in zebrafish which was restored by NCALD suppression. Importantly, reduced NCALD restores both impaired endocytosis caused by SMN loss in cell culture and MN function across various SMA models, including zebrafish, worm, and mice. Showing that suppression of NCALD counteracts SMA opens novel therapeutic avenues for this insidious disease.

Highlights

LowNCALD level acts as a SMA protective modifier in SMN1-deleted subjects

SMN loss reduces $Ca^{2+}$-influx and impairs endocytosis, causing MN defects

NCALD suppresses endocytosis via binding clathrin at low $Ca^{2+}$-concentrations NCALD reduction restores MN and NMJ function in SMA worms, zebrafish and mice Introduction Paradoxically, mutations in some ubiquitously expressed housekeeping genes impair only a specific organ or even a specific cell type. A particularly remarkable example is spinal muscular atrophy (SMA), one of the most common autosomal recessive disorders. SMA is a neuromuscular disease caused by functional absence of the survival motor neuron 1 gene (SMN1). An almost identical copy gene, SMN2, is present in all SMA patients and determines the severity of SMA. Due to a silent mutation affecting an exotic splicing enhancer, SMN2 produces only about 10% of correctly spliced full-length transcript and protein. Consequently, SMN2, cannot compensate for lack of SMN1. About 50% of patients develop the most severe type I SMA and usually carry two SMN2 copies, whereas the remaining 50% of patients develop milder type II or III SMA and usually carry three to four SMN2 copies.

SMN is an essential protein involved in snRNP biogenesis and splicing. Despite this fundamental role, SMA patients or SMA mice carrying human SMN2 transgenes and murine Smn knockout show prominent structural and functional disturbances at motor neuron (MN) and MN circuitry but especially on the level of presynapses of neuromuscular junction (NMJ) (Karya et al., 2008; Kong et al, 2009; Murray et al., 2008; Ruiz et al, 2010). Despite this knowledge, it is still unclear why mainly motor neurons are affected and which signaling pathways and cellular functions are disturbed by reduced SMN levels.

In extremely rare instances, we and others identified SMA discordant families, in which some siblings or parents of SMA patients show a homozygous SMN1 deletion together with three or four SMN2 copies, but are clinically asymptomatic. We hypothesized that the asymptomatic individuals are protected by genetic modifiers and the identification of the modifier would unravel essential cellular processes disturbed in SMA. Previously, we reported the first fully protective SMA modifier in women, conferred by the X-linked gene Plastin 3 (PLS3). PLS3 is a $Ca^{2+}$-dependent F-actin bundling protein that influences the G/F-actin ratio, which is essential for many processes related to neurotransmitter release at the presynaptic site (Ackermann et al., 2013; Hao le et al, 2012; Oprea et al, 2008). We demonstrated in an SMA mouse model overexpressing PLS3 that PLS3 counteracts the poor axonal connectivity at the presynaptic level and the impaired NMJ development and maturation by restoring all F-actin-dependent processes essential in synaptic vesicle recycling and neurotransmission.

Here, we identify NCALD, a neuronal $Ca^{2+}$ sensor protein, as an SMA protective modifier in humans. We demonstrate that either knockdown of NCALD or overexpression of PLS3 in various SMA animal models restore NMJ and motor function, thereby ameliorating SMA pathology. Furthermore, endocytosis is identified as a crucial common functional denominator of NCALD and PLS3. PLS3 has been reported to be important in endocytosis in yeast; moreover, NCALD interacts with clathrin, which is essential in coating of endocytotic vesicles (Haucke et al., 2011; Ivings et al., 2002; Kubler and Riezman, 1993). We show that 1) endocytosis is impaired in SMA but restored by NCALD knockdown or PLS3 overexpression, 2) low SMN levels reduce $Ca^{2+}$ influx, which is not restored by low NCALD levels, 3) NCALD binds clathrin only in the absence or low $Ca^{2+}$ levels and thus acts as an $Ca^{2+}$-dependent inhibitor of endocytosis, and 4) moderate reduction of SMN and moderate blockage of clathrin-dependent endocytosis act in a genetically synergistic manner causing massive motor axon impairment in zebrafish, which is however restored upon NCALD knockdown. Together, these findings identify endocytosis as a critically impaired cellular process in SMA, which is restored by low NCALD levels in MN that acts as a $Ca^{2+}$-dependent regulator of endocytosis.

Results

Figure 15A:
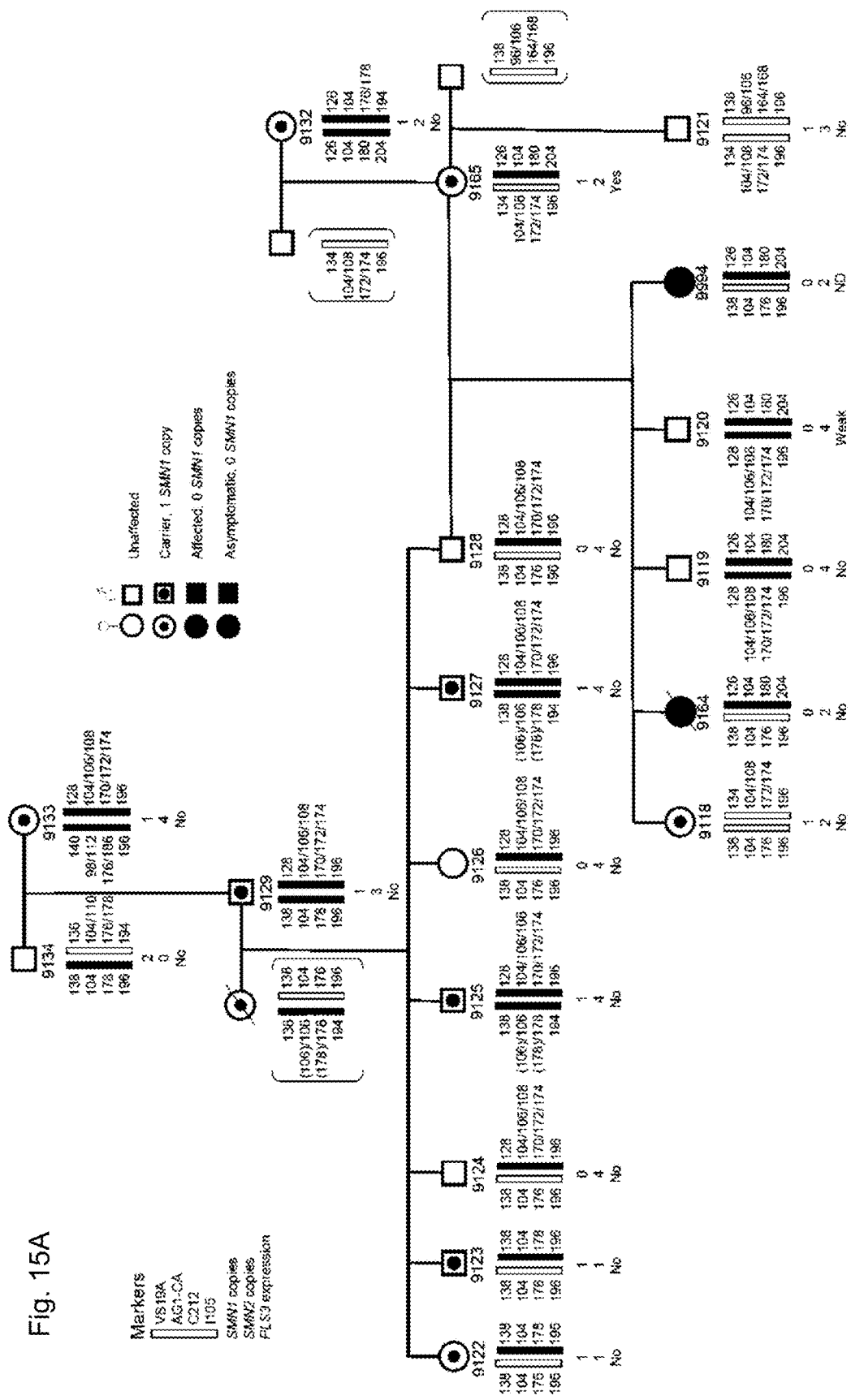
FIG. 15 shows the genome-wide linkage and transcriptome analysis uncovered NCALD as candidate modifier of SMA.

Identification of NCALD as a Potential SMA Modifier by Genome-Wide Linkage and Transcriptome-Wide Differential Expression Analysis In a four-generation Mormon family from Utah, we identified seven individuals carrying homozygous SMN1 deletions, two of whom were affected by type I SMA whereas five were fully asymptomatic at ages ranging from 8 to 40 years, except a reported increased photosensitivity when moving rapidly from a dark to bright environment (FIG. 15A). Full clinical pictures and investigations are given in the Supplementary Information.

Haplotype analysis using multicopy polymorphic markers from the SMA region showed a cosegregation of three different SMA alleles in this family (FIG. 15A). Importantly, all five asymptomatic individuals showed homozygous absence of SMN1 and four SMN2 copies. This resembles a genotype associated with type II or III SMA, whereas the two type I SMA patients carried no SMN1 and two SMN2 copies (FIG. 15A). Sequencing of the entire SMN2 coding region excluded any further variant that may affect SMN2 splicing or expression. Similar levels of SMN RNA and protein were found in lymphoblastoid cell lines (LBs) compared to other typical type III SMA patients, thus excluding both cis and trans-acting factors regulating SMN2. No increased PLS3 levels—potential modifier—were measured (FIG. 15A, array data stored at GEO). We concluded that these individuals are protected by a new SMA modifier.

Figure 15B:
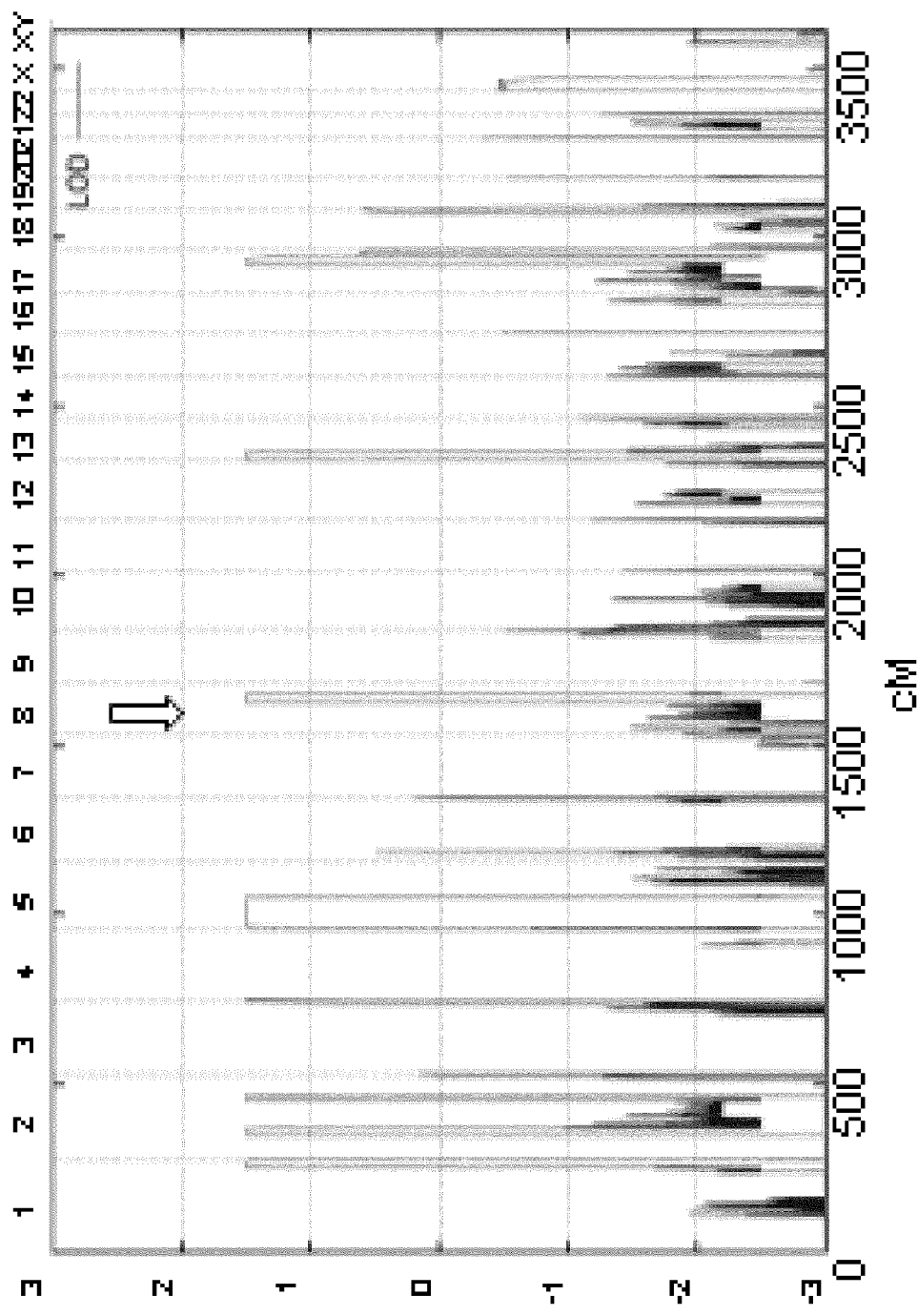
Figure 15C:
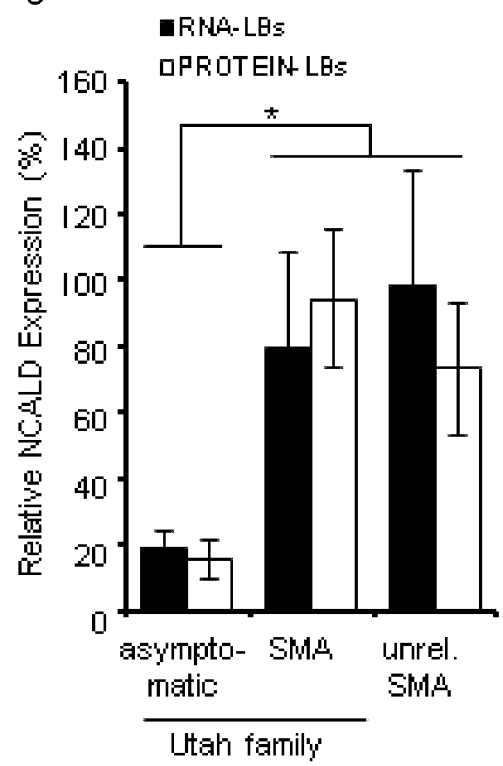
Figure 15D:
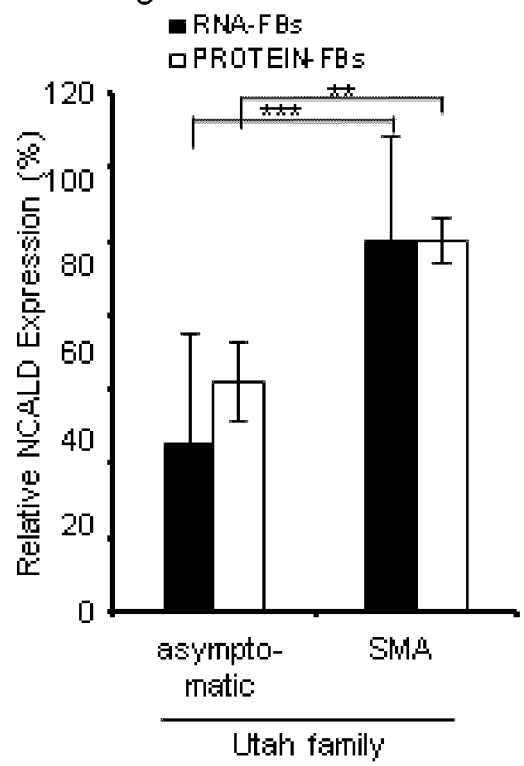

To identify this SMA modifier and the potential genetic difference in the Utah family, we applied a combined strategy using linkage analysis together with transcriptome-wide differential expression analysis followed by a targeted re-sequencing analysis. Whole genome linkage study was performed including all available 14 family members. A parametric linkage analysis assuming a dominant mode of inheritance revealed eight positive peaks with a maximum LOD score of 1.5 (FIG. 15B). In parallel, a transcriptome-wide differential expression analysis with 12 RNA samples isolated from LBs was performed. Expression results of 25, 000 transcripts were evaluated as described in the Supplemental Information. The 12 samples were grouped as follows: group 1, the five asymptomatic members of the Utah family; group 2, the two SMA patients of the Utah family; and group 3, five independent type III SMA patients carrying four SMN2 copies. First, significantly differentially expressed genes (p<0.05) between group 1 and 2 and group 1 and 3 were identified. Subsequently, an intersection between the two tables and common transcripts, significantly up- or downregulated towards the same direction was created, which resulted in 17 transcripts (Table S1). Out of these, NCALD (neurocalcin delta) was represented by two independent probes showing a 4-5 fold downregulation in asymptomatic individuals versus the other two groups. Most importantly, NCALD was the only transcript localized in one of the eight linked regions on chromosome 8q22.3 (between SNPs rs28144 and rs958381), making it an extremely likely candidate. Microanay data were confirmed by qRT-PCR and similar protein expression levels were found in LBs as well as in fibroblast cell lines (FIGS. 15C and 15D).

Targeted re-sequencing of about ~3 Mb genomic DNA comprising NCALD using a Nimblegene custom-designed array in five family members and detailed genetic analysis given in the Supplementary information and Table S2 let us to conclude that additional transregulatory or epigenetic factors might cause the NCALD downregulation in the Utah family or that there has to be another molecular cause not unraveled by our approach.

What is Known about NCALD?

NCALD belongs to a family of fourteen neuronal calcium sensor (NCS) proteins which are highly conserved across species and mainly linking $Ca^{2+}$-signals with neuronal functions (reviewed in (Di Sole et al., 2012)). NCALD encodes a small protein that is present in two forms: 18 kDa ($Ca^{2+}$-bound) and 22 kDa (non-$Ca^{2+}$-bound). It contains two pairs of EF-hand domains and an N-terminal myristoyl anchor that enables a switch from cytosolic to membrane-bound form in a $Ca^{2+}$-dependent manner (Hidaka and Okazaki, 1993;). It is highly expressed in brain, but also found in blood, skin and liver. It is detected in cerebral neurons, spinal motor neurons, and is particularly abundant in axonal growth cones (lino et at, 1998). Overexpression of NCALD inhibits neurite outgrowth (Yamatani et al., 2010). NCALD has an important role as a $Ca^{2+}$-sensing protein in phototransduction (Venkataraman et at, 2008) which most likely explains the photosensitivity in the asymptomatic SMN1-deleted individuals of the Utah family. Moreover, NCALD has been reported to interact with clathrin and actin (Ivings et al., 2002), suggesting a role in endocytosis and synaptic vesicle recycling (reviewed in Haucke et at, 2011). Since NCALD is also abundant in axonal growth cones of spinal motor neurons, we considered it as a plausible candidate as SMA modifier.

Figure 16A:
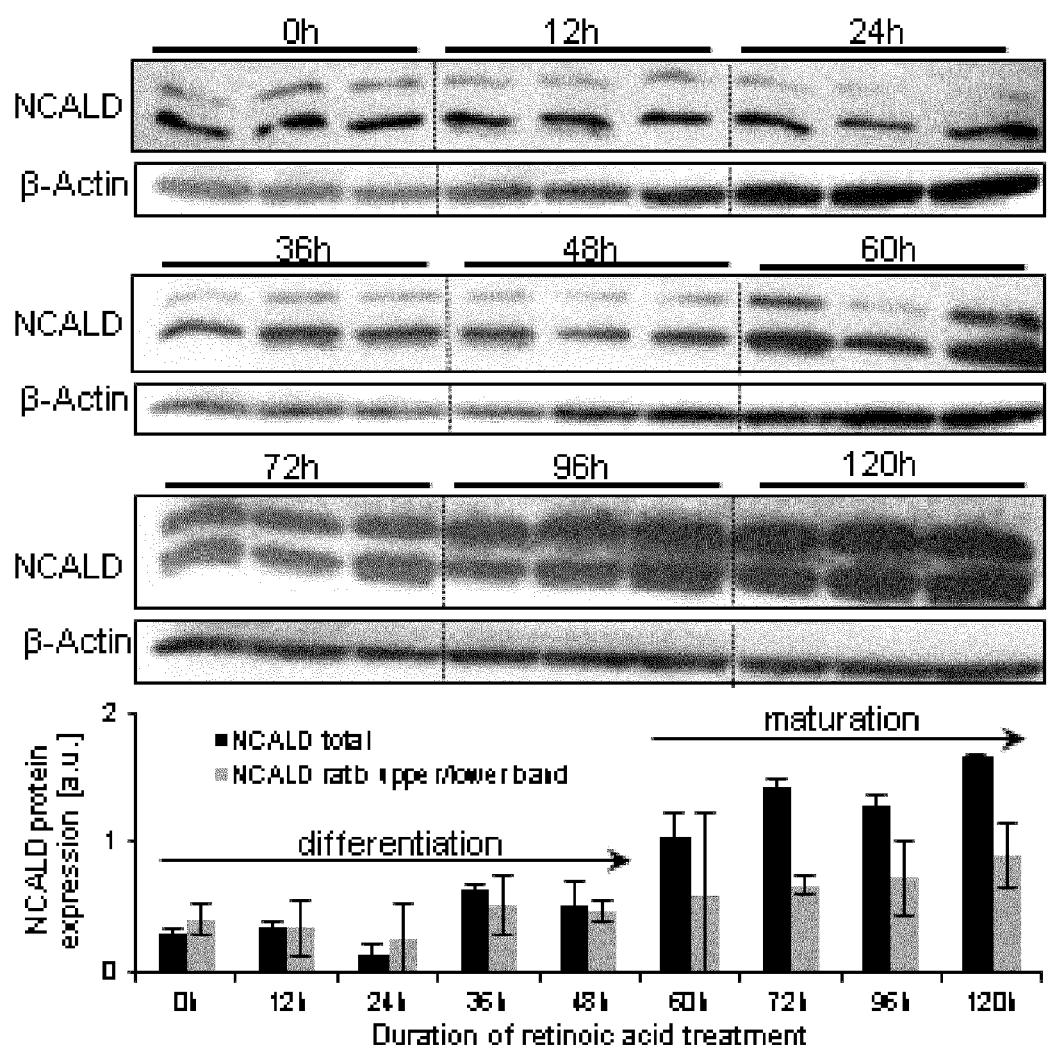
Figure 16B:
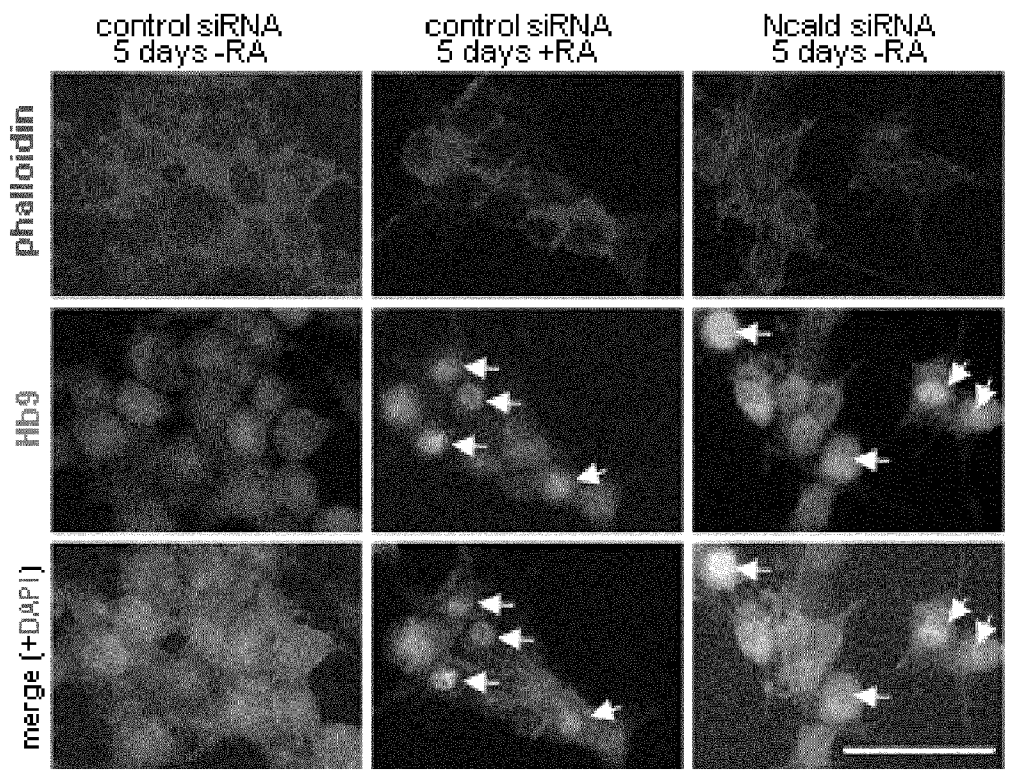
Figure 16C:
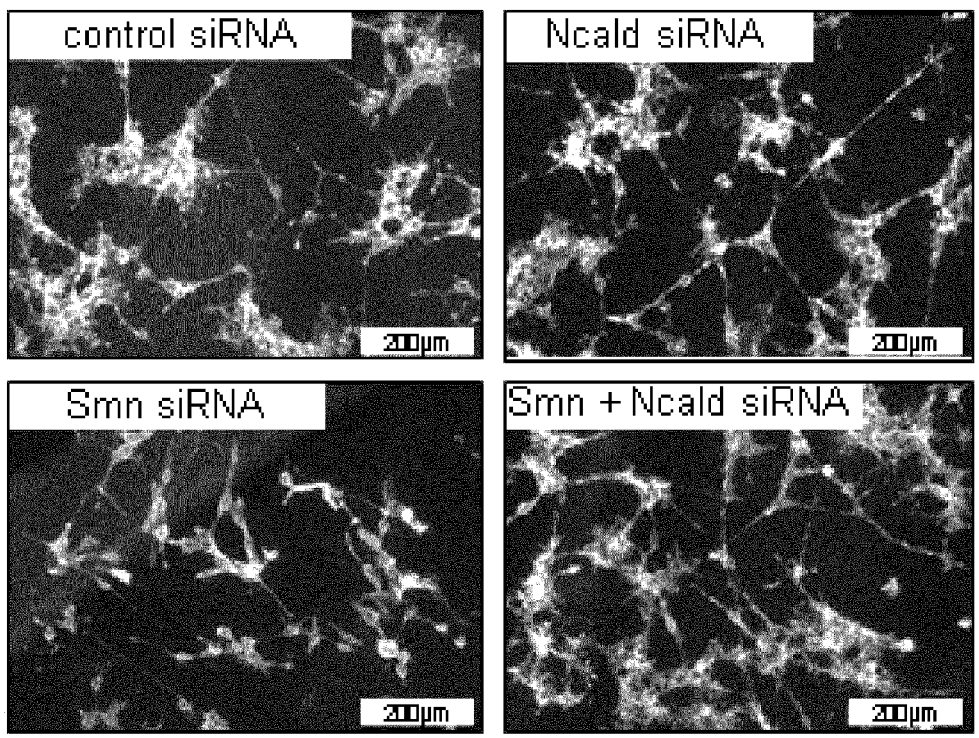
Figure 16D:
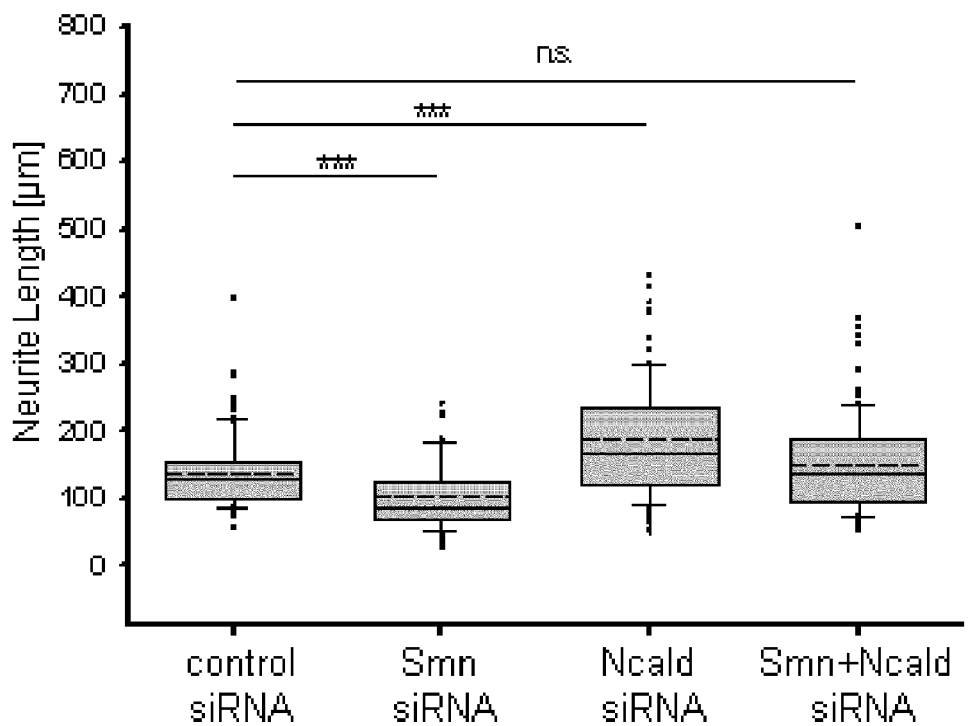
Figure 16E:
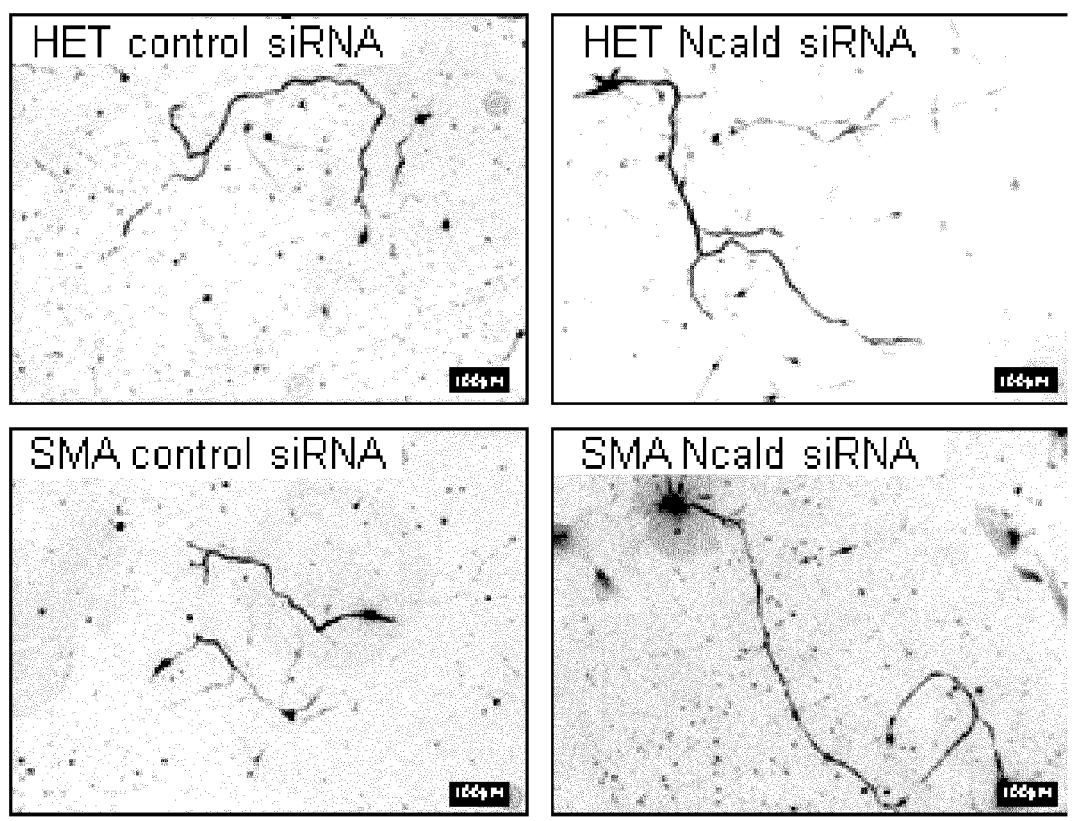
Figure 16F:
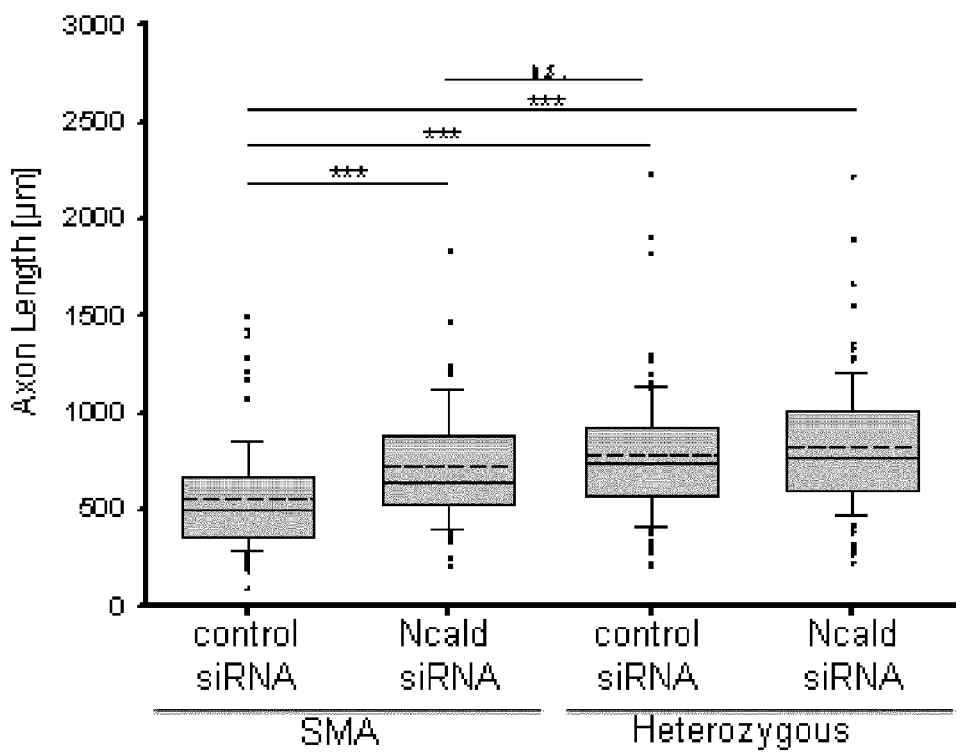

Downregulation of Ncald/Restores Neurite and Axonal Growth in Cultured SMA Motor Neurons To test whether NCALD influences axonal outgrowth, we first analyzed the expression of NCALD in NSC34 cells treated with retinoic acid to induce MN differentiation. While in the first 48 h of early MN differentiation, NCALD expression was low, a massive increase and a switch of ratio between the $Ca^{2+}$-bound and non-$Ca^{2+}$-bound NCALD forms was observed during later maturation (next 3-5 days), suggesting different requirements during the two developmental phases (FIG. 16A). Next, we tested the impact of Ncald down regulation by siRNA in NSC34 cells. Strikingly, Ncald downregulation induced MN differentiation (indicated by Hb9-staining) and induced neurite outgrowth in NSC34 cells even without retinoic acid (FIG. 16B). We further tested the impact of NCALD knockdown on SMA background. As expected, Smn depletion by siRNA in NSC34 cells impaired neurite outgrowth, whereas double knockdown of Smn+Ncald restored neurite length after three days reaching levels similar to controls (FIGS. 16C and 16D). By contrast, overexpression of NCALD in retinoic acid-treated NSC34 cells impaired neurite outgrowth and induced plasma membrane blebbing (FIG. 23). Concordant results were obtained in cultured primary MN from SMA versus heterozygous control mouse embryos. As previously shown, SMA MN show reduced axon length as compared to controls, which was significantly ameliorated by Ncald knockdown (FIGS. 16E and 16F). These findings indicate that reduced NCALD levels counteract the impaired axonal development of SMN-deficient MN.

Reduced Ncald Restores Axonal Growth in Zebrafish smn Morphants

Figure 17A:
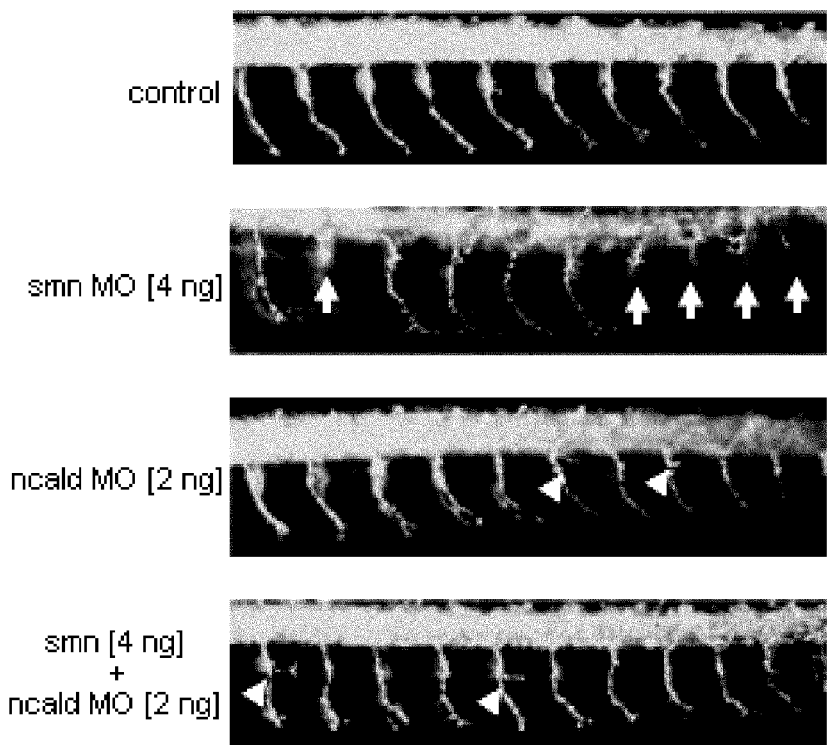
Figure 17B:
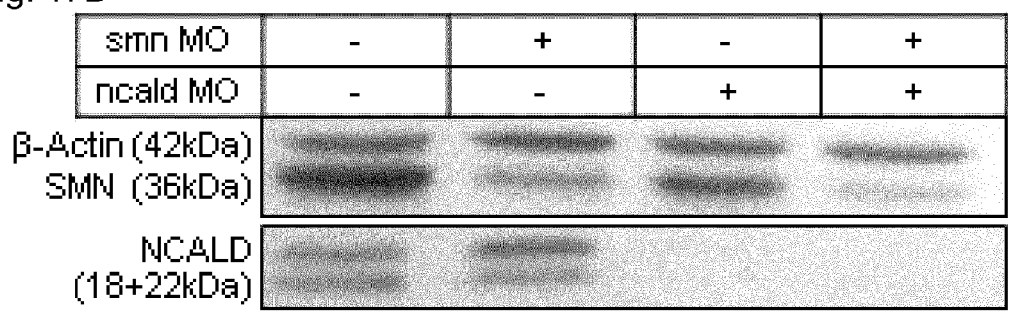
Figure 17C:
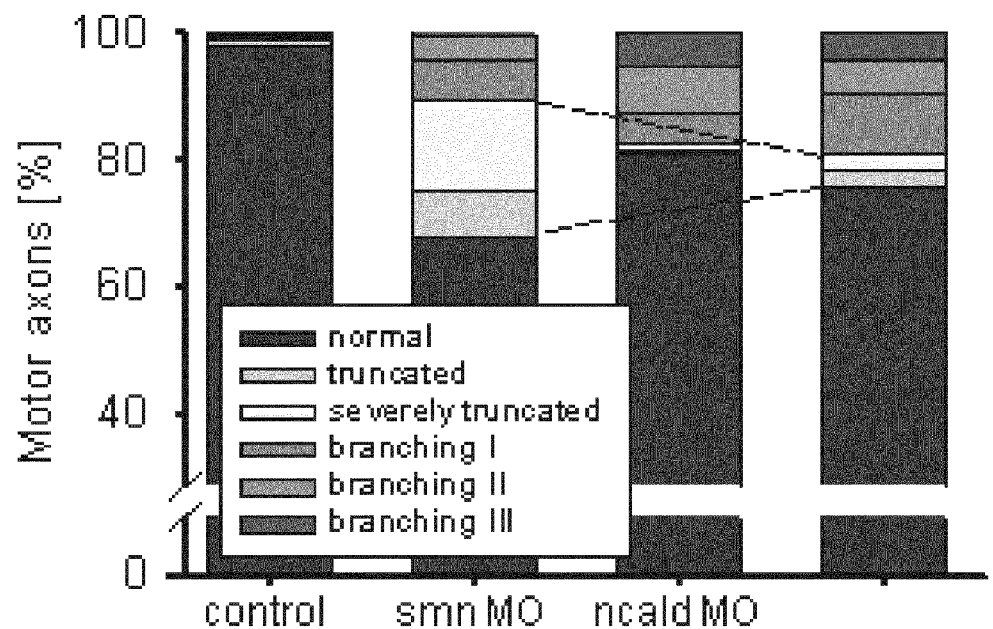
Figure 24A:
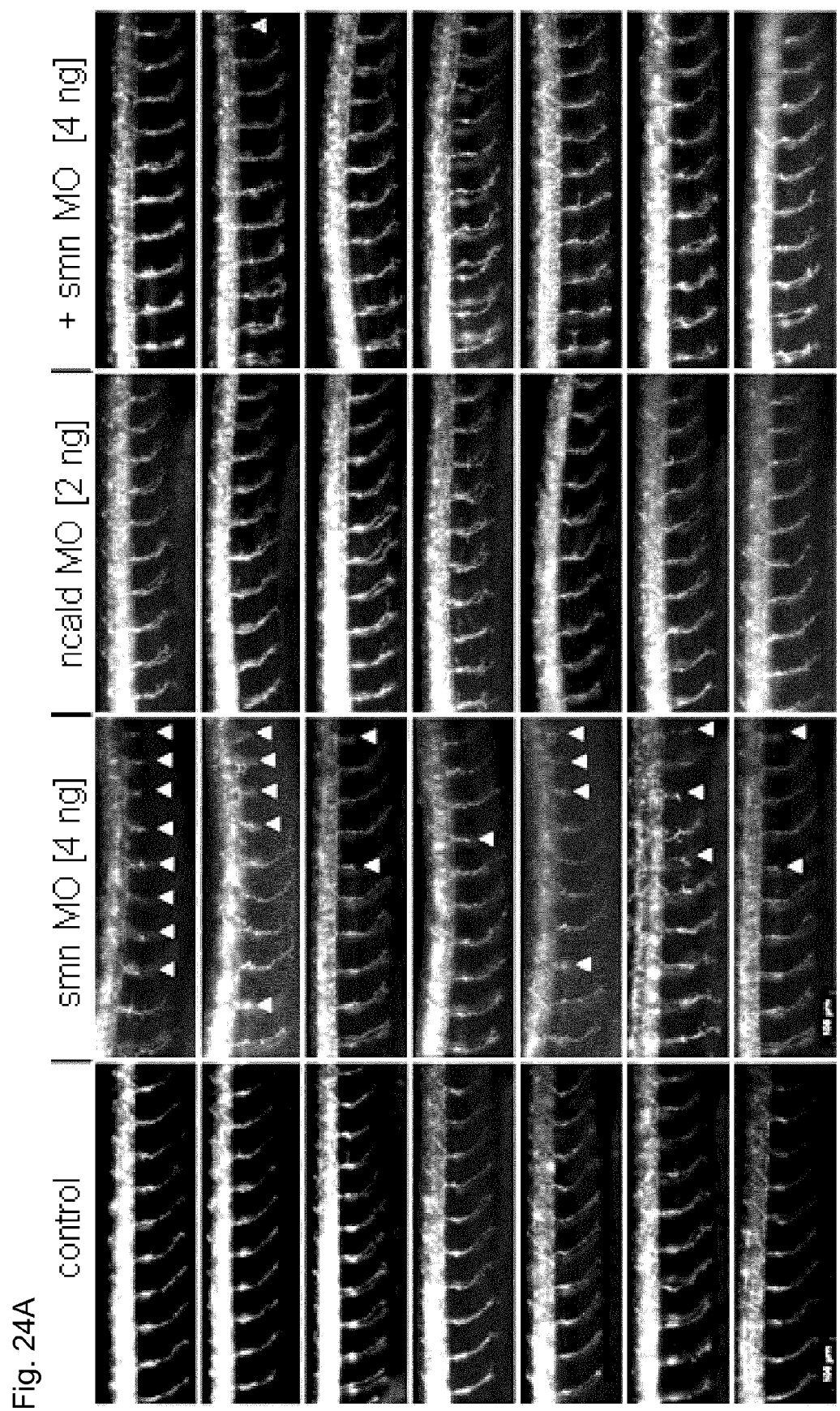
Figure 24B:
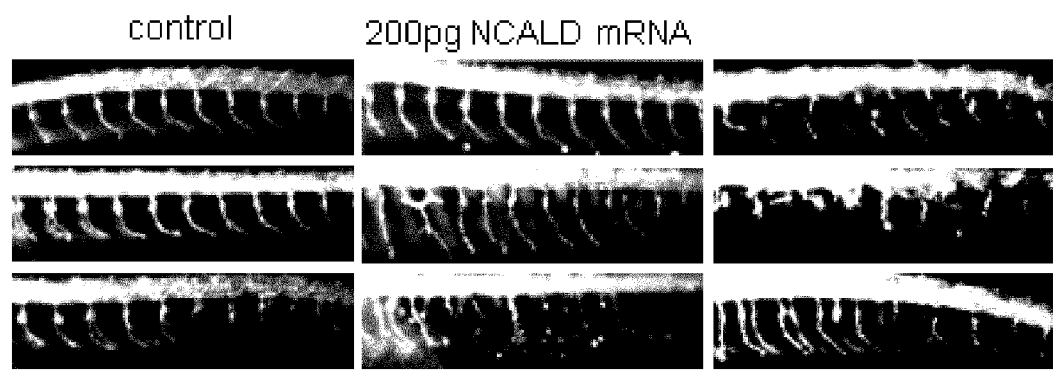
Figure 24C:
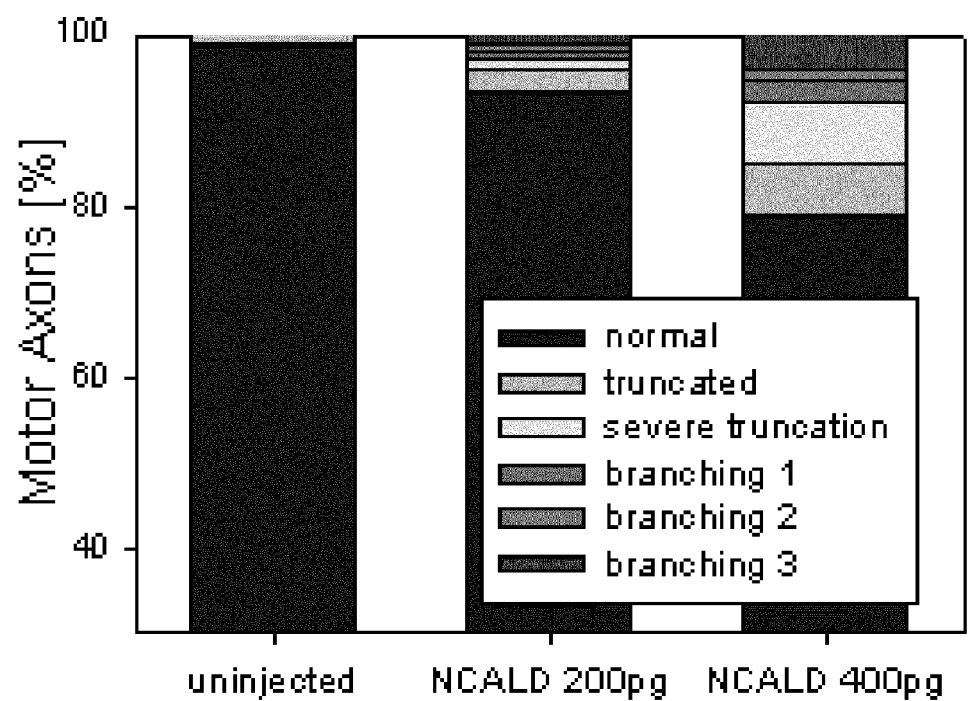

Human NCALD and its ortholog in zebrafish are 98% identical, suggesting an important conserved function across vertebrates. Based on the results obtained in cultured MN, we investigated the modifying effect of ncald in vivo in an mnxl:eGFP-expressing transgenic zebrafish model by either knocking down either smn, ncald or both with antisense morpholinos (MO). Knockdown of smn resulted in massive motor axon-specific outgrowth defects such as truncations and ectopic branches which were both rescued by PLS3 overexpression as previously shown (FIG. 17A). Knockdown of ncald alone led to an enhanced branching of motor axons, whereas most importantly double knockdown of smn+ncald fully rescued the truncated motor axon defect associated with Smn deficiency (FIGS. 17A, 17C and 24A). The efficiency of the knockdown was confirmed by Western blot analysis (FIG. 17B). We also found that overexpression of human NCALD mRNA in zebrafish caused massive truncation and branching of motor axons (FIGS. 24B and 24C), resembling the phenotype of smn morphant zebrafish (FIG. 17A) and the effect seen inNSC34 cells.

Knockdown of ncald Restores NMJ Functionality of Zebrafish smn Morphants

Figure 17D:
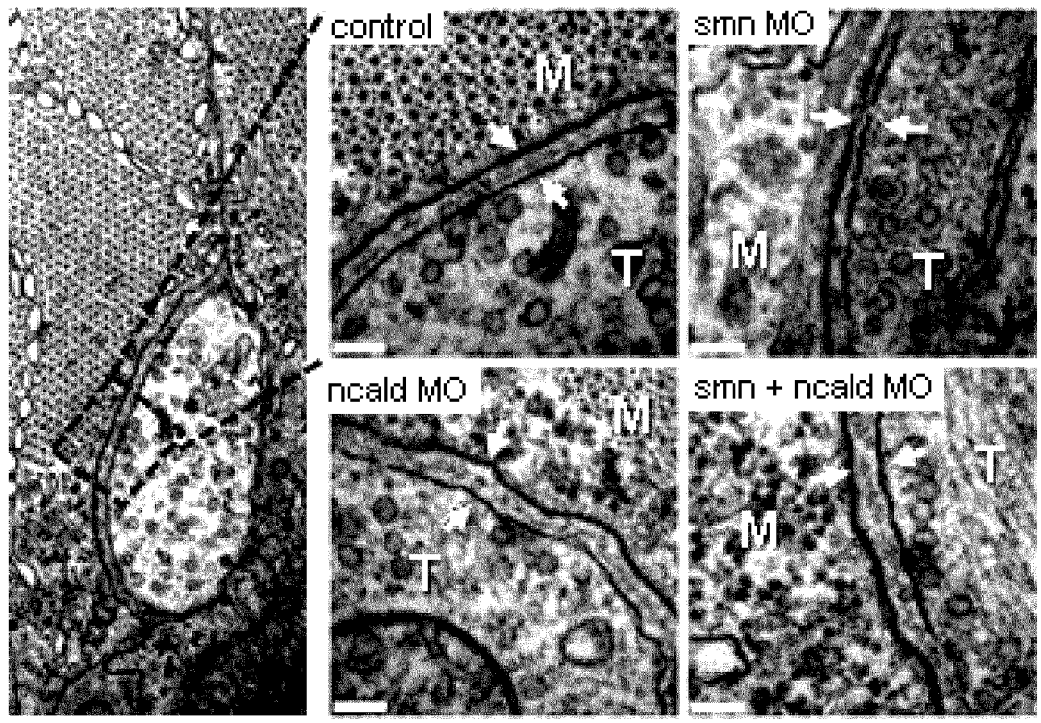
Figure 17E:
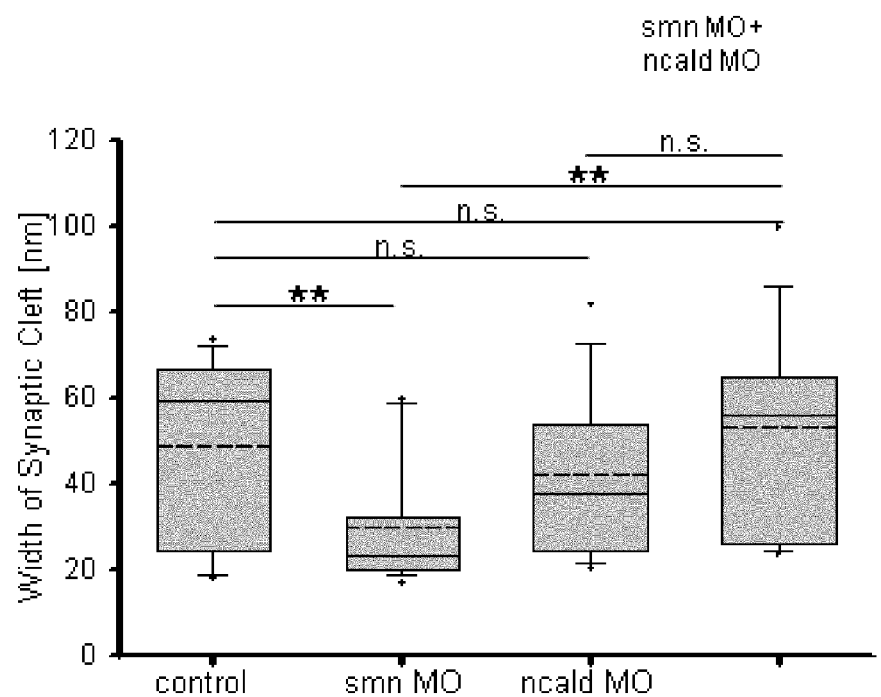

During maturation of NMJs in the zebrafish, the width of the synaptic cleft increases, which is essential in neurotransmission. TEM-based ultrastructural analysis of synaptic clefts of zebrafish NMJs in 34 hpf old zebrafish embryos revealed a delayed maturation of NMJs in smn morphants (FIG. 17D-E). The neuromuscular synaptic cleft of smn morphants is significantly smaller than in control fish or ncald morphants. Double knockdown of smn and ncald significantly restored synaptic maturation, resulting in a cleft width similar to controls (FIG. 17D). These NMJ changes also had profound implications on motor ability.

Figure 17G:
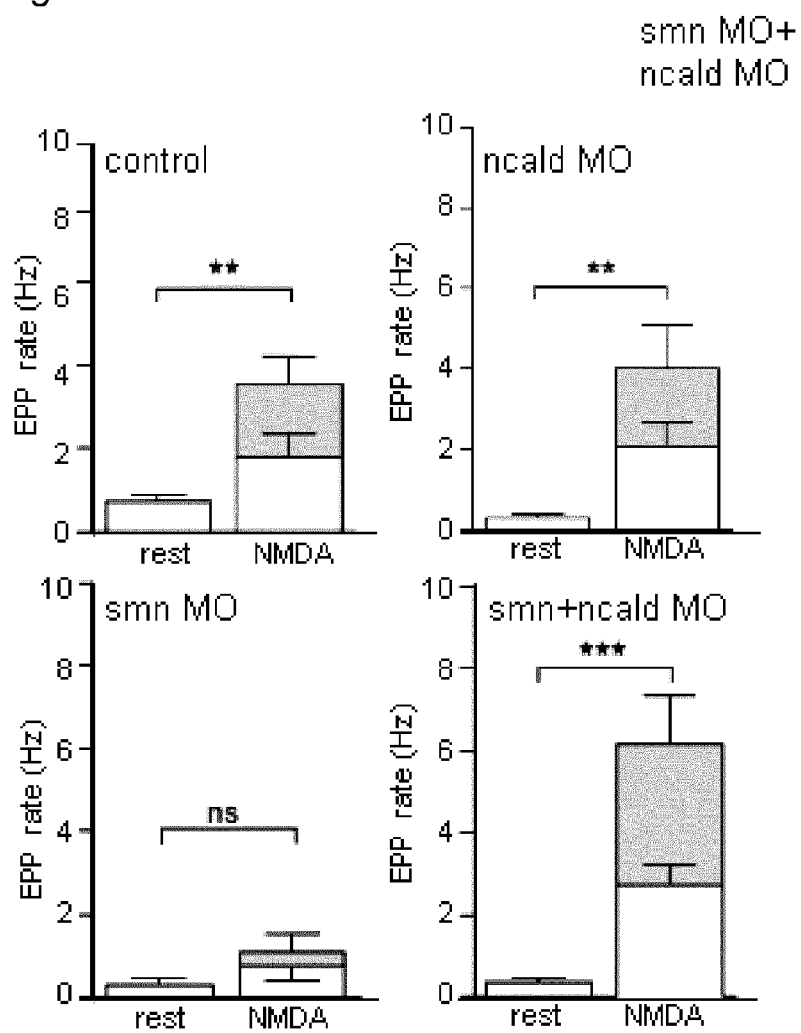

To test the functionality of neuromuscular synapses between caudal primary MN and ventral fast muscle cells we performed whole-cell patch clamp recordings in current clamp mode from muscle cells during motor neuron stimulation in wild types and smn, ncald and smn+ncald morphants. One muscle cell per animal was recorded between the $1^{st}$ and $10^{th}$ myotome counted from the end of the yolk (FIG. 17F). The experiments were performed in two steps. First, we recorded spontaneous endplate potentials at rest (without stimulation) and, second, we recorded endplate potentials during the stimulation of the MN by NMDA. In the wild-type zebrafish we recorded at rest small endplate potentials (0.75±0.16 Hz, n=12) that were mostly not tetrodotoxin (TTX) sensitive (FIGS. 25D and 25E) and most resembled miniature endplate potentials (mEPPs). During NMDA stimulation, the mEPP frequency did not significantly increase, but we additionally observed large TTX sensitive endplate potentials and muscle action potentials that were induced by MN spike evoked transmission (1.6±0.37 Hz; n=12). In the smn morphants we found a significantly lower spontaneous mEPP frequency (0.32±0.16 Hz; n=10; p<0.025, compared to wt) and during NMDA stimulation we observed only occasional action potentials (0.37±0.17 Hz; n=10; p<0.05, compared to wt). In the smn+ncald morphants the spontaneous mEPP frequency (0.38±0.11 Hz; n=12; p<0.05, compared to wt) was slightly increased and the frequency of large NMDA-induced EPP (3.46±1.02 Hz; n=12; p<0.05, compared to wt) was restored to wild-type levels (FIGS. 17F and 17G). The resting and NMDA induced electrical EPP activity in the ncald morphants did not differ from wild-type controls (FIGS. 17F and 3G). In line with these electrophysiological data, swimming velocity after electrical stimulation was reduced in smn morphants, but rescued in smn+ncald morphants (FIG. 25B). Together, these results show that a reduction of Ncald levels rescues neural circuit function at NMJs of smn morphants.

Figure 18A:
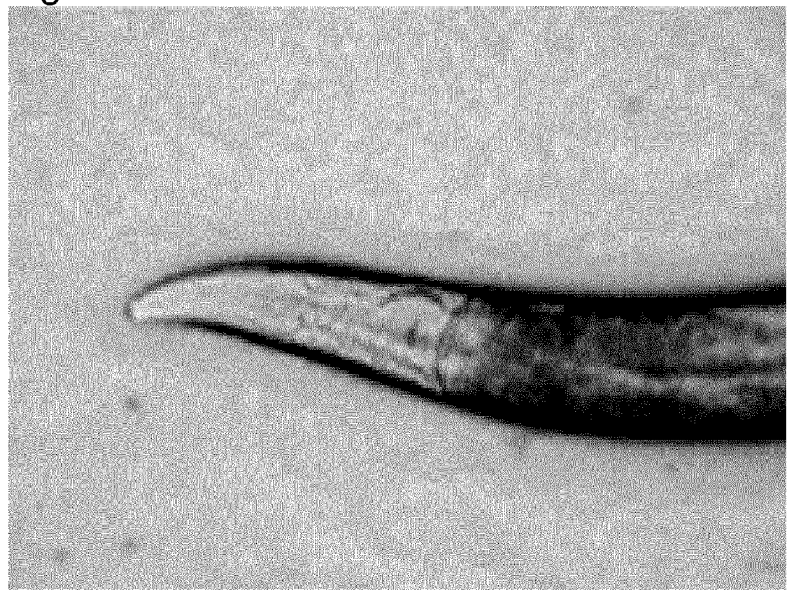
Figure 19A:
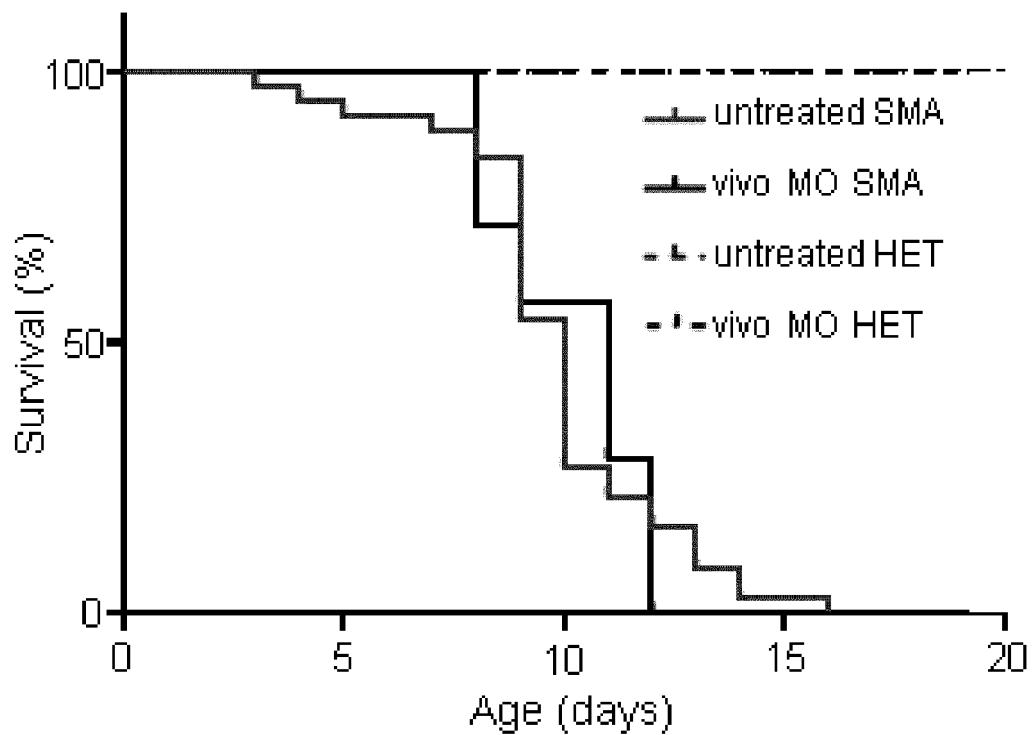

NCALD Depletion or PLS3 Overexpression Counteract the SMA Phenotype in *C elegans* and Ameliorate SMN Loss of Function Defects Previously, we have shown that *C elegans* lacking the SMN ortholog smn-1, referred to here as Cesmn-1, display pharyngeal pumping defects: this neuromuscular defect is exacerbated by loss of the *C elegans* PLS3 ortholog (FIG. 19A). Here, we tested the impact of NCALD ortholog loss-of-function or human PLS3 overexpression in the *C elegans* SMA model. The *C elegans* ortholog of NCALD is encoded by neuronal calcium sensor-1 (ncs-1). ncs-1 knockdown by RNA interference (RNAi) or introduction of the ncs-1(qa401) loss of function allele significantly ameliorated the pumping defects of Cesmn-1 animals (FIGS. 18B and 18C, p=0.01 and 0.004, respectively). Furthermore, overexpression of human PLS3 also ameliorated the pharyngeal pumping defects of Cesmn-1 animals (FIG. 18D, p=0.01). These results confirm that NCALD and PLS3 are cross-species modifiers of the SMN loss-of-function-induced neuromuscular defects.

Ncald Downregulation Ameliorates Motoric Phenotype in SMA Mice

Figure 19B:
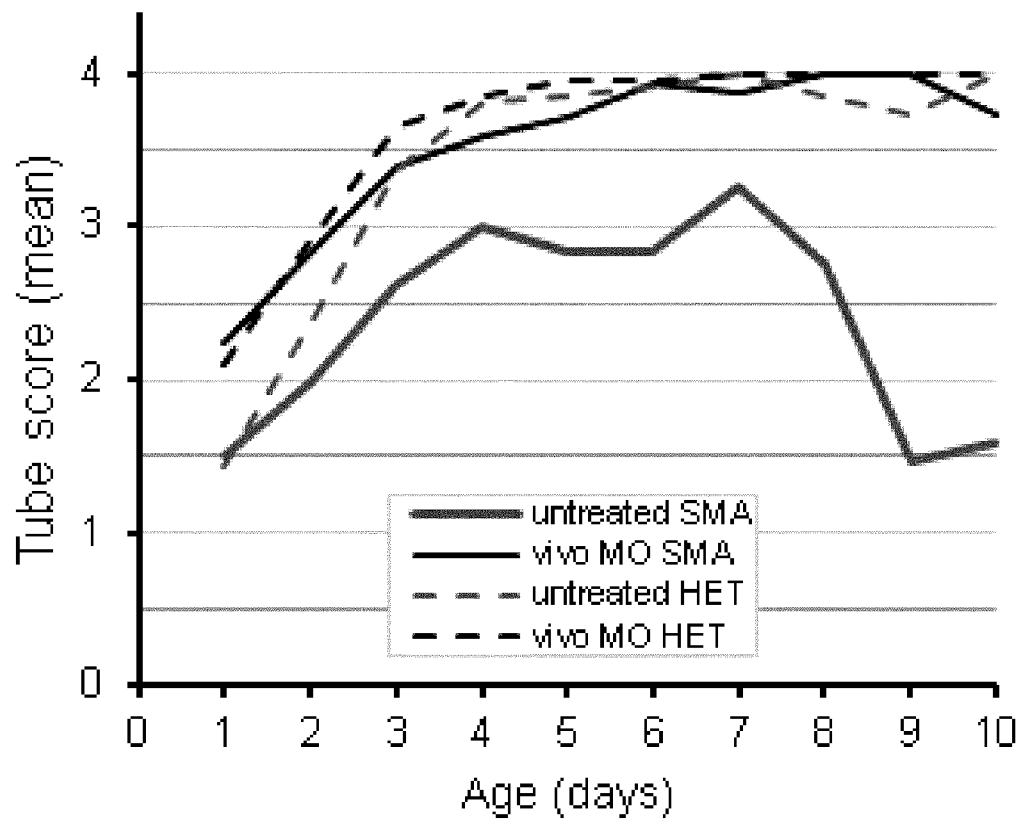
Figure 19C:
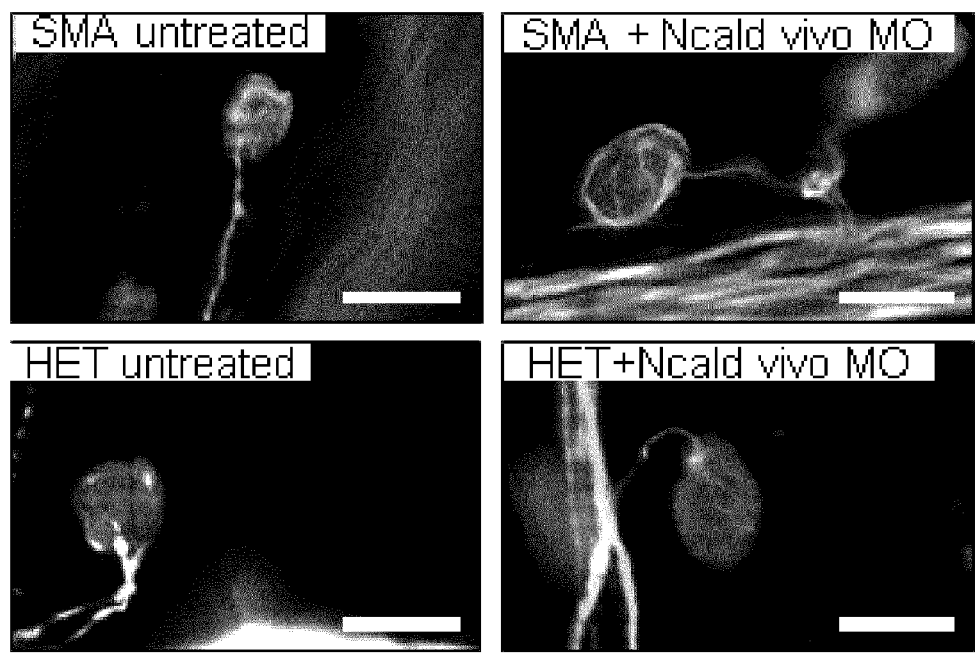
Figure 19D:
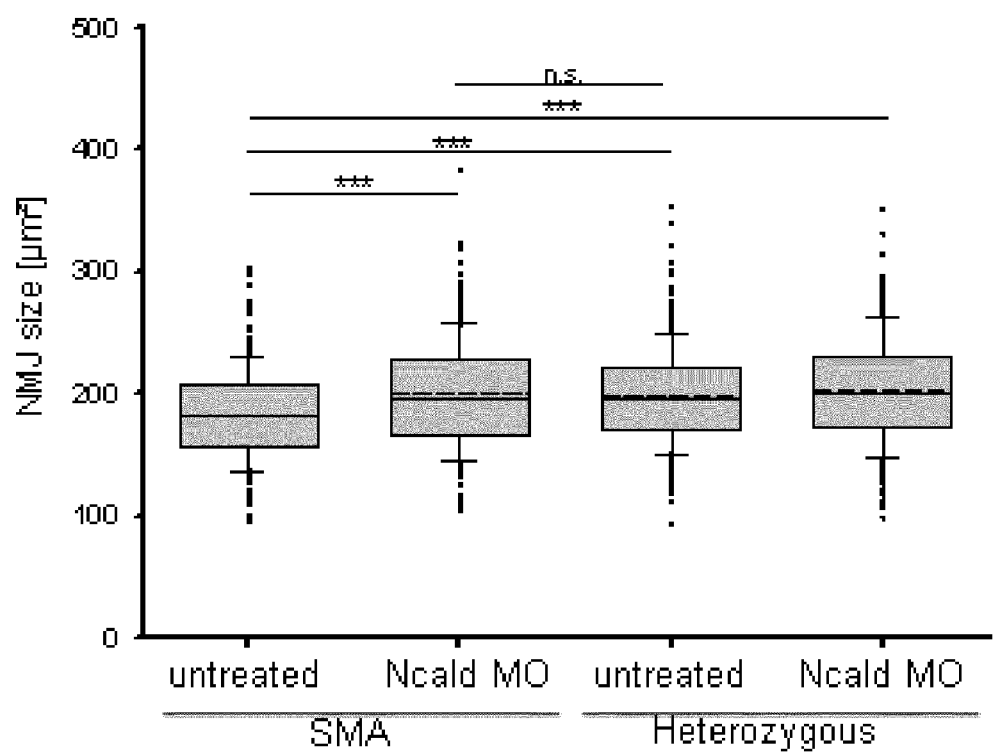
Figure 19E:
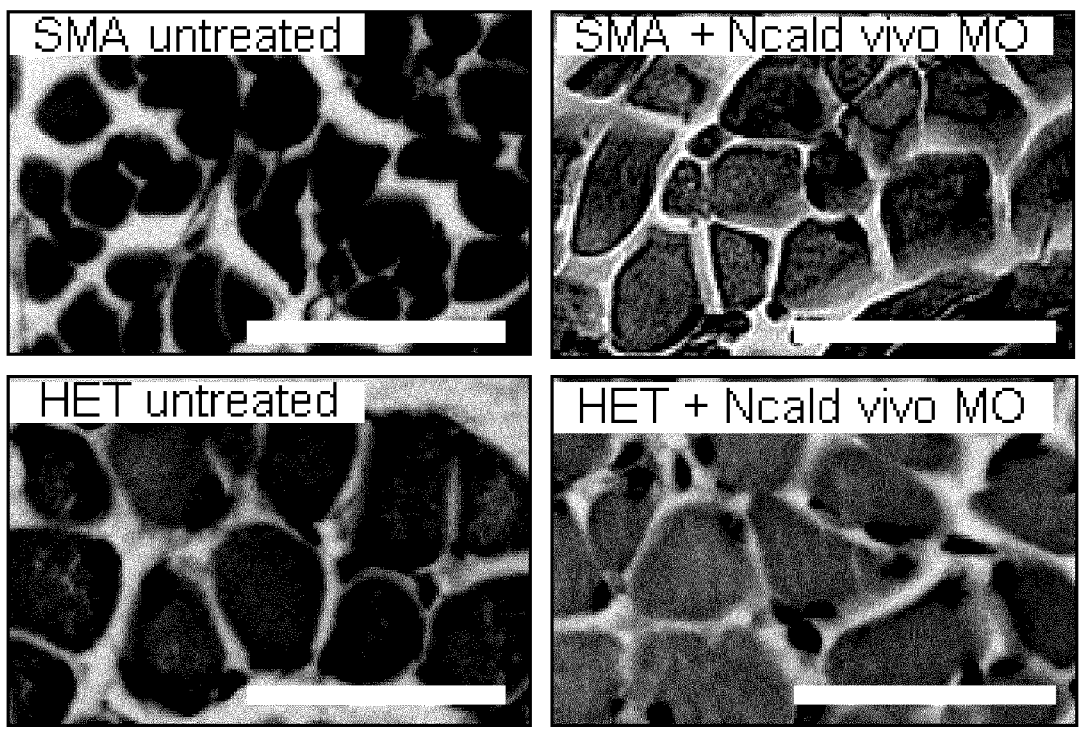
Figure 19F:
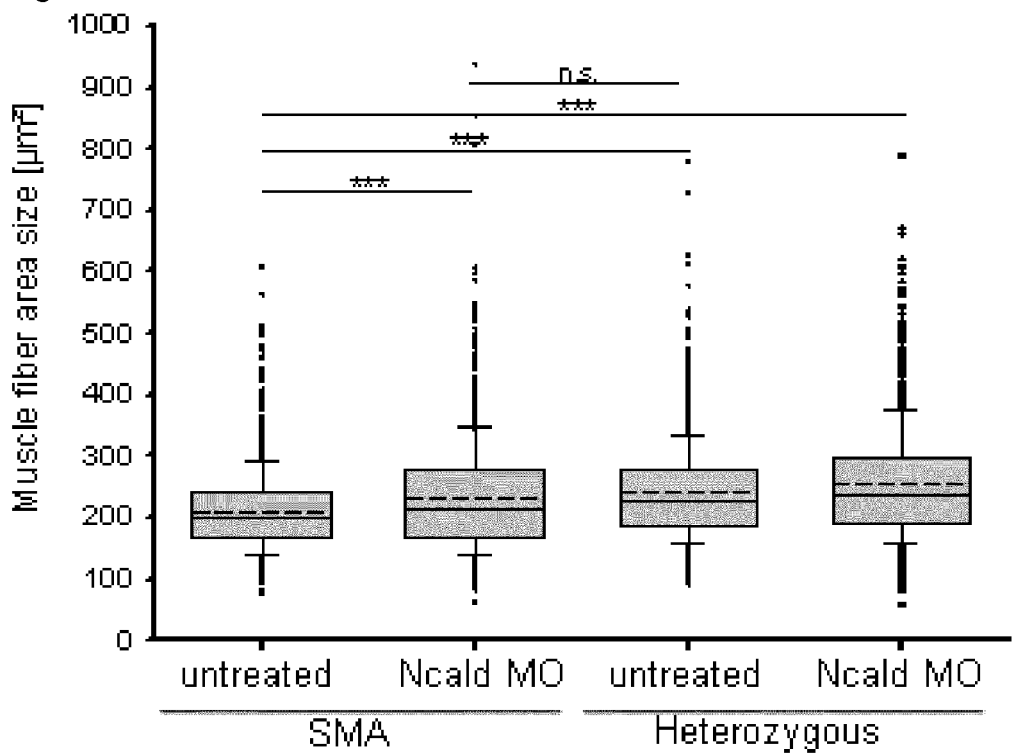
Figure 26A:
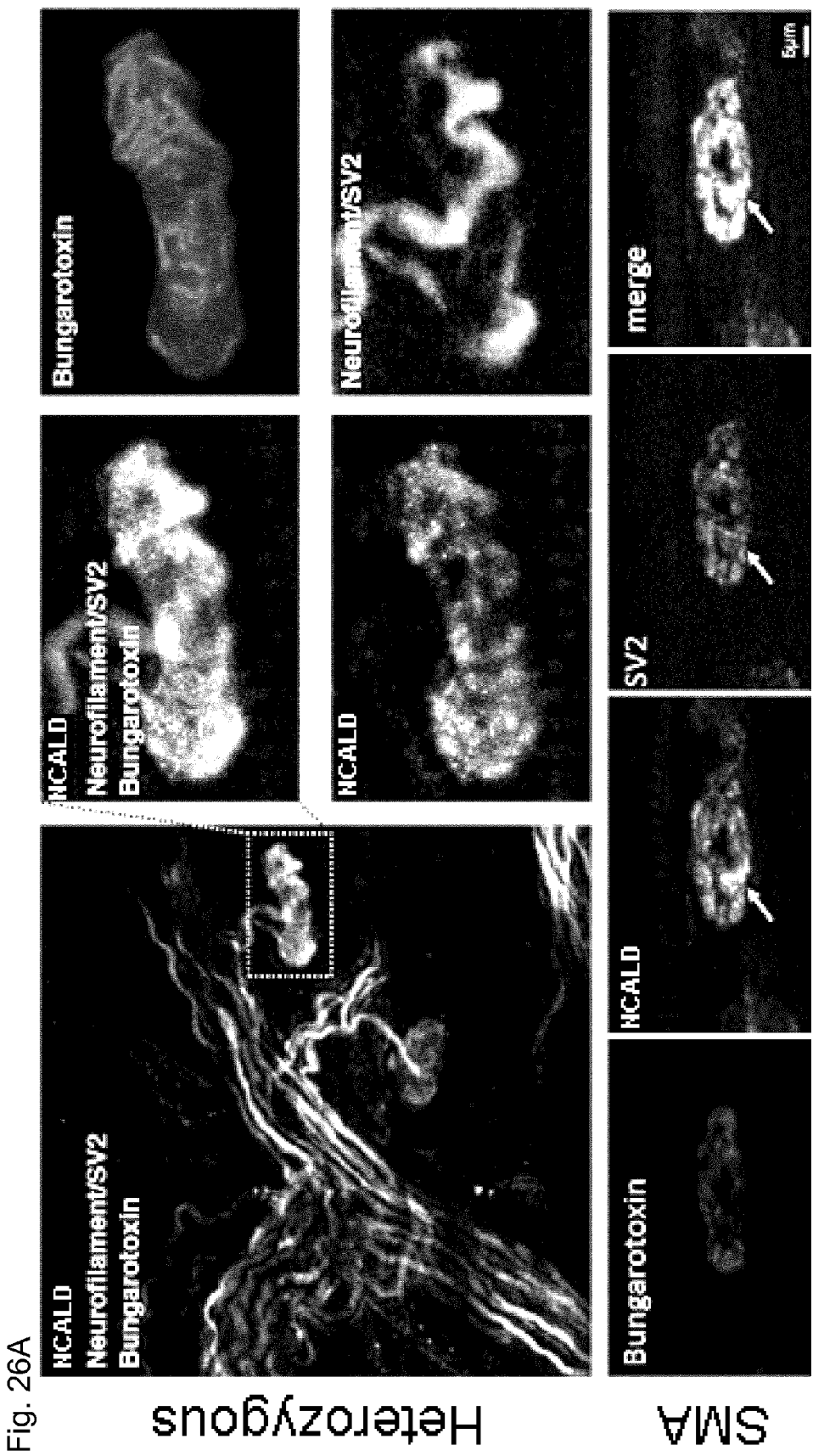
Figure 26B:
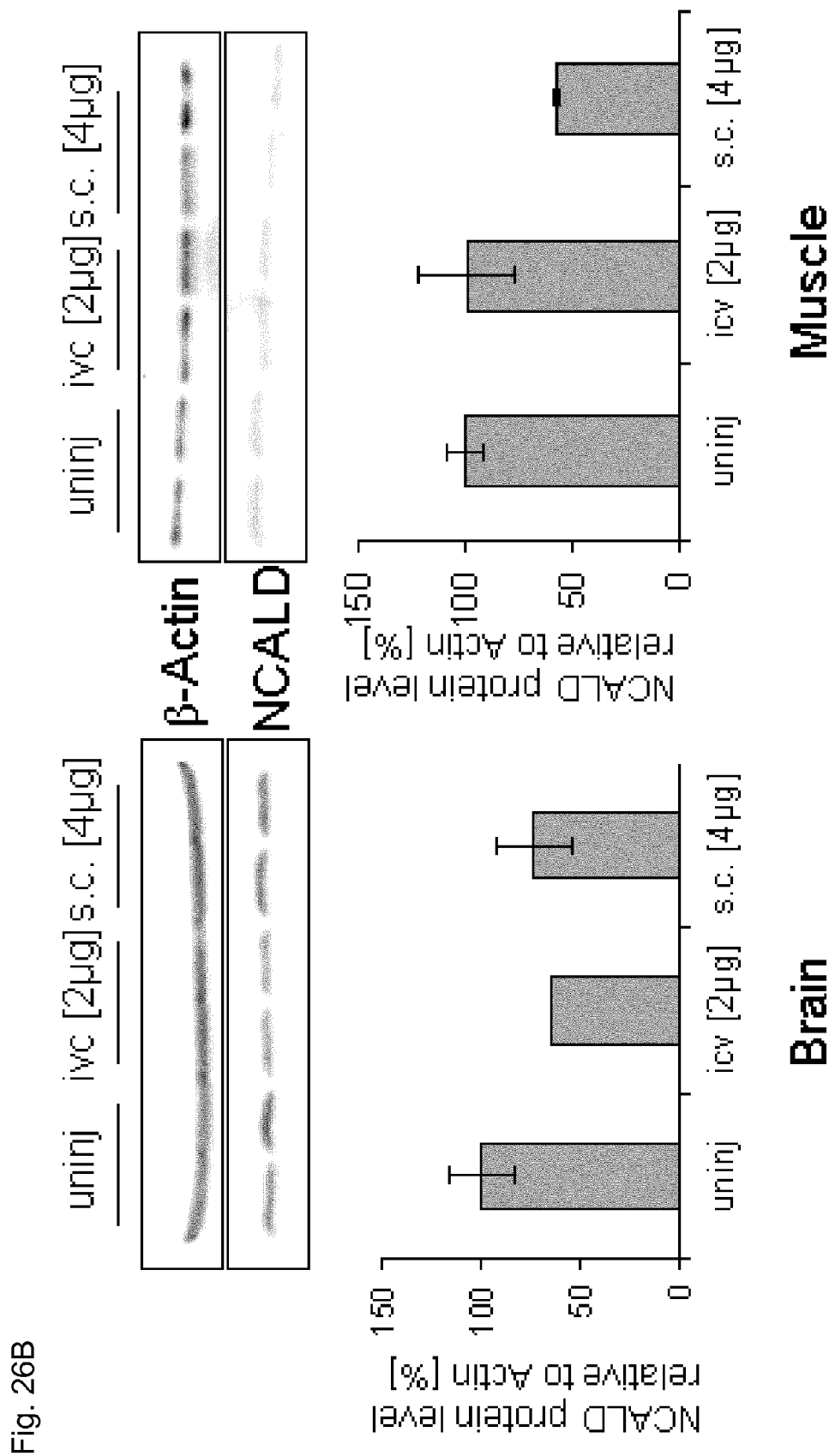
Figure 26C:
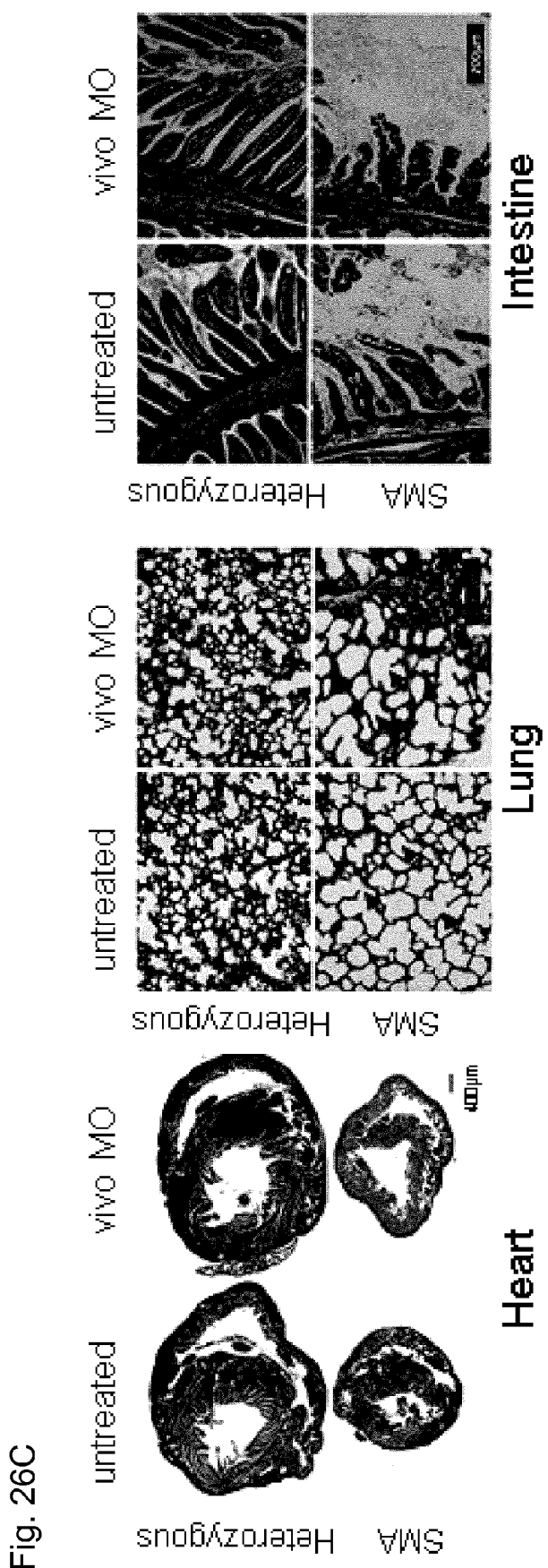

Since maturation, maintenance and function of NMJs are severely impaired in SMA mice, we first analyzed the expression of NCALD in NMJs. NCALD was clearly expressed at the presynaptic site and partly overlapped in localization with SV2, a presynaptic maker (FIG. 26A). To test whether downregulation of Ncald improves the SMA phenotype in a severe mouse model for SMA, vivo MOs against Ncald were injected (s.c.). As previously shown, splice correction antisense oligonucleotides against SMN2 (Hua et al., 2011) act efficiently when injected subcutaneously after birth (P2/3) before the blood brain barrier is fully developed (FIG. 26B). We injected vivo MO at postnatal day 1 (2 mg/kg) and continued with injections every other day. The mean survival was not improved (mean survival: 10 days in control and in MO-treated mice (p=0.78)) (FIG. 19A). However, the motor ability of the Ncald-downregulated mice was significantly improved to the level of heterozygous littermates as shown by a neonate motor test, the tube test (FIG. 19B). Since we observed increased axonal outgrowth in cultured primary MN and improved NMJ maturation and functionality in zebrafish, we investigated the NMJs of SMA mice treated with Ncald vivo MO. The NMJ size in TVA muscles of 10-day-old mice is reduced in SMA mice ($Smn^{ko/ko}$; $SMN2^{tg/0}$ compared to control littermates (heterozygous mice $Smn^{wt/ko}$; $SMN2^{tg0}$, which was restored to control levels by Ncald downregulation, indicating a protective effect on NMJ development (FIGS. 19C and 19D). This positive impact on NMJ level turned into a significant increase in muscle fiber size in the quadriceps femoris muscle (FIGS. 19E and 19F) and in improved motor abilities (FIG. 19B). However, despite improved motor function abilities, reduced NCALD levels in neuronal tissues could not improve survival of this severe SMA mouse model, due to severe organ impairment of lung, intestine and heart (FIG. 26C). which is in agreement with previous observation related to severe SMA mouse models. In conclusion, the cellular mechanism by which NCALD protects MN function is specific to neurons and, since NCALD is very weakly or not expressed in these other organs, NCALD cannot be involved in the impaired cellular processes of these tissues.

Low SMN Levels Decrease $Ca^{2+}$ Influx in NSC34 and PC12 cells, which is not Restored by Reduced NCALD Levels.

Figure 20A:
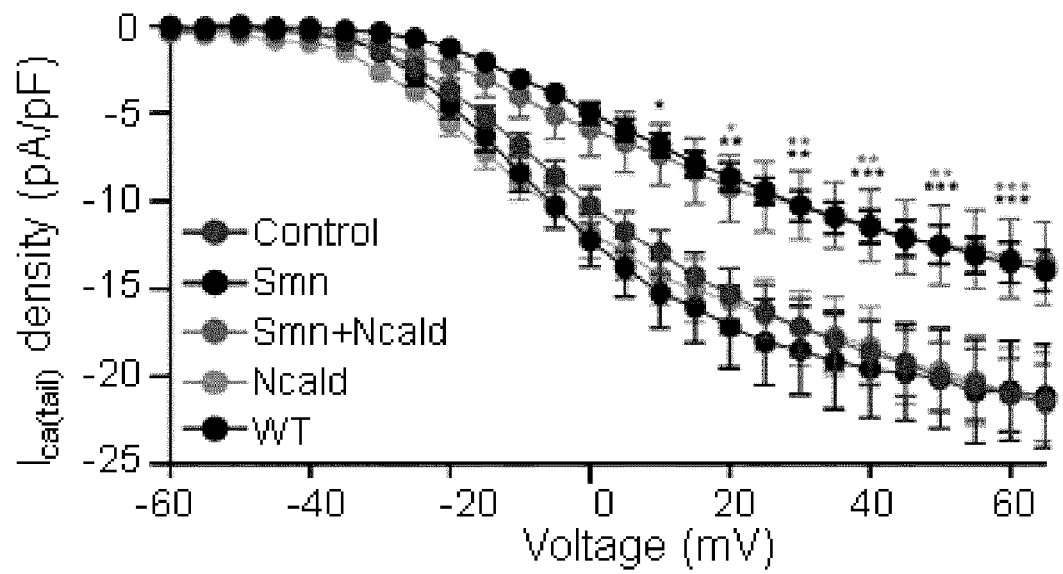

Since NCALD is a $Ca^{2+}$ sensor and impaired $Ca^{2+}$ homeostasis in SMA has been reported (Ruiz et at, 2010), we asked if low SMN levels modulate voltage-dependent $Ca^{2+}$ currents ($I_{Ca}$) in MN-like cells. We used whole-cell patch-clamp recordings and ratiometric $Ca^{2+}$ imaging with fura-2. In a first series of experiments, we recorded $I_{Ca}$ of RA-differentiated NSC34 cells untreated, treated with control (scrambled) RNA, Smn siRNA, Ncald siRNA, or Smn/Ncald siRNA and analyzed the tail currents, which are independent of the driving force during a series of varying voltage pulses. In NSC34 cells Smn downregulation significantly reduced the voltage dependent $Ca^{2+}$ influx, which could not be restored by additional Ncald reduction (FIG. 20A). In a second series of experiments, ratiometric $Ca^{2+}$ imaging with fura-2 also revealed a reduced voltage-dependent $Ca^{2+}$ influx (induced by KCl) in SMN-reduced PC12 cells compared to controls (FIG. 27B). These data show that low SMN levels impair $Ca^{2+}$ influx, which is not restored by NCALD knockdown and that NCALD rescues synaptic transmission in a different way.

Endocytosis and Synaptic Vesicle Recycling is Disturbed in SMA and Rescued by Downregulation of NCALD We next sought a common pathway impacted by both SMA modifiers. Since NCALD directly binds clathrin (Ivings et al., 2002) and PLS3 knockdown in yeast impairs endocytosis (Ivings et al., 2002; Kubler and Riezman, 1993), we hypothesized that low SMN levels may impair endocytosis, which in turn is rescued by NCALD suppression or PLS3 overexpression. Performing coimmunoprecipitation studies in NSC34 cells, we found that NCALD interacts with clathrin only in the absence of $Ca^{2+}$ (FIG. 20B) or at low $Ca^{2+}$ levels (data not shown), thus, only in unstimulated neurons. Furthermore, TEM analyses after immunogold staining of ultrathin sections of wild-type zebrafish embryos revealed colocalization of Ncald and clathrin in the presynaptic sites of NMJs (FIG. 20C).

To study the effect of SMN, PLS3 and NCALD on endocytosis, we applied FITC-dextran internalization assays in various cell culture systems. In primary fibroblast cell lines derived from SMA patients (n=10), endocytosis rates were strongly reduced compared to controls (n=3) (FIG. 20D), but highly restored in fibroblasts derived from asymptomatic individuals of the Utah family (n=5). Since human fibroblasts derived from SMA discordant families overexpressing PLS3 in LBs do not overexpress PLS3 in fibroblasts, we used murine embryonic fibroblasts lines (MEFs) from SMA embryos ubiquitously overexpressing a PLS3 transgene. Compared to SMA, SMA-PLS3 MEFs markedly restored endocytosis (FIG. 20F).

In addition, Smn knockdown in NSC34 neurons led to significantly reduced FITC-dextran uptake, which was rescued by concomitant downregulation of Ncald. Strikingly, Ncald downregulation alone increased the rate of endocytosis by 1.3-fold, demonstrating that low NCALD levels already facilitate endocytosis (FIGS. 20E and 27F), in line with the SMA-opposing phenotypes obtained upon single ncald knockdown in zebrafish (FIGS. 17A, 17F and 17G).

Finally, to investigate whether endocytosis and the found Smn-Ncald-clathrin network is also relevant for SMA in vivo, we returned to the zebrafish system, applying pharmacological inhibition of endocytosis. Treatment of zebrafish with subphenotypical concentrations of smn MO (2 ng) in combination with Pitstop2, an inhibitor of clathrin, caused an synergistic effect resulting in significant elevation in the number of truncated motor axons (FIG. 20G), similar to the effect caused upon knockdown of smn with high smn MO dose (FIG. 18A,C). Also treatment with Dynasore, an inhibitor of the endocytosis-driving GTPase dynamin, resulted either alone or in combination with low smn MO in an SMA-like axonal truncations (FIG. 20G). However, additional treatment with ncald MO rescued either phenotype (FIG. 20G). Together, this suggests that SMN and clathrin interact genetically to promote endocytosis and MN axogenesis, whereas NCALD negatively interferes with the SMN-stimulated function of clathrin.

Discussion

Here, we describe a novel naturally occurring SMA modifier in human, NCALD. Reduced NCALD expression fully protects individuals from developing SMA despite lacking SMN1 and carrying only four SMN2 copies, which usually causes a type II or III SMA. Thus, unlike PLS3, which alleviates SMA pathology upon overexpression, reduced NCALD acts as genetic suppressor of SMA. Understanding these naturally unique protecting processes turned out to be a powerful tool to unravel the genuine molecular and cellular pathomechanisms of SMA and its dysfunction in axonal growth and neurotransmission. Neurotransmitter release is a fundamental, well conserved biological mechanism, which is important for function, survival and maintenance of neuronal circuits. For repeated release, subsequent endocytosis is important (Stevens, 2003). Endo- and exocytosis are regulated by the $Ca^{2+}$ dynamics within the presynaptic terminals (Sudhof, 2012).

In SMA impaired neurotransmission, disturbed $Ca^{2+}$ homeostasis, a decreased synaptic vesicle number and reduced F-actin caging surrounding the reserve pool of synaptic vesicles have been reported (Kariya et al., 2008; Kong et al., 2009; Murray et at., 2008; Ruiz et al., 2010). In NSC34 and PC12 cells, we found that low SMN levels cause clear reduction of $Ca^{2+}$ influx, which is in agreement with recently published measurements in SMA fish and mislocalization of calcium channels in SMA (Jablonka et al., 2007; See et al., 2014). However, in contrast to SMA pathology, $Ca^{2+}$ influx was not restored by reduced NCALD levels, suggesting that NCALD downregulation counteracts NMJ dysfunction by a different pathway. Since depletion of the PLS3 ortholog in yeast has been reported to dramatically impair endocytosis and NCALD binds clathrin and actin, two major components of endocytosis (Haucke et al., 2011; Ivings et al., 2002; Kubler and Riezman, 1993), we postulare that reduced SMN may disturb endocytosis, possibly due to the decreased $Ca^{2+}$ levels, whereas either NCALD knockdown or PLS3 overexpression can compensate for the SMN loss. Indeed, we demonstrated in 1) human and murine fibroblasts derived from SMA patients or SMA mice, and 2) NSC34 cells treated with Smn siRNAs that endocytosis was decreased in SMA and rescued by either NCALD knockdown or PLS3 overexpression. Furthermore, we demonstrated that in zebrafish chemical inhibition of endocytosis per se caused MN axogenesis defects as in SMA, that it did so in a tight genetic interaction with SMA, and that the latter effect could be reversed upon concomitant loss of Ncald (FIG. 20G).

Figure 20B:
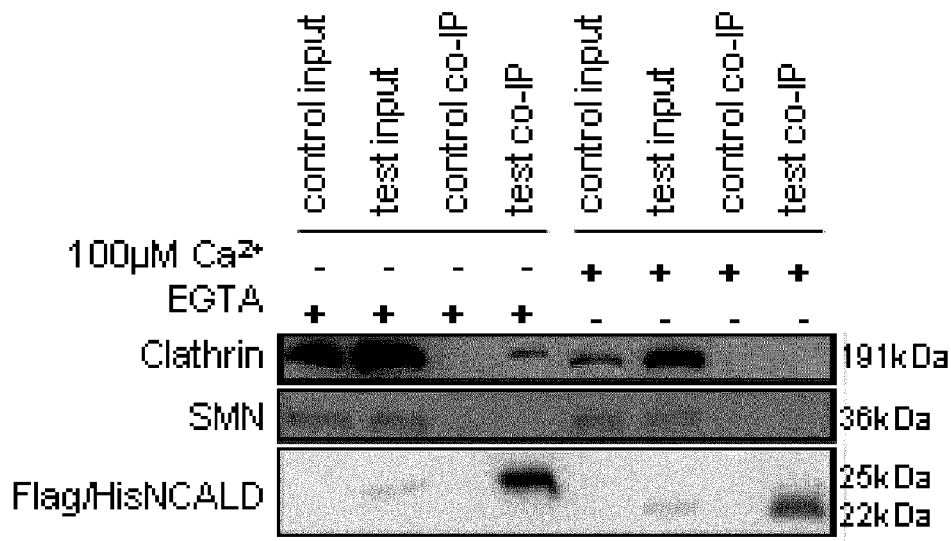
Figure 20C:
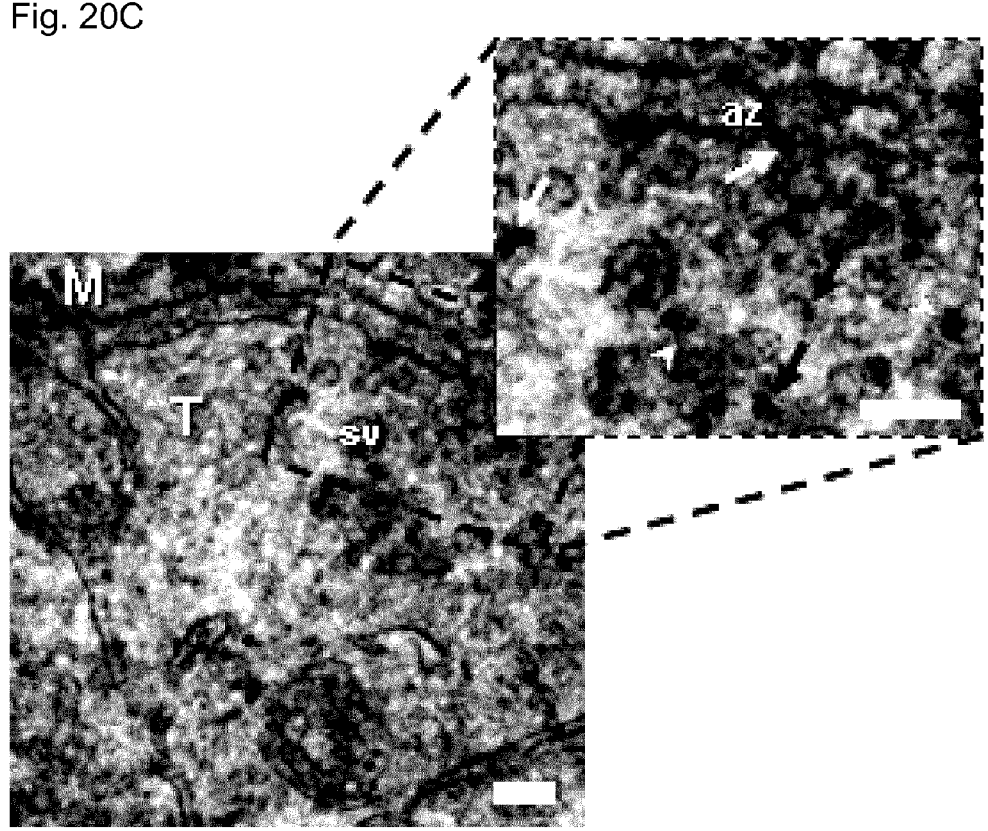
Figure 20D:
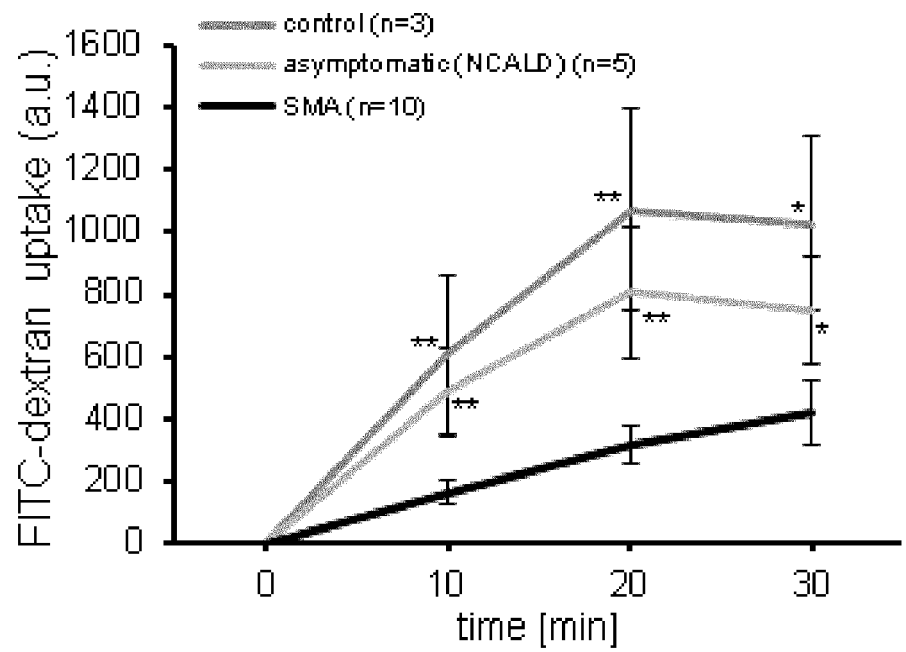
Figure 20E:
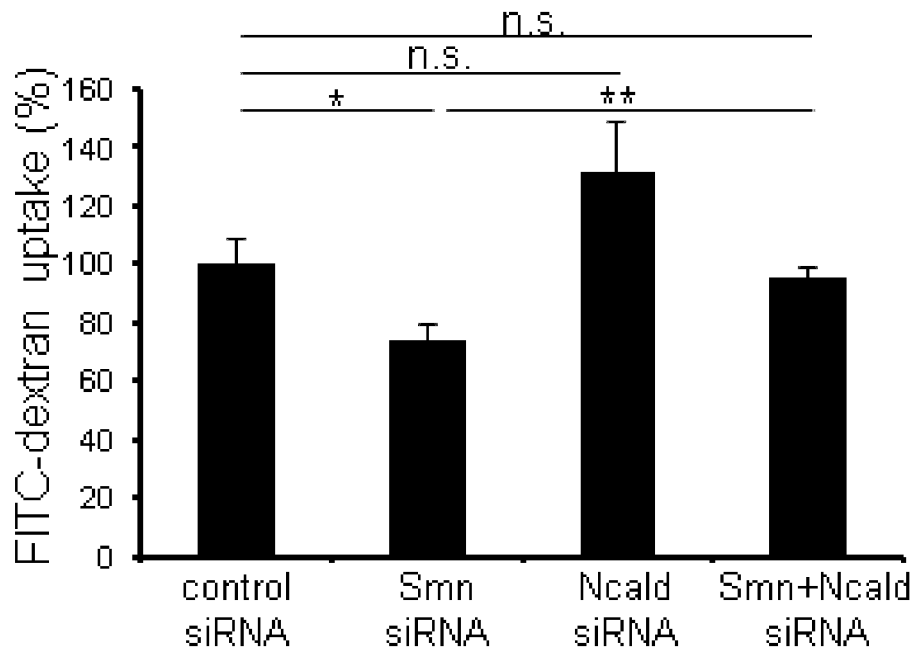
Figure 20F:
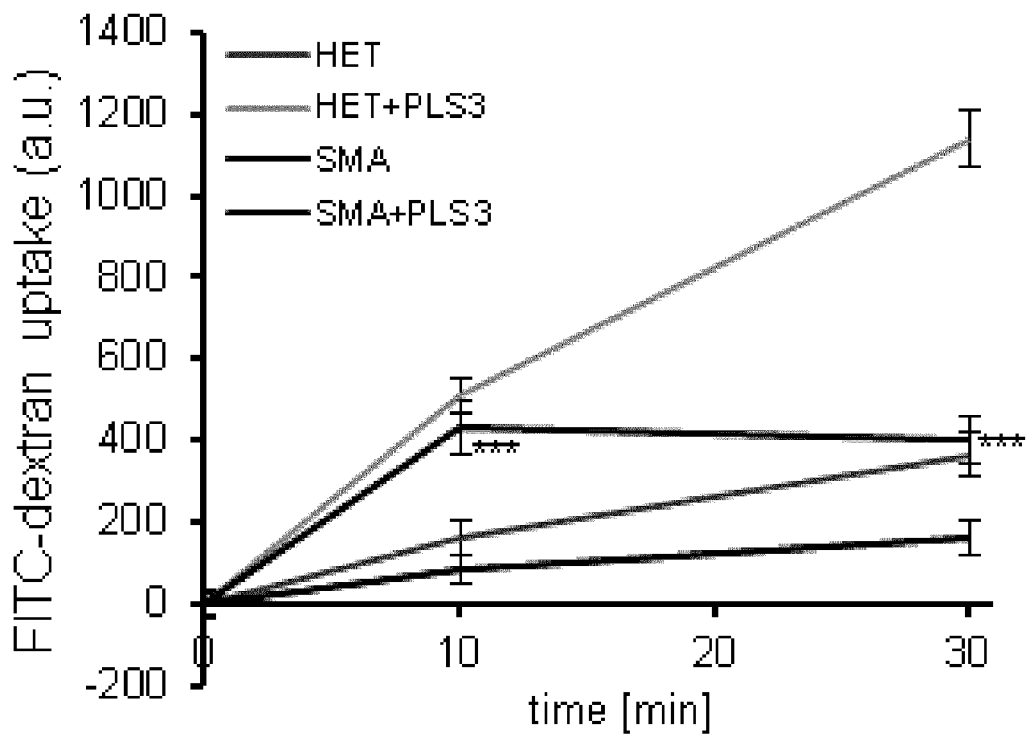

Importantly, we also found that NCALD binds clathrin only at low $Ca^{2+}$ levels, as present in un-stimulated wild-type MN, but not at high $Ca^{2+}$ levels, as present during action potentials in MN terminals (FIG. 20B). For SMA MN, with low $Ca^{2+}$ levels even during action potentials, we predict that NCALD constantly binds clathrin, thereby inhibiting its function in endocytosis. However, low NCALD levels, as present in asymptomatic individuals, allow free clathrin to be used in endocytosis even when $Ca^{2+}$ levels remain reduced (FIG. 21).

Along the same lines, the protective effect of PLS3 overexpression can be explained. F-actin is crucial in the initial steps of endocytosis but also in synaptic vesicle recycling (Haucke et al., 2011). Loss of PLS3 impairs endocytosis in yeast (Kubler and Riezman, 1993) and in NSC34 cells (own results in the lab). Therefore, overexpression of PLS3, which facilitates F-actin bundling (Oprea et al., 2008), may enhance endocytosis and counteract impaired endocytosis found in SMA.

Intriguingly, impaired endocytosis might underlie the different aspects of the SMA phenotype, including axonal outgrowth and NMJ maturation in addition to presynaptic functionality. Thus, in addition to neurotransmitter recycling in presynaptic terminals (Sudhof, 2012), endocytosis-driven internalization of membrane and proteins at the leading edge of the growth cone is crucial for axonal outgrowth and branching, possibly underlying the MN axogenesis defects in SMA zebrafish. Since endocytosis is crucial in every cell, its dysfunction may also explain the defects of the other organs affected in SMA. Most importantly, we found that NCALD knockdown rescues or ameliorates the SMA pathology not only in humans but also in three different animal models, suggesting a common pathway across species.

In agreement with this concept, two other proteins connected to endocytosis cause various forms of SMA. Mutations in UBA-1, an E1 Ubiquitin-Activating Enzyme involved in monoubiquitination serving as signal for endocytosis and trafficking of cell surface proteins, has been associated to X-linked SMA. BICD2, which causes dominant SMA when mutated, binds to clathrin heavy chain to promote its transport and augments synaptic vesicle recycling. These findings provide additional evidence that disturbances in synaptic vesicle recycling are underlying SMA pathology in general. Our findings are further strongly supported by data in *C elegans* in which two of our collaborators providing evidence for disturbed endocytotic trafficking at synaptic level and for increased resistance against infections in SMA which may explain the high carrier frequency in the population of 1:35.

Ideally, we would like to identify the proteins whose impaired function disturbed $Ca^{2+}$ influx in SMA and decreased endocytosis. So far, a large number of differential expression analyses on transcriptome and/or proteome levels including synaptosomes, spinal cord, brain and muscle in various SMA animal models have been carried out. Each of the analyses led to the identification of hundreds of up- or downregulated transcripts or proteins, whose importance in the etiology of SMA is difficult to dissect. In contrast, NCALD and PLS3, although per se not altered in SMA, rescue the SMA phenotype in humans and across various animal models upon SMN-independent activity alterations. These findings, together with the identification of endocytosis as a crucial process affected in SMA, will hopefully facilitate the identification of the relevant direct SMN targets, which are likely to interfere, in one of the other way, with PLS3,NCALD and/or endocytosis.

Our findings are further strongly supported by data in *C elegans* in which two of our collaborators providing evidence for disturbed endocytotic trafficking at synaptic level and for increased resistance against infections in SMA which may explain the high carrier frequency in the population of 1:35.

To summarize, NCALD is a novel protective SMA modifier that together with PLS3 allowed identifying endocytosis as a crucially affected process in SMA. This may open new avenues for SMA therapy in addition to SMN upregulation or SMN replacement therapies. Moreover, reduced NCALD levels might even be beneficial for other motor neuron and neurodegenerative disorders with impaired F-actin dynamics and $Ca^{2+}$-homeostasis as recently shown for Alzheimer disease, where NCALD is highly upregulated (Suszynska-Zajczyk et al., 2014).

Experimental Procedures

The experimental proceedings are laid out in more detail in the section Extended Experimental Procedures (Supplemental Information) below.

Patient DNA, Fibroblast Cell Lines and Lymphoblastoid Cell Lines

Informed written consent was obtained from each subject or their legal guardians for all biological samples according to the Declaration of Helsinki. The study was approved by the Ethical Committee of the University of Cologne (04-138). Clinical information and patient cohort is given in the Supplemental Information.

Genotype Analysis, Transcriptome Analysis, Whole Linkage Analysis, Targeted Re-Sequencing All molecular genetic analyses are described in detail in the Supplemental Information.

Animal Models

All zebrafish experiments were performed with the transgenic line tg(mnx1-GFP)$^{m12TG}$, approved by the local animal protection committee (LANUV NRW; reference number 84-02.04.2012A251). All *C. elegans* experiments are described in the Supplementary Information. All mouse experiments were approved by LANUV NRW (reference number 9.93.2.10.31.07.186). SMA mice were obtained from Jackson's Laboratory (FVB.Cg-Tg(SMN2)2Hung Smn1tm1Hung/J, Stock Number: 005058).

Primary Neuronal Cultures

Primary MN were isolated from embryonic day 15 (E15) SMA and heterozygous (control) mice and transfection was performed one day after seeding. Motor axon length was measured in DIV8 (days in vitro).

Voltage-Dependent $Ca^{2+}$ Influx

In differentiated NSC34 cells $Ca^{2+}$ currents were measured using whole cell patch clamp recordings, while $Ca^{2+}$ influx into differentiated PC12 cells was measured using ratiometric $Ca^{2+}$ imaging with fura-2.

Zebrafish Electrophysiology

Experiments were conducted with decapitated 72 hpf zebrafish embryos. To characterize the motor axon-muscle connectivity, the endplate potentials of single muscle cells were measured by whole cell patch clamp recordings, before and during motor neuron stimulation with NMDA.

Immunogold and Ultrastructural Analysis Using Transmission Election Microscopy in the Zebrafish 48 hpf zebrafish larvae were fixed in 4% PFA for 30 min and postfixed in 0.6% glutaraldehyde for another day. Gold-labeled secondary antibodies were used for co-localization studies of Ncald and Clathrin. Image acquisition of ultra-thin sections with a thickness of 0.1 mm was performed using the TEM CM10 (Philips) microscope with the Orius SC200W 1 Gatan camera and the Digital Micrograph software.

Immunoblot and Immunostaining

Fluorescence-based immunostainings and Western blots were performed in primary cells (fibroblasts, motor or hippocampal neurons), canines (NSC34, PC12), zebrafish (znp1 staining, to visualize motor axons) and in mouse TVAs for NMJs. For detailed protocols and information about antibodies see Supplemental Information.

Downregulation of Gene Expression

In vitro and in vivo knockdown was performed in multiple cells (primary neuronal cells, neuronal cell lines) and species (*C. elegans*, zebrafish and mouse) using siRNA, RNAi and antisense oligonucleotides see Supplemental Information.

Endocytosis Assays

To unravel differences in endocytosis performance, cells (fibroblasts and NSC34) were starved and subsequently incubated with FITC-dextran. FITC-uptake after respective incubation times was quantified either by microscopic analysis or by FACS.

The in vivo effect of inhibition of endocytosis on MN outgrowth was investigated by the use of the pharmacological inhibitors Pitstop2 and Dynasore (both Abcam) in the SMA zebrafish model. Motor axons of treated zebrafish larvae were analyzed by fluorescence microscopy.

Statistics

If not mentioned otherwise, all statistical analyses were performed by use of the software programs Excel 2013 (Microsoft), GraphPad Prism (GraphPad Software) and Sigma Plot 11 (Systat Software) and ANOVA Mann-Whitney U-test, Fisher's exact test or unpaired Student's t-tests were used All data are represented as mean±SEM.

Database

The microarray data are stored at GEO under the reference number . . . (will be provided, as soon as available).

References

Additional references not included in Example 1

Ackermann, B., Krober, S., Torres-Benito, L., Borgmann, A., Peters, M., Hosseini Barkooie, S. M., Tejero, R., Jakubik, M., Schreml, J., Milbradt, J., et al. (2013). Plastin 3 ameliorates spinal muscular atrophy via delayed axon pruning and improves neuromuscular junction functionality. Hum Mol Genet 22, 1328-1347.

Di Sole, F., Vadnagara, K., Moe, O. W., and Babich, V. (2012). Calcineurin homologous protein: a multifunctional Ca2+-binding protein family. Am J Physiol Renal Physiol 303, F165-179.

Hao le, T., Wolman, M., Granato, M., and Beattie, C. E. (2012). Survival motor neuron affects plastin 3 protein levels leading to motor defects. J Neurosci 32, 5074-5084.

Haucke, V., Neher, E., and Sigrist, S. J. (2011). Protein scaffolds in the coupling of synaptic exocytosis and endocytosis. Nat RevNeurosci 12,127-138.

Hidaka, H., and Okazaki, K (1993). Neurocalcin family. a novel calcium-binding protein abundant in bovine central nervous system. Neurosci Res 16, 73-77.

Iino, S., Kobayashi, S., and Hidaka, H. (1998). Neurocalcin-immunopositive nerve terminals in the muscle spindle, Golgi tendon organ and motor endplate. Brain Res 808, 294-299.

Ivings, L., Pennington, S. R, Jenkins, R, Weiss, J. L., and Burgoyne, R. D. (2002). Identification of Ca2+-dependent binding partners for the neuronal calcium sensor protein neurocalcin delta: interaction with actin, clathrin and tubulin. Biochem J 363, 599-608.

Jablonka, S., Beck, M., Lechner, B. D., Mayer, C., and Sendiner, M. (2007). Defective Ca2+ channel clustering in axon terminals disturbs excitability in motoneurons in spinal muscular atrophy. J Cell Biol179, 139-149.

Kariya, S., Park, G. H., Maeno-Hikichi, Y., Leykekhman, O., Lutz, C., Arkovitz, M. S., Landmesser, L. T., and Monani, U. R (2008). Reduced SMN protein impairs maturation of the neuromuscular junctions in mouse models of spinal muscular atrophy. Hum Mol Genet 17, 2552-2569.

Kong, L., Wang, X., Choe, D. W., Polley, M., Burnett, B. G., Bosch-Marce, M., Griffin, J. W., Rich, M. M., and Sumner, C. J. (2009). Impaired synaptic vesicle release and immaturity of neuromuscular junctions in spinal muscular atrophy mice. J Neurosci 29, 842-851.

Kubler, E., and Riezman, H. (1993). Actin and fimbrin are required for the internalization step of endocytosis in yeast. Embo J 12, 2855-2862.

Ruiz, R., Casanas, J. J., Torres-Benito, L., Cano, R, and Tabares, L. (2010). Altered intracellular Ca2+ homeostasis in nerve terminals of severe spinal muscular atrophy mice. J Neurosci 30, 849-857.

Stevens, C. F. (2003). Neurotransmitter release at central synapses. Neuron 40, 381-388.

Sudhof, T. C. (2012). Calcium control of neurotransmitter release. Cold Spring Harb Perspect Biol 4, a011353.

Suszynska-Zajczyk, J., Luczak, M., Marczak, L., and Jakubowski, H. (2014). Hyperhomocysteinemia and Bleomycin Hydrolase Modulate the Expression of Mouse Brain Proteins Involved in Neurodegeneration. J Alzheimers Dis.

Venkataraman, V., Duda, T., Ravichandran, S., and Sharma, R. K. (2008). Neurocalcin delta modulation of ROS-GC1, a new model of Ca(2+) signaling. Biochemistry 47, 6590-6601.

Yamatani, H., Kawasaki, T., Mita, S., Inagaki, N., and Hirata, T. (2010). Proteomics analysis of the temporal changes in axonal proteins during maturation. Dev Neurobiol 70, 523-537.

Extended Experimental Procedures (Supplemental Information)

Clinical Investigation of SMA Patients and Asymptomatic Family Members of the Utah Family Informed written consent (or parental consent and assent where appropriate) was obtained from all participating family members under University of Utah Institutional Review Board Protocol #8751 entitled Clinical and Genetics Studies in Spinal Muscular Atrophy. DNA was extracted from whole blood samples using routine protocols in all subjects; skin biopsies for fibroblast cultures were performed on a subset of individuals. All individuals with homozygous SMN deletion agreed to participate in additional detailed clinical investigations, including a fit physical and neurological examination, electrophysiologic investigations inclusive of maximum ulnar compound muscle action potential amplitudes (CMAP) and motor unit number estimation to assess peripheral motor nerve function (using Vikingquest electromyography system, Natus and previously published protocol www.smaoutcomes.org); dual energy X-ray absorptiometry (DEXA) scans to assess whole body composition and bone density (XR-26 system, Norland Corporation, Fort Atkinson, Wis.). A summary of phenotypes and investigations for SMN1 deleted individuals is detailed below. History of evolution of clinical symptoms is additionally provided for the proband, 9164 and affected sister 9994 with SMA type I.

The proband was a female infant (FIG. 15A, 9164, SMA type I) born full-term following an uneventful pregnancy and delivery. In retrospect, parents noted hypotonia from about 2 weeks of age. Neurologic evaluation at age 3.8 months revealed generalized weakness and hypotonia, absent head control, areflexia and paradoxical breathing indicating intercostal muscle weakness. She had limited antigravity proximal limb movements. Ulnar CMAP was already significantly diminished: 0.9 mV (normal>5 mV) and MUNE 8 (normal>150). She received nocturnal noninvasive ventilatory support with bilevel respiratory support (BIPAP) from age 5.5 months. Nasogastric tube was required from 7 months and she received gastrostomy tube at 8.7 months. DEXA scan performed at 12 months of age revealed severely diminished fat-fire lean body mass for age. She died of respiratory failure at 3 years of age when her ventilator was inadvertently unplugged.

Unaffected brother (FIG. 15A, 9119, SMN1 deleted, asymptomatic) was born full-term following an uneventful pregnancy, BW 6 lbs 14 oz. Prenatal diagnosis via amniocentesis was performed prior to the delivery. He was examined and followed closely prospectively from birth Neurologic examination at2 weeks, and 2, 3, 6, 9 and 12 months was normal. He sat by six months, stood by 9 months and walked independently by 10 months. CMAP was initially 3.8 mV at 2 weeks of age and progressively increased over the ensuing months, to reach a maximum of ~9 mV by 9 months of age. MUNE values were normal, and DEXA scan revealed normal body composition. He was evaluated on a yearly basis, and continued to develop normally. At 11 years of age, his neurologic exam is entirely normal; he can perform 20 squats without difficulty and he is normally active for age. He demonstrates a squint when going from dark to bright environments.

Unaffected brother (FIG. 15A, 9120, SMN1 deleted, asymptomatic) was born full-term following an uneventful pregnancy and delivery, birth weight 8 lbs 2 oz. Examination at 1 day of age was normal. Detailed investigations performed at 3 months of age revealed normal CMAP (10.3 mV) and MUNE (~150) values. Developmental proceeded normally, he sat by 6 months and walked by 12 months. DEXA at 8 months demonstrated normal body composition. He demonstrated some modest speech delay, and was a bit clumsy but neurologic examination remained normal. At 9 years of age, he remains neurologically normal. He is normally active and can do 20 squats without evident difficulty or fatigue. He is photosensitive, with a prominent squint when going from dim to bright environment; this is especially notable in family photos taken outdoors.

Affected SMA type I sister (FIG. 15A, 9994) was born 10 days post-term via induced vaginal delivery. At day 1 of life, she appeared clinically normal. However, by 4 days of age, she was hypotonic, with reduced spontaneous voluntary limb movements and evident tongue fasiculations. She was areflexic but still had good suck, cry and head control and proximal antigravity limb movements. She had bilateral wrist drop and poor coloration of distal extremities. CMAP at 4 days of age was low (2.7 mV) and fell precipitously to 0.8 mV by 3 weeks of age, indicating rapidly progressive distal denervation. She received Nissan and gastrostomy-tube surgery at six weeks of age, and was on nocturnal BIPAP support by 3 months of age. She had numerous hospitalizations in the first year for acute on chronic respiratory failure, usually in the setting of apparent viral infections, including respiratory syncytial virus. She underwent tracheostomy at 22 months of age for increasing respiratory instability; however, support was withdrawn at 5 years of age after a critical illness with sepsis and multi-organ failure.

Unaffected father (FIG. 15A, 9128, asymptomatic, homozygous SMN1 deletion) underwent detailed clinical investigation at 30 years of age, when carrier testing indicated an apparent homozygous SMN1 deletion. Detailed neurologic examination was entirely normal. Maximum ulnar CMAP (11.3 mV) and MUNE (150) values were normal. Whole body DEXA scan indicated normal body composition. He remains clinically unaffected at 40 years of age, without evidence of proximal muscle weakness or fatigability. He admits to photosensitivity, wears sunglasses most days, and has a characteristic squint in photos taken outdoors.

Unaffected paternal uncle (FIG. 15A, 9127, asymptomatic, homozygous SMN1 deletion) underwent detailed clinical investigation at 27 years of age. Detailed neurologic examination was normal, with no evident weakness or fatigability. Maximum ulnar CMAP (152 mV) and MUNE (234) values were normal. DEXA indicated normal body composition. At 37 years of age, he remains clinically asymptomatic. He was not examined for clinically evident photosensitivity.

Unaffected paternal uncle (FIG. 15A, 9125, asymptomatic, homozygous SMN1 deletion) underwent detailed clinical investigation at 25 years of age. Detailed neurologic examination was normal, with no evident weakness or fatigability. Maximum ulnar CMAP (14.9 mV) and MUNE (160) values were normal. DEXA indicated normal body composition. At 35 years of age, he remains clinically asymptomatic. He was not examined for clinically evident photosensitivity.

Unaffected paternal aunt (FIG. 15A, 9123, asymptomatic, homozygous SMN1 deletion) underwent detailed clinical investigation at 22 years of age. Neurologic examination was normal, without evident weakness or fatigability. Maximum ulnar CMAP (10.6) and MUNE (160) values were normal. DEXA indicated normal body composition. At 32 years of age, she remains clinically asymptomatic. She was not examined for clinically evident photosensitivity.

Patient DNA, Fibroblast Cell Lines and Lymphoblastoid Cell Lines

Informed written consent was obtained from each subject or their legal guardians for all biological samples according to the Declaration of Helsinki. The study has been approved by the Ethical Committee of the University of Cologne (04-138).

DNA was extracted from EDTA blood samples, primary fibroblast cell lines established from skin biopsies and lymphoblastoid cell lines from EDTA blood using standard protocols.

SMN1 and SMN2 copy number were determined by quantitative real-time PCR or MLPA analysis (MRC Holland) as previously described.

Haplotype analysis was carried out using multicopy polymorphic markers Ag1-CA (D5S1556) localized in the promoter of the SMN genes and C212 (D5F14951/S2) localized around 12 kb upstream of the SMN promoter as previously described. Polymorphic marker VS19A (D5S435) localized proximal and MIT I105 (D5S351) distal to the SMN genes were analysed as described.

Sequencing of the entire coding region of the SMN2 genes from RT-PCR products obtained from RNA isolated from lymphoblastoid cell lines was carried out as described in detail. Quantitative analysis of PLS3 RNA expression was catried out as previously described. An overview of the used cell lines is given below.

TABLE 1

Human fibroblast and EBV-transformed lymphoblastoid cell lines (LCL) derived from SMA patients, carriers and asymptomatic individuals used in this work.

| Phenotype | SMN1/SMN2 | DNA# | Fibroblast# | LCL# |
|---|---|---|---|---|
| Utah Family | | | | |
| SMA type I | 0/2 | 9994 | ML83 | B9994 |
| SMA type I | 0/2 | 9164 | ML84 | B9164 |
| asymptomatic | 0/4 | 9120 | ML113 | B9120 |
| asymptomatic | 0/4 | 9119 | ML114 | B9119 |
| asymptomatic | 0/4 | 9128 | ML115 | B9128 |
| asymptomatic | 0/4 | 9124 | ML117 | B9124 |
| asymptomatic | 0/4 | 9126 | ML118 | B9126 |
| carrier | 1/3 | 9129 | ML146 | B9129 |
| carrier | 1/1 | 9122 | | B9122 |
| carrier | 1/1 | 9123 | | B9123 |
| carrier | 1/4 | 9125 | | B9125 |
| carrier | 1/4 | 9127 | | B9127 |
| carrier | 1/4 | 9133 | | B9133 |
| carrier | 1/0 | 9134 | | B9134 |
| carrier | 1/2 | 9165 | | B9165 |
| Independent SMA patients | | | | |
| SMA type III | 0/3 | 326 | | BW70 |
| SMA type II | 0/4 | 798 | | BW174 |
| SMA type II | 0/4 | 1086 | | BW214 |
| SMA type III | 0/4 | 2349 | | BW303 |
| SMA type III | 0/4 | 1141 | | BW232 |
| SMA type II | 0/4 | 146 | | T110/91 |
| SMA type III | 0/4 | 906 | | BW184 |
| SMA type III | 0/4 | 106 | | T77/91 |
| SMA type III | 0/4 | 530 | | BW145 |
| SMA type III | 0/5 | 6241 | | LN498 |
| SMA type III | 0/4 | 6981f | ML69 | |
| SMA type I | 0/2 | 3413 | ML17 | |
| SMA type III | 0/3 | 2027 | ML12 | BW332 |
| SMA type I | 0/3 | 4043 | ML16 | |
| SMA type III | 0/3 | 2026 | ML14 | BW333 |
| SMA type III | 0/4 | 11268c | ML106 | |
| SMA type II | 0/3 | 785 | ML5 | |
| SMA type I | 0/2 | 4814b | ML39 | |
| control | | | ML32 | |
| control | | | ML35 | |
| control | | | ML44 | |

Genome-wide Linkage Analysis

The genome-wide scan was performed by genotyping 14 individuals of the Utah family using Affymetrix GeneChip Human Mapping 10K Array, version 2.0 (Affymetrix, Santa Clara, Calif.). This version of the Mapping 10K array comprises a total of 10,024 SNPs with a mean intermarker distance of 258 kb, equivalent to 0.36 cM. Parametric linkage analysis was performed by the program ALLEGRO assuming autosomal dominant inheritance with full penetrance, a disease allele frequency of 0.0001. Haplotypes were reconstructed with ALLEGRO and presented graphically with HaploPainter. All data handling was performed using the graphical user interface ALOHOMORA.

Transcriptome Analysis

For expression profiling, 400 ng of total RNA were linearly amplified and biotinylated using the Illumina® TotalPrep™ RNA Amplification Kits (Ambion) according to the manufacturer's instructions. Human HT-12v3 bead arrays (Illumina, San Diego, Calif.) were hybridized with 750ng cRNA for 18 h at 58° C. according to the Illumina® Whole-Genome Gene Expression with IntelliHyb Seal System Manual. Arrays were washed three times with buffer E1BC, High-Temp Wash Buffer and 100% ethanol, respectively, stained with streptavidine-Cy3 and again washed with buffer E1BC. Raw fluorescence intensities were recorded on a BeadArray Reader GX (Illumina). Average signal intensities without background correction were performed with BeadStudio 3.1 software (Illumina). All subsequent data analysis steps were performed in the statistical programming environment R (version 2.10-0; www.r-project.org) with several bioconductor packages (version 2.6.1; www.bioconductor.org). First, signal intensities were normalized with VSN and non-informative probes were removed based on detection p-values. The signals were then averaged for the individual subgroups and a linear model was designed capturing the influence of the patient group on gene expression levels. Differences between subgroups were extracted as contrasts and analyzed with the moderated F-test (empirical Bayes method) including a correction step for multiple testing with the 5%-FDR-based method of Benjamini and Hochberg (Benjamini and Hochberg, 1995). To attribute significant regulations to individual contrasts, a decision matrix was generated based on the function "decide test" within the "limma" package, where significant up- or downregulations are represented by values of 1 or −1, respectively.

Target Re-Sequencing

To identify a potential variant regulating differential NCALD expression, the complete NCALD locus±1 Mb (chr8:101,505,353-104,404,346) was sequenced in five family members (9129, 9124, 9128, 9119, 9165). Massive parallel sequencing of whole-blood genomic DNA was performed at the Radboud University Medical Center Nijmegen using a 5500×1 sequencing instrument (Life Technologies). Capture of the nearly 3 Mb genomic DNA from chromosome 8, for which unique sequence capture probes were possible, was performed using a 385K NimbleGen Sequence Capture Array (Roche).

On average, we obtained 2.7 Gb of mappable sequence data per individual after multiplex sequencing. Colour space reads were mapped to the hg19 reference genome with LifeTechnologies BioScope software version 1.3. On average, 94% of bases originated from the target region, resulting in a mean coverage of 544-fold. In total, 99.8% of the targeted region was covered ≥20 times. Single-nucleotide variants were subsequently called by the DiBayes algorithm using high-stringency calling settings, and small insertions and deletions were detected using the Small Indel Tool. Variant annotation was performed using an in-house analysis pipeline.

On average 2,723 variants were called per sample. Based on the previously obtained haplotype data, we filtered for heterozygous variants shared between the individuals 9129, 9124, 9128, 9119 but not present in 9165. This yielded in 43 variants of which 21 were previously annotated SNPs. None of the 43 variants was located in the coding region of NCALD, and only the SNP rs147264092 in intron 1 with a minor allele frequency of 0.1079 (1000 Genome database) was located in UTR of NCALD (Table S2). Subsequent screening of potential variants by Sanger sequencing of 50 unrelated SMA patients identified several symptomatic individuals carrying the same alleles thus refusing a protective role of the respective variant (FIG. 22). About 600 kb upstream of NCALD, we identified a 17 bp deletion (nt103783522-38, rs150254064; with a MAF of 0.056 in the 1000 Genome database) linked to the modifier haplotype and located adjacent to a H3K27AC block (http://genome.ucsc.edu/ENCODE). Sanger sequencing of this variant in the entire family showed perfect co-segregation with the modifier haplotype. However, since the 17 bp deletion was also present in 8/50 independent SMA patients, we excluded this as a sole cause either.

Cell Culture

Quantitative RT-PCR

For the quantification of RNA expression of NCALD of either human lymphoblastoid cell lines or human primary fibroblasts, RNA was extracted using RNeasy kit (Qiagen) according to the manufacturer's protocol. After determining the exact RNA concentration by the use of Quant-iT RNA Assay Kit (Invitrogen), 150 ng RNA was reverse transcribed to cDNA (Quantitect Reverse Transcription Kit, Qiagen). For NCALD cDNA measurements, exactly 9 ng of cDNA was used for the realtime PCR (LightCycler, Roche). Realtime PCR was performed in triplicates according to the manufacturer's protocol (annealing temperature 68° C., primers for NCALD cDNA are 5'-GGAATGCCCAGAGC-CCCAGTGT-3' (SEQ ID NO: 20) and 5'-GCCCCAAC-CCCCGAGTCTTACG-3' (SEQ ID NO: 21)). Standard curve-based absolute transcript quantification was performed by the use of Excel software (Microsoft). For statistical evaluation, the Student's t-test was applied. For quantitative measurements of SMN and PLS3, protocols were used as published earlier.

Western Blot Analysis

Protein levels in cells were quantified by the use of semi-quantitative western blots. Cells were harvested on ice and lysed in RIPA buffer (Sigma) containing protease inhibitors (Complete Mini, Roche). Western blots were performed as previously reported. The following primary antibodies were used for overnight incubation: anti-beta-actin (mouse monoclonal, 1:10000, Sigma), anti-SMN (MANSMA7, mouse monoclonal, 1:1000, Hybridoma Bank), anti-PLS3 (rabbit polyclonal, 1:1000, Eurogentec) and anti-NCALD (rabbit polyclonal, 1:1000, Proteintech). The following secondary antibodies were used (incubation 1 h, 1:10,000): anti-rabbit-HRP (GE Healthcare), anti-mouse-HRP (Sigma). Signal detection with Chemiluminescence reagent (Super Signal West Pico, Thermo Scientific) was performed according to the manufacturer's protocol.

siRNA-mediated Knockdown

To downregulate the expression of a specific gene small interfering RNAs (siRNA) were used (see Table below). The siRNA stocks (Qiagen) were first diluted to a final concentration of 1 µM in RNAse-free water. Transfection of cells (including NSC34, PC12, primary hippocampal and primary motor neurons) was performed by the use of the lipofection substance Dharmafect 1 (Thermo Scientific) for all siRNA experiments. Transfection was carried out according to the manufacturer's protocol. As a control of transfection efficiency, siTOX (Dharmacon) siRNA was used and AllStars Negative Control siRNA (Qiagen) sewed as a negative control. All cells transfected with siTOX induced apoptosis, demonstrating good transfection rate. Knockdown efficiency of the individual siRNA was confirmed by subsequent quantitative Western blotting. Subsequently to the respective incubation time, cells were either harvested for protein isolation, or were further analysed by immunostaining. Every knockdown experiment was performed at least in triplicates.

TABLE 2

| Species | Name (gene) | Target Sequence (5'→3') |
|---|---|---|
| mouse | Mm_Smn1_5 | AAGAAGGAAAGTGCTCACATA (SEQ ID NO: 22) |
| mouse | Mm_Ncald_2 | CAGGTGATTCACCCATTATAA (SEQ ID NO: 23) |
| rat | Rn_SMN1_1 | CCCGACCTGTGAAGTAGCTAA (SEQ ID NO: 24) |
| rat | Rn_Ncald_1 | AGAGACTTCCTAGCAATTTAA (SEQ ID NO: 25) |

Transient Overexpression

Human NCALD cDNA was cloned into pcDNA™ 3.1/CT-GFP TOPO using the following primers NCALD-FWD 5'-ATGGGGAAACAGAACAGCAAG-3' (SEQ ID NO: 26) and NCALD-REV 5'-GAACTGGCCGGCACTGCTC-3' (SEQ ID NO: 27) (Integrated DNA Technologies) and the manufacturer's protocol (Invitrogen).

To transiently overexpress NCALD-GFP (humNCALD-GFP, pcDNA3.1) or PLS3-V5 plasmids were transfected by the use of the lipofection reagent Dharmafect1 (Thermo Scientific) according to the manufacturer's protocol. This transfection was carried out for either primary motor neurons, primary hippocampal neurons, PC12 cells, or NSC34 cells.

NCALD Co-Immunoprecipitation

NSC34 cells transiently transfected with either pcDNA™ 6FLAG-His-NCALD or a control vector were lysed ([50 mM Tris/HCl, 5% (w/v) glycerol, 270 mM sucrose, 0.5% (v/v) Tween 20, 0.1% (v/v) β-mercaptoethanol, with added EDTA-fice protease inhibitor cocktail (Complete Mini, EDTA-free, Roche), pH7.5]. In order to investigate if the interactions are calcium-dependent, immunoprecipitation were carried out in 1 mM EGTA/1 mM EDTA or in the presence of 100 μM fire $Ca^{2+}$. Transfected NSC34 cells were subjected to immunoprecipitation using FLAG M2 affinity beads (Sigma Aldrich). The mixture was gently agitated overnight at 4° C. Bound proteins were eluted in laemlli buffer (240 mM Tris-HCl, pH 6.8, 6% SDS, 30% (v/v) glycerol, 0.06% bromophenol blue (w/v), 16% (v/v) β-mercaptoethanol) prior to SDS/PAGE. The proteins were transferred to a nitrocellulose membrane which was probed with antibodies against SMN (MANSMA7, mouse monoclonal, 1:1000, Hybridoma Bank), NCALD (rabbit polyclonal, 1:1000, Proteintech) and clathrin heavy chain (mouse monoclonal, 1:1000, Sigma Aldrich).

Primary Motor Neuron Culture

All animal experimental procedures were performed in agreement with animal protocols approved by the Landesamt für Natur, Umwelt and Verbraucherschutz Nordrhein-Westfalen (LANUV). Spinal cords were dissected from E14.5 SMA and heterozygous mouse embryos. Neurons were singularized with Trypsin and DNAse treatment, sieved, and plated on poly-D-lysine/Laminin coated coverslips. Some 1×10⁵ cells were seeded in 12-well plates for electrophysiology and 30,000 cells for immunostaining experiments. Culture conditions for these neurons were, as described before, as follows neurobasal medium with B27 supplement, 2 mM L-glutamine, 1× pen-strep (Invitrogen) containing 50 ng/μl, BDNF, 50 ng/μl GCNF and 50 ng/μl CNTF (Peprotech) at 37° C. in a humidified incubator with 5% $CO_2$. Immunostainings were performed as described previously.

Immunocytochemistry

For immunostainings, neuronal cells (NSC34, primary motor neurons) were grown on laminin-coated glass coverslips in 12-well plates. In brie, after washing with PBS (VWR), cells were fixed in 4% PFA in PBS containing 4% Sucrose (AppliChem). Cells were permeabilized in PBS-T (PBS containing 0.2% Tween20 (AppliChem)) and blocked in blocking solution (PBS-T including 5% BSA (Sigma) and 5% FCS (Biochrom)). Cells were incubated with blocking solution containing primary antibodies (α-HB9-antibody (1:100), monoclonal mouse, Hybridoma Bank; α-Synaptic vesicle 2 (1:150), monoclonal mouse (SV2-c), Hybridoma Bank α-Neurofilament (1:150), monoclonal mouse (2H3-c) Hybridoma Bank; α-Choline Acetyltransferase (ChAT) (1:150), goat, Millipore) over night at 4° C. After washing in PBS, cells were incubated for 1 h in the dark with respective secondary antibody labelled with Alexafluor488 or Alexaluor568 (Invitrogen) in blocking solution (optionally) containing phalloidin-Alexafluor568 (Invitrogen). Then, cells were washed and mounted on objects slides using Mowiol (Sigma) for later microscopic analysis using AxioImager M2 (Zeiss).

Enclocytosis Assay

One day before the measurement, some 15,000 fibroblasts per well (4-well EZ slides, Millipore) were plated out in 500 μl normal DMEM growth medium (Invitrogen). Cells were starved for 10 minutes in starvation media (DMEM transparent (HEPES), 2% FKS) at 37° C. For endocytosis, cells were treated with FITC dextran solution (5 mg/ml FITC-dextran in starvation medium) for respective time period at 37° C. Subsequently, medium was removed and cells were washed three times with ice-cold PBS on ice and fixed in 4% paraformaldehyde for ten minutes. After subsequent washing (2 times in PBS) cells were stained with Alexafluor 568 phalloidin (Invitrogen, 2 hours at 4° C.). Then, after washing cells were stained with DAPI and mounted with Mowiol (Sigma). Finally, FITC fluorescence was monitored at the fluorescence microscope (Axiolmager M2, Zeiss) and quantified using the Zen software (Zeiss) and evaluated with Excel (Microsoft).

Flow cytometry Analysis

NSC34 cells were transfected with control, Smn, Ncalci and Smn-Ncald siRNAs for 48 hours. The cells were starved for 6 hours, incubated with 5 mg/ml of FITC-dextran (Sigma) for 20 minutes at 37° C. The cells were washed and trypsinized (Trypsin solution, Sigma) on ice. After two times washing with 1% BSA solution in PBS, intake of FITC-Dextran was measured with BD FACSCalibur machine. Dead cells were excluded by propidium iodide staining (10 μg/ml, Sigma). The FACS data was analyzed with Cyflogic software (www.cyflogic.com).

Zebrafish Experiments
Zebrafish Injection and Analysis

Sequences of the used antisense Morpholinos (MO) were designed against the translational start codons of the respective genes (Gene Tools, LLC) (sequences see Table below).

TABLE 3

| Species | Name (gene) | Sequence (5'→3') |
|---|---|---|
| zebrafish | smn_MO | CGACATCTTCTGCACCATTGGC (SEQ ID NO: 28) |
| zebrafish | ncaldb_ATG_MO | GGAGCTTGCTGTTTTGTTTTCCCAT (SEQ ID NO: 29) |

TABLE 3-continued

| Species | Name (gene) | Sequence (5'→3') |
|---|---|---|
| zebrafish | Standard Control oligo (SEQ ID NO: 30) | CCTCTTACCTCAGTTACAATTTATA |

For NCALD mRNA injections, human NCALD cDNA was cloned into pCS2+ mRNA expression vector and in vitro transcribed using the mMESSAGE mMACHINE® SP6 Transcription Kit (Ambion) according to the manufacturer's protocol. Zebrafish embryos were injected between the one- and four-cell stage. For visualization of the motor neuron phenotype, embryos obtained from TL/EK wildtype and TUEK-hb9-GFP crossings were used Zebrafish embryos were injected with the respective dose of the individual MOs or mRNA in aqueous solution containing 0.05% phenol red and 0.05% rhodamine-dextran. To ensure equal distribution of the injected solution six hours after injection embryos were sorted according to homogeneity of the rhodamine fluorescence signal. Only embryos with equal rhodamine fluorescence were used for further analysis.

Immunohistochemistry for Motor Axon Quantification

For immunohistochemistry, zebrafish were manually dechorionated and fixed in 4% PFA-PBS at 34 hours post fertilization. To permeabilize the larvae for the following antibody staining, collagenase digest of the whole animal was performed. To visualize the primary motor axons, fish were incubated at 4° C. over night in 500 µl PBS-T/1% DMSO/10% FCS containing znp-1 antibody (1:300, Hybridoma Bank). Fish were stained in PBS-T/1% DMSO/10% FCS containing secondary donkey anti-mouse antibody labelled with Alexafluor 488 (1:200, Invitrogen) after all-day washing in PBS-T/1% FCS/1% BSA (changing solution every hour). After repeated washing in PBS-T and PBS, fish were stored in 80% glycerol/20% PBS in the dark at 4° C. Labelled fish were embedded in low-melting agarose micro slides and analysed using a fluorescence microscope (AxioImager M2, Zeiss). The structure of each of the first ten motor axons posterior to the yolk was analysed, rated as: 1) normal, 2) truncated (truncation ventral from midline), 3) severely truncated (shorter than midline), 4) branched I (branching ventral from midline), 5) branched II (branching at midline), or 6) branched BI (branching dorsal from midline) and statistically evaluated using Excel (Microsoft).

Western Blot Analysis of Zebrafish Material

To analyse the protein levels in zebrafish, semi-quantitative western blots were performed as follows. After gentle spin-down of dechorionated 48 hpf old larvae, fish were sacrificed by incubation on ice and lysed in RIPA buffer (Sigma) containing protease inhibitors (Complete Mini, Roche). Wester blots were performed as previously reported. The following primary antibodies were used for overnight incubation: anti-beta-actin (zebrafish) (rabbit polyclonal, 1:1000, Anaspec); anti-SMN (MANSMA7, mouse monoclonal, 1:1000, Hybridoma Bank) and anti-NCALD (rabbit polyclonal, 1:1000, Proteintech). The following secondary antibodies were used (incubation 1 h, 1:10,000): anti-rabbit-HRP (GE Healthcare), anti-mouse-HRP (Sigma). Signal detection with Chemiluminescence reagent (Super Signal West Pico, Thermo Scientific) was carried out according to standard protocols.

Ultrastructural Analysis using Transmission Electron Microscopy of Zebrafish 48 hpf zebrafish larvae were fixed in 4% PFA for 30 mm and postfixed in 0.6% glutaraldehyde for another day. Samples were then prepared and embedded in resin as previously described. The thickness of semi-thin and ultra-thin sections was 0.5 and 0.1 mm, respectively. For immunogold stainings, in brie pre-stained sections were blocked and afterwards incubated with primary antibodies (anti-clathrin, 1:50, anti-NCALD, 1:50) and washed in PBS; after that sections were stained with gold-labelled secondary antibodies (donkey anti-mouse 6 nm gold, 1:100; goat anti-rabbit 20 nm gold 1:100; Abeam). Image acquisition was performed using the TEM CM10 (Philips) microscope with the Orius SC200W 1 Gatan camera and the Digital Micrograph software.

Motor Behaviour Analysis of Zebrafish

To analyse the swimming behaviour of zebrafish morphants, high-speed imaging was performed. In brief 30 zebrafish larvae, all treated with each respective morpholino, were placed in a 10 cm petri dish containing fish embryo medium. To trigger a swimming response, fish were stimulated with an electrical impulse (60 V; delay: 60 ms, duration: 4 ms, frequency: 6 pps (SD9 Stimulator)). Swimming behaviour was recorded with 120 frames per second using a high-speed camera (FC-100, Casio). Quality of the high-speed video was optimized for analysis (Adobe) and afterwards swimming velocity and distance was analysed using LoliTrack software (Loligo Systems).

Endocytosis Inhibitor Treatment

Dynasore (dynamin inhibitor) and Pitstop2 (clathrin inhibitor) (both Abcam) were dissolved as stock solution (50 mM) in DMSO and stored at −20° C. Zebrafish were treated with the respective concentrations starting at 16 hpf. To do so, fish were dechorionated and substance was added to the embryo medium. Fish larvae were incubated at 28° C. in an incubator on a rocking platform (20 rpm) until fixed in PBS-PFA at 34 hpf. Subsequently fish were stained with znp-1 antibody, as described above.

Electrophysiology

Zebrafish

Experiments were conducted with zebrafish embryos (wildtype (wt) controls, Smn-, Ncald-, and smn+ncald-morphants) 72 hours post fertilization. The animals were anesthetized with 0.02% tricaine (in saline; E10521, Sigma-Aldrich, Taufkirchen, Germany) for 1-2 min and then rinsed with saline. The saline contained (in mM): 134 NaCl, 2.9 KCl, 2.1 $CaCl_2$, 1.2 $MgCl_2$, 10 HEPES, 10 Glucose adjusted to pH 7.8 withNaOH. The fish were decapitated and pinned under saline in a Sylgard-coated (SYLG184, Dow Coming, Midland, Mich.) recording chamber (~3 ml volume). The skin was peeled off using a sharp tungsten pin and fine forceps and the preparation was incubated in 3 M formamide (in saline; 6749.1, Carl Roth GmbH, Karlsruhe) for 2 min to prevent muscle contractions. After rinsing the preparation, the superficial layer of ventral slow muscle cells was removed by gently scratching with a fine tungsten pin to expose deeper lying fast skeletal muscle cells. Remaining superficial slow muscles in the segments of interest were removed with a low resistance pipette (~2 MΩ). If not stated otherwise the preparation was continuously superfused with saline at a flow rate of ~2 ml·$min^{-1}$. Experiments were carried out at ~25° C. Muscle cells were visualized with a fixed-stage upright microscope (Zeiss Axio Examiner, Carl Zeiss Microscopy GmbH, Jena, Germany), using a 40× water immersion objective (W Plan-Apochromat, 40×; 1.0 numerical aperture; 2.5 mm waking distance; Zeiss) with infrared-differential interference contrast and fluorescence optics. Fast muscle cells were identified by their orientation to the spinal cord and by their ability to generate action potentials.

Ca$^{2+}$ Influx Measurements in NSC34 and PC12

Whole cell recordings were performed at 24° C. following the methods described by Hamill (1981). Electrodes (tip resistance between 2.5 and 3 MΩ) were fashioned from bomsilicate glass (0.86 mm OD, 1.5 mm ID, GB150-8P, Science Products, Hofheim, Germany) with a temperature-controlled pipette puller (PIP5, HEKA Elektronik, Lambrecht, Germany), and filled with a solution containing (in mM) 133 CsCl, 1 CaCl$_2$, 2 MgCl$_2$, 10 HEPES and 10 EGTA, adjusted to pH 7.2 (with NaOH), resulting in an osmolarity of 415 mOsm. During the experiments, the cells were superfused constantly with saline solution containing (in mM) 84 NaCl, 20 CsCl, 2.5 KCl, 10 CaCl$_2$, 2 MgCl$_2$, 10 HEPES and 30 glucose, adjusted to pH 7.3, resulting in an osmolarity of 310 mOsm. To isolate the Ca$^{2+}$ currents we used a combination of pharmacological blockers and ion substitution Transient voltage gated Na+ currents were blocked by tetrodotoxin (10-6 M TTX, T-550, Alomone, Jerusalem, Israel). 4-Aminopyridine (4 AP, 4×10-3 M, A78403, Sigma) was used to block transient K$^+$ currents (IA; nomenclature adapted from Connor and Stevens 1971) and tetraethylammonium (TEA, 2×10-3, T2265, Sigma) blocked sustained K$^+$ currents (IK(V)) as well as Ca$^{2+}$-activated K$^+$ currents (IK(Ca)). In addition the pipette solution did not contain potassium. Whole cell voltage-clamp recordings were made with an EPC10 patch-clamp amplifier (HEKA Elektronk) that was controlled by the program Patchmaster (V2×53, HEKA-Elektionik) running under Windows. The electrophysiological signals were low-pass filtered at 2.9 kHz with a 3 pole Bessel filter. The data were sampled at intervals of 50 µs (20 kHz). Compensation of the offset potential and capacitance was performed using the 'automatic mode' of the EPC10 amplifier. The liquid junction potential between intracellular and extracellular solution (see Neher 1992) of 2.5 mV (calculated with Patcher's PowerTools plug-in from http://www.mpibpc.gwdg.de/abtei-lungen/140/software/index.html for Igor Pro (WaveMetrics,Portland, Oreg.)) was also compensated. Whole-cell capacitance was determined by using the capacitance compensation (C-slow) of the EPC10. To remove uncompensated leakage and capacitive currents, a p/6 protocol was used. Voltage errors due to series resistance (RS) were minimized using the RS compensation of the EPC10. RS was compensated to 70-80% with a time constant (τ) of 100 µs. Stimulus protocols used for each set of experiments are provided in the results.

Statistical Analysis

Data were analyzed using Spike2 and statistical analysis was performed in GraphPad Prism (version 5.05, GraphPad Software, San Diego, Calif., USA). All calculated values are expressed as mean±standard error. The EEP frequencies for each cell were measured as mean frequencies over 30 s intervals. Frequencies before and during NMDA application were compared by a paired t-test for each group. A Kruskal-Wallis test followed by Dunns multiple comparisons was used to compare EPP frequencies in different groups. A significance level of 0.05 was accepted for all tests.

*Caenorhabditis elegans* experiments

*Caenorhabditis elegans* strains

LM99 smn-1(ok355)I/hT2(I;III), HA1981 +/hT2(I;III), HA2530 +/hT2(I;III);ncs-1(qa401)X, HA2531 smn-1(ok355)I/hT2(I;III);ncs-1(qa401)X, HA2599 +/hT2(I;III); uIs72, HA2623 smn-1(ok355)I/hT2(I;III);uIs72, HA2629 +/hT2(I;III);rtSi28 IV, HA2627 +/hT2(I;III)πSi27 IV, HA2628 smn-1(ok355)I/hT2(I;III); rtSi28, HA2626 smn-1(ok355)I/hT2(I;III);rtSi27 strains were maintained at 20° C. under standard conditions. +/hT2 strains used as control far genetic background; RNAi studies were undertaken in a sensitized background (transgene uIs72) expressing the SID-1 double stranded RNA channel in neurons. rtSi27 and rtSi28 were generated by Mos1-mediated single-copy insertion of pHA #607 and pHA #606, respectively. Construction: dpy-30 promoter from pS235 was inserted using SphI and NheI sites into pPD49.26. Human PLS3 coding sequences amplified from pcDNA3.1_PLS3.V5-His6 TOPO (5'-GAACGCTAGCATGGATGAGATGGCTACCAC-3' (SEQ ID NO: 31), 5'-CAGGGGAATGAAGAGAGTGTAAC-CCGGGGTTC-3' (SEQ ID NO: 32)) and inserted behind dpy-30p. Either the promoter or promoter/PLS3 sequences were inserted into a modified pCFJ66 using SphI/NheI or SphI/XmaI sites, respectively, creating pHA #606 dpy-30p:: unc-54UTR, unc-119(+) and pHA #607 dpy-30p::PLS3:: unc-54UTR, unc-119(+). Plasmids were injected at 50 ng/ul as described. All integrated transgenes were backcrossed to wild type at least three times before final strain construction.

*C elegans* Pharyngeal Pumping

The pharyngeal pumping assay was performed as previously described in the last larval stage. A pharyngeal grinder movement in any axis was scored as a pumping event. Average pumping rates (±SEM) were combined from at least three independent trials (n≥25 animals in total). For the RNAi knockdown, second generation (F2) animals were reared on either control vector L4440 or C44C1.3/ncs-1 (RNAi) in HT115. ncs-1 RNAi clone contains genomic DNA amplified by primers 5'-AAATCGTCTAGCTGTAGT-GTCGC-3' (SEQ ID NO: 33) and 5'-TTGTGCTCCCTA-CACTTTGTTTT-3' (SEQ ID NO: 34) inserted into L4440. The clone was verified by sequencing.

Microscopy

If not mentioned otherwise, all microscopic experiments were performed with a fully motorized fluorescence microscope AxioImager M2 (Zeiss). This microscope was equipped with an ApoTome (Zeiss) for better picture quality. All measurements (fluorescence intensity, length, surface size etc.) were performed using the Zen software (Zeiss) and evaluated with Excel (Microsoft) or SigmaPlot (Systat Software).

Mouse Experiements

Breeding

All mice used in this work were housed in micro-isolation chambers in the mouse facility of the Institute of Genetics, Cologne. Whenever necessary, mice were humanely euthanized according to protocols set forth by the 'Landesamt für Natur, Umwelt und Verbraucherschutz NRW'. The animal breeding and all mouse experiments were approved by the local animal protection committee. The animal experiment application form was confirmed. All in vivo experiments were performed under the reference number 9.93.2.10.31.07.292. SMA mice (FVB.Cg-Tg(SMN2) 2Hung Smn1tm1Hung/J, Jackson's Laboratory Stock Number 005058) were bred as published previously. In brief breeding pairs consisted of one mouse that was homozygous for the human SMN2 transgene and the Smn knockout (Smn$^{-/-}$;SMN2$^{tg/tg}$) allele and the other mouse was heterozygous for the knock-out (Smn$^{-/+}$) allele, which resulted in pups that all were heterozygous for the transgene and to 50% either homozygous (SMA) or heterozygous (HET) for the knock-out allele.

TABLE 4

For genotyping the primers were used as following: gDNA

| | | | |
|---|---|---|---|
| mouse | murine KO fw | Genotyping mouse | ATAACACCACCACTCTTACTC (SEQ ID NO: 35) |
| mouse | murine KO rev1 | Genotyping mouse | AGCCTGAAGAACGAGATCAGC (SEQ ID NO: 36) |
| mouse | murine KO rev2 | Genotyping mouse | TAGCCGTGATGCCATTGTCA (SEQ ID NO: 37) |
| human | Human SMN2 fw | Genotyping mouse | CGAATCACTTGAGGGCAGGAGTTTG (SEQ ID NO: 38) |
| human | Human SMN2 rev | Genotyping mouse | AACTGGTGGACATGGCTGTTCATTG (SEQ ID NO: 39) |

Mouse Motor Ability Test

The motor ability of SMA-like and heterozygous control mice was measured by applying the so called tube test, as described previously. This method has the advantage that it can be performed with neonates. In brief, each pup was placed one by one headfirst into a vertical 50 ml reaction tube. The ability of the mouse to hold itself by the strength of the hind limbs was rated from 4 (best score wide spreading) to 1 (bad score, hind limbs in a clasped position). The tube test was performed daily and measurements were evaluated with Excel (Microsoft).

Vivo Morpholino Treatment

After finding the right application method (i.c.v. or s.c.) and the adequate treatment concentration, each mouse was treated with 2 $\mu g/g_{mouse}$ (concentration 1 $\mu g/\mu l$) of Vivo-Morpholino with the sequence AGCTTGCTGTTCT-GTTTCCCCATTC (SEQ ID NO: 4) (Gene Tools,) subcutaneously every other day, starting from postnatal day 1.

Mouse Tissue Analysis

As described previously muscle or lung biopsies, or whole organs (heart, intestine) of symptomatic mice (PND10) were fixed in 4% paraformaldehyde (PFA) over night and afterwards dehydrated with the help of an infiltration machine (Leica). Subsequently, biopsies were embedded in paraffin and cut with the help of microtome (Leica) into 8 $\mu m$ thick sections. To compare structures of heart, lung and intestine, H&E staining was performed and overview pictures were taken using brightfield microscopy AxioImager M2 (Zeiss).

Quantification of Muscle Fiber Size

To quantify the size of the muscle fibers, cross-sections of the rectus femoris muscle were stained with an H&E staining. The surface area size of 300 muscle fibers per animal was measured with the help of Zen computer software (Zeiss). For each genotype (3 mice per genotype), the mean muscle fiber size was evaluated (Microsoft Excel).

Quantification of NMJ Size

The area of the NMJs was measured (in $\mu m^2$) as previously reported. Therefore, the transversus abdominis (TVA) was prepared at PND10, fixed in 4% PFA for 15 minutes were stained with anti-Neurofilament M (1:100, Hybridoma Bank) and SV2 (1:100, Hybridoma Bank) (subsequently stained with goat anti mouse secondary antibody (1:250) labeled with AlexaFlour 488, Millipore), which labels the neurons, and α-Bungarotoxin (1:1000, labeled with rhodamine, Invitrogen), which binds to the muscular acetycholine-receptors (AChR). The surface area of the post-synapse of 100 NMJ per animal was measured with the help of Zen computer software (Zeiss).

Mouse Fibroblasts from PLS3 Mice

Murine embryonic fibroblasts were derived from E13.5 embryos of following genotypes: $Smn^{-/-}; SMN2^{tg/tg}$, $Smn^{-/+}; SMN2^{tg/tg}$, $Smn^{-/-}; SMN2^{tg/tg}, PLS3V5^{tg/0}$, $Smn^{+/-}; SMN2^{tg/tg}; PLS3V5^{tg/0}$. MEFs were prepared as described in. Briefly, embryos were dissected, rinsed with PBS and the head and internal organs were removed. The remaining tissues were homogenized with a sterile syringe plumber through a 70 $\mu m$ cell filter (BD Falcon) which was subsequently flushed with 10 ml DMEM medium (Invitrogen) supplemented with 10% FCS (Invitrogen), 100 U/ml penicillin (PAA), 100 $\mu l/ml$ streptomycin (PAA). Cells were sedimented by 5 min centrifugation at 300 g, resuspended in 6 ml medium and plated on 6-well tissue culture dishes (Sarstedt). MEFs were cultured at 37° C., 5% $CO_2$ and 90% humidity.

Statistical Analysis

Whenever the significance of the RNA expression levels as well as the changed protein levels were tested, it was performed by the use of a directional student's t-test for uncorrelated samples. In all cases, three levels of statistical significance were distinguished: *=P<0.05,=P<0.01 and *=P<0.001.

A Wilcoxon's rank-sum test was performed in order to determine the significance in the increase of survival (the shift of the Kaplan-Meier curves) of the SMA mice after vivo morpholino treatment. Each value is given as a mean of three experiments±SEM if not indicated otherwise.

The significance in the differences of NMJ and muscle fiber surface area size, motor axon length, NSC34 neurite length and width of the synaptic cleft as well was determined by the use of a directional students t-test for uncorrelated samples. NMJ and muscle fiber surface area size, motor axon length, NSC34 neurite length and width of the synaptic cleft are presented in boxplot diagram, reflecting mean and median values. If not mentioned otherwise, all statistical analyses were performed by use of the software programs Excel 2013 (Microsoft) and Sigma Plot 11 (Systat Software).

SUPPLEMENTAL TABLE S1

Transcripts significantly up or downregulated in asymptomatic Utah family members as compared to affected siblings or unrelated SMA patients carrying also four SMN2 copies

| ID | Symbol | Name | Group1-Group2 | Group1-Group3 | Group1-Group2 (logFC) | Group1-Group3 (logFC) |
|---|---|---|---|---|---|---|
| 7040477 | PLOD2 | procollagen-lysine, 2-oxoglutarate 5-dioxygenase 2 | −1 | −1 | −3.176 | −2.503 |
| 60093 | NCALD | neurocalcin delta | −1 | −1 | −2.779 | −2.226 |
| 520553 | NCALD | neurocalcin delta | −1 | −1 | −3.034 | −2.155 |
| 4610047 | RANBP1 | RAN binding protein 1 | −1 | −1 | −0.930 | −0.863 |
| 7320746 | NA | NA | −1 | −1 | −0.784 | −0.742 |

SUPPLEMENTAL TABLE S1-continued

| | | | | | | | |
|---|---|---|---|---|---|---|---|
| 7510543 | NA | NA | | −1 | −1 | −1.040 | −0.674 |
| 5820086 | TREH | trehalase (brush-border membrane glycoprotein) | | −1 | −1 | −1.352 | −0.647 |
| 5870196 | NA | NA | | −1 | −1 | −1.074 | −0.627 |
| 2750475 | D4S234E | DNA segment on chromosome4 (unique) 234 expressed sequence | | 1 | 1 | 2.899 | 2.224 |
| 1070450 | NA | NA | | 1 | 1 | 1.911 | 0.950 |
| 1710189 | RHBDF1 | rhomboid 5 homolog 1 (*Drosophila*) | | 1 | 1 | 1.325 | 0.870 |
| 6200367 | FICD | formiminotransferase cyclodeaminase | | 1 | 1 | 1.134 | 0.825 |
| 6270152 | NA | NA | | 1 | 1 | 0.716 | 0.615 |
| 5220338 | MPEG1 | macrophage expressed 1 | | 1 | 1 | 0.724 | 0.605 |
| 2940296 | NA | NA | | 1 | 1 | 0.968 | 0.543 |
| 6350307 | NA | NA | | 1 | 1 | 0.701 | 0.535 |
| 6280360 | SPG7 | spastic paraplegia 7 (pure and complicated autosomal recessive) | | 1 | 1 | 0.746 | 0.443 |

The rows continue the corresponding rows of previous Table S1.

| ID | AveExpr | F | P.Value | adj.P.Val | Chr | Refseq | Entrez |
|---|---|---|---|---|---|---|---|
| 7040477 | 7.666 | 9.017 | 0.003 | 0.599 | 3q23-q24 | NM_000935, NM_182943, NP_000926, NP_891988 | 5352 |
| 60093 | 9.578 | 7.806 | 0.006 | 0.648 | 8q22.2 | NM_001040624, NM_001040625, NM_001040626, NM_001040627, NM_001040628, NM_001040629, NM_001040630, NM_032041, NP_001035714, NP_001035715, NP_001035716, NP_001035717, NP_001035718, NP_001035719, NP_001035720, NP_114430 | 83988 |
| 520553 | 8.840 | 9.084 | 0.003 | 0.599 | 8q22.2 | NM_001040624, NM_001040625, NM_001040626, NM_001040627, NM_001040628, NM_001040629, NM_001040630, NM_032041, NP_001035714, NP_001035715, NP_001035716, NP_001035717, NP_001035718, NP_001035719, NP_001035720, NP_114430 | 83988 |
| 4610047 | 10.730 | 16.879 | 0.000 | 0.461 | 22q11.21 | NM_002882, NP_002873 | 5902 |
| 7320746 | 4.311 | 10.141 | 0.002 | 0.599 | NA | NA | NA |
| 7510543 | 4.630 | 8.344 | 0.005 | 0.632 | NA | NA | NA |
| 5820086 | 4.289 | 14.092 | 0.001 | 0.461 | 11q23.3 | NM_007180, NP_009111 | 11181 |
| 5870196 | 4.859 | 11.006 | 0.002 | 0.599 | NA | NA | NA |
| 2750475 | 6.164 | 8.573 | 0.004 | 0.622 | 4p16.3 | NM_001040101, NM_014392, NP_001035190, NP_055207 | 27065 |
| 1070450 | 5.176 | 11.702 | 0.001 | 0.581 | NA | NA | NA |
| 1710189 | 5.202 | 8.600 | 0.004 | 0.622 | 16p13.3 | NM_022450, NP_071895 | 64285 |
| 6200367 | 3.712 | 9.478 | 0.003 | 0.599 | 21q22.3 | NM_006657, NM_206965, NP_006648, NP_996848 | 10841 |
| 6270152 | 4.336 | 8.414 | 0.004 | 0.626 | NA | NA | NA |
| 5220338 | 5.487 | 9.268 | 0.003 | 0.599 | 11q12.1 | NM_001039396, NP_001034485 | 219972 |
| 2940296 | 4.477 | 12.872 | 0.001 | 0.507 | NA | NA | NA |
| 6350307 | 4.320 | 9.506 | 0.003 | 0.599 | NA | NA | NA |
| 6280360 | 10.279 | 9.233 | 0.003 | 0.599 | 16q24.3 | NM_003119, NM_199367, NP_003110, NP_955399 | 6687 |

| ID | E9R_034a01_4 | E9R_034a02_2 | E9R_034a3_2 | E9R_034a04_2 | E9R_034a05_2 | E9R_034b01 | E9R_034b02 |
|---|---|---|---|---|---|---|---|
| 7040477 | 5.73 | 5.74 | 5.98 | 6.63 | 6.38 | 10.71 | 7.83 |
| 60093 | 6.42 | 8.75 | 10.44 | 6.67 | 8.65 | 11.51 | 10.42 |
| 520553 | 6.00 | 7.92 | 9.73 | 5.77 | 7.76 | 10.95 | 9.99 |
| 4610047 | 10.12 | 10.50 | 10.16 | 10.02 | 10.28 | 11.28 | 11.01 |
| 7320746 | 4.18 | 4.03 | 3.97 | 3.64 | 3.54 | 4.61 | 4.70 |
| 7510543 | 4.46 | 4.53 | 3.91 | 4.35 | 3.63 | 5.38 | 5.05 |
| 5820086 | 3.97 | 4.03 | 3.61 | 3.61 | 3.75 | 5.28 | 5.02 |
| 5870196 | 4.06 | 4.19 | 4.90 | 4.61 | 4.34 | 5.35 | 5.63 |
| 2750475 | 7.80 | 7.75 | 8.39 | 8.73 | 5.21 | 4.61 | 4.74 |
| 1070450 | 5.84 | 6.19 | 6.47 | 5.78 | 5.18 | 4.23 | 3.73 |
| 1710189 | 6.86 | 5.22 | 5.67 | 5.87 | 5.30 | 4.52 | 4.40 |
| 6200367 | 4.87 | 3.99 | 3.86 | 4.10 | 4.41 | 3.28 | 2.94 |
| 6270152 | 4.32 | 4.77 | 4.55 | 4.74 | 5.17 | 4.05 | 3.94 |
| 5220338 | 5.70 | 5.82 | 5.55 | 6.15 | 6.09 | 5.01 | 5.27 |
| 2940296 | 4.79 | 4.63 | 4.81 | 4.97 | 5.13 | 4.06 | 3.73 |
| 6350307 | 4.39 | 4.82 | 4.71 | 4.67 | 4.72 | 4.05 | 3.87 |
| 6280360 | 10.76 | 10.52 | 10.34 | 10.69 | 10.63 | 9.76 | 9.92 |

| ID | E9R_034c01_4 | E9R_034c02_2 | E9R_034c03_2 | E9R_034c04_4 | E9R_034c05_2 |
|---|---|---|---|---|---|
| 7040477 | 8.95 | 11.05 | 6.95 | 8.81 | .23 |
| 60093 | 10.49 | 10.81 | 9.90 | 11.41 | 9.45 |
| 520553 | 9.63 | 9.88 | 9.20 | 10.49 | 8.75 |
| 4610047 | 11.07 | 11.12 | 10.91 | 10.83 | 11.45 |
| 7320746 | 4.40 | 5.00 | 4.50 | 4.39 | 4.78 |
| 7510543 | 4.85 | 4.75 | 4.97 | 4.40 | 5.27 |
| 5820086 | 4.09 | 3.94 | 4.69 | 4.85 | 4.64 |
| 5870196 | 4.70 | 5.12 | 5.07 | 5.26 | 5.09 |
| 2750475 | 6.10 | 5.14 | 5.60 | 3.45 | 6.47 |
| 1070450 | 5.28 | 3.94 | 5.66 | 5.03 | 4.79 |

SUPPLEMENTAL TABLE S1-continued

| | | | | | |
|---|---|---|---|---|---|
| 1710189 | 4.61 | 4.98 | 4.73 | 5.24 | 5.02 |
| 6200367 | 3.81 | 3.48 | 3.76 | 3.04 | 3.01 |
| 6270152 | 4.03 | 4.12 | 4.31 | 3.96 | 4.10 |
| 5220338 | 5.22 | 5.22 | 5.08 | 5.28 | 5.47 |
| 2940296 | 4.24 | 4.35 | 4.10 | 4.42 | 4.50 |
| 6350307 | 3.99 | 4.03 | 4.39 | 4.08 | 4.12 |
| 6280360 | 10.35 | 10.06 | 10.16 | 10.12 | 10.03 |

SUPPLEMENTAL TABLE S2

Variants co-segregating with the modifying haplotype based on targeted re-sequencing of 3 Mb of the region around NCALD

| Child | % variation | Start position | End position | reference | mutation | reads | variation reads |
|---|---|---|---|---|---|---|---|
| 1.02E+08 | 36.73469 | 1.02E+08 | 1.02E+08 | A | C | 98 | 36 |
| 1.02E+08 | 39.07285 | 1.02E+08 | 1.02E+08 | TA | | 151 | 59 |
| 1.02E+08 | 32.69231 | 1.02E+08 | 1.02E+08 | | G | 572 | 187 |
| 1.02E+08 | 23.05238 | 1.02E+08 | 1.02E+08 | G | | 529 | 122 |
| 1.02E+08 | 41.68865 | 1.02E+08 | 1.02E+08 | C | T | 379 | 158 |
| 1.02E+08 | 22.81369 | 1.02E+08 | 1.02E+08 | AA | T | 263 | 60 |
| 1.02E+08 | 46.27329 | 1.02E+08 | 1.02E+08 | C | T | 644 | 298 |
| 1.02E+08 | 31.55556 | 1.02E+08 | 1.02E+08 | | A | 450 | 142 |
| 1.02E+08 | 43.83838 | 1.02E+08 | 1.02E+08 | | T | 495 | 217 |
| 1.02E+08 | 24.73573 | 1.02E+08 | 1.02E+08 | | A | 473 | 117 |
| 1.02E+08 | 36.53846 | 1.02E+08 | 1.02E+08 | T | A | 104 | 38 |
| 1.02E+08 | 27.92793 | 1.02E+08 | 1.02E+08 | | TA | 555 | 155 |
| 1.02E+08 | 44.21769 | 1.02E+08 | 1.02E+08 | AAC | G | 294 | 130 |
| 1.02E+08 | 47.61905 | 1.02E+08 | 1.02E+08 | ACACACACACACATAT (SEQ ID NO: 40) | | 63 | 30 |
| 1.02E+08 | 49.01055 | 1.02E+08 | 1.02E+08 | C | G | 657 | 322 |
| 1.02E+08 | 31.81818 | 1.02E+08 | 1.02E+08 | TTCCTTTCTTTTTCCTTCC (SEQ ID NO: 41) | | 22 | 7 |
| 1.02E+08 | 22.95082 | 1.02E+08 | 1.02E+08 | CAGA | | 366 | 84 |
| 1.02E+08 | 34.86005 | 1.02E+08 | 1.02E+08 | | T | 393 | 137 |
| 1.02E+08 | 45.13761 | 1.02E+08 | 1.02E+08 | C | T | 545 | 246 |
| 1.02E+08 | 42.73504 | 1.02E+08 | 1.02E+08 | C | G | 351 | 150 |
| 1.02E+08 | 45.96774 | 1.02E+08 | 1.02E+08 | C | T | 496 | 228 |
| 1.03E+08 | 30.98592 | 1.03E+08 | 1.03E+08 | TC | | 852 | 264 |
| 1.03E+08 | 34.18941 | 1.03E+08 | 1.03E+08 | | TA | 623 | 213 |
| 1.03E+08 | 36.25498 | 1.03E+08 | 1.03E+08 | | CT | 502 | 182 |
| 1.04E+08 | 36.82008 | 1.04E+08 | 1.04E+08 | A | G | 478 | 176 |
| 1.04E+08 | 40.31891 | 1.04E+08 | 1.04E+08 | C | T | 439 | 177 |
| 1.04E+08 | 20.85308 | 1.04E+08 | 1.04E+08 | CCAGAAGAGGGCICTGA (SEQ ID NO: 42) | | 422 | 88 |
| 1.04E+08 | 20.96386 | 1.04E+08 | 1.04E+08 | | CGG | 415 | 87 |
| 1.04E+08 | 79.1762 | 1.04E+08 | 1.04E+08 | | C | 437 | 346 |

SUPPLEMENTAL TABLE S2-continued

Variants co-segregating with the modifying haplotype based on targeted re-sequencing of 3 Mb of the region around NCALD

| | | | | | | | | % variation | Abberation | Score | Novel allele mean QV | Unique starts | SNP id | SNP state | SNP reference |
|---|---|---|---|---|---|---|---|---|---|---|---|---|---|---|---|
| 1.04E+08 | 49.89154 | 1.04E+08 | 1.04E+08 | | CAG | 461 | 230 | 36.73469 | substitution | 0 | 31 | 16 | | | |
| 1.04E+08 | 48.07396 | 1.04E+08 | 1.04E+08 | | AGG | 649 | 312 | 39.07285 | deletion | 1 | | | | | |
| 1.04E+08 | 57.57576 | 1.04E+08 | 1.04E+08 | | A | 429 | 247 | 32.69231 | insertion | 1 | | | rs148206390, | Overlapping location | T |
| 1.04E+08 | 43.65942 | 1.04E+08 | 1.04E+08 | G | A | 552 | 241 | 23.06238 | deletion | 1 | | | | | |
| 1.04E+08 | 55.82329 | 1.04E+08 | 1.04E+08 | | C | 249 | 139 | 41.68865 | substitution | 0 | 31 | 56 | | | |
| 1.04E+08 | 26.78019 | 1.04E+08 | 1.04E+08 | | T | 646 | 173 | 22.81369 | deletion | 1 | | | | | |
| 1.04E+08 | 40.91954 | 1.04E+08 | 1.04E+08 | G | A | 435 | 178 | 46.27329 | substitution | 0 | 37 | 67 | | | |
| 1.04E+08 | 39.783 | 1.04E+08 | 1.04E+08 | | G | 553 | 220 | 31.55556 | insertion | 1 | | | rs148380835, | Overlapping location | C |
| 1.04E+08 | 29.30233 | 1.04E+08 | 1.04E+08 | | AC | 430 | 126 | 43.83838 | insertion | 1 | | | rs146361232, | Overlapping location | A |
| 1.04E+08 | 31.46067 | 1.04E+08 | 1.04E+08 | | GGG | 534 | 168 | 24.73573 | insertion | 1 | | | rs141249250, | Overlapping location | C |
| 1.04E+08 | 36.68122 | 1.04E+08 | 1.04E+08 | C | | 458 | 168 | 36.53846 | substitution | 0 | 35 | 5 | rs143075072, rs33986428, | Overlapping location | TT |
| 1.04E+08 | 49.88764 | 1.04E+08 | 1.04E+08 | A | G | 445 | 222 | 27.92793 | insertion | 1 | | | rs144748760, | Overlapping location | C |
| 1.04E+08 | 37.3913 | 1.04E+08 | 1.04E+08 | | AT | 345 | 129 | 44.21769 | deletion | 1 | | | rs35890983, rs57873812, rs10568391, rs34102669, | Overlapping location | A |
| 1.04E+08 | 30.58637 | 1.04E+08 | 1.04E+08 | | CACT | 631 | 193 | 47.61905 | deletion | 1 | | | rs10551908, rs66528948, rs56819980, rs80196784, rs3133528, rs66578263, rs60645177, | Overlapping location | — |

The rows continue the corresponding Rows of previous Table S2.

SUPPLEMENTAL TABLE S2-continued

Variants co-segregating with the modifying haplotype based on targeted re-sequencing of 3 Mb of the region around NCALD

| | | | | | | |
|---|---|---|---|---|---|---|
| 49.01065 | substitution | 0 | 37 | 60 | | |
| 31.81818 | deletion | 1 | | | rs148290228, rs111969072, rs71276936, rs3081248, rs111318848, rs113871735, rs2386925, | Overlapping C location |
| 22.95082 | deletion | 1 | | | | |
| 34.86005 | insertion | 1 | | | rs144916577, | Overlapping G location |
| 45.13761 | substitution | 0 | 37 | 57 | | |
| 42.73504 | substitution | 0 | 35 | 51 | | |
| 45.96774 | substitution | 0 | 32 | 54 | | |
| 30.98592 | deletion | 1 | | | | |
| 34.18941 | insertion | 1 | | | rs149400338, | Overlapping G location |
| 36.25498 | insertion | 1 | | | rs147264092, | Overlapping A location |
| 36.82008 | substitution | 0 | 35 | 50 | | |
| 40.31891 | substitution | 0 | 37 | 45 | | |
| 20.85308 | deletion | 1 | | | | |
| 20.96386 | insertion | 1 | | | rs148418188, | Overlapping T location |
| 79.1762 | insertion | 1 | | | rs141327290, | Overlapping A location |
| 49.89154 | insertion | 1 | | | rs149000904, | Overlapping T location |
| 48.07396 | insertion | 1 | | | rs141286298, | Overlapping T location |
| 57.57576 | insertion | 1 | | | rs144300572, | Overlapping G location |
| 43.65942 | substitution | 0 | 37 | 61 | | |
| 55.82329 | insertion | 1 | | | rs142705941, | Overlapping A location |
| 26.78019 | insertion | 1 | | | rs148391224, | Overlapping A location |
| 40.91954 | substitution | 0 | 34 | 41 | | |
| 39.783 | insertion | 1 | | | | |
| 29.30233 | insertion | 1 | | | rs147406348, | Overlapping A location |
| 31.46067 | insertion | 1 | | | rs138166283, rs147744297, | Overlapping A location |
| 36.68122 | deletion | 1 | | | | |
| 49.88764 | substitution | 0 | 38 | 57 | | |
| 37.3913 | deletion | 1 | | | | |
| 30.58637 | deletion | 1 | | | | |

SUPPLEMENTAL TABLE S2-continued

Variants co-segregating with the modifying haplotype based on targeted re-sequencing of 3 Mb of the region around NCALD

| % variation | SNP variant | Gene name | Gene id |
|---|---|---|---|
| 36.73469 | | | |
| 39.07285 | | ANKRD46 | NM_198401 |
| 32.69231 | —, G, | | |
| 23.06238 | | SNX31 | NM_152628 |
| 41.68865 | | SNX31 | NM_152628 |
| 22.81369 | | SNX31 | NM_152628 |
| 46.27329 | | SNX31 | NM_152628 |
| 31.55556 | —, A, | | |
| 43.83838 | —, T, | | |
| 24.73573 | —, A, | | |
| 36.53846 | —, TT, —, | | |
| 27.92793 | —, TA, | | |
| 44.21769 | —, T, G, —, —, | | |
| 47.61905 | —, CA, —, T, C, —, CA, CACACACA, | PABPC1 | NM_002568 |
| 49.01065 | | | |
| 31.81818 | —, TTCCTTTCTTTTTCCTTCC (SEQ ID NO: 43), —, TTT, —, —, TTT, C, C, T, | | |
| 22.95082 | | | |
| 34.86005 | —, T, | | |
| 45.13761 | | | |
| 42.73504 | | | |
| 45.96774 | | | |
| 30.98592 | | GRHL2 | NM_024915 |
| 34.18941 | —, AT, TA, | GRHL2 | NM_024915 |
| 36.25498 | —, CT, | NCALD | NM_032041 |
| 36.82008 | | ODF1 | NM_024410 |
| 40.31891 | | | |
| 20.85308 | | | |
| 20.96386 | —, CGG, | | |
| 79.1762 | —, C, | AZIN1 | NM_148174 |
| 49.89154 | —, CAG, | AZIN1 | NM_148174 |
| 48.07396 | —, AGG, | AZIN1 | NM_148174 |
| 57.57576 | —, A, | AZIN1 | NM_148174 |
| 43.65942 | | | |
| 55.82329 | —, C, | | |
| 26.78019 | —, T, | | |
| 40.91954 | | | |

SUPPLEMENTAL TABLE S2-continued

Variants co-segregating with the modifying haplotype based on targeted re-sequencing of 3 Mb of the region around NCALD

| | | | | |
|---|---|---|---|---|
| 39.783 | | | | |
| 29.30233 | —, AC, | | | |
| 31.46067 | | —, GGG, —, GG, | | |
| 36.68122 | | | | |
| 49.88764 | | | FZD6 | NM_001164615 |
| 37.3913 | | | | |
| 30.58637 | | | | |

---

The invention claimed is:

1. A method for the treatment or prevention of a patient suffering from or being at risk of developing a neuronal disorder associated with a pathological calcium homeostasis and/or disturbed neuromuscular transmission comprising administering to said patient a sufficient amount of an inhibitor of neurocalcin delta (NCALD), wherein said inhibitor of NCALD knocks down the expression of NCALD in comparison to an untreated control.

2. The method according to claim 1, wherein said inhibitor is an oligonucleotide or an oligonucleotide analogue.

3. The method according to claim 1, wherein said inhibitor is an oligonucleotide having a sequence homology of at least 80% to any of SEQ ID NOs: 2-6 or 15-19.

4. The method according to claim 1, wherein said inhibitor is
   (a) covalently and/or non-covalently bound to at least one cell-penetrating peptide and/or at least one membrane disrupting peptide;
   (b) included in or covalently and/or non-covalently bound to a liposome;
   (c) included in or covalently and/or non-covalently bound to a micelle;
   (d) included in or covalently and/or non-covalently bound to a polymersome;
   (e) included in an episome;
   (f) covalently and/or non-covalently bound to or included in a microbead and/or nanobead; and/or
   (g) covalently and/or non-covalently bound to a non-toxic polymer.

5. The method according to claim 1, wherein the patient is further administered with an HDAC inhibitor.

6. The method according to claim 1, wherein the patient is further administered with an agent increasing survival motor neuron (SMN) activity.

7. The method according to claim 1, wherein said inhibitor knocks down the NCALD expression.

8. The method according to claim 1, wherein said inhibitor is an oligonucleotide or an oligonucleotide analogue selected from the group consisting of:
   (a) an antisense oligonucleotide;
   (b) an antisense oligonucleotide analogue;
   (c) an interfering oligonucleotide;
   (d) an oligonucleotide modifying the splicing of pre-mRNA;
   (e) an oligonucleotide analogue modifying the splicing of pre-mRNA; and
   (f) an oligonucleotide encoding for one or more of the aforementioned (a)-(e).

9. The method according to claim 1, wherein said inhibitor is an oligonucleotide has a sequence of any of SEQ ID NOs: 2-6 or 15-19.

10. The method according to claim 1, wherein the disorder is a motoneuron disease.

11. The method according to claim 1, wherein the disorder is selected from the group consisting of spinal muscular atrophy (SMA), amyotrophic lateral sclerosis (ALS), hereditary motor neuron disease (HMN) or a neurodegenerative disorder.

12. The method according to claim 1, wherein the disorder is selected from the group consisting of Parkinson's disease, Frontotemporal Dementia, Alzheimer's disease, Ataxia, Morbus Huntington, and polyglutamic acid disease.

13. The method according to claim 1, wherein the patient is further administered with an agent increasing survival motor neuron (SMN) activity selected from the group consisting of:
   (a) an agent increasing the expression rate of SMN;
   (b) an agent increasing the rate of functional SMN;
   (c) an agent comprising genetic material encoding for functional SMN;
   (d) an agent stabilizing the SMN; or inhibiting the proteasomal degradation of SMN;
   (e) an agent that is increasing activity of the SMN; and
   (f) replacement by gene therapy expressing SMN1 in an self-complementary adenovirus vector.

* * * * *